US007153889B2

(12) United States Patent
Altenbach et al.

(10) Patent No.: US 7,153,889 B2
(45) Date of Patent: Dec. 26, 2006

(54) BICYCLIC-SUBSTITUTED AMINES AS HISTAMINE-3 RECEPTOR LIGANDS

(75) Inventors: Robert J. Altenbach, Chicago, IL (US); Lawrence A. Black, Libertyville, IL (US); Sou-Jen Chang, Prairie View, IL (US); Marlon D. Cowart, Round Lake Beach, IL (US); Ramin Faghih, Lake Forest, IL (US); Gregory A. Gfesser, Waukegan, IL (US); Yi-Yin Ku, Buffalo Grove, IL (US); Huaqing Liu, Buffalo Grove, IL (US); Kirill A. Lukin, Mundelein, IL (US); Diana L. Nersesian, Gurnee, IL (US); Yu-ming Pu, Gurnee, IL (US); Padam N. Sharma, Gurnee, IL (US); Youssef L. Bennani, Shaker Heights, OH (US); Michael P. Curtis, Kenosha, WI (US)

(73) Assignee: Abbott Laboratories, Abbott Park, IL (US)

( * ) Notice: Subject to any disclaimer, the term of this patent is extended or adjusted under 35 U.S.C. 154(b) by 183 days.

(21) Appl. No.: 10/689,735

(22) Filed: Oct. 22, 2003

(65) Prior Publication Data

US 2004/0152704 A1 Aug. 5, 2004

Related U.S. Application Data

(60) Provisional application No. 60/425,376, filed on Nov. 12, 2002.

(51) Int. Cl.
*C07C 13/465* (2006.01)
(52) U.S. Cl. .......................................... 514/765; 585/26
(58) Field of Classification Search ................ 514/243, 514/765; 585/26
See application file for complete search history.

(56) References Cited

U.S. PATENT DOCUMENTS

| 1,860,286 | A | | 5/1932 | Hartman et al. | |
|---|---|---|---|---|---|
| 3,489,756 | A | | 1/1970 | Bolhofer et al. | 260/247.7 |
| 3,639,476 | A | | 2/1972 | Eberle et al. | 260/563 |
| 4,327,022 | A | * | 4/1982 | Bailey | 540/484 |
| 6,225,328 | B1 | | 5/2001 | Bernardon | 514/356 |
| 6,300,352 | B1 | * | 10/2001 | Cheshire et al. | 514/357 |
| 6,358,515 | B1 | | 3/2002 | Ogata et al. | 424/401 |

FOREIGN PATENT DOCUMENTS

| CH | 149 007 | | 11/1931 |
|---|---|---|---|
| GB | 1 122 756 | | 8/1968 |
| GB | 1178400 | | 1/1970 |
| WO | WO 94/17079 | | 8/1994 |
| WO | WO 95/01426 | | 1/1995 |
| WO | WO 95/09159 | | 4/1995 |
| WO | WO 98/38156 | | 9/1998 |
| WO | WO 9838156 | * | 9/1998 |
| WO | WO 98/57931 | | 12/1998 |
| WO | 00/06254 | | 2/2000 |
| WO | 00/27815 | | 5/2000 |
| WO | 02/074758 | | 9/2002 |
| WO | 03/093237 | | 11/2003 |

OTHER PUBLICATIONS

Azzolina et al. "Chemical and biological profile of racemic and optically active dialkylaminoalkylnaphtalenes with analgesic activity," Tetrahedron Asymmetry, vol. 13, (2002), pp. 1073-1081.*
Airaksinen et al., "Histamine Neurons in Human Hypothalamus: Anatomy in Normal and Alzeimer Diseased Brains," Neuroscience 44(2):465-481 (1991).
Andrés et al., "A Simple Steroselective Synthesis Of Enantiopure 2-Substituted Pyrrolidines and Piperidines From Chiral (*R*)-Phenylglycinol-Derived Bicyclic 1,3-Oxazolidines," Eur. J. Org. Chem. 1719-1726 (2000).
Aranyos et al., "Novel Electron-Rich Bulky Phosphine Ligands Facilitate the Palladium-Catalyzed Preparation of Diaryl Ethers," J. Am Chem. Soc. 121:4369-4378 (1999).
Baston et al., "A New Route To 6-Aryl-Substituted 3,4-Dihydronaphthalene Derivates Via Pd (O)-Catalyzed Cross-Coupling Reaction of Aryl Zinc Chlorides With an Aryl Triflate," Synthetic Communication 28(14):2725-2729 (1998).
Bjenning et al., "Peripherally Administered Ciproxifan Elevates Hypothalamic Histamine Levels And Potently Reduces Food Intake in the Sprague Dawley Rat," Histamine Research In The New Mellennium, Proceedings Of The International Sendai Histamine Symposium Held In Sendai, Japan, Nov. 22-25, 2000, p. 449-450.

(Continued)

*Primary Examiner*—James O. Wilson
*Assistant Examiner*—Jason H. Johnsen
(74) *Attorney, Agent, or Firm*—Portia Chen

(57) ABSTRACT

Compounds of formula (I)

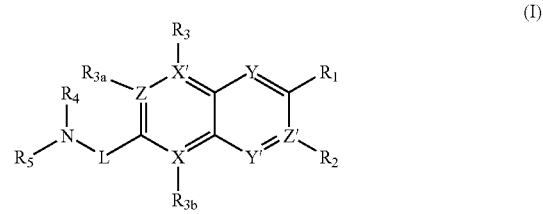

are useful in treating conditions or disorders prevented by or ameliorated by histamine-3 receptor ligands. Also disclosed are pharmaceutical compositions comprising the histamine-3 receptor ligands, methods for using such compounds and compositions, and a process for preparing compounds within the scope of formula (I).

31 Claims, No Drawings

OTHER PUBLICATIONS

Dai et al., "The First General Method For Palladium-Catalyzed Negishi Cross-Coupling Of Aryl And Vinyl Chlorides: Use of Commercially Available Pd(P(t-Bu)$_3$)$_2$ as a Catalyst," J. Am. Chem Soc. 123:2719-2724 (2001).

De Almeida et al., "Memory Facilitation by Histamine," Arch. Int. Pharmacodyn., 283:193-198 (1986).

Delaunois et al., "Modulation Of Acetylcholine, Capsaicin and Substance P Effects by Histamine H$_3$ Receptors in Isolated Perfused Rabbit Lungs," European Journal Of Pharmacology, 277:243-250 (1995).

Dimitriadou et al., "Functional Relationship Between Mast Cells and C-Sensitive Nerve Fibres Evidenced by Histamine H$_3$-Receptor Modulation in Rat Lung and Spleen," Clinical Science, 87:151-163 (1994).

Dohle et al., "Copper-Mediated Cross-Coupling of Functionalized Arylmagnesium Reagents with Functionalized Alkyl and Benzylic Halides," Organic Letters 3(18):2871-2873 (2001).

Duméry et al., "Development of Amygdaloid Cholinergic Mediation of Passive Avoidance Learning in the Rat," Exp. Brain. Res., 67:61-69 (1987).

Ellingboe et al., "Antihyperglycemic Activity of Novel Naphthalenyl 3H-1,2,3,5-Oxathiadiazole 2-Oxides," J. Med. Chem. 36:2485-2493 (1993).

Elworthy et al., "The Configurational Stability of Chiral Lithio α-Amino Carbanions. The Effect of Li-O vs. Li-N Complexation," Tetrahedron 50(20):6089-6096 (1994).

Fitzsimons et al., "Histamine Receptors Signalling in Epidermal Tumor Cell Lines With H-ras Gene Alterations," Inflamm. Res., 47, Supplement 1, S50-S51 (1998).

Fox et al., "Effects of Histamine H$_3$ Receptor Ligands GT-2331 And Ciproxifan in a Repeated Acquisition Response in the Spontaneously Hypertensive Rat Pup," Behavioural Brain Research 131:151-161 (2002).

Gaffield et al., "Chiroptical Properties of N-Nitrosopyrrolidines and N-Nitrosamino Acids," Tetrahedron 37:1861-1869 (1981).

Haas et al., "Subcortical Modulation of Synaptic Plasticity in the Hippocampus," Behavioural Brain Research, 66:41-44 (1995).

Hartwig, "Transition Metal Catalyzed Synthesis of Arylamines and Aryl Ethers From Aryl Halides and Triflates: Scope And Mechanism," Angew. Chem. Int. Ed. 37:2046-2067 (1998).

Hatta et al., "Activation of Histamine H$_3$ Receptors Inhibits Carrier-Mediated Norepinephrine Release in a Human Model of Protracted Myocardial Ischemia[1,2]," The Journal Of Pharmacology And Experimental Therapeutics, 283(2):494-500 (1997).

Imamura et al., "Activation Of Histamine H$_3$-Receptors Inhibits Carrier-Mediated Norepinephrine Release During Protracted Myocardial Ischemia," Circulation Research, 78(3):475-481 (1996).

Imamura et al., "Histamine H$_3$- Receptor-Mediated Inhibition Of Calcitonin Gene-Related Peptide Release From Cardiac C Fibers," Circulation Research, 78(5):863:869(1996).

Itoh et al., "Thioperamide, A Histamine H$_3$ Receptor Antagonist, Powerfully Suppresses Peptide YY-Induced Food Intake In Rats," Biol. Psychiatry 45:475-481 (1999).

Kamei et al., "Influence Of Certain H$_1$-Blockers On The Step-Through Active Avoidance Response In Rats," Psychopharmacology, 102:312-318 (1990).

Kamei et al., "Participation Of Histamine In The Step-Through Active Avoidance Response And Its Inhibition By H$_1$-Blockers," Japan J. Pharmacol., 57:473-482 (1991).

Karrer et al., Helvetica Chimica Acta. 34(270):2202-2210 (1951).

Kiyomori et al., "An Efficient Copper-Catalyzed Coupling Of Aryl Halides With Imidazoles," Tetrahedron Letters 40:2657-2660 (1999).

Klapars et al., "A General And Efficient Copper Catalyst For The Amidation of Aryl Halides And The N-Arylation Of Nitrogen Heterocycles," J. Am. Chem. Soc. 123:7727-7729 (2001).

Kwong et al., "Copper-Catalyzed Coupling Of Alkylamines And Aryl Iodides: An Efficient System Even In An Air Atmosphere," Organic Letters 4(4):581-584 (2002).

Leurs et al., "The Histamine H$_3$-Receptor: A Target For Developing New Drugs," Progress In Drug Research, 39:127-165 (1992).

Leurs et al., "The Medicinal Chemistry And Therapeutic Potentials Of Ligands Of The Histamine H$_3$ Receptor," Progress In Drug Research, 45:107-165 (1995).

Leurs et al., "Therapeutic Potential Of Histamine H$_3$ Receptor Agonists And Antagonists," Trends In Pharm. Sci., 19:177-183 (1998).

Levi et al., "Histamine H$_3$-Receptors: A New Frontier In Myocardial Ischemia," The Journal Of Pharmacology And Experimental Therapeutics, 292(3):825-830 (2000).

Li et al., "Highly Active, Air-Stable Versatile Palladium Catalysts For The C-C, C-N, And C-S Bond Formations Via Cross-Coupling Reactions Of Aryl Chlorides," J. Org. Chem. 66:8677-8681 (2001).

Li et al., "The First Phosphine Oxide Ligand Precursors For Transition Metal Catalyzed Cross-Coupling Reactions: C-C, C-N, And C-S Bond Formation On Unactivated Aryl Chlorides," Angew. Chem. Int. Ed. 40(8):1513-1516 (2001).

Lin et al., "Involvement Of Histaminergic Neurons In Arousal Mechanisms Demonstrated With H$_3$- Receptor Ligands In The Cat," Brain Research, 523:325-330 (1990).

Lipshutz et al., "Efficient Scavenging Of Ph$_3$P And Ph$_3$P=O With High-Loading Merrifield Resin," Organic Letters 3(12):1869-1871 (2001).

Lipshutz et al., "Substitution Reactions Of Aryl *Chlorides* With Organozinc Reagents Catalyzed By Ni(0)," Tetrahedron Letters 40:197-200 (1999).

Littke et al., "Versatile Catalysts For The Suzuki Cross-Coupling Of Arylboronic Acids With Aryl And Vinyl Halides And Triflates Under Mild Conditions," J. Am. Chem. Soc. 122:4020-4028 (2000).

Marcoux et al., "A General Copper-Catalyzed Synthesis Of Diaryl Ethers," J. Am. Chem. Soc. 119:10539-10540 (1997).

Matsubara et al., "UK-14,304, R(-) ∀-Methyl-Histamine And SMS 201-995 Block Plasma Protein Leakage Within Dura Mater By Prejunctional Mechanisms," European Journal Of Pharmacology, 224:145-150 (1992).

Mazurkiewicz-Kwilecki et al., "Changes In The Regional Brain Histamine And Histidine Levels In Postmortem Brains Of Alzheimer Patients," Can. J. Physiol. Pharmacol, 67: 75-78 (1989).

McLeod et al., "Histamine H$_3$ Antagonists," Progress In Resp. Research 31:133-134 (2001).

Miyaura et al., "Palladium-Catalyzed Cross-Coupling Reactions Of Organoboron Compounds," Chem. Rev. 95:2457-2483 (1995).

Mohanakrishnan et al., "Pd(0)-Mediated Cross Coupling Of 2-Iodoestradiol With Organozinc Bromides: A General Route To The Synthesis Of 2-Alkynyl, 2-Alkenyl And 2-Alkylestradiol Analogs," Synlett. 7:1097-1099 (1999).

Molander et al., "Cross-Coupling Reactions Of Primary Alkylboronic Acids With Aryl Triflates And Aryl Halides," Tetrahedron 58:1465-1470 (2002).

Monti et al., "Effects Of Selective Activation Or Blockade Of The Histamine H$_3$ Receptor On Sleep And Wakefulness," European Journal Of Pharmacology, 205:283-287 (1991).

Monti et al., "Sleep And Waking During Acute Histamine H$_3$ Agonist BP2.94 Or H$_3$ Antagonist Carboperamide (MR 16155) Administration In Rats," Neuropsychopharmacology, 15(1):31-35 (1996).

Murakami et al., "AQ-0145, A Newly Developed Histamine H$_3$ Antagonist, Decreased Seizure Susceptibility Of Electrically Induced Convulsions In Mice," Meth. Find. Exp. Clin. Pharmacol. 17(C):70-73 (1995).

Nijhuis et al., "Stereochemical Aspects Of The "*Tert*-Amino Effect." 2. Enantio- And Diastereoselectivity In The Synthesis Of Quinolines, Pyrrolo [1,2-α]Quinolines, And [1,4]Oxazino[4,3-α]Quinolines," J. Org. Chem. 54:209-216 (1989).

Onodera et al., "Neuropharmacology Of The Histaminergic Neuron System In The Brain And Its Relationship With Behavioral Disorders," Progress In Neurobiology, 42:685-702 (1994).

Palomo et al., "Phosphazene Bases For The Preparation Of Biaryl Thioethers From Aryl Iodides And Arenethiols," Tetrahedron Letters 41:1283-1286 (2000).

Palucki et al., "Palladium-Catalyzed Intermolecular Carbon-Oxygen Bond Formation: A New Synthesis Of Aryl Ethers," J. Am. Chem. Soc. 119:3395-3396 (1997).

Pan et al., "Histaminergic Ligands Attenuate Barrel Rotation in Rats Following Unilateral Labyrinthectomy," Meth. Find Exp. Clin. Pharmacol 20(9):771-777 (1998).

Panula et al., "Brain Histamine In Pathophysiological Conditions And Brain Diseases," The Histamine $H_3$ Receptor, 243-253 (1998).

Perez-Garcia et al., "Effects Of Histamine $H_3$ Receptor Ligands In Experimental Models Of Anxiety And Depression," Psychopharmacology 142:215-220 (1999).

Phillips et al., "Recent Advances In Histamine $H_3$ Receptor Agents," Annual Reports In Medicinal Chemistry, 33:31-40 (1998).

Rouleau, "Bioavailability, Antinociceptive And Antiiflammatory Properties Of BP 2-94, A Histamine $H_3$ Receptor Agonist Prodrug," The Journal Of Pharmacology And Experimental Therapeutics, 281(3):1085-1094 (1997).

Sakai et al., "Effects Of Thioperamide, A Histamine $H_3$ Receptor Antagonist, On Locomotor Activity And Brain Histamine Content In Mast Cell-Deficient W/W$^v$ Mice," Life Sciences, 48:2397-2404 (1991).

Schopfer et al., "A General Palladium-Catalysed Synthesis Of Aromatic And Heteroaromatic Thioethers," Tetrahedron 57:3069-3073 (2001).

Schwartz et al., "Histaminergic Transmission in the Mammalian Brain," Physiological Reviews 71(1):1-51 (1991).

Schwartz et al., "Histamine," Psychopharmacology: The Fourth Generation Of Progress, 397-405 (1995).

Shaywitz et al., "Dopaminergic But Not Noradrenergic Mediation Of Hyperactivity And Performance Deficits In The Developing Rat Pup," Psychopharmacology, 82:73-77 (1984).

Sugahara et al., "A Facile Copper-Catalyzed Ullmann Condensation: N-Arylation Of Heterocyclic Compounds Containing an -NHCO- Moiety," Chem. Pharm. Bull. 45(4):719-721 (1997).

Suzuki, "Recent Advances In The Cross-Coupling Reactions Of Organoboron Derivatives With Organic Electrophiles, 1995-1998," Journal Of Organometallic Chemistry 576:147-168 (1999).

Szelag, "Role Of Histamine $H_3$-Receptors In The Proliferation Of Neoplastic Cells In Vitro," Med. Sci. Monit., 4(5):747-755 (1998).

Tedford et al., "Cognition And Locomotor Activity In The Developing Rat: Comparisons Of Histamine $H_3$ Receptor Antagonists And ADHD Therapeutics," Society For Neuroscience Abstr., 22:22 (1996).

Tedford et al., "Pharmacological Characterization Of GT-2016, A Non-Thiourea-Containing Histamine $H_3$ Receptor Antagonist: In Vitro And In Vivo Studies," The Journal Of Pharmacology And Experimental Therapeutics, 275(2):598-604 (1995).

Tedford, "Clinical Application Of HA $H_3$ Receptor Antagonists In Learning And Memory Disorders," The Histamine $H_3$ Receptor 269-286 (1998).

Toshimitsu et al., "Preparation, Structure, And Reactivity Of Pentacoordinate Disilanes Bearing An 8-Charcogeno-1-Naphthyl Group And A Heteroatom On The Same Silicon Atom," Heteroatom Chemistry 12(5):392-397 (2001).

Wada et al., "Is The Histaminergic Neuron System A Regulatory Center For Whole-Brain Activity?," Trends In Neurosciences, 14(9):415-418 (1991).

Wolfe et al., "Rational Development Of Practical Catalysts For Aromatic Carbon-Nitrogen Bond Formation," Acc. Chem. Res. 37:805-818 (1998).

Wolfe et al., "Simple, Efficient Catalyst System For The Palladium-Catalyzed Amination Of Aryl Chlorides, Bromides, And Triflates," J. Org. Chem. 65:1158-1174 (2000).

Yamada et al., "A Biogenetic-Type Asymmetric Cyclization Syntheses Of Optically Active α-Cyclocitral And Trans-α-Damascone," Tetrahedron Letters 5:381-384 (1973).

Yamamoto et al., "Ullmann Condensation Using Copper Or Copper Oxide As The Reactant. Arylation Of Active Hydrogen Compound (Imides, Amides, Amines, Phenol, Benzoic Acid, And Phenylacetylene)," Can. J. Chem. 61:86-91 (1983).

Yang et al., "Palladium-Catalyzed Animation Of Aryl Halides And Sulfonates," Journal Of Organometallic Chemistry 576:125-146 (1999).

Yates et al., "Effects Of A Novel Histamine $H_3$ Receptor Antagonist, GT-2394, On Food Intake And Weight Gain In Sprague-Dawley Rats," Abstracts, Society For Neuroscience, 102.10:219 (Nov. 2000).

Yokoyama et al., "Effect Of Thioperamide, A Histamine $H_3$ Receptor Antagonist, On Electrically Induced Convulsions In Mice," Journal Of Pharmacology, 234:129-133 (1993).

Yokoyama et al., "Histamine And Seizures Implications For The Treatment Of Epilepsy," CNS Drugs, 5(5):321-330 (1996).

Zou et al., "Ag(I)-Promoted Suzuki-Miyaura Cross-Couplings Of N-Alkylboronic Acids," Tetrahedron Letters 42:7213-7215 (2001).

Bachman et al., "Quinoline Derivatives from 2- and 4-Chloroquinolines," Journal of Organic Chemistry, American Chemical Society. Easton, US 9:302-309 (1944).

Coutts et al., "Calmodulin Antagonists as Potential Antifungal Agents," Pesticide Science, Elsevier Applied Science Publisher. Barking, GB 51(1):99-101 (1997).

Vernsten et al., "Halogen Substituted Aryl Alkamine Ethers," Journal of the American Chemical Society 78:5398-5400 (1956).

Wear et al., "The Synthesis of Some Quinoxaline Derivatives," Journal of the American Chemical Society 72:2893-2894 (1950).

* cited by examiner

BICYCLIC-SUBSTITUTED AMINES AS HISTAMINE-3 RECEPTOR LIGANDS

The present application claims the benefit under 35 U.S.C. 119 to United States Provisional Application No. 60/425,376, filed Nov. 12, 2002, the entire disclosure of that application being incorporated herein by reference.

BACKGROUND OF THE INVENTION

1. Technical Field

The invention relates to bicyclic-substituted amine compounds, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302:832–837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117–123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can demonstrate antagonist, agonist or partial agonist activity. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to substituted amines and, more particularly, bicyclic-substituted amines. Accordingly, one aspect of the invention relates to compounds of formula (I):

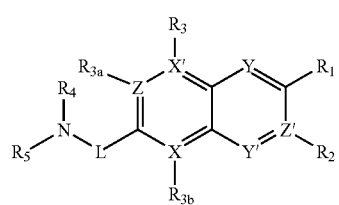

(I)

or a pharmaceutically acceptable salt, ester, amide, or prodrug thereof, wherein:

Y, and Y' are each independently selected from the group consisting of CH, CF, and N;

X, X', Z, and Z' are each independently C or N;

one of $R_1$ and $R_2$ is selected from the group consisting of halogen, cyano, and $L_2R_6$;

the other of $R_1$ and $R_2$ is selected from the group consisting of hydrogen, alkyl, alkoxy, aryl, cycloalkyl, halogen, cyano, and thioalkoxy, provided that $R_2$ is absent when Z' is N;

$R_3$ is absent when X' is N or $R_3$ is selected from the group consisting of hydrogen, alkyl, alkoxy, halogen, cyano, and thioalkoxy;

$R_{3a}$ is absent when Z is N or $R_{3a}$ is selected from the group consisting of hydrogen, methyl, alkoxy, halogen, and cyano;

$R_{3b}$ is absent when X is N or $R_{3b}$ is selected from the group consisting of hydrogen, alkyl, alkoxy, halogen, hydroxy, cyano, and thioalkoxy;

$R_4$ and $R_5$ are each independently selected from the group consisting of alkyl, haloalkyl, hydroxyalkyl, alkoxyalkyl, cycloalkyl, cycloalkylalkyl and $(NR_AR_B)$alkyl, or $R_4$ and $R_5$ taken together with the nitrogen atom to which each is attached form a non-aromatic ring of the formula:

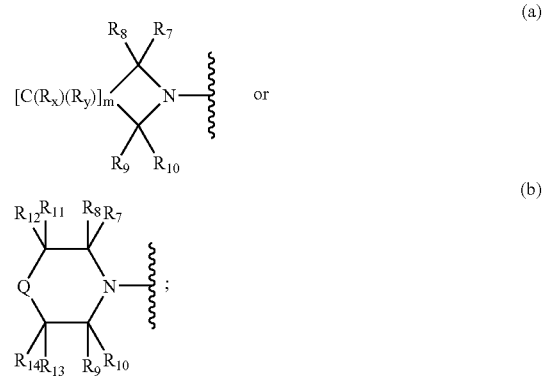

$R_6$ is selected from the group consisting of aryl, heteroaryl, heterocycle, and cycloalkyl;

$R_7$, $R_8$, $R_9$, and $R_{10}$ at each occurrence are each independently selected from the group consisting of hydrogen, hydroxyalkyl, fluoroalkyl, and alkyl; or one of the pair $R_7$ and $R_8$ or the pair $R_9$ and $R_{10}$ is taken together to form a $C_3$–$C_6$ ring, wherein 0, 1, or 2 heteroatoms selected from O, N, or S replace a carbon atom in the ring;

$R_{11}$, $R_{12}$, $R_{13}$, and $R_{14}$ are each independently selected from the group consisting of hydrogen, hydroxy, hydroxyalkyl, alkyl, and fluoro;

Q is selected from the group consisting of a bond, O, S, and $NR_{15}$;

L is —$[C(R_{16})(R_{17})]_n$— or —$[C(R_{16})(R_{17})]_pO$—;

$L_2$ is a bond or $L_2$ is selected from the group consisting of —O—, —C(=O)—, —S—, —$[C(R_{18})(R_{19})]_q$—, —O—[C$(R_{18})(R_{19})]_q$—, —NH— and —N(alkyl)-;

$R_{15}$ is selected from the group consisting of hydrogen, alkyl, acyl, amido, and formyl;

$R_{16}$ and $R_{17}$ at each occurrence are independently selected from the group consisting of hydrogen, alkyl, alkoxy, and fluoro;

$R_{18}$ and $R_{19}$ at each occurrence are each independently selected from the group consisting of hydrogen, hydroxy, alkyl, alkoxy, and fluoro;

$R_x$ and $R_y$ at each occurrence are each independently selected from the group consisting of hydrogen, hydroxy, alkyl, alkoxy, alkylamino, dialkylamino, and fluoro, or one of $R_x$ or $R_y$ represents a covalent bond when taken together with $R_x$ or $R_y$ on an adjacent carbon atom such that a double bond is represented between the adjacent carbon atoms;

m is an integer from 1 to 5;

n is an integer from 1 to 6;

p is an integer from 2 to 6; and q is an integer from 1 to 4;

wherein 0, 1, or 2 of X, X', Y, Y', Z, and Z' can be nitrogen; provided that $R_3$ is absent when X' is N; $R_{3a}$ is absent when Z is N; $R_2$ is absent when Z' is N; and $R_{3b}$ is absent when X is N.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating and/or preventing conditions and disorders related to $H_3$ receptor modulation in mammals. More particularly, the method is useful for conditions and disorders related to memory and cognition processes, neurological processes, cardiovascular function, and body weight.

Processes for making compounds of the invention also are contemplated.

The compounds, compositions comprising the compounds, methods for making the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" as used herein, means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein, means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein, means a —$NH_2$ group.

The term "aryl" as used herein, means a monocyclic aromatic ring system. Representative examples of aryl include, but are not limited to, phenyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkylcarbonyl, formyl, haloalkoxy, haloalkyl, halogen, hydroxy, hydroxyalkyl, mercapto, nitro, thioalkoxy, $NR_AR_B$, and $(NR_AR_B)$sulfonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl" as used herein, means an arylalkoxy group, as defined herein, appended to the parent molecular moiety through a carbonyl group, as defined herein. Representative examples of arylalkoxycarbonyl include, but are not limited to, benzyloxycarbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein, means a —C(=O)— group.

The term "carboxy" as used herein, means a —CO$_2$H group, which may be protected as an ester group —CO$_2$-alkyl.

The term "cyano" as used herein, means a —CN group.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycoalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halogen, hydroxy, hydroxyalkyl, methylenedioxy, thioalkoxy, and —NR$_A$R$_B$.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylcarbonyl" as used herein, means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "dialkylamino" as used herein, means two independent alkyl groups, as defined herein, appended to the parent molecular moiety through a nitrogen atom. Representative examples of dialkylamino include, but are not limited to, dimethylamino, diethylamino, ethylmethylamino, butylmethylamino.

The term "ethylenedioxy" as used herein, means a —O(CH$_2$)$_2$O— group wherein the oxygen atoms of the ethylenedioxy group are attached to the parent molecular moiety through one carbon atom forming a five-membered ring or the oxygen atoms of the ethylenedioxy group are attached to the parent molecular moiety through two adjacent carbon atoms forming a six-membered ring.

The term "fluoro" as used herein means —F.

The term "fluoroalkyl" as used herein, means at least one fluoro group, as defined herein, appended to the parent molecular moiety through an alkyl group, as defined herein. Representative example of fluoroalkyl include, but are not limited to, fluoromethyl, difluoromethyl, trifluoromethyl, pentafluoroethyl, and 2,2,2-trifluoroethyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring, or a ring wherein two carbon atoms in the ring are replaced with one O or S atom and one N atom. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridazinonyl, pyridinyl, pyridinonyl, pyrimidinyl, pyrrolyl, tetrazolyl, thiadiazolyl, thiazolyl, thienyl or thiophenyl, triazinyl, and triazolyl. Specific heteroaryl groups include, but are not limited to, 2H-pyridazin-3-one-2-yl.

The heteroaryl groups of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, formyl, haloalkoxy, haloalkyl, halogen, hydroxy, hydroxyalkyl, mercapto, nitro, thioalkoxy, —NR$_A$R$_B$, (NR$_A$R$_B$)carbonyl, and (NR$_A$R$_B$)sulfonyl.

The term "heterocycle," as used herein, refers to a three-, four-, five-, six-, seven-, or eight-membered ring containing one, two, or three heteroatoms independently selected from the group consisting of nitrogen, oxygen, and sulfur. Rings containing at least four members can be saturated or unsaturated. For example, the four- and five-membered ring has zero or one double bond. The six-membered ring has zero, one, or two double bonds. The seven- and eight-membered rings have zero, one, two, or three double bonds. The heterocycle groups of the invention can be attached to the parent molecular moiety through a carbon atom or a nitrogen atom. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, dihydrothiazolyl, and thiomorpholinyl. Representative examples of non-nitrogen containing heterocycles include, but are not limited to, tetrahydrofuryl and tetrahydropyranyl.

The heterocycles of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halogen, hydroxy, hydroxyalkyl, mercapto, nitro, oxo, thioalkoxy, —$NR_AR_B$, and ($NR_AR_B$)sulfonyl.

The term "hydroxy" as used herein means a —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyidimethylsilyl, t-butyidiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein, means a —SH group.

The term "methylenedioxy" as used herein, means a —$OCH_2O$— group wherein the oxygen atoms of the methylenedioxy are attached to the parent molecular moiety through two adjacent carbon atoms.

The term "—$NR_AR_B$" as used herein, means two groups, $R_A$ and $R_B$, which are appended to the parent molecular moiety through a nitrogen atom. $R_A$ and $R_B$ are independently selected from hydrogen, alkyl, acyl and formyl. Representative examples of —$NR_AR_B$ include, but are not limited to, amino, dimethylamino, methylamino, acetylamino, and acetylmethylamino.

The term "($NR_AR_B$)alkyl" as used herein, means an —$NR_AR_B$ group, as defined herein, appended to the parent molecular moiety through an alkyl group, as defined herein. Representative examples of ($NR_AR_B$)alkyl include, but are not limited to, 2-(methylamino)ethyl, 2-(dimethylamino)ethyl, 2-(amino)ethyl, 2-(ethylmethylamino)ethyl, and the like.

The term "($NR_AR_B$)carbonyl" as used herein, means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "($NR_AR_B$)sulfonyl" as used herein, means a —$NR_AR_B$ group, as defined herein, appended to the parent molecular moiety through a sulfonyl group, as defined herein. Representative examples of ($NR_AR_B$)sulfonyl include, but are not limited to, aminosulfonyl, (methylamino)sulfonyl, (dimethylamino)sulfonyl and (ethylmethylamino)sulfonyl.

The term "nitro" as used herein means a —$NO_2$ group.

The term "nitrogen protecting group" as used herein, means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O)$_2$C=O, a diaryl anhydride, for example as represented by (aryl-O)$_2$C=O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "hydroxy protecting group" or "O-protecting group" or "oxygen protecting group" means a substituent which protects hydroxy groups against undesirable reactions during synthetic procedures. Examples of hydroxy protecting groups include, but are not limited to, substituted methyl ethers, for example, methoxymethyl, benzyloxymethyl, 2-methoxyethoxymethyl, 2-(trimethylsilyl)ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, tert-butyldimethylsilyl and tert-butyldiphenylsilyl; cyclic acetals and ketals, for example, methylene acetal, acetonide, and benzylidene acetal; cyclic ortho esters, for example, methoxymethylene; cyclic carbonates; and cyclic boronates.

The term "oxo" as used herein means (=O).

The term "sulfonyl" as used herein means a —$S(O)_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

As used herein, the term "antagonist" encompasses and describes compounds that prevent receptor activation by an $H_3$ receptor agonist alone, such as histamine, and also encompasses compounds known as "inverse agonists". Inverse agonists are compounds that not only prevent receptor activation by an $H_3$ receptor agonist, such as histamine, but also inhibit intrinsic $H_3$ receptor activity.

Compounds of the Invention

Compounds of the invention can have the general formula (I) as described above.

As previously described, Y, and Y' each can be CH, CF, or N, and X, X', Z, and Z' each can be independently selected from C or N.

$R_1$ can be halogen, cyano, or $L_2R_6$, wherein $L_2$ is selected from the group consisting of a bond, —O—, —C(=O)—, —S—, —[C($R_{18}$)($R_{19}$)]$_q$—, as defined herein, —O—[C($R_{18}$)($R_{19}$)]$_q$—, as defined herein, —NH—, and —N(alkyl)-, and $R_6$ is selected from the group consisting of aryl, heteroaryl, heterocycle, and cycloalkyl.

Typically, the substituent for $R_1$ is selected from bromo, cyano, or $L_2R_6$. Specific examples of groups for $R_1$ wherein the substituent is halogen or cyano include, but are not limited to, bromo and cyano.

Preferably $L_2$ is selected from a bond, —O—, —C(=O)—, —S—, or —[C($R_{18}$)($R_{19}$)]$_q$—. Specific groups for $L_2$ include, but are not limited to, —CH(OH)—, —C(=O)—, and where $L_2$ is a bond.

$L_2$ as a bond is most preferred. Preferred groups for $R_6$ are aryl, heteroaryl, and cycloalkyl. The aryl, heteroaryl, and heterocyclic groups can be unsubstituted or substituted, for example as described in the Definition of Terms.

Examples of aryl groups for $R_6$ can include, but are not limited to, phenyl. The phenyl groups can be substituted with at least 0, 1, or 2 substituents. Preferred substituents for aryl are cyano, halogen, —NR$_A$R$_B$, alkoxy, hydroxyalkyl, alkylcarbonyl, alkoxycarbonyl, cycloalkylcarbonyl, thioalkoxy, alkylsulfonyl, and haloalkyl. The more preferred substituent is cyano. Specific examples include, but are not limited to, 4-chlorophenyl, 3-cyanophenyl, 4-cyanophenyl, 3,5-difluorophenyl, 4-(dimethylamino)phenyl, 4-ethoxyphenyl, 3-fluorophenyl, 4-fluorophenyl, 3-hydroxymethylphenyl, 4-(1-hydroxy-1-methylethyl)phenyl, 3-(methylcarbonyl)phenyl, 4-(methylcarbonyl)phenyl, 4-(methylsulfanyl)phenyl, 4-(methylsulfonyl)phenyl, 4-methoxyphenyl, 4-(cyclopropylcarbonyl)phenyl, 4-(methoxycarbonyl)phenyl, and 4-(trifluoromethyl)phenyl.

One particular embodiment is a compound of formula (I) wherein $R_1$ is $L_2R_6$, $L_2$ is a bond and $R_6$ is aryl wherein the aryl is phenyl substituted with 0, 1, or 2 substituents selected from the group consisting of cyano, halogen, —NR$_A$R$_B$, alkoxy, hydroxyalkyl, alkylcarbonyl, alkoxycarbonyl, cycloalkylcarbonyl, alkylsulfonyl, haloalkyl, and thioalkoxy.

Specific heteroaryl groups for $R_6$ can include, but are not limited to, furyl, imidazolyl, isothiazolyl, isoxazolyl, oxadiazolyl, oxazolyl, pyrazinyl, pyrazolyl, pyridazinyl, pyridazinonyl, pyridinonyl, pyridinyl, pyrimidinyl, pyrrolyl, tetrazolyl, thiadiazolyl, thiazolyl, thienyl, triazinyl, and triazolyl. Specific heteroaryl groups for the invention include, but are not limited to, for example, furan-3-yl, pyrazin-2-yl, pyrazol-3-yl, pyrazol-4-yl, pyridin-2-yl, pyridin-3-yl, pyridin-4-yl, pyrimidin-2-yl, pyrimidin-5-yl, pyrrol-2-yl, 1,3-thiazol-2-yl, 1,3-thiazol-5-yl, thiophen-3-yl, and thiophen-2-yl. Also included as heteroaryl groups of the invention are 2H-pyridazin-3-one, particularly 2H-pyridazin-3-one-2-yl, and 1H-pyridin-2-one, particularly 1H-pyridin-2-one-1-yl. A preferred heteroaryl group is 2H-pyridazin-3-one-2-yl.

The heteroaryl groups can be substituted with at least 0, 1, 2, or 3 substituents. Preferred substituents for the heteroaryl groups are —NR$_A$R$_B$, halogen, alkyl, cyano, alkoxyimino, alkoxycarbonyl, (NR$_A$R$_B$)carbonyl, alkylcarbonyl, haloalkyl, and alkoxy. Specific examples of substituted heteroaryl groups for the invention include, but are not limited to, 2-aminopyrimidin-5-yl, 3-bromoisoxazol-5-yl, 3-chloropyridin-4-yl, 6-chloropyridin-3-yl, 5-cyanopyridin-3-yl, 3-cyano-2,6-dimethylpyridin-3-yl, 2,6-dichloropyridin-3-yl, 2,6-dimethylpyridin-3-yl, 1,3-dimethylpyrazol-4-yl, 1,5-dimethylpyrazol-4-yl, 3,5-dimethylpyrazol-4-yl, 5-cyanothien-2-yl, 2-cyanopyrimidin-5-yl, 2,5-dimethylfur-3-yl, 3,5-dimethylthien-2-yl, 5-(ethoxyiminomethyl)thien-2-yl, 6-fluoropyridin-3-yl, 2,6-difluoropyridin-3-yl, 4-(ethoxycarbonyl)-3-methylisoxazol-5-yl, 3,5-dimethylisoxazol-4-yl, 3-(ethoxycarbonyl)isoxazol-5-yl, 3-methylpyrazin-2-yl, 6-fluoropyridin-3-yl, 6-methylpyridin-3-yl, 2,6-dimethyl-5-(aminocarbonyl)pyridin-3-yl, 2,6-dimethyl-5-(methylcarbonyl)pyridin-3-yl, 4-hydroxy-2-(trifluoromethyl)pyridin-3-yl, 6-(methylcarbonyl)pyridin-2-yl, 2,4-dimethoxypyrimidin-5-yl, 6-methoxypyridin-3-yl, 5-methoxypyridin-3-yl, 2,4-dimethylthiazol-5-yl, 2,4-dimethyloxazol-5-yl, 6-chloropyridazin-3-yl, 6-methoxypyridazin-3-yl, 6-methylpyridazinonyl, 4-methylpyridinonyl, and 1-(tert-butoxycarbonyl)pyrrol-2-yl.

A particular embodiment is a compound of formula (I) wherein $R_1$ is $L_2R_6$, $L_2$ is a bond, and $R_6$ is selected from the group consisting of furyl, isoxazolyl, oxazolyl, pyrazinyl, pyrazolyl, pyridinyl, pyridinonyl, pyridazinyl, pyridazinonyl, pyrimidinyl, pyrrolyl, thiazolyl, and thienyl, substituted with 0, 1, 2, or 3 substituents selected from the group consisting of —NR$_A$R$_B$, halogen, alkyl, cyano, alkoxyimino, alkoxycarbonyl, (NR$_A$R$_B$)carbonyl, alkylcarbonyl, haloalkyl, and alkoxy.

Heterocycle groups for $R_6$ can include, but are not limited to, azepanyl, azetidinyl, aziridinyl, azocanyl, dihydrothiazolyl, morpholinyl, piperazinyl, piperidinyl, pyrrolidinyl, pyrrolinyl, thiomorpholinyl, and tetrahydropyridinyl, as well as non-nitrogen containing heterocycles, for example, tetrahydrofuryl and tetrahydropyranyl. Heterocycles can be substituted with 0, 1, or 2 substituents as described in the Definition of Terms. Specific examples of heterocycles for the invention include, but are not limited to, morpholin-4-yl, thiomorpholin-4-yl, and 4,5-dihydrothiazol-2-yl. Preferred heterocycles are dihydrothiazolyl, morpholinyl, piperidinyl, pyrrolidinyl, thiomorpholinyl, and tetrahydropyranyl.

Specific cycloalkyl groups for $R_6$ can include, but are not limited to, cyclopropyl, cyclobutyl, cyclopentyl, and cyclohexyl.

$R_2$ in a compound of formula (I) is absent when Z' is N. $R_2$ also can be independently selected from the group consisting of hydrogen, alkyl, alkoxy, aryl, cycloalkyl, halogen, cyano, and thioalkoxy when Z' is C. Preferred groups for $R_2$ are hydrogen, alkyl, and cycloalkyl. Alternatively, $R_2$ can be halogen, cyano, or $L_2R_6$, as defined for $R_1$. In compounds wherein $R_2$ is a group of the formula $L_2R_6$, $R_1$ can be selected from the group consisting of hydrogen, alkyl, alkoxy, aryl, cycloalkyl, halogen, cyano, and thioalkoxy.

$R_3$ in a compound of formula (I) is absent when X' is N. In addition, $R_3$ can be independently selected from the group consisting of hydrogen, alkyl, alkoxy, cycloalkyl, halogen, cyano, and thioalkoxy when X' is C. Preferred groups for $R_3$ are hydrogen, alkyl, and cycloalkyl.

$R_{3a}$ in a compound of formula (I) is absent when Z is N. In addition, $R_{3a}$ can be independently selected from the group consisting of hydrogen, methyl, alkoxy, halogen, and cyano when Z is C. Preferred groups for $R_{3a}$ are hydrogen and methyl.

$R_{3b}$ in a compound of formula (I) is absent when X is N. In addition, $R_{3b}$ can be independently selected from the group consisting of hydrogen, alkyl, alkoxy, halogen, hydroxy, cyano, and thioalkoxy when X is C. Preferred groups for $R_{3b}$ are hydrogen and hydroxy.

$R_4$ and $R_5$ in a compound of formula (I) are each independently selected from the group consisting of alkyl, haloalkyl, hydroxyalkyl, alkoxyalkyl, cycloalkyl, cycloalkylalkyl, and $(NR_AR_B)$alkyl. Preferred compounds of formula (I), wherein $R_4$ and $R_5$ are independently selected are those wherein $R_4$ and $R_5$ are each independently selected from methyl, ethyl, and propyl, particularly isopropyl.

$R_4$ and $R_5$ also can be taken together with the nitrogen atom to which each is attached form a non-aromatic ring of the formula:

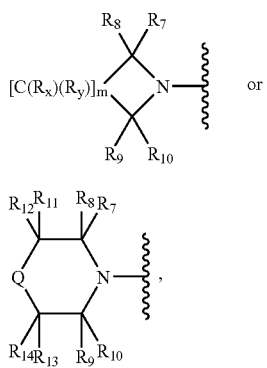

wherein $R_7$, $R_8$, $R_9$, $R_{10}$, $R_{11}$, $R_{12}$, $R_{13}$, $R_{14}$, $R_x$, $R_y$, and m are as described herein.

In one embodiment, $R_4$ and $R_5$ taken together with the nitrogen atom to which each is attached form a 4- to 8-membered non-aromatic ring represented by formula (a).

$R_7$, $R_8$, $R_9$, and $R_{10}$ each can be independently selected from the group consisting of hydrogen, hydroxyalkyl, fluoroalkyl, and alkyl. Alternatively, each pair of $R_7$ and $R_8$ or $R_9$ and $R_{10}$ taken together can form a $C_3$–$C_6$ ring, including the carbon atom to which each is attached. The $C_3$–$C_6$ ring can include 0, 1, or 2 heteroatoms selected from O, N, or S to replace a carbon atom in the ring. Examples of $C_3$–$C_6$ rings can include, but are not limited to, cyclopropyl, cyclobutyl, cyclopentyl, cyclohexyl, azetidinyl, pyrrolidinyl, oxirane, and the like.

$R_x$ and $R_y$ each can be independently selected from hydrogen, hydroxy, alkyl, alkoxy, alkylamino, dialkylamino, and fluoro. Also, one of $R_x$ and $R_y$ can represent a bond when taken with $R_x$ or $R_y$ on an adjacent carbon atom, such that a double bond is represented between the adjacent carbon atoms.

The value represented by m can be selected from 1 to 5, inclusive. Preferred values for m are 2 and 3.

Compounds of formula (I) also are those wherein $R_4$ and $R_5$ are taken together with the nitrogen atom to which each is attached to form a non-aromatic ring of formula (b), wherein $R_7$, $R_8$, $R_9$, and $R_{10}$ are as previously defined for a ring of formula (a); $R_{11}$, $R_{12}$, $R_{13}$, and $R_{14}$ are each independently selected from the group consisting of hydrogen, hydroxy, hydroxyalkyl, alkyl, and fluoro; and Q is a bond or Q is selected from the group consisting of O, S, and $NR_{15}$, wherein $R_{15}$ is selected from the group consisting of hydrogen, alkyl, acyl, amido, and formyl. Preferably, $R_7$, $R_8$, $R_9$, and $R_{10}$ are each independently selected from hydrogen, methyl, ethyl, fluoromethyl, and hydroxymethyl. $R_{11}$, $R_{12}$, $R_{13}$, and $R_{14}$ preferably each are hydrogen. Alternatively, it is preferred that $R_{11}$ and $R_{12}$ are hydrogen, $R_{13}$ and $R_{14}$ are each independently selected from hydrogen or alkyl, and $R_7$, $R_8$, $R_9$, and $R_{10}$ are as previously defined.

Compounds wherein $R_4$ and $R_5$ taken together with the nitrogen atom to which each is attached to form a 4- to 8-membered non-aromatic ring of formula (a) can include, but are not limited to, those wherein the 4- to 8-membered non-aromatic ring is selected from azetidinyl, azepanyl, azepinyl, pyrrolidinyl, pyrrolinyl, piperidinyl, piperazinyl, and tetrahydropyridinyl. The ring can be substituted with 0, 1, or 2 substituents as previously described for heterocycle groups in the Definition of Terms. Preferred substituents are selected from the group consisting of alkyl, halogen, hydroxyalkyl, fluoroalkyl, and $-NR_AR_B$.

Groups for $R_4$ and $R_5$ also can be taken together with the nitrogen atom to which each is attached to form a 4- to 8-membered non-aromatic ring of formula (a) or formula (b), wherein the ring is substituted with at least one substituent selected from hydroxy, alkyl, halogen, fluoroalkyl, or hydroxyalkyl.

More specific groups for $R_4$ and $R_5$ include, for example, those wherein $R_4$ and $R_5$ are taken together with the nitrogen atom to which each is attached to form a 4- to 8-membered non-aromatic ring selected from morpholinyl and thiomorpholinyl, and unsubstituted or substituted pyrrolidinyl, for example, methylpyrrolidinyl, ethylpyrrolidinyl, dimethylaminopyrrolidinyl, isopropylpyrrolidinyl, isobutylpyrrolidinyl, hydroxymethylpyrrolidinyl, and fluoromethylpyrrolidinyl. Pyrrolidinyl, and particularly methylpyrrolidinyl, for example 2-methylpyrrolidinyl, are preferred.

In one embodiment, groups for $R_4$ and $R_5$ are taken together with the nitrogen atom to which each is attached to form a non-aromatic ring of formula (a) or formula (b) and at least one of the substituents $R_7$, $R_8$, $R_9$, and $R_{10}$ is selected from hydroxyalkyl, fluoroalkyl, or alkyl. In this embodiment, at least one of $R_7$, $R_8$, $R_9$, and $R_{10}$ can be selected from methyl, ethyl, fluoromethyl, or hydroxymethyl, and the like. In such embodiment, it is particularly preferred that one substituent represented by $R_7$, $R_8$, $R_9$, and $R_{10}$ is alkyl, and particularly methyl, and the other three substituents are hydrogen.

One specific embodiment relates to compounds having the formula (I) wherein $R_4$ and $R_5$ taken together with the nitrogen atom to which each is attached form a non-aromatic ring of formula (b) and Q is $NR_{15}$. In such embodiment, $R_{15}$ preferably is selected from hydrogen, alkyl, amido, or formyl.

The moiety represented by L can be $-[C(R_{16})(R_{17})]_n-$ or $-[C(R_{16})(R_{17})]_pO-$, wherein $R_{16}$ and $R_{17}$ are each independently selected from the group consisting of hydrogen, alkyl, alkoxy, and fluoro, and n is an integer selected from 1 to 6, inclusive, and p is an integer selected from 2 to 6, inclusive. $R_{16}$ and $R_{17}$ preferably are hydrogen. The preferred value of n is 2 or 3. The preferred value for p is 2.

$L_2$ can be a bond or selected from $-O-$, $-C(=O)-$, $-S-$, $-[C(R_{18})(R_{19})]_q-$, $-NH-$, $-N(alkyl)-$, wherein $R_{18}$ and $R_{19}$ are each independently selected from the group consisting of hydrogen, hydroxy, alkyl, alkoxy, and fluoro, and q is an integer selected from 1 to 4, inclusive. The alkyl group of $-N(alkyl)-$ preferably contains from 1 to 6 carbons. Compounds of the invention can have the formula (I) wherein $L_2$ is $[C(R_{18})(R_{19})]_q-$, $R_{18}$ and $R_{19}$ are hydrogen, and q is 1, 2, 3 or 4. The preferred value for q is 1.

Preferred compounds of formula (I) are those wherein $R_1$ is a group $L_2R_6$, wherein $L_2$ is a bond and $R_6$ is heteroaryl or heterocycle; $R_2$, $R_3$, $R_{3a}$, and $R_{3b}$ are hydrogen; L is $-[C(R_{16})(R_{17})]_n-$; n is 2; $R_{16}$ and $R_{17}$ are hydrogen at each occurrence; $R_4$ and $R_5$ are taken together to form a methylpyrrolidinyl ring of formula (a), wherein one of $R_7$, $R_8$, $R_9$, and $R_{10}$ is methyl and the remaining three substituents are hydrogen; Y and Y' are CH; X, X', Z, and Z' are C. A preferred heteroaryl group is pyridazinonyl and, more particularly, 2H-pyridazin-3-one-2-yl.

With respect to the ring system, 0, 1, or 2 atoms represented by X, X', Y, Y', Z, and Z' can be nitrogen.

Compounds of the invention can have the formula (I) wherein Y and Y' are CH; X, X', Z, and Z' are C; and $R_2$, $R_3$, $R_{3a}$, and $R_{3b}$ are hydrogen.

Alternatively, compounds of the invention have formula (I) wherein Y and Y' are CH; X, X', and Z are C; $R_3$, $R_{3a}$, and $R_{3b}$ are hydrogen; Z' is N; and $R_2$ is absent.

Compounds of the invention also can have the formula (I) wherein Y and Y' are CH; X', Z', and Z are C; $R_2$, $R_3$, and $R_{3a}$ are hydrogen; X is N; and $R_{3b}$ is absent.

The invention also includes compounds having the formula (I) wherein Y and Y' are CH; X, X', and Z' are C; $R_2$, $R_3$, and $R_{3b}$ are hydrogen; Z is N; and $R_{3a}$ is absent.

In another embodiment, compounds of the invention can have formula (I) wherein Y is CH; X, X', Z, and Z' are C; $R_2$, $R_3$, $R_{3a}$, and $R_{3b}$ are hydrogen; and Y' is N.

In yet another embodiment, compounds of the invention have formula (I) wherein Y and Y' are CH; X and Z' are C; $R_2$ and $R_{3b}$ are hydrogen; X' is N; Z is N; and $R_3$ and $R_{3a}$ are absent.

Yet another embodiment relates to compounds of the invention having the formula (I) wherein X, X', Z, and Z' are C; $R_2$, $R_3$, $R_{3a}$, and $R_{3b}$ are hydrogen; Y is N; and Y' is N.

Still yet another embodiment relates to compounds of the invention having the formula (I) wherein Y' is CH; X, X', and Z are C; $R_3$, $R_{3a}$, and $R_{3b}$ are hydrogen; Y is N; Z' is N; and $R_2$ is absent.

Another embodiment relates to compounds of the invention having the formula (I) wherein Y' is CH; X, Z, and Z' are C; $R_2$, $R_{3a}$, and $R_{3b}$ are hydrogen; Y is N; X' is N; and $R_3$ is absent.

Still yet another embodiment relates to compounds of the invention having the formula (I) wherein Y' is CH; X, X', and Z' are C; $R_2$, $R_3$, and $R_{3b}$ are hydrogen; Y is N; Z is N; and $R_{3a}$ is absent.

Still yet another embodiment relates to compounds of the invention having the formula (I) wherein Y is CH; X, X', and Z are C; $R_3$, $R_{3a}$, and $R_{3b}$ are hydrogen; Y' is N; Z' is N; and $R_2$ is absent.

Still yet another embodiment relates to compounds of the invention having the formula (I) wherein Y and Y' are CH; Z' and Z are C; $R_2$ and $R_{3a}$ are hydrogen; X' is N; X is N; and $R_3$ and $R_{3b}$ are absent.

Compounds of the invention also can have the formula (I) wherein Y' is CH; X, X', Z and Z' are C; $R_2$, $R_3$, $R_{3a}$, and $R_{3b}$ are hydrogen; and Y is N.

In yet another embodiment, compounds of the invention have formula (I) wherein Y and Y' are CH; X' and Z' are C; $R_2$ and $R_3$ are hydrogen; X is N; Z is N; and $R_{3a}$ and $R_{3b}$ are absent.

Still yet another embodiment relates to compounds of the invention having the formula (I) wherein Y is CH; X, Z', and Z are C; $R_2$, $R_{3a}$, and $R_{3b}$ are hydrogen; Y' is N; X' is N; and $R_3$ is absent.

When substituents represented by $R_2$, $R_3$, $R_{3a}$, and $R_{3b}$ are present, Z', X', Z, and X respectively, represent a carbon atom to allow for the substituents represented by $R_2$, $R_3$, $R_{3a}$, and $R_{3b}$. Specific examples of compounds of the invention include, but are not limited to:

4-(6-{2-[(2R)-2-methyl-1-pyrrolidinyl]ethyl}-2-naphthyl) benzonitrile;
(2R)-1-[2-(6-bromo-2-naphthyl)ethyl]-2-methylpyrrolidine;
1-[3-(6-{2-[(2R)-2-methyl-1-pyrrolidinyl]ethyl}-2-naphthyl)phenyl]ethanone;
2-[3-(6-{2-[(2R)-2-methyl-1-pyrrolidinyl]ethyl}-2-naphthyl)phenyl]-2-propanol;
6-{2-[(2R)-2-methyl-1-pyrrolidinyl]ethyl}-2-naphthonitrile;
4-(6-{[(2R)-2-methyl-1-pyrrolidinyl]methyl}-2-naphthyl) benzonitrile;
3-(6-{2-[(2R)-2-methyl-1-pyrrolidinyl]ethyl}-2-naphthyl) benzonitrile;
4-(6-{2-[(2R)-2-methyl-1-pyrrolidinyl]ethyl}-2-naphthyl) pyridine;
3-(6-{2-[(2R)-2-methyl-1-pyrrolidinyl]ethyl}-2-naphthyl) pyridine;
(3-fluorophenyl)(6-{2-[(2R)-2-methyl-1-pyrrolidinyl] ethyl}-2-naphthyl)methanol;
3,5-dimethyl-4-(6-{2-[(2R)-2-methyl-1-pyrrolidinyl]ethyl}-2-naphthyl)isoxazole;
4-(6-{2-[(2S)-2-(hydroxymethyl)-1-pyrrolidinyl]ethyl}-2-naphthyl)benzonitrile;
4-(6-{2-[(3R)-3-hydroxy-1-pyrrolidinyl]ethyl}-2-naphthyl) benzonitrile;
4-{6-[2-(2-isobutyl-1-pyrrolidinyl)ethyl]-2-naphthyl}benzonitrile;
4-{6-[2-(2-isopropyl-1-pyrrolidinyl)ethyl]-2-naphthyl}benzonitrile;
4-(6-{2-[(3R)-3-(dimethylamino)-1-pyrrolidinyl]ethyl}-2-naphthyl)benzonitrile;
4-{6-[2-(diethylamino)ethyl]-2-naphthyl}benzonitrile;
4-{6-[2-(dimethylamino)ethyl]-2-naphthyl}benzonitrile;
4-(6-{2-[ethyl(isopropyl)amino]ethyl}-2-naphthyl)benzonitrile;
4-(6-{2-[tert-butyl(methyl)amino]ethyl}-2-naphthyl)benzonitrile;
4-(6-{2-[(2S)-2-methyl-1-pyrrolidinyl]ethyl}-2-naphthyl) benzonitrile;
4-(6-{2-[(2R)-2-methyl-1-piperidinyl]ethyl}-2-naphthyl) benzonitrile;
4-{6-[2-(2,5-dihydro-1H-pyrrol-1-yl)ethyl]-2-naphthyl}benzonitrile;
4-(6-{2-[methyl(propyl)amino]ethyl}-2-naphthyl)benzonitrile;
4-(6-{2-[(2-hydroxyethyl)(methyl)amino]ethyl}-2-naphthyl)benzonitrile;
5-(6-{2-[(2R)-2-methyl-1-pyrrolidinyl]ethyl}-2-naphthyl) pyrimidine;
4-(6-{2-[(2R)-2-methyl-1-pyrrolidinyl]ethyl}-2-naphthyl) morpholine;
2-(6-{2-[(2R)-2-methyl-1-pyrrolidinyl]ethyl}-2-naphthyl)-1,3-thiazole;
4-(6-{2-[(2S)-2-(fluoromethyl)-1-pyrrolidinyl]ethyl}-2-naphthyl)benzonitrile;
(3-fluorophenyl)(6-{2-[(2R)-2-methyl-1-pyrrolidinyl] ethyl}-2-naphthyl)methanone;
2-(6-{2-[(2R)-2-methyl-1-pyrrolidin-1-yl]-ethyl}-2-naphthalen-2-yl)-2-3-one;
2-methoxy-5-(6-{2-[(2R)-2-methyl-1-pyrrolidinyl]ethyl}-2-naphthyl)pyridine;
4-(6-{2-[(2R)-2-(hydroxymethyl)-1-pyrrolidinyl]ethyl}-2-naphthyl)benzonitrile;
4-{6-[2-(2-methyl-1-pyrrolidinyl)ethyl]-2-naphthyl}benzonitrile;
4-{6-[2-(1-pyrrolidinyl)ethyl]-2-naphthyl}benzonitrile;
4-(6-{2-[(2R)-2-methyl-1-pyrrolidinyl]ethyl}-2-naphthyl) thiomorpholine;
1-{2-[(6-bromo-2-naphthyl)oxy]ethyl}pyrrolidine;

3-{6-[2-(1-pyrrolidinyl)ethoxy]-2-naphthyl}benzonitrile;
3-{6-[2-(1-pyrrolidinyl)ethoxy]-2-naphthyl}pyridine;
3-(6-{2-[(2R)-2-methyl-1-pyrrolidinyl]ethoxy}-2-naphthyl)benzonitrile;
3-(6-{2-[(2R)-2-methyl-1-pyrrolidinyl]ethoxy}-2-naphthyl)pyridine;
4-(2-{2-[(2R)-2-methyl-1-pyrrolidinyl]ethyl}-6-quinolinyl)benzonitrile;
6-(4-fluorophenyl)-2-{2-[(2R)-2-methyl-1-pyrrolidinyl]ethyl}quinoline;
3-(2-{2-[(2R)-2-methyl-1-pyrrolidinyl]ethyl}-6-quinolinyl)benzonitrile;
1-[3-(2-{2-[(2R)-2-methyl-1-pyrrolidinyl]ethyl}-6-quinolinyl)phenyl]ethanone;
6-(4-methoxyphenyl)-2-{2-[(2R)-2-methyl-1-pyrrolidinyl]ethyl}quinoline;
2-{2-[(2R)-2-methyl-1-pyrrolidinyl]ethyl}-6-[4-(trifluoromethyl)phenyl]quinoline;
2-{2-[(2R)-2-methyl-1-pyrrolidinyl]ethyl}-6-[4-(methylsulfonyl)phenyl]quinoline;
6-(3,5-difluorophenyl)-2-{2-[(2R)-2-methyl-1-pyrrolidinyl]ethyl}quinoline;
(3-fluorophenyl)(2-{2-[(2R)-2-methyl-1-pyrrolidinyl]ethyl}-6-quinolinyl)methanone;
2-{2-[(2R)-2-methyl-1-pyrrolidinyl]ethyl}-6-(3-pyridinyl)quinoline;
4-(3-{2-[(2R)-2-methyl-1-pyrrolidinyl]ethyl}-7-isoquinolinyl)benzonitrile;
3-(3-{2-[(2R)-2-methyl-1-pyrrolidinyl]ethyl}-7-isoquinolinyl)benzonitrile;
6-{2-[(2R)-2-methyl-1-pyrrolidinyl]ethyl}-2-(3-pyridinyl)quinoline;
6-{2-[(2R)-2-methyl-1-pyrrolidinyl]ethyl}-2-(4-pyridinyl)quinoline;
6-{2-[(2R)-2-methyl-1-pyrrolidinyl]ethyl}-2-(2-pyridinyl)quinoline;
6-{2-[(2R)-2-methyl-1-pyrrolidinyl]ethyl}-2-(1,3-thiazol-2-yl)quinoline;
2-(2,4-dimethyl-1,3-thiazol-5-yl)-6-{2-[(2R)-2-methyl-1-pyrrolidinyl]ethyl}quinoline;
6-{2-[(2R)-2-methyl-1-pyrrolidinyl]ethyl}-2-(2-pyrazinyl)quinoline;
1-[6-(6-{2-[(2R)-2-methyl-1-pyrrolidinyl]ethyl}-2-quinolinyl)-2-pyridinyl]ethanone;
4-(2-{2-[(2R)-2-methyl-1-pyrrolidinyl]ethyl}-6-quinoxalinyl)benzonitrile;
4-(3-{2-[(2R)-2-methyl-1-pyrrolidinyl]ethyl}-6-quinoxalinyl)benzonitrile;
7-(2,6-difluoro-3-pyridinyl)-3-{2-[(2R)-2-methyl-1-pyrrolidinyl]ethyl}isoquinoline;
3-{2-[(2R)-2-methyl-1-pyrrolidinyl]ethyl}-7-(3-pyridinyl)isoquinoline;
3-(benzyloxy)-2-methyl-6-{2-[(2R)-2-methyl-1-pyrrolidinyl]ethyl}quinoline;
2-cyclopropyl-6-{2-[(2R)-2-methyl-1-pyrrolidinyl]ethyl}quinoline;
4-(6-{2-[(2R)-2-methyl-1-pyrrolidinyl]ethyl}-2-quinolinyl)benzonitrile;
2,6-dimethyl-5-(6-{2-[(2R)-2-methyl-1-pyrrolidinyl]ethyl}-2-quinolinyl)nicotinonitrile;
2-(3-methyl-2-pyrazinyl)-6-{2-[(2R)-2-methyl-1-pyrrolidinyl]ethyl}quinoline;
ethyl 5-(6-{2-[(2R)-2-methyl-1-pyrrolidinyl]ethyl}-2-quinolinyl)-3-isoxazolecarboxylate;
5-(6-{2-[(2R)-2-methyl-1-pyrrolidinyl]ethyl}-2-quinolinyl)-2-thiophenecarbonitrile;
ethyl 5-(6-{2-[(2R)-2-methyl-1-pyrrolidinyl]ethyl}-2-quinolinyl)-2-thiophenecarboximidoate;
2-(2,4-dimethyl-1,3-oxazol-5-yl)-6-{2-[(2R)-2-methyl-1-pyrrolidinyl]ethyl}quinoline;
ethyl 3-methyl-5-(6-{2-[(2R)-2-methyl-1-pyrrolidinyl]ethyl}-2-quinolinyl)-4-isoxazolecarboxylate;
4-(7-{2-[(2R)-2-methyl-1-pyrrolidinyl]ethyl}-3-isoquinolinyl)benzonitrile;
6-{2-[(2R)-2-methyl-1-pyrrolidinyl]ethyl}-2-(4-methoxyphenyl)quinoxaline;
7-{2-[(2R)-2-methyl-1-pyrrolidinyl]ethyl}-2-(4-methoxyphenyl)quinoxaline;
6-{2-[(2R)-2-methyl-1-pyrrolidinyl]ethyl}-2-phenylquinoxaline;
7-{2-[(2R)-2-methyl-1-pyrrolidinyl]ethyl}-2-phenylquinoxaline;
6-{2-[(2R)-2-methyl-1-pyrrolidinyl]ethyl}-2-(3-pyridinyl)quinazoline;
6-methyl-2-{6-[2-((2R)-2-methyl-pyrrolidin-1-yl)-ethyl]-naphthalen-2-yl}-2H-3-one;
5-{6-[2-((2R)-2-methyl-pyrrolidin-1-yl)-ethyl]-naphthalen-2-yl}-pyrimidine-2-carbonitrile;
1-{6-[2-(2(R)-methyl-pyrrolidin-1-yl)-ethyl]-naphthalen-2-yl}-1H-pyridin-2-one;
5-{6-[2-(2(R)-methyl-pyrrolidin-1-yl)-ethyl]-naphthalen-2-yl}-nicotinonitrile;
4-methyl-1-{6-[2-(2(R)-methyl-pyrrolidin-1-yl)-ethyl]-naphthalen-2-yl}-1H-pyridin-2-one;
2-{6-[2-((2R)-2-methyl-pyrrolidin-1-yl)-ethyl]-naphthalen-2-yl}-pyrazine;
2-{6-[2-((2R)-2-methyl-2,5-dihydro-pyrrol-1-yl)-ethyl]-naphthalen-2-yl}-2H-pyridazin-3-one;
4-(6-{2-[(2-dimethylamino-ethyl)-methyl-amino]-ethyl}-naphthalen-2-yl)-benzonitrile;
4-{6-[2-(4-methyl-piperazin-1-yl)-ethyl]-naphthalen-2-yl}-benzonitrile;
2-(2,5-dimethyl-furan-3-yl)-6-{2-[(2R)-2-methyl-1-pyrrolidinyl]ethyl}-quinoline;
6-{2-[(2R)-2-methyl-1-pyrrolidinyl]ethyl}-2-(4-methylsulfanyl-phenyl)-quinoline;
2-(6-methyl-pyridin-3-yl)-6-{2-[(2R)-2-methyl-1-pyrrolidinyl]ethyl}-quinoline;
2-(1,3-dimethyl-1H-pyrazol-4-yl)-6-{2-[(2R)-2-methyl-1-pyrrolidinyl]ethyl}-quinoline;
6-{2-[(2R)-2-methyl-1-pyrrolidinyl]ethyl}-2-thiophen-3-yl-quinoline;
6-{2-[(2R)-2-methyl-1-pyrrolidinyl]ethyl}-2-pyrimidin-5-yl-quinoline;
2-(2,6-dimethyl-pyridin-3-yl)-6-{2-[(2R)-2-methyl-1-pyrrolidinyl]ethyl}-quinoline;
1-[2,6-dimethyl-5-(6-{2-[(2R)-2-methyl-1-pyrrolidinyl]ethyl}-quinolin-2-yl)-pyridin-3-yl]-ethanone;
6-{2-[(2R)-2-methyl-1-pyrrolidinyl]ethyl}-2-(2H-pyrazol-3-yl)-quinoline;
2-(3-bromo-isoxazol-5-yl)-6-{2-[(2R)-2-methyl-1-pyrrolidinyl]ethyl}-quinoline;
2-(6-chloro-pyridin-3-yl)-6-{2-[(2R)-2-methyl-1-pyrrolidinyl]ethyl}-quinoline;
2-(3,5-dimethyl-thiophen-2-yl)-6-{2-[(2R)-2-methyl-1-pyrrolidinyl]ethyl}-quinoline;
6-{2-[(2R)-2-methyl-1-pyrrolidinyl]ethyl}-2-thiophen-2-yl-quinoline;
2-furan-3-yl-6-{2-[(2R)-2-methyl-1-pyrrolidinyl]ethyl}-quinoline;
2-(4,5-dihydro-thiazol-2-yl)-6-{2-[(2R)-2-methyl-1-pyrrolidinyl]ethyl}-quinoline;

1-[4-(6-{2-[(2R)-2-methyl-1-pyrrolidinyl]ethyl}-quinolin-2-yl)-phenyl]-ethanone;
3-(6-{2-[(2R)-2-methyl-1-pyrrolidinyl]ethyl}-quinolin-2-yl)-2-trifluoromethyl-pyridin-4-ol;
2-(3,5-dimethyl-1H-pyrazol-4-yl)-6-{2-[(2R)-2-methyl-1-pyrrolidinyl]ethyl}-quinoline;
6-{2-[(2R)-2-methyl-1-pyrrolidinyl]ethyl}-2-(1H-pyrazol-4-yl)-quinoline;
2,6-dimethyl-5-(6-{2-[(2R)-2-methyl-1-pyrrolidinyl]ethyl}-quinolin-2-yl)-nicotinamide;
2-[2-(2R-methyl-pyrrolidin-1-yl)-ethyl]-6-pyridin-4-yl-quinoline;
6-(6-methoxy-pyridin-3-yl)-2-[2(R)-(2-methyl-pyrrolidin-1-yl)-ethyl]-quinoline;
6-(2,6-difluoro-pyridin-3-yl)-2-[2-(2(R)-methyl-pyrrolidin-1-yl)-ethyl]-quinoline;
6-(6-chloro-pyridin-3-yl)-2-[2-(2(R)-methyl-pyrrolidin-1-yl)-ethyl]-quinoline;
6-(2,6-dichloro-pyridin-3-yl)-2-[2-(2(R)-methyl-pyrrolidin-1-yl)-ethyl]-quinoline;
2-[2-(2(R)-methyl-pyrrolidin-1-yl)-ethyl]-6-pyrazin-2-yl-quinoline;
2-[2-(2(R)-methyl-pyrrolidin-1-yl)-ethyl]-6-pyrimidin-5-yl-quinoline;
6-(2,4-dimethoxy-pyrimidin-5-yl)-2-[2-(2(R)-methyl-pyrrolidin-1-yl)-ethyl]-quinoline;
dimethyl-(4-{2-[2-(2(R)-methyl-pyrrolidin-1-yl)-ethyl]-quinolin-6-yl}-phenyl)-amine;
1-(4-{2-[2-(2(R)-methyl-pyrrolidin-1-yl)-ethyl]-quinolin-6-yl}-phenyl)-ethanone;
6-(4-chloro-phenyl)-2-[2-(2(R)-methyl-pyrrolidin-1-yl)-ethyl]-quinoline;
6-(2,6-dimethyl-pyridin-3-yl)-2-[2-(2(R)-methyl-pyrrolidin-1-yl)-ethyl]-quinoline;
6-(5-methoxy-pyridin-3-yl)-2-[2-(2(R)-methyl-pyrrolidin-1-yl)-ethyl]-quinoline;
6-(3,5-dimethyl-isoxazol-4-yl)-2-[2-(2(R)-methyl-pyrrolidin-1-yl)-ethyl]-quinoline;
4-{2-[2-(2(R)-methyl-pyrrolidin-1-yl)-ethyl]-quinolin-6-yl}-benzoic acid methyl ester;
2-[2-(2(R)-methyl-pyrrolidin-1-yl)-ethyl]-6-(4-methylsulfanyl-phenyl)-quinoline;
6-(6-fluoro-pyridin-3-yl)-2-[2-(2(R)-methyl-pyrrolidin-1-yl)-ethyl]-quinoline;
5-{2-[2-(2(R)-methyl-pyrrolidin-1-yl)-ethyl]-quinolin-6-yl}-nicotinonitrile;
2,4-dimethoxy-5-{6-[2-((2R)-methyl-pyrrolidin-1-yl)-ethyl]-naphthalen-2-yl}-pyrimidine;
2,6-difluoro-3-{6-[2-((2R)-2-methyl-pyrrolidin-1-yl)-ethyl]-naphthalen-2-yl}-pyridine;
cyclopropyl-(4-{6-[2-((2R)-2-methyl-pyrrolidin-1-yl)-ethyl]-naphthalen-2-yl}-phenyl)-methanone;
3-methoxy-6-{6-[2-((2R)-2-methyl-pyrrolidin-1-yl)-ethyl]-naphthalen-2-yl}-pyridazine;
4-{6-[2-(2-methyl-piperidin-1-yl)-ethyl]-naphthalen-2-yl}-benzonitrile;
4-{6-[2-((2R)-2-ethyl-pyrrolidin-1-yl)-ethyl]-naphthalen-2-yl}-benzonitrile;
2-{6-[2-((2S)-2-methyl-pyrrolidin-1-yl)-ethyl]-naphthalen-2-yl}-2H-pyridazin-3-one;
2-[6-((2R)-2-piperidin-1-yl-ethyl)-naphthalen-2-yl]-2H-pyridazin-3-one;
2-{6-[2-(tert-butyl-methyl-amino)-ethyl]-naphthalen-2-yl}-2H-pyridazin-3-one;
2-[6-(2-diethylamino-ethyl)-naphthalen-2-yl]-2H-pyridazin-3-one;
2-[6-(2-morpholin-4-yl-ethyl)-naphthalen-2-yl]-2H-pyridazin-3-one;
2-{6-[2-(ethyl-methyl-amino)-ethyl]-naphthalen-2-yl}-2H-pyridazin-3-one;
2-{6-[2-((2S)-2-fluoromethyl-pyrrolidin-1-yl)-ethyl]-naphthalen-2-yl}-2H-pyridazin-3-one;
2-{6-[2-(2-hydroxymethyl-pyrrolidin-1-yl)-ethyl]-naphthalen-2-yl}-2H-pyridazin-3-one;
2-{6-[2-((R)-2-ethyl-pyrrolidin-1-yl)-ethyl]-naphthalen-2-yl}-2H-pyridazin-3-one;
2-[6-(2-azetidin-1-yl-ethyl)-naphthalen-2-yl]-2H-pyridazin-3-one;
2-{6-[2-((2S)-2-fluoromethyl-azetidin-1-yl)-ethyl]-naphthaien-2-yl}-2H-pyridazin-3-one;
2-{6-[2-((2S)-2-hydroxymethyl-azetidin-1-yl)-ethyl]-naphthalen-2-yl}-2H-pyridazin-3-one;
2-{6-[2-((2R,5R)-2,5-Dimethyl-pyrrolidin-1-yl)-ethyl]-naphthalen-2-yl}-2H-pyridiazin-3-one;
2-{6-[2-((2R,6S)-2,6-dimethyl-piperidin-1-yl)-ethyl]-naphthalen-2-yl}-2H-pyridiazin-3-one;
2-{6-[2-((R)3-hydroxy-piperidin-1-yl)-ethyl]-naphthalen-2-yl}-2H-pyridazin-3-one;
2-{6-[2-((R)-2-methyl-piperidin-1-yl)-ethyl]-naphthalen-2-yl}-2H-pyridazin-3-one;
2,6-dimethyl-3-{6-[2-((2R)-2-methyl-pyrrolidin-1-yl)-ethyl]-naphthalen-2-yl}-pyridine;
5-{6-[2-((R)-2-methyl-pyrrolidin-1-yl)-ethyl]-naphthalen-2-yl}-thiazole;
2-{6-[2-((R)-2-methyl-pyrrolidin-1-yl)-ethyl]-naphthalen-2-yl}-pyrimidine;
3-chloro-6-{6-[2-((R)-2-methyl-pyrrolidin-1-yl)-ethyl]-naphthalen-2-yl}-pyridazine;
5-{6-[2-((R)-2-methyl-pyrrolidin-1-yl)-ethyl]-naphthalen-2-yl}-pyrimidin-2-ylamine;
2-methyl-5-{6-[2-((2R)-2-methyl-pyrrolidin-1-yl)-ethyl]-naphthalen-2-yl}-pyridine;
3-bromo-7-(2-pyrrolidin-1-yl-ethyl)-[1,5]naphthyridine;
3-bromo-7-[2-(2R-2-methyl-pyrrolidin-1-yl)-ethyl]-[1,5]naphthyridine;
3-bromo-7-(2-piperidin-1-yl-ethyl)-[1,5]naphthyridine;
3-(2,6-dimethyl-pyridin-3-yl)-7-[2-(2R-2-methyl-pyrrolidin-1-yl)-ethyl]-[1,5]naphthyridine;
3-(2,4-dimethoxy-pyrimidin-5-yl)-7-[2-(2R-2-methyl-pyrrolidin-1-yl)-ethyl]-[1,5]naphthyridine;
3-(2,6-dimethyl-pyridin-3-yl)-7-(2-pyrrolidin-1-yl-ethyl)-[1,5]naphthyridine;
3-(2,4-dimethoxy-pyrimidin-5-yl)-7-(2-pyrrolidin-1-yl-ethyl)-[1,5]naphthyridine;
3-(2,6-dimethyl-pyridin-3-yl)-7-(2-piperidin-1-yl-ethyl)-[1,5]naphthyridine;
3-(2,4-dimethoxy-pyrimidin-5-yl)-7-(2-piperidin-1-yl-ethyl)-[1,5]naphthyridine;
3-[2-(2(R)-methyl-pyrrolidin-1-yl)-ethyl]-7-pyridin-4-yl-isoquinoline;
7-(6-methoxy-pyridin-3-yl)-3-[2-(2(R)-methyl-pyrrolidin-1-yl)-ethyl]-isoquinoline;
3-[2-(2(R)-methyl-pyrrolidin-1-yl)-ethyl]-7-pyrimidin-5-yl-isoquinoline;
7-(6-fluoro-pyridin-3-yl)-3-[2-(2(R)-methyl-pyrrolidin-1-yl)-ethyl]-isoquinoline;
5-{3-[2-(2(R)-methyl-pyrrolidin-1-yl)-ethyl]-isoquinolin-7-yl}-nicotinonitrile;
7-(3-chloro-pyridin-4-yl)-3-[2-(2(R)-methyl-pyrrolidin-1-yl)-ethyl]-isoquinoline;
7-bromo-3-[2-((2R)-2-methyl-pyrrolidin-1-yl)-ethyl]-cinnolin-4-ol;

4-{3-[2-(2-methyl-pyrrolidin-1-yl)-ethyl]-cinnolin-7-yl}-benzonitrile;
7-bromo-4-chloro-3-[2-((2R)-2-methyl-pyrrolidin-1-yl)-ethyl]-cinnoline;
4-{4-hydroxy-3-[2-((2R)-2-methyl-pyrrolidin-1-yl)-ethyl]-cinnolin-7-yl}-benzonitrile;
4-{4-isopropoxy-3-[2-((2R)-2-methyl-pyrrolidin-1-yl)-ethyl]-cinnolin-7-yl}-benzonitrile;
4-{3-[2-(4-methyl-piperazin-1-yl)-ethyl]-cinnolin-7-yl}-benzonitrile;
4-[3-(2-piperidin-1-yl-ethyl)-cinnolin-7-yl]-benzonitrile;
4-[3-(2-pyrrolidin-1-yl-ethyl)-cinnolin-7-yl]-benzonitrile;
4-{3-[2-((2R)-2-methyl-pyrrolidin-1-yl)-ethyl]-cinnolin-7-yl}-benzonitrile;
4-{3-[2-((2R)-2-hydroxymethyl-pyrrolidin-1-yl)-ethyl]-cinnolin-7-yl}-benzonitrile;
4-[3-(2-morpholin-4-yl-ethyl)-cinnolin-7-yl]-benzonitrile;
4-{3-[2-(4-methyl-piperidin-1-yl)-ethyl]-cinnolin-7-yl}-benzonitrile;
4-{3-[2-(ethyl-methyl-amino)-ethyl]-cinnolin-7-yl}-benzonitrile;
7-(2,6-dimethyl-pyridin-3-yl)-3-[2-((2R)-2-methyl-pyrrolidin-1-yl)-ethyl]-cinnoline;
7-(2,4-dimethoxy-pyrimidin-5-yl)-3-[2-((2R)-2-methyl-pyrrolidin-1-yl)-ethyl]-cinnoline;
7-(6-methoxy-pyridin-3-yl)-3-[2-((2R)-2-methyl-pyrrolidin-1-yl)-ethyl]-cinnoline;
3-{3-[2-((2R)-2-methyl-pyrrolidin-1-yl)-ethyl]-cinnolin-7-yl}-benzonitrile;
5-{3-[2-((2R)-2-methyl-pyrrolidin-1-yl)-ethyl]-cinnolin-7-yl}-nicotinonitrile;
7-(4-fluoro-phenyl)-3-[2-((2R)-2-methyl-pyrrolidin-1-yl)-ethyl]-cinnoline;
2-{3-[2-((2R)-2-methyl-pyrrolidin-1-yl)-ethyl]-cinnolin-7-yl}-pyrrole-1-carboxylic acid tert-butyl ester;
(3-{3-[2-((2R)-2-methyl-pyrrolidin-1-yl)-ethyl]-cinnolin-7-yl}-phenyl)-methanol;
7-(3,5-difluoro-phenyl)-3-[2-((2R)-2-methyl-pyrrolidin-1-yl)-ethyl]-cinnoline;
3-[2-((2R)-2-methyl-pyrrolidin-1-yl)-ethyl]-7-thiophen-3-yl-cinnoline;
7-(4-chloro-phenyl)-3-[2-((2R)-2-methyl-pyrrolidin-1-yl)-ethyl]-cinnoline;
7-(4-ethoxy-phenyl)-3-[2-((2R)-2-methyl-pyrrolidin-1-yl)-ethyl]-cinnoline;
3-[2-((2R)-2-methyl-pyrrolidin-1-yl)-ethyl]-7-(1H-pyrrol-2-yl)-cinnoline; and
2-(1,5-dimethyl-1H-pyrazol-4-yl)-6-{2-[(2R)-2-methyl-1-pyrrolidinyl]ethyl}-quinoline; or a pharmaceutically acceptable salt thereof.

A preferred compound is 2-(6-{2-[(2R)-2-methyl-1-pyrrolidin-1-yl]-ethyl}-2-naphthalen-2-yl)-2H-pyridazin-3-one, which also can be named 2-(6{2-[(2R)-2-methyl-1-pyrrolidinyl]ethyl}-2-naphthyl)-3(2H)-pyridazinone.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Ac for acetyl; atm for atmosphere(s); BINAP for 2,2'-bis(diphenylphosphino)-1,1'-binaphthyl; Boc for butyloxycarbonyl; Bu for butyl; DCM for dichloromethane; DMAP for 4-(N,N-dimethylamino)pyridine; DMF for N,N-dimethylformamide; DMSO for dimethylsulfoxide; Et for ethyl; EtOH for ethanol; EtOAc for ethyl acetate; HPLC for high pressure liquid chromatography; IPA for isopropyl alcohol; IPAC or IPAc for isopropyl acetate; LDA for lithium diisopropylamide; NBS for N-bromosuccinimide; NIS for N-iodosuccinimide; Me for methyl; MeOH for methanol; Ms for methanesulfonyl; MTBE for tert-butyl methyl ether; Pd for palladium; tBu for tert-butyl; TEA for triethylamine; TFA for trifluoroacetic acid; THF for tetrahydrofuran; and Ts for p-MePhS(O)$_2$—.

The compounds of this invention can be prepared by a variety of synthetic procedures. Representative procedures are shown in, but are not limited to, Schemes 1–24.

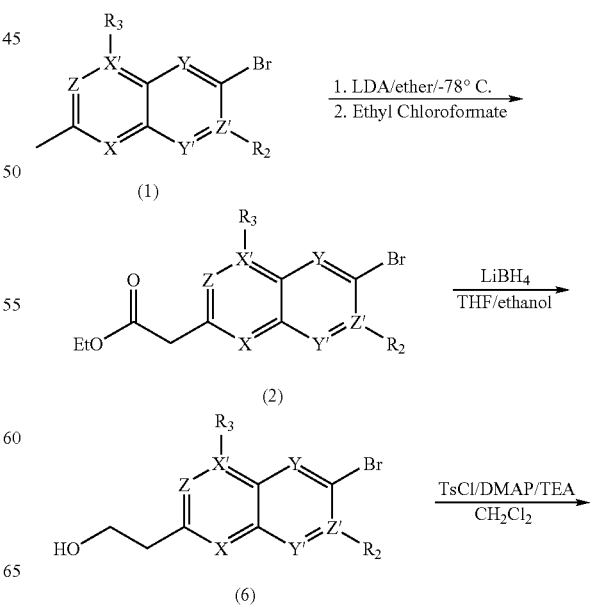

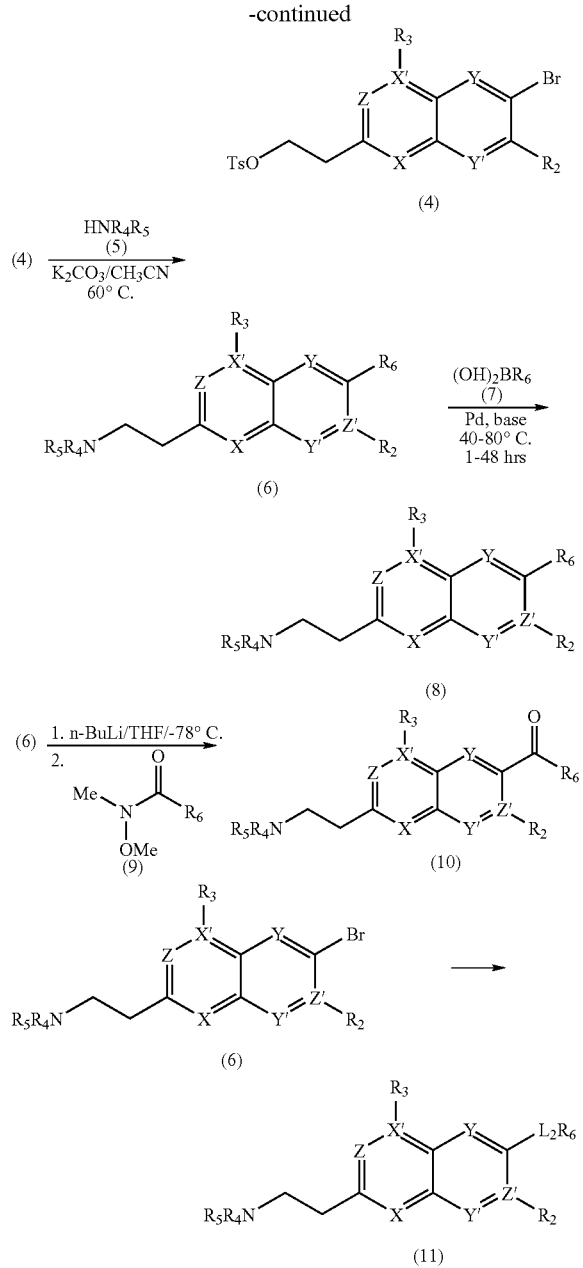

sodium carbonate and an amine of formula (5) with or without heat to provide amines of formula (6).

The Suzuki reaction can be used to produce compounds of formula (I), wherein $R_1$ is an aryl, heteroaryl, heterocyclic, or cycloalkyl ring. In such a Suzuki reaction, compounds of formula (I) wherein $R_1$ is a triflate or halogen are reacted with boronic acids of formula (7), a metal catalyst such as, but not limited to, palladium diacetate or $Pd(PPh_3)_4$, optionally with a Pd ligand added such as (dicyclohexylphosphinyl)biphenyl or trifurylphosphine, and a base such as, but not limited to, aqueous 0.2 M $K_3PO_4$ to provide products of formula (I) wherein $R_1$ is an aryl, heteroaryl, heterocyclic or cycloalkyl ring. Boronic acid esters of formula (7a) can be used in place of boronic acids. Boronic acids can be esterified to the corresponding boronic acid esters with alcohols such as methanol or with diols such as pinacol. Likewise, amines of formula (6) can be subjected to the Suzuki reaction to provide amines of formula (8).

There are many aryl, heteroaryl, and heterocyclic boronic acids and boronic acid esters that are available commercially or that can be prepared as described in the scientific literature of synthetic organic chemistry. The preparation of boronic acid and boronic acid ester reagents suitable for incorporating into the synthetic methods for preparing compounds of formula (I) are more specifically described in Reference Example 2 herein.

Alternatively, using the Stille coupling, compounds of formula (8) may be prepared from compounds of formula (6) by treatment with aryl, heteroaryl, and heterocyclic stannanes ($Me_3SnR_6$, $Bu_3SnR_6$), a palladium source such as tris(dibenzylidineacetone)dipalladium (CAS #52409-22-0) or palladium diacetate, and a ligand such as tri(2-furyl) phosphine (CAS #5518-52-5) or triphenyl arsine in a solvent, for example in DMF at 25–150° C. While many organotin reagents for the Stille coupling are commercially available or described in the literature, new organotin reagents can be prepared from arylhalides, aryltriflates, heteroarylhalides, heteroaryltriflates by reaction with distannanes like $(Me_3Sn)_2$ (hexamethyl distannane) in the presence of a palladium source like $Pd(Ph_3P)_4$. Such methods are described, for instance, in Krische, et. al., Helvetica Chimica Acta 81(11):1909–1920 (1998), and in Benaglia, et al., Tetrahedron Letters 38:4737–4740 (1997). These reagents can be reacted with (6) to give (8) as described under Suzuki conditions, or for example under the conditions reported by Littke, Schwartz, and Fu, Journal of the American Chemical Society 124:6343–6348 (2002).

Compounds of formula (8) wherein the $R_6$ group is a nitrogen-containing heteroaryl or heterocyclic ring linked to the bicyclic core group through a nitrogen may be prepared by heating compounds of formula (6) with the H—$R_6$ ($R_6$=heteroaryl or heterocyclic group) with a base such as, but not limited to, sodium t-butoxide or cesium carbonate, in the presence of a metal catalyst such as, but not limited to copper metal or CuI, palladium diacetate, and also optionally with a ligand such as, but not limited to, BINAP, tri-tertbutylphosphine in solvents such as dioxane, toluene and pyridine. References that describe these methodologies may be found in the following references: J. Hartwig et al., Angew. Chem. Int. Ed. 37:2046–2067 (1998); J. P. Wolfe et al., Acc. Chem. Res., 13:805–818 (1998); M. Sugahara et al., Chem. Pharm. Bull., 45:719–721 (1997); J. P. Wolfe et al., J. Org. Chem., 65:1158–1174, (2000); F. Y. Kwong et al., Org. Lett., 4:581–584, (2002); A. Klapars et al., J. Amer. Chem. Soc., 123:7727–7729 (2001); B. H. Yang et al., J. Organomet. Chem., 576:125–146 (1999); and A. Kiyomori et al., Tet. Lett., 40:2657–2640 (1999). Additional references Compounds of formula (8) and (10), wherein X, X', Y, Y', Z, Z', $R_2$, $R_3$, $R_4$, and $R_5$ are as defined in formula (I) and $R_6$ is aryl or heteroaryl, can be prepared as described in Scheme 1. Bromides of formula (1), purchased or prepared using methodolgy known to those of ordinary skill in the art, can be treated with lithium diisopropylamine and a chloroformate such as, but not limited to, ethyl chloroformate to provide esters of formula (2). Esters of formula (2) can be treated with a reducing agent such as, but not limited to, lithium borohydride to provide alcohols of formula (3). Alcohols of formula (3) can be treated with a base such as, but not limited to, triethylamine and a sulfonate such as, but not limited to, methanesulfonyl chloride or p-toluensulfonyl chloride or triflic anhydride to provide sulfonates of formula (4). Sulfonates of formula (4) can be treated with an optional base such as, but not limited to, potassium carbonate or may also be found in Hartwig, J. Org. Chem., 64(15): 5575–5580 (1999), where compounds of structure (6) can be transformed to compounds of structure (8) or (11) by reaction with amines, anilines, amides with tris-tert-butyl phosphine and a palladium source such as Pd(OAc)$_2$. Compounds of structure (6) can be transformed to heterocyclic or heteroaryl compounds of structure (8) where the R$_6$ moiety is, for instance, a N-pyridazinone by heating with 3(2H)-pyridazinone (or an optionally functionalized heterocycle that contains an acidic NH group in the heterocycle, such as pyridin-2-one) with copper powder and base as described in WO 0024719, p.127, Example 62.

Compounds of formula (6) can also be treated with an organolithium reagent such as, but not limited to, n-butyllithium, methyllithium, or tert-butyllithium and an amide of formula (9) to provide compounds of formula (10).

Compounds of formula (11), wherein L$_2$ is —NH— or —N(alkyl)- and R$_6$ is as defined for a compound of formula (I) can be prepared by heating compounds of formula (6) with a compound of formula H$_2$N—R$_6$ or HN(alkyl)-R$_6$ with a base such as, but not limited to sodium t-butoxide or cesium carbonate in the presence of a metal catalyst such as, but not limited to copper metal or CuI, palladium diacetate, and also optionally with a ligand such as, but not limited to, BINAP, tri-tertbutylphosphine in solvents such as dioxane, toluene, pyridine. References that describe these methodologies may be found in the following references: J. Hartwig, et al., Angew. Chem. Int. Ed., 37:2046–2067 (1998); J. P. Wolfe et al., Acc. Chem. Res., 13:805–818 (1998); J. P. Wolfe et al., J. Org. Chem., 65:1158–1174 (2000); F. Y. Kwong et al., Org. Lett., 4:581–584, (2002); and B. H. Yang et al., J. Organomet. Chem., 576:125–146 (1999).

Compounds of formula (11), wherein L$_2$ is oxygen and R$_6$ is defined in formula (I) can be prepared by heating compounds of formula (6) with a compound of formula HOR$_6$ using a base such as but not limited to sodium hydride in a solvent such as toluene or N,N-dimethylformamide in the presence of a metal containing catalyst such as CuI or palladium diacetate. References that describe these methodologies may be found in the following references: J. Hartwig et al., Angew. Chem. Int. Ed., 37:2046–2067 (1998); J.-F. Marcoux et al., J. Am. Chem. Soc., 119:10539–10540 (1997); A. Aranyos et al., J. Amer. Chem. Soc., 121:4369–4378 (1999); M. Palucki et al., J. Amer. Chem. Soc., 119:3395–3396 (1997); and T. Yamamoto et al., Can. J. Chem., 61:86–91 (1983). Additional methodologies useful for the synthesis of compounds of formula (11), wherein the L$_2$ is oxygen and R$_6$ is defined in formula (1) can be found in the following references: A. Aranyos et al., J. Amer. Chem. Soc., 121:4369–4378 (1999); and E. Baston et al., Synth. Commun., 28:2725–2730 (1998).

Compounds of formula (11), wherein L$_2$ is sulfur and R$_6$ is as defined for a compound of formula (I) can be prepared by heating compounds of formula (6) with a compound of formula HSR$_6$ using a base with or without a metal catalyst such as CuI or palladium diacetate in the presence of a base in a solvent such as dimethylformamide or toluene. References that describe these methodologies may be found in the following references: G. Y. Li et al., J. Org. Chem., 66:8677–8681 (2001); G. Y. Li et al., Angew. Chem. Int. Ed., 40:1513–1516 (2001); U. Schopfer et al., Tetrahedron, 57:3069–3074 (2001); and C. Palomo et al., Tet. Lett., 41:1283–1286 (2000). Additional methodologies useful for the synthesis of compounds of formula (11), wherein the L$_2$ is oxygen and R$_6$ is defined in formula (1) can be found in the following reference A. Toshimitsu et al., Het. Chem., 12:392–397 (2001).

Compounds of formula (11), wherein L$_2$ is —[C(R$_{18}$)(R$_{19}$)]$_q$ and R$_6$, R$_{18}$ and R$_{19}$ are as defined for a compound of formula (I) and q=1, can be prepared from compounds of formula (10). Compounds of formula (10) can be manipulated by reactions well known to those skilled in the art of organic chemistry such as the Grignard reaction, catalytic hydrogenation, metal hydride reaction, alkylation of alcohols, fluorination with (diethylamino)sulfur trifluoride, fluorination with [bis(2-methoxyethyl)amino]sulfur trifluoride to provide compounds of formula (11), wherein L$_2$ is —[C(R$_{18}$)(R$_{19}$)]$_q$ and R$_6$, R$_{18}$ and R$_{19}$ are defined in for a compound of formula (I) and q=1.

Compounds of formula (11), wherein L$_2$ is —[C(R$_{18}$)(R$_{19}$)]$_q$ and R$_6$, R$_{18}$, R$_{19}$ and q are as defined for a compound of formula (I) can be prepared by cross-coupling reactions known to those skilled in the art. Examples of these reactions are the Kumada, Suzuki, Heck, Stille, Suzuki-Miyaaura, Tamao-Kamuda and Sonogashira reaction. Suitable reagents, for example, alkyl Grignard reagents, boronic acids or ester, tin intermediates, alkenes and alkynes can be coupled with compounds of formulas (6) in the presence of a metal catalyst such as palladium, nickel, silver or indium, to prepare compounds of formula (11) wherein L$_2$ is a substituted or unsubstituted alkyl, alkenyl or alkynyl chain. Compounds of formula (11) wherein L$_2$ is an alkenyl or alkynyl chain can be reduced to compounds of formula (11) wherein L$_2$ is an alkyl by methods known to those skilled in the art such as catalytic hydrogenation. References that describe these methodologies may be found in the following references: G. A. Molander et al., Tetrahedron, 58:1465–1470 (2002); W. Dohle et. al., Org. Left., 3:2871–2873 (2001); G. Zou et al, Tet. Left., 42:7213–7216 (2001); A. J. Suzuki, Organomet. Chem., 576:147–168 (1999); A. F. Liftke, J. Amer. Chem. Soc., 122:4020–4028 (2000); N. Miyaura et al., Chem. Rev., 95:2457–2483 (1995); H. Horie et al., J. Mater. Chem., 11:1063–1071 (2001); C. Dai et al., J. Amer. Chem. Soc., 123:2719–2724 (2001); F. Diederich et al., Metal-catalyzed Cross-Coupling Reactions, Wiley-VCH; Weinheim, 1998; A. Mohanakrishnan et al., Syn. Lett., 7:1097–1099 (1999); B. H. Lipshutz et al., Org. Lett., 3:1869–1872 (2001); B. H. Lipshutz et al., Tet. Lett., 40:197–200 (1999); and J. Tsuji, Palladium Reagents and Catalysts-Innovations in Organic Synthesis, John Wiley & Sons: New York, 1995.

Scheme 2

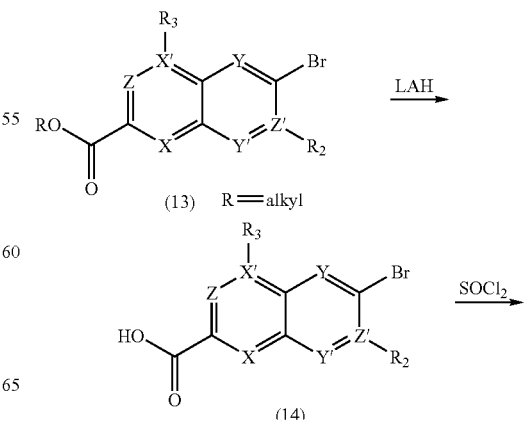

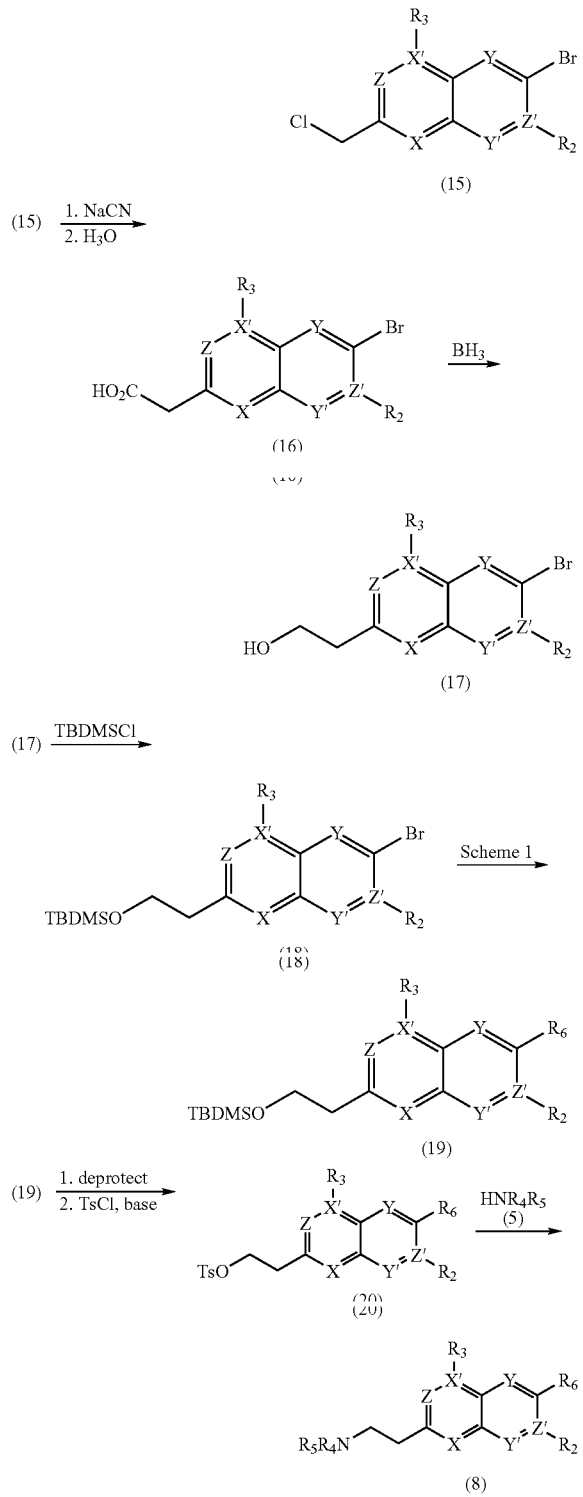

formula (14) can be treated with thionyl chloride to provide chlorides of formula (15). Chlorides of formula (15) can be treated with sodium cyanide or potassium cyanide to provide the nitrile which can be treated with aqueous acid to provide acids of formula (16). Acids of formula (16) can be treated with a reducing agent such as, but not limited to, diborane or borane THF complex to provide alcohols of formula (17). Alcohols of formula (17) can be treated with a hydroxy-protecting reagent such as, but not limited to, tert-butyldimethylsilyl chloride. The protected compounds of formula (18) can be processed as described in Scheme 1 to provide compounds of formula (19). Compounds of formula (19) can be deprotected using methods known to those of ordinary skill in the art and then treated with a sulfonyl chloride such as, but not limited to, methanesulfonyl chloride or p-toluensulfonyl chloride to provide sulfonates of formula (20). Sulfonates of formula (20) can be treated with an amine of formula (5) to provide compounds of formula (8).

Scheme 3

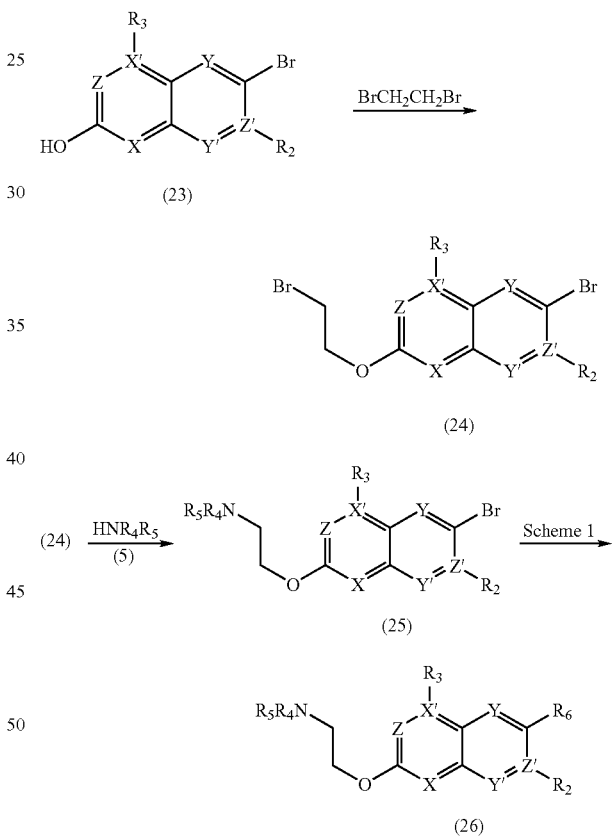

Compounds of formula (26), wherein X, X', Y, Y', Z, Z', $R_2$, $R_3$, $R_4$, and $R_5$ are as defined in formula (I) and $R_6$ is aryl or heteroaryl, can be prepared as described in Scheme 3. Hydroxy compounds of formula (23), purchased or prepared using methods known to those of ordinary skill in the art, can be treated with 1,2-dibromoethane to provide bromides of formula (24). Bromides of formula (24) can be treated with amines of formula (5) to provide compounds of formula (25). Compounds of formula (25) can be processed as described in Scheme 1 to provide compounds of formula (26).

Alternatively, compounds of formula (8), wherein X, X', Y, Y', Z, Z', $R_2$, $R_3$, $R_4$, and $R_5$ are as defined in formula (I) and $R_6$ is aryl or heteroaryl, can be prepared as described in Scheme 2. Esters of formula (13) can be treated with a reducing agent such as, but not limited to, lithium aluminum hydride to provide alcohols of formula (14). Alcohols of

Scheme 4

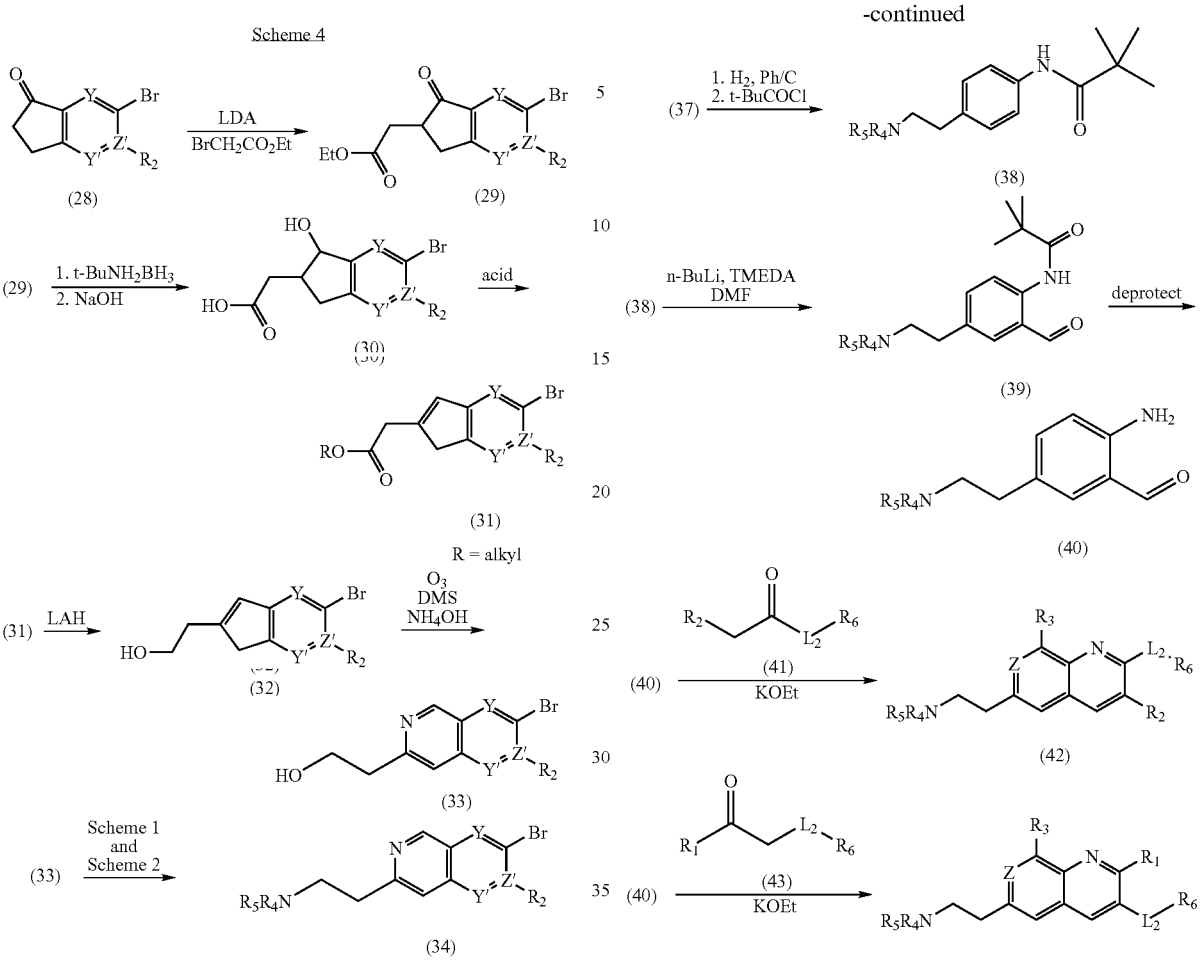

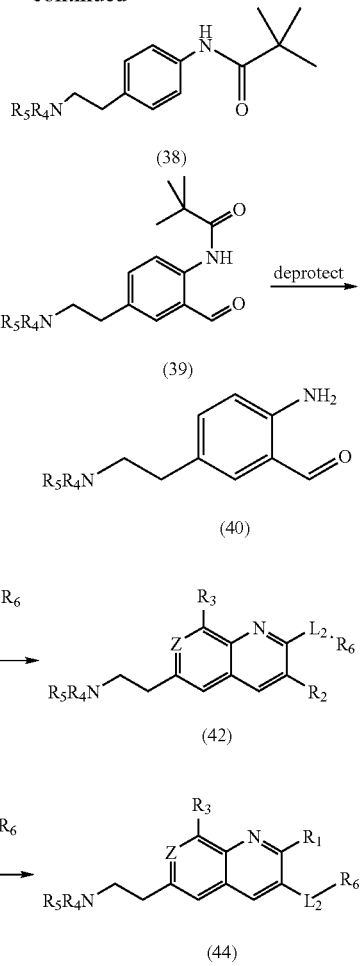

Compounds of formula (34), wherein Y, Y', Z', $R_2$, $R_4$, and $R_5$ are as defined in formula (I) and $R_6$ is aryl or heteroaryl, can be prepared as described in Scheme 4. Indanones of formula (28) can be treated with a base such as, but not limited to, lithium diisopropylamide and ethyl bromoacetate to provide esters of formula (29). Esters of formula (29) can be treated with tert-butylamineborane and then an aqueous basic solution such as, but not limited to, sodium hydroxide in water to provide hydroxyacids of formula (30). Hydroxyacids of formula (30) can be treated with a strong acid such as, but not limited to, concentrated sulfuric acid with heat in a solvent such as methanol to provide esters of formula (31). Esters of formula (31) can be treated with a reducing agent such as, but not limited to, lithium aluminum hydride to provide alcohols of formula (32). Alcohols of formula (32) can be treated with ozone followed by dimethylsulfide and ammonium hydroxide to provide isoquinolines of formula (33). Isoquinolines of formula (33) can be processed as described in Schemes 1 and 2 to provide compounds of formula (34).

Scheme 5

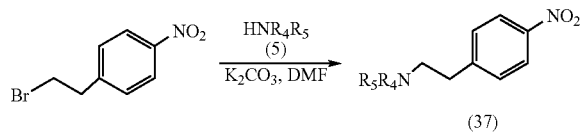

Compounds of formula (42), wherein $R_2$, $R_3$, $R_4$, $R_5$ and $R_6$ are as defined in formula (I) and $L_2$ is $-[C(R_{18})(R_{19})]_q-$ or a bond can be prepared as described in Scheme 5. 1-(2-Bromoethyl)-4-nitrobenzene can be treated with amines of formula (5) to provide amines of formula (37). Amines of formula (37) can be treated with palladium on carbon under a hydrogen atmosphere to provide anilines which can then be treated with a nitrogen protecting reagent such as, but not limited to, trimethylacetyl chloride to provide protected anilines of formula (38). Protected anilines of formula (38) can be treated with an organolithium reagent such as, but not limited to, n-butyllithium, sec-butyllithium, or tert-butyllithium and N,N-dimethylformamide to provide aldehydes of formula (39). The aniline of aldehydes of formula (39) can be deprotected using methods well know to those skilled in the art such as, but not limited to, heating in aqueous hydrochloric acid to provide aldehydes of formula (40). Aldehydes of formula (40) can be treated with ketones of formula (41) and a base such as, but not limited to, potassium ethoxide to provide compounds of formula (42).

Compounds of formula (44), wherein $R_1$, $R_3$, $R_4$, $R_5$ and $R_6$ are as defined in formula (I) and $L_2$ is $-[C(R_{18})(R_{19})]_q-$ or a bond can be prepared as described in Scheme 5. Aldehydes of formula (40) can be treated with ketones of formula (43) and a base such as, but not limited to, potassium ethoxide to provide compounds of formula (44).

Compounds of formula (41) and (43) can be purchased commercially or synthesized from procedures which are known to those skilled in the art.

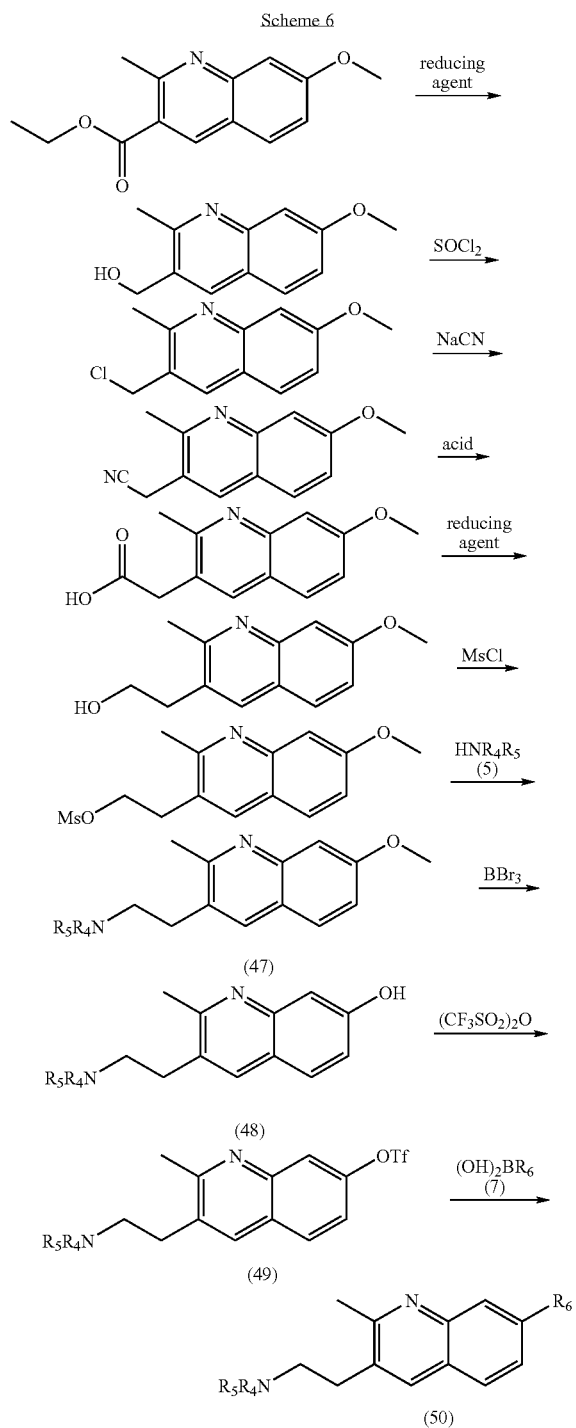

Compounds of formula (50), wherein $R_4$ and $R_5$ are as defined in formula (I) and $R_6$ is aryl or heteroaryl, can be prepared as described in Scheme 6. Ethyl 7-methoxy-2-methyl-3-quinolinecarboxylate can be prepared using the procedures described in Synthetic Comm., 17(14):1647–1653 (1987). Ethyl 7-methoxy-2-methyl-3-quinolinecarboxylate can be treated with a reducing agent, such as, but not limited to, lithium aluminum hydride or sodium borohydride, to provide (7-methoxy-2-methyl-3-quinolinyl)methanol. (7-Methoxy-2-methyl-3-quinolinyl)methanol can be treated with a chlorinating reagent, such as, but not limited to, thionyl chloride to provide 3-(chloromethyl)-7-methoxy-2-methylquinoline. 3-(Chloromethyl)-7-methoxy-2-methylquinoline can be treated with sodium cyanide or potassium cyanide to provide (7-methoxy-2-methyl-3-quinolinyl)acetonitrile. (7-Methoxy-2-methyl-3-quinolinyl)acetonitrile can be treated with acid, such as, but not limited to, glacial acetic acid and concentrated sulfuric acid, in water and 1,4-dioxane with heat to provide (7-methoxy-2-methyl-3-quinolinyl)acetic acid. (7-Methoxy-2-methyl-3-quinolinyl)acetic acid can be treated with a reducing agent, such as, but not limited to, $B_2H_6$, borane-THF complex, or borane-pyridine complex, to provide 2-(7-methoxy-2-methyl-3-quinolinyl)ethanol. 2-(7-Methoxy-2-methyl-3-quinolinyl)ethanol can be treated with methanesulfonyl chloride and a base, such as, but not limited to, triethylamine or diisopropylamine to provide 2-(7-methoxy-2-methyl-3-quinolinyl)ethyl methanesulfonate. 2-(7-Methoxy-2-methyl-3-quinolinyl)ethyl methanesulfonate can be treated with an amine of formula (5) to provide amines of formula (47). Amines of formula (47) can be treated with $BBr_3$ to provide hydroxy compounds of formula (48). Hydroxy compounds of formula (48) can be treated with trifluoromethanesulfonic anhydride or trifluoromethanesulfonyl chloride to provide triflates of formula (49). Triflates of formula (49) can be treated with boronic acids of formula (7) as described in Scheme 1 to provide compounds of formula (50).

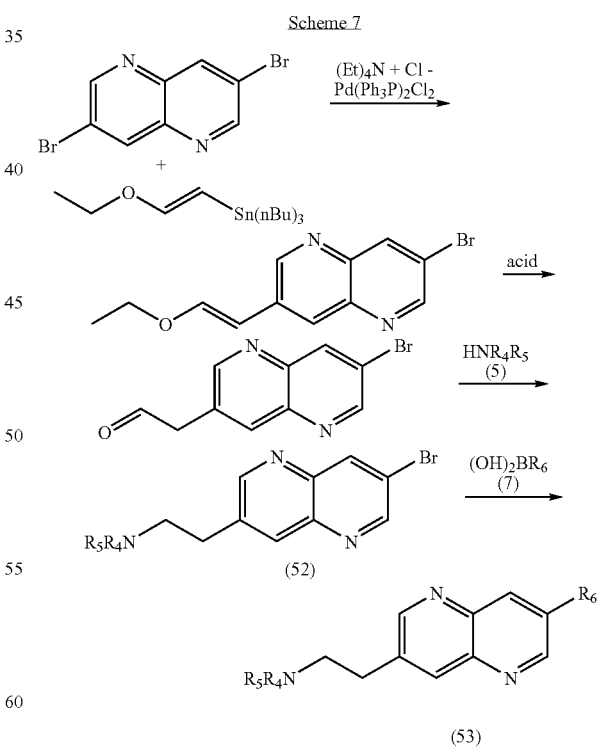

1,5-Naphthyridines of formula (53), wherein $R_4$ and $R_5$ are as defined in formula (I) and $R_6$ is aryl or heteroaryl, can be prepared as described in Scheme 7. 3,7-Dibromo-[1,5] naphthyridine, prepared as described by W. W. Paudler, J.

Org. Chem., 33:1384 (1968), can be treated with (2-ethoxyvinyl)tributylstannane, a halide source, such as, but not limited to, tetraethylammonium chloride, and a palladium source, such as, but not limited to, dichlorobis(triphenylphosphine)palladium(II) in a solvent, such as, but not limited to, N,N-dimethylformamide with heat (about 50° C. to about 150° C.) to provide 3-bromo-7-[2-ethoxyvinyl]-1,5-naphthyridine. 3-Bromo-7-[2-ethoxyvinyl]-1,5-naphthyridine can be treated with an acid, such as, but not limited to, formic acid at about 0° C. to about 60° C. in a solvent, such as, but not limited to, 1,2-dichloroethane to provide (7-bromo-1,5-naphthyridin-3-yl)acetaldehyde. Alternatively, 3-bromo-7-[2-ethoxyvinyl]-1,5-naphthyridine in a solvent, such as, but not limited to, tetrahydrofuran can be treated with an aqueous acid, such as, but not limited to, hydrochloric acid at about 0° C. to about 60° C. to provide (7-bromo-1,5-naphthyridin-3-yl)acetaldehyde. (7-Bromo-1,5-naphthyridin-3-yl)acetaldehyde can be treated with an amine of formula (5) under reductive amination conditions, such as, but not limited to, sodium triacetoxyborohydride and an acid, such as, but not limited to, acetic acid in a solvent, such as, but not limited to, 1,2-dichloroethane at about 0° C. to about 50° C. to povide amines of formula (52). Amines of formula (52) can be treated with boronic acids of formula (7), a palladium source, such as, but not limited to, tris(dibenzylideneacetone)dipalladium(0), a ligand, such as, but not limited to, tri(tert-butyl)phosphine, and a base, such as, but not limited to, potassium fluoride in a solvent, such as, but not limited to, tetrahydrofuran at about 20° C. to about 80° C. to provide 1,5-naphthyridines of formula (53).

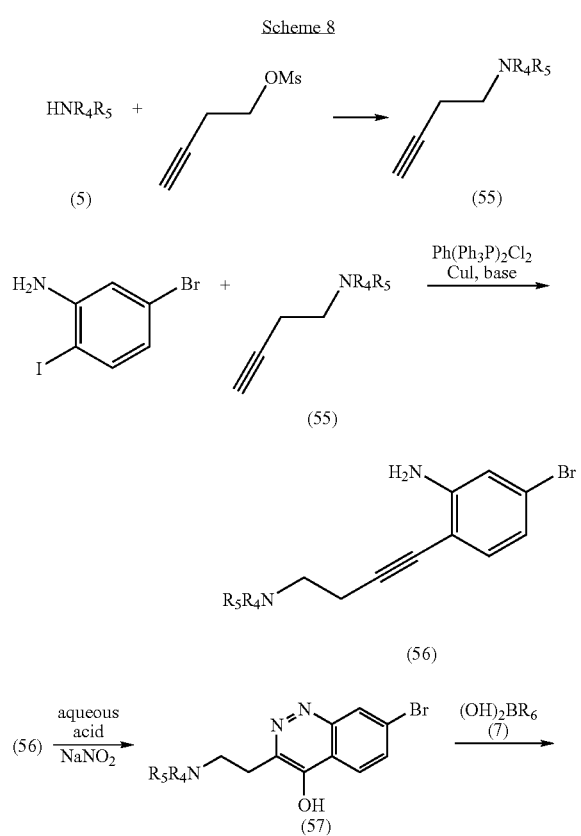

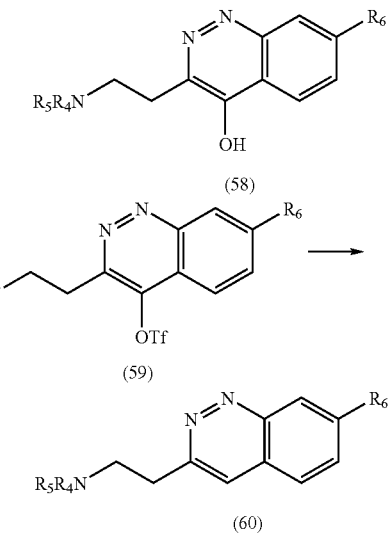

Cinnolines of formula (60), wherein $R_4$ and $R_5$ are as defined in formula (I) and $R_6$ is aryl or heteroaryl, can be prepared as described in Scheme 8. Amines of formula (5) can be treated with 3-butynyl methanesulfonate at room temperature with stirring for about 1 hour and then heated at about 50° C. for about 24 hours. The mixture is allowed to cool to room temperature, and filtered. The filtrate is diluted with acetonitrile to provide a 0.1 M solution of alkynes of formula (55) for use in subsequent steps. 5-Bromo-2-iodophenylamine, prepared as described by Sakamoto in Chem. Pharm. Bull., 35:1823 (1987), can be treated with alkynes of formula (55), a source of palladium(II), such as, but not limited to, $Pd(Ph_3P)_2Cl_2$, CuI, and a base, such as, but not limited to, triethylamine in an organic solvent, such as, but not limited to, DMF at about 50° C. to about 80° C. to provide alkynes of formula (56). Alkynes of formula (56) can be treated with aqueous acid, such as but not limited to aqueous HCl in the presence of sodium nitrite at about 0° C. to about 100° C. to provide hydroxy cinnolines of formula (57). Hydroxy cinnolines of formula (57) can be treated with boronic acids of formula (7) as described in Scheme 1 to provide hydroxy cinnolines of formula (58). Hydroxy cinnolines of formula (58) can be treated with N-phenylbis(trifluoromethanesulfonimide) and a base, such as, but not limited to, diisopropylethylamine in an organic solvent, such as, but not limited to, 1,2-dichloroethane at about 25° C. to about 40° C. to provide triflates of formula (59). Triflates of formula (59) can be treated with a catalytic palladium source, such as, but not limited to, palladium(II) acetate and a hydrogen donor, such as, but not limited to, formic acid at about 25° C. to about 50° C. to provide cinnolines of formula (60).

Scheme 9

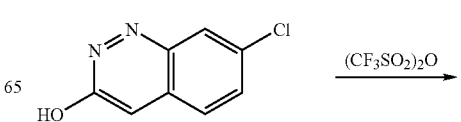

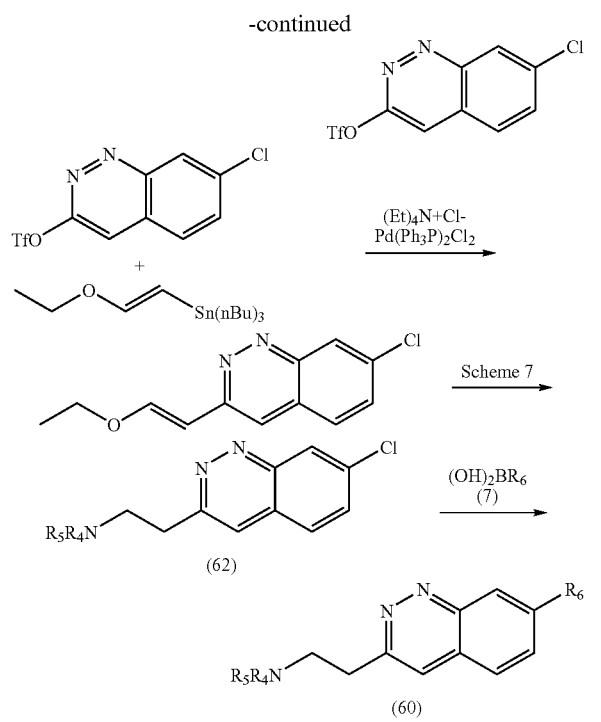

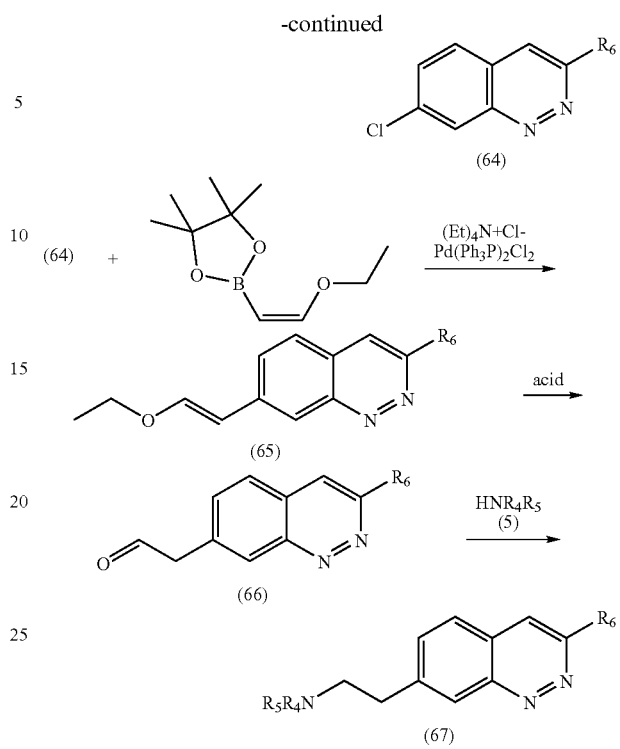

Cinnolines of formula (60), wherein $R_4$ and $R_5$ are as defined in formula (I) and $R_6$ is aryl or heteroaryl, also can be prepared as described in Scheme 9. 7-Chloro-3-cinnolinol, prepared as described by H. E. Baumgarten, J. Het. Chem., 6:333 (1969), can be treated with trifluoromethanesulfonyl chloride or trifluoromethanesulfonic anhydride and a base, such as, but not limited to, triethylamine or pyridine in a solvent, such as, but not limited to, dichloromethane at about 0° C. or room temperature to provide 7-chloro-3-cinnolinyl trifluoromethanesulfonate. 7-Chloro-3-cinnolinyl trifluoromethanesulfonate can be treated with (2-ethoxyvinyl)tributylstannane, a halide source, such as, but not limited to, tetraethylammonium chloride, and a palladium source, such as, but not limited to, dichlorobis(triphenylphosphine) palladium(II) in a solvent, such as, but not limited to, N,N-dimethylformamide at about 50° C. to about 150° C. to provide 7-chloro-3-(2-ethoxyvinyl)cinnoline. 7-Chloro-3-(2-ethoxyvinyl)cinnoline can be processed as described in Scheme 7 to provide amines of formula (62). Amines of formula (62) can be treated with boronic acids of formula (7), a palladium source, such as, but not limited to, dichloro(di-tert-butylphosphinous acid)palladium(II) dimer) or tris(dibenzylideneacetone)dipalladium(0), tri(tert-butyl)phosphine, and a base, such as, but not limited to, cesium fluoride, in a solvent, such as, but not limited to, 1,4-dioxane at about 30° C. to about 120° C. to provide cinnolines of formula (60).

Cinnolines of formula (67), wherein $R_4$ and $R_5$ are as defined in formula (I) and $R_6$ is aryl or heteroaryl, can be prepared as described in Scheme 10. 7-Chloro-3-cinnolinyl trifluoromethanesulfonate, prepared as described in Scheme 9, can be treated with boronic acids of formula (7), a palladium source, such as, but not limited to, tris(dibenzylideneacetone)dipalladium(0), tricyclohexylphosphine (or triphenylphosphine or tri(tert-butyl)phosphine), and a base, such as, but not limited to, potassium fluoride, in a solvent, such as, but not limited to, tetrahydrofuran at about 20° C. to about 80° C. to provide chlorides of formula (64). Chlorides of formula (64) can be treated with 2-(2-ethoxyvinyl)-4,4,5,5-tetramethyl-[1,3,2]dioxaborolane, prepared as described by C. M. Vogels in Chem. Commun. (2000) 1, 51, a palladium source, such as, but not limited to, tris(dibenzylideneacetone)dipalladium(0), tri(tert-butyl)phosphine or, in place of both, dichloro(di-tert-butylphosphinous acid)palladium(II) dimer and a base such as cesium fluoride, in a solvent, such as, but not limited to, 1,4-dioxane at about 30° C. to about 120° C. to provide ethers of formula (65). Ethers of formula (65) can be processed as described in Scheme 7 to provide cinnolines of formula (67).

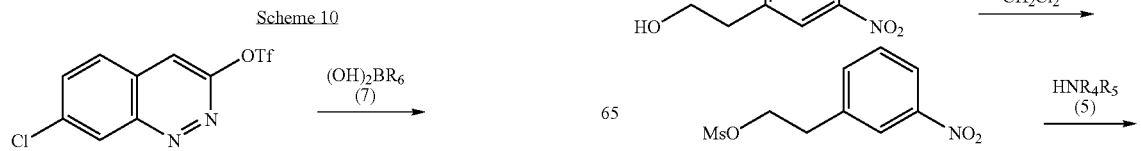

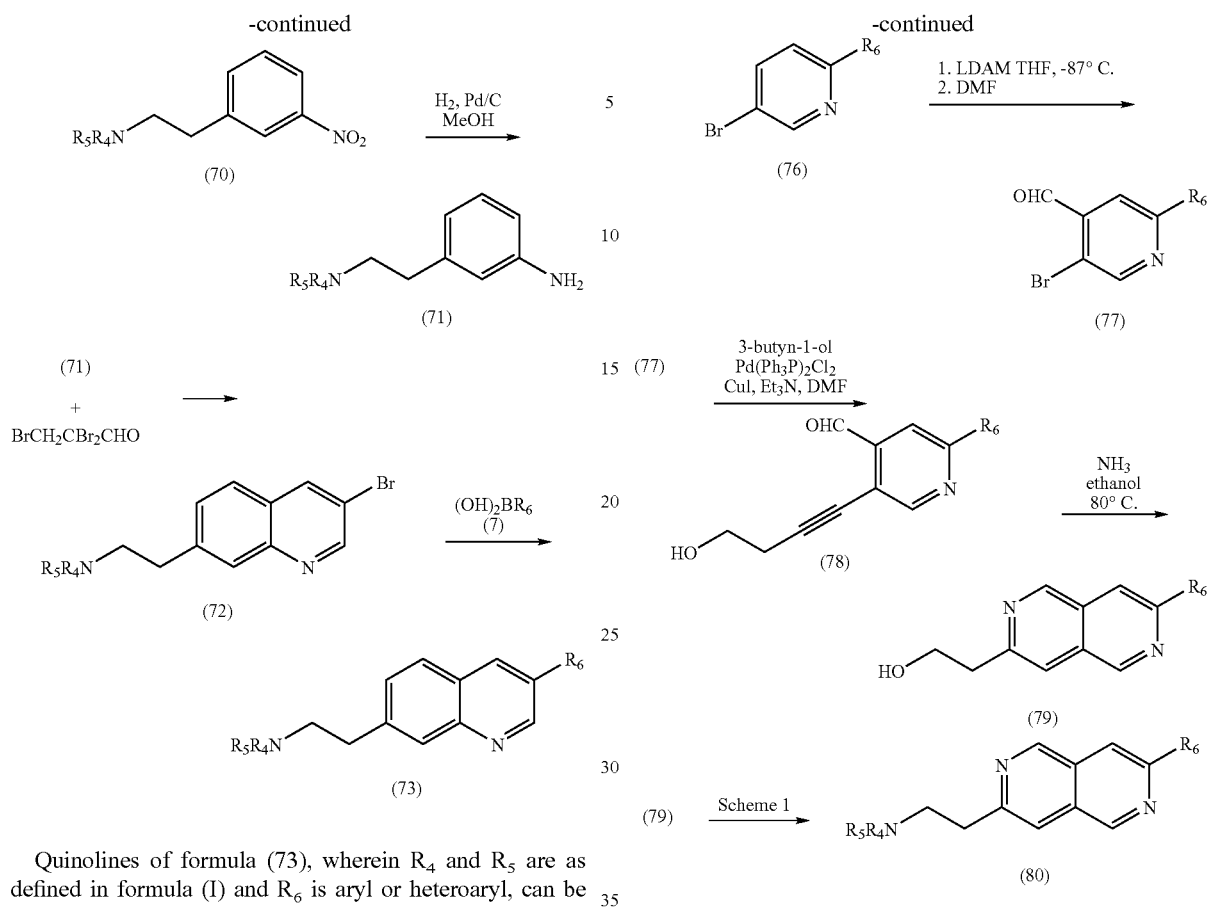

Quinolines of formula (73), wherein $R_4$ and $R_5$ are as defined in formula (I) and $R_6$ is aryl or heteroaryl, can be prepared as described in Scheme 11. 2-(3-Nitrophenyl) ethanol, CAS 100-27-6, can be treated with methanesulfonyl chloride (or toluenesulfonyl chloride), and a base, such as, but not limited to, triethylamine in a solvent, such as, but not limited to, methylene chloride to provide 2-(3-nitrophenyl) ethyl methanesulfonate. 2-(3-Nitrophenyl)ethyl methanesulfonate can be treated with amines of formula (5) and a base, such as, but not limited to, potassium carbonate in a solvent, such as, but not limited to, acetonitrile to provide amines of formula (70). Amines of formula (70) can be treated with hydrogen with a palladium source, such as but not limited to palladium on carbon in a solvent, such as, but not limited to, methanol, ethanol, or ethyl acetate to provide anilines of formula (71). Anilines of formula (71) can be treated with 2,2,3-tribromopropanal as described in S. W. Tinsley, J. Amer. Chem. Soc. 77:4175–4176 (1955), to provide quinolines of formula (72). Quinolines of formula (72) can be treated with boronic acids of formula (7) and treated as described in Scheme 1 to provide quinolines of formula (73).

Naphthyridines of formula (80), wherein $R_4$ and $R_5$ are as defined in formula (I) and $R_6$ is aryl or heteroaryl, can be prepared as described in Scheme 12. 3-Bromo-1-(phenoxycarbonyl)pyridinium chloride can be treated with Grignard reagents of formula (75) as described in D. Comins et al., J. Het. Chem. 1239–1243 (1983) to provide compounds of formula (76). Compounds of formula (76) can be treated with a base, such as, but not limited to, lithium diisopropylamide and N,N-dimethylformamide, as described in Numata et al, Synthesis, 1999, 306–311, to provide compounds of formula (77). Compounds of formula (77) can be treated with 3-butyn-1-ol, CuI, a base, such as, but not limited to, triethylamine, and palladium source, such as, but not limited to, $Pd(PPh_3)_2Cl_2$ in a solvent, such as but not limited to N,N-dimethylformamide to provide alkynes of formula (78). Alkynes of formula (78) can be treated with ammonia at about 80° C. in a solvent, such as, but not limited to, ethanol to provide naphthyridines of formula (79). Naphthyridines of formula (79) can be processed as described in Scheme 1 to provide naphthyridines of formula (80).

Scheme 12

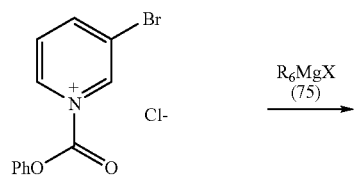

Scheme 13

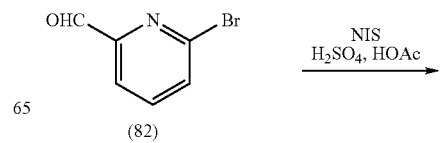

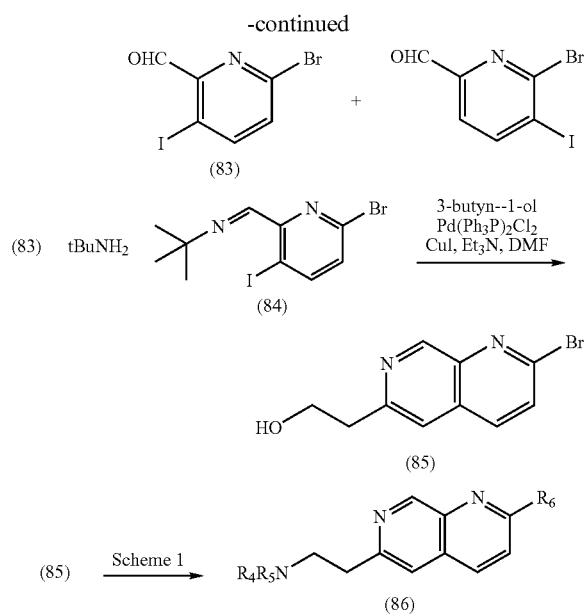

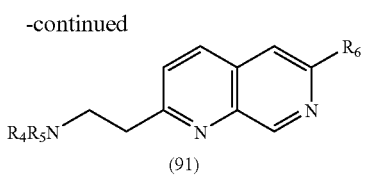

Naphthyridines of formula (91), wherein $R_4$ and $R_5$ are as defined in formula (I) and $R_6$ is aryl or heteroaryl, can be prepared as described in Scheme 14. Imines of formula (84), prepared as described in Scheme 13, can be treated with alkynes of formula (88), CuI, a base, such as, but not limited to, triethylamine or diisopropylamine, and a palladium source, such as, but not limited to, Pd(PPh$_3$)$_2$Cl$_2$ in a solvent, such as but not limited to N,N-dimethylformamide to provide naphthyridines of formula (89). Naphthyridines of formula (89) can be treated with an alkyllithium reagent, such as, but not limited to, methyllithium, n-butyllithium, sec-butyllithium, or t-butyllithium, and ethylene oxide in a solvent, such as, but not limited to, THF or diethyl ether to provide alcohols of formula (90). Alcohols of formula (90) can be treated as described in Scheme 1 to provide naphthyridines of formula (91).

Naphthyridines of formula (86), wherein $R_4$ and $R_5$ are as defined in formula (I) and $R_6$ is aryl or heteroaryl, can be prepared as described in Scheme 13. 6-Bromo-2-pyridinecarbaldehyde can be treated with N-iodosuccinimide in sulfuric acid and acetic acid to provide 6-bromo-3-iodo-2-pyridinecarbaldehyde and 6-bromo-5-iodo-2-pyridinecarbaldehyde. 6-Bromo-3-iodo-2-pyridinecarbaldehyde can be treated with tert-butylamine in a solvent, such as, but not limited to, THF to provide imine (84). Imine (84) can be treated with 3-butyn-1-ol, CuI, a base, such as, but not limited to, triethylamine or diisopropylamine, and a palladium source, such as, but not limited to, Pd(PPh$_3$)$_2$Cl$_2$ in a solvent, such as but not limited to N,N-dimethylformamide to provide alcohols of formula (85). Alcohols of formula (85) can be processed as described in Scheme 1 to provide naphthyridines of formula (86).

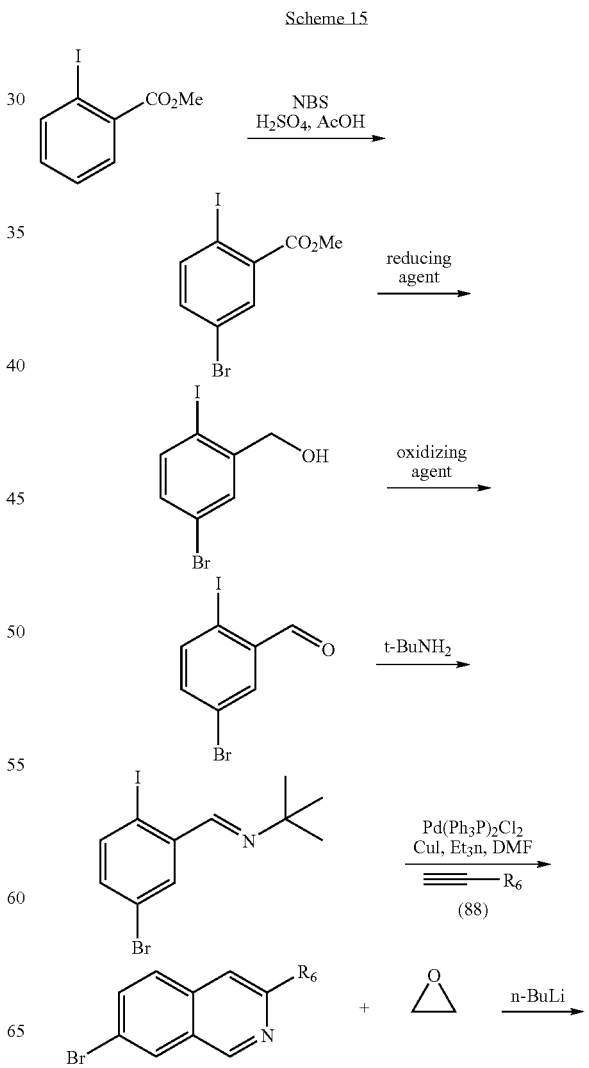

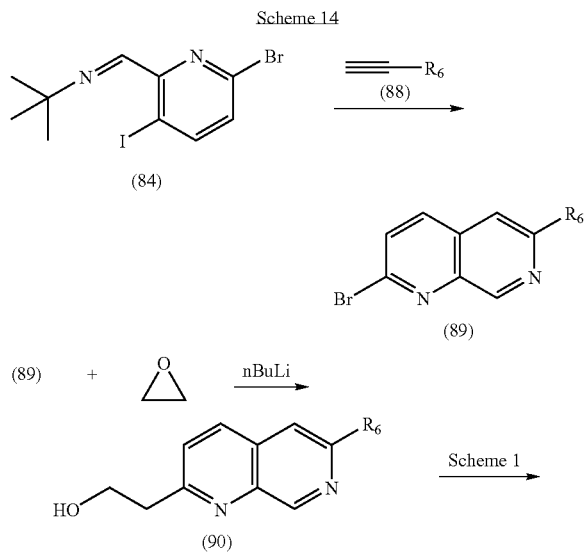

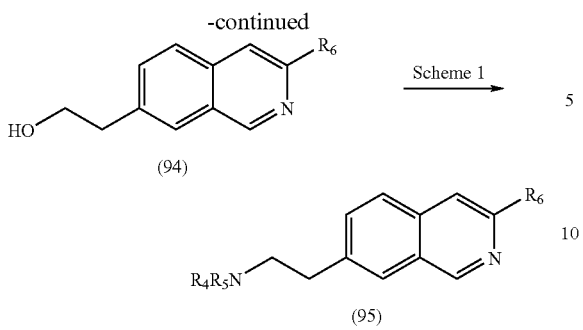

Isoquinolines of formula (95), wherein $R_4$ and $R_5$ are as defined in formula (I) and $R_6$ is aryl or heteroaryl, can be prepared as described in Scheme 15. Methyl 2-iodobenzoate can be treated with N-bromosuccinimide in acetic acid and sufuric acid to provide methyl 5-bromo-2-iodobenzoate. Methyl 5-bromo-2-iodobenzoate can be treated with a reducing agent, such as, but not limited to, sodium borohydride or lithium aluminum hydride in a solvent, such as, but not limited to, THF, ethanol, or a mixture thereof, to provide (5-bromo-2-iodophenyl)methanol. (5-Bromo-2-iodophenyl) methanol can be treated with an oxidizing agent, such as, but not limited to, pyridinium chlorochromate, pyridinium dichromate, $MnO_2$, a peracid such as meta-chloroperoxybenzoic acid, or Swern conditions ($DMSO/Cl(CO)_2Cl/TEA$) to provide 5-bromo-2-iodobenzaldehyde. 5-Bromo-2-iodobenzaldehyde can be treated with tert-butylamine in a solvent, such as, but not limited to, THF to provide N-[(5-bromo-2-iodophenyl)methylene]-N-(tert-butyl)amine. N-[(5-Bromo-2-iodophenyl)methylene]-N-(tert-butyl) amine can be treated with alkynes of formula (88), CuI, a base, such as, but not limited to, triethylamine or diisopropylamine, and a palladium source, such as, but not limited to, $Pd(PPh_3)_2Cl_2$ in a solvent, such as but not limited to N,N-dimethylformamide to provide isoquinolines of formula (93). Isoquinolines of formula (93) can be treated with an alkyllithium reagent, such as, but not limited to, methyllithium, n-butyllithium, sec-butyllithium, or t-butyllithium, and ethylene oxide in a solvent, such as, but not limited to, THF or diethyl ether to provide alcohols of formula (94). Alcohols of formula (94) can be treated as described in Scheme 1 to provide isoquinolines of formula (95).

Scheme 16

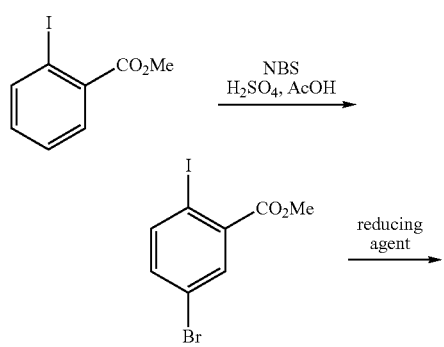

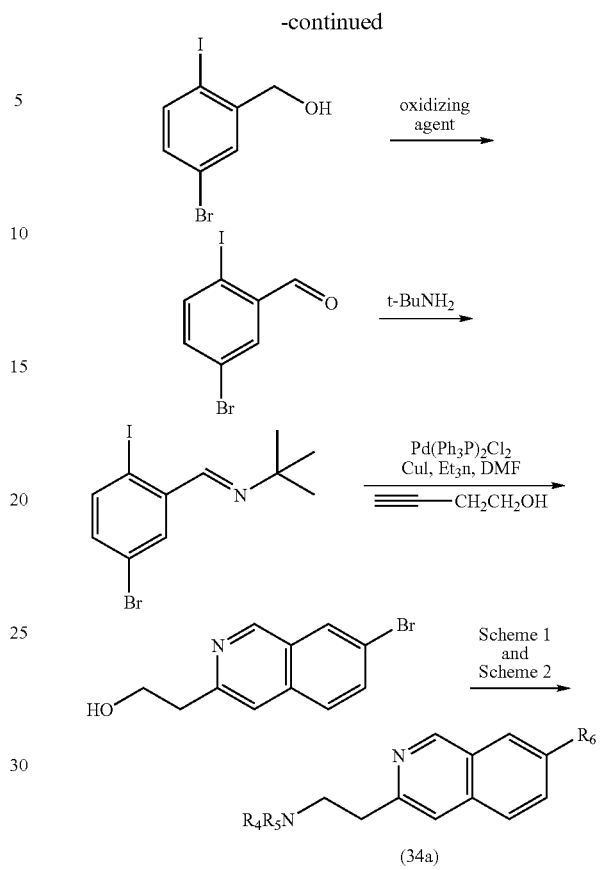

Isoquinolines of formula (34a) are a subgenus of compounds (34), wherein X, Y', and Z' are all carbon atoms, for instance CH, and $R_4$ and $R_5$ are as defined in formula (I) and $R_6$ is aryl or heteroaryl, and the compounds of the subgenus (34a) can be prepared as described in Scheme 16. Methyl 2-iodobenzoate can be treated with N-bromosuccinimide in acetic acid and sufuric acid to provde methyl 5-bromo-2-iodobenzoate. Methyl 5-bromo-2-iodobenzoate can be treated with a reducing agent, such as, but not limited to, sodium borohydride or lithium aluminum hydride in a solvent, such as, but not limited to, THF, ethanol, or a mixture thereof, to provide (5-bromo-2-iodophenyl)methanol. (5-Bromo-2-iodophenyl)methanol can be treated with an oxidizing agent, such as, but not limited to, pyridinium chlorochromate, pyridinium dichromate, $MnO_2$, a peracid such as meta-chloroperoxybenzoic acid, or Swern conditions ($DMSO/Cl(CO)_2Cl/TEA$) to provide 5-bromo-2-iodobenzaldehyde. 0.5-Bromo-2-iodobenzaldehyde can be treated with tert-butylamine in a solvent, such as, but not limited to, THF to provide N-[(5-bromo-2-iodophenyl)methylene]-N-(tert-butyl)amine. N-[(5-Bromo-2-iodophenyl)methylene]-N-(tert-butyl)amine can be treated with the alkyne but-3-yn-1-ol, CuI, a base, such as, but not limited to, triethylamine or diisopropylamine, and a palladium source, such as, but not limited to, $Pd(PPh_3)_2Cl_2$ in a solvent, such as, but not limited to, N,N-dimethylformamide to provide an isoquinoline. The 2-hydroxyethylisoquinoline can be treated as described in Scheme 1 to provide isoquinolines of formula (34a).

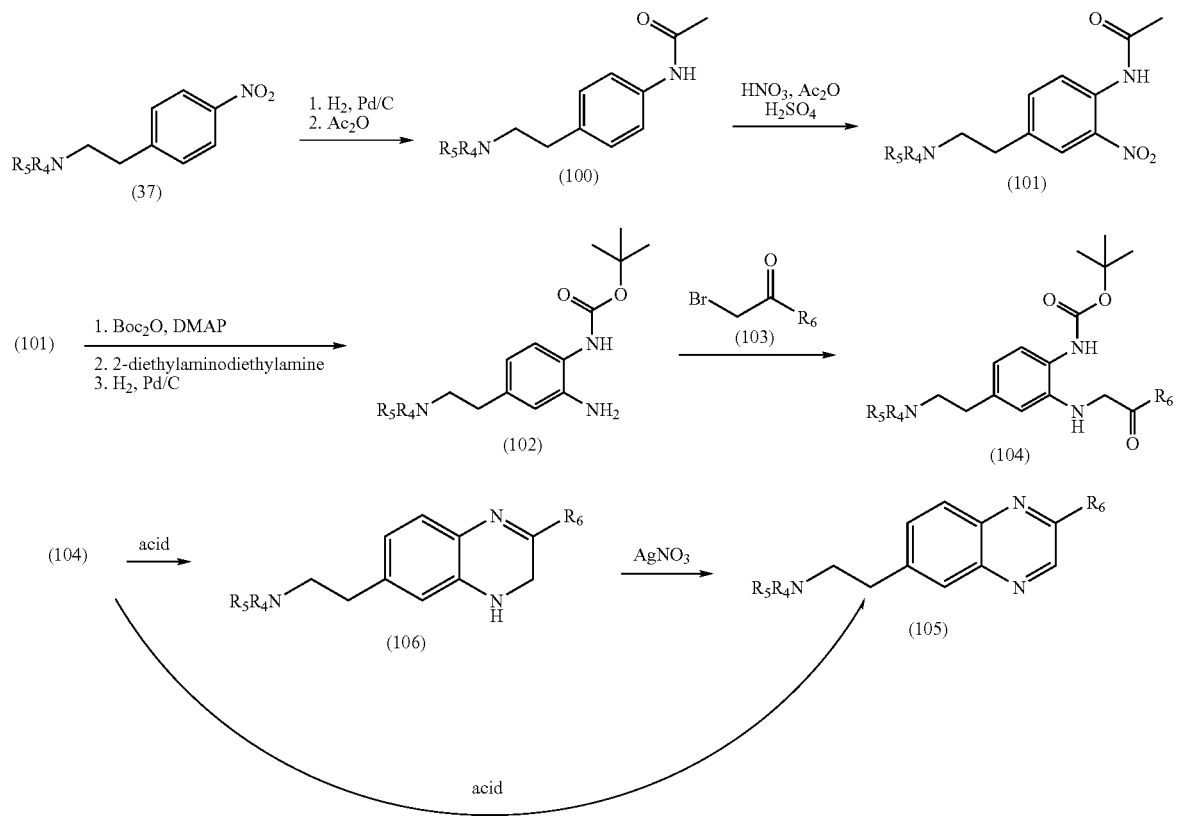

Scheme 17

Quinoxalines of formula (105), wherein $R_4$ and $R_5$ are as defined in formula (I) and $R_6$ is aryl, heteroaryl, heterocycle, or cycloalkyl, can be prepared as described in Scheme 17. Amines of formula (37), prepared as described in Scheme 5, can be treated with palladium on carbon under a hydrogen atmosphere to provide anilines that can then be treated with acetic anhydride in a solvent such as a mixture of sulfuric acid and water to provide acetamides of formula (100). Acetamides of formula (100) can be nitrated using conditions well known to those skilled in the art such as, but not limited to, nitric acid in sulfuric acid in the presence of acetic anhydride to provide acetamides of formula (101). Acetamides of formula (101) can be converted to Boc protected nitroanilines using a procedure described in Grehen, L, et. al, Acta Chem. Scand. Ser. B. 41, 1, 18–23, in which the acetamide is reacted with di-tert-butyidicarbonate in the presence of 4-dimethylaminopyridine followed by treatment with 2-diethylaminodiethylamine to provide a Boc protected nitroaniline which can be treated with palladium on carbon under a hydrogen atmosphere to provide anilines of formula (102). Anilines of formula (102) can be reacted with an acetyl bromide of formula (103) to provide amines of formula (104). Amines of formula (104) can be treated with an acid such as trifluoroacetic acid with heating to provide quinoxalines of formula (105). Treatment of amines of formula (104) may result in the formation of dihydroquinoxalines of formula (106). Dihydroquinoxalines of formula (106) may be oxidized with an oxidant such as silver nitrate to provide quinoxalines of formula (105).

Scheme 18

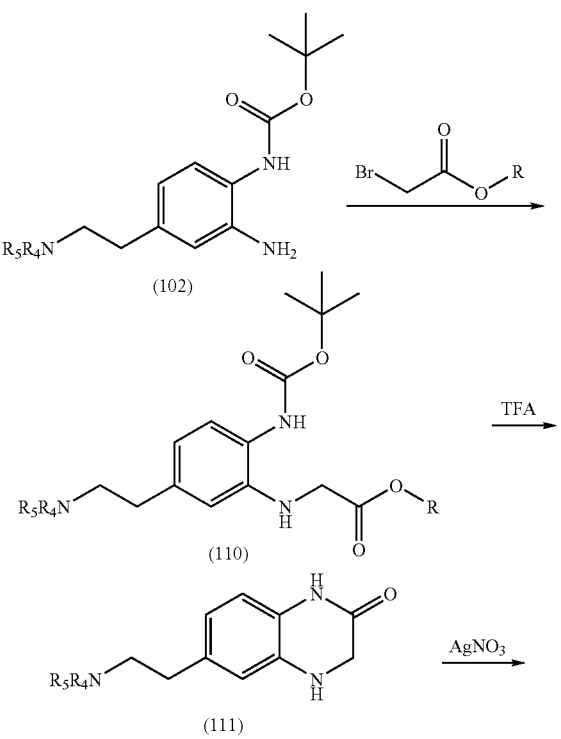

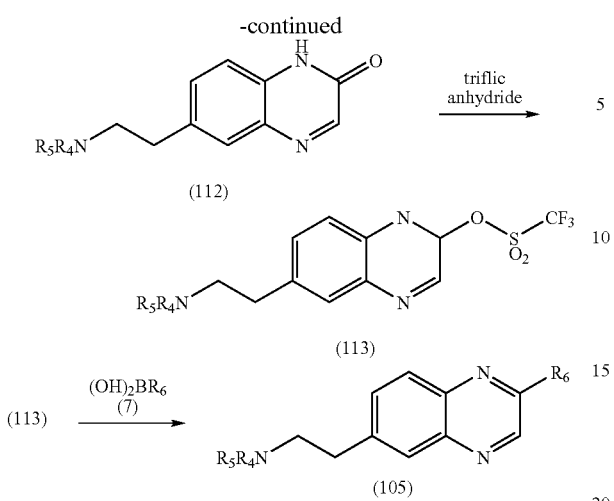

An alternate route to quinoxalines of formula (105), wherein $R_4$ and $R_5$ are as defined in formula (I) and $R_6$ is aryl or heteroaryl, is described in Scheme 18. Anilines of formula (102), prepared as described in Scheme 17, can be reacted with a bromoacetate to provide anilines of formula (110). Anilines of formula (110) can be treated with an acid such as, but not limited to, trifluoroacetic acid with heating to provide dihydroquinoxalinones of formula (111). Dihydroquinoxalinones of formula (111) can be oxidized using an oxidizing agent such as, but not limited to, silver nitrate to provide quinoxalinones of formula (112). Quinoxalinones of formula (112) can be treated with triflic anhydride in the presence of a base such as 2,6-lutidine in a solvent such as dichloromethane to provide triflates of formula (113). Triflates of formula (113) can be treated with boronic acids of formula (7) as described in Scheme 1 to provide quinoxalines of formula (105).

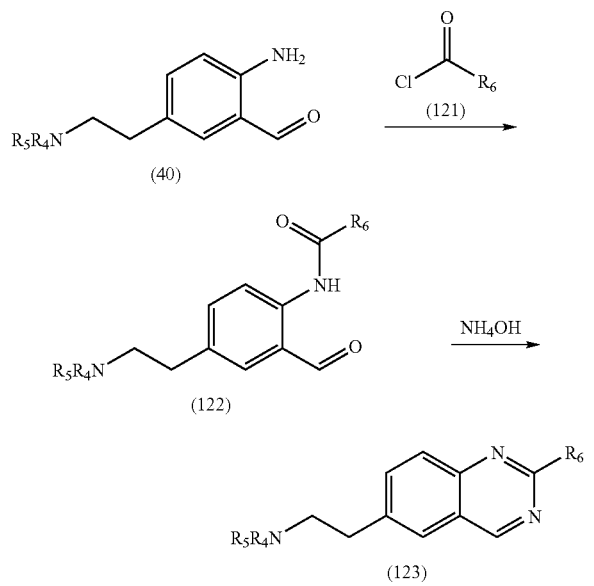

Quinazolines of formula (123), wherein $R_4$ and $R_5$ are as defined in formula (I) and $R_6$ is aryl, heteroaryl, heterocycle, or cycloalkyl, can be prepared as described in Scheme 19. Anilines of formula (40), prepared as described in Scheme 5, can be treated with acid chlorides of formula (121) in the presence of a base such as pyridine in a solvent such as dichloromethane to provide amides of formula (122). Amides of formula (122) can be treated with a source of ammonia, such as aqueous ammonium hydroxide, and heated to provide quinazolines of formula (123).

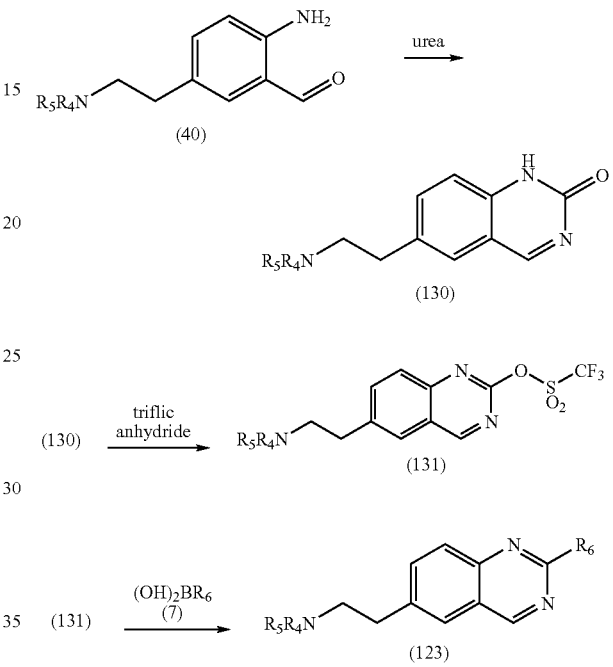

Quinazolines of formula (123), wherein $R_4$ and $R_5$ are as defined in formula (I) and $R_6$ is aryl or heteroaryl can also be prepared as described in Scheme 20. Anilines of formula (40), prepared as described in Scheme 5, can be teated with urea and heated as described in Troeger, et. al. Prakt. Chem. 117, 1927, 181, to provide quinazolinones of formula (130). Quinazolinones of formula (130) can be treated with triflic anhydride in the presence of a base such as 2,6-lutidine in a solvent such as dichloromethane to provide triflates of general strucure (131). Triflates of formula (131) can be treated with boronic acids of general structure (7) as described in Scheme 1 to provide quinoxalines of formula (123).

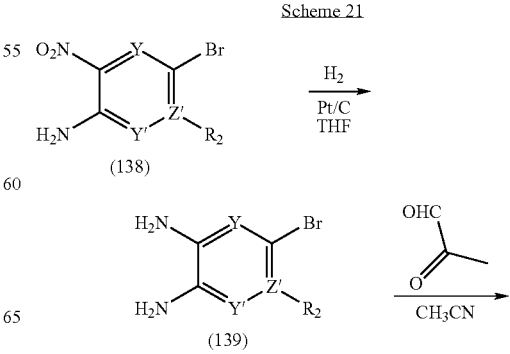

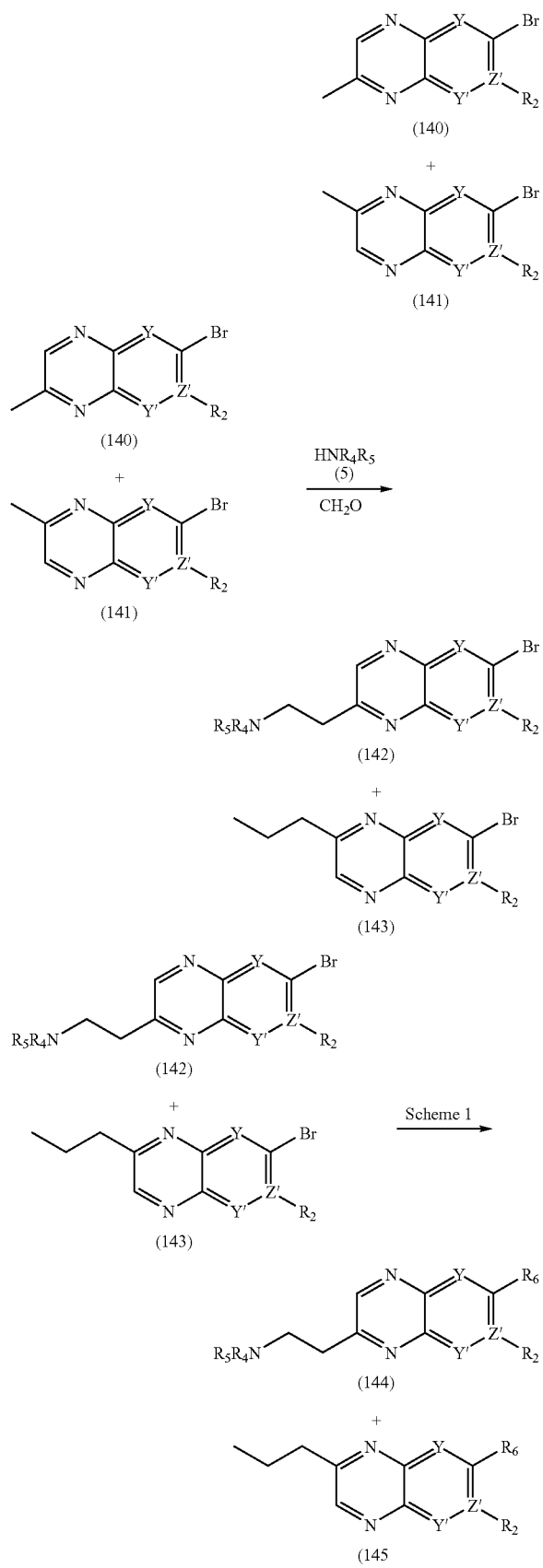

Compounds of formula (144) and (145), wherein Y, Y', Z', $R_2$, $R_4$, and $R_5$ are as defined in formula (I) and $R_6$ is aryl or heteroaryl, can be prepared as described in Scheme 21. Nitrobenzenes of formula (138) can be treated with a reducing agent such as, but not limited to, platinum on carbon under a hydrogen atmosphere to provide diaminobenzenes of formula (139). Diaminobenzenes of formula (139) can be treated with 2-oxopropanal to provide a mixture of bromides of formula (140) and (141). Bromides of formula (140) and (141) can be treated with formaldehyde and amines of formula (5) to provide a mixture of aminobromides of formula (142) and (143). Aminobromides of formula (142) and (143) can be processed as described in Scheme 1 to provide compounds of formula (144) and (145).

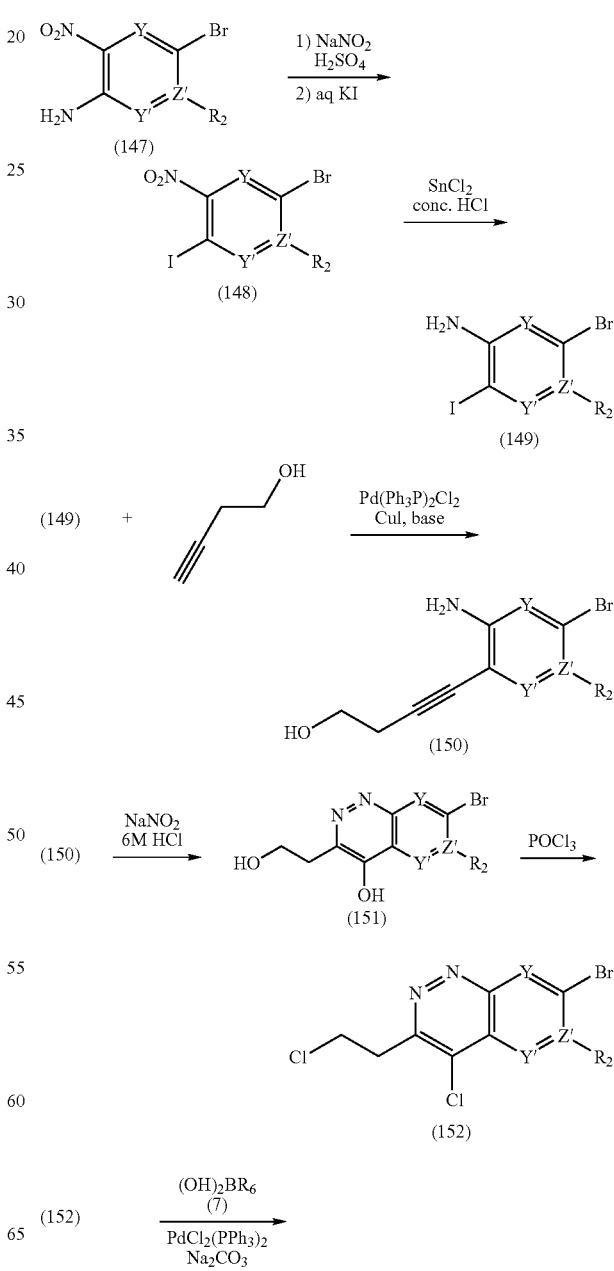

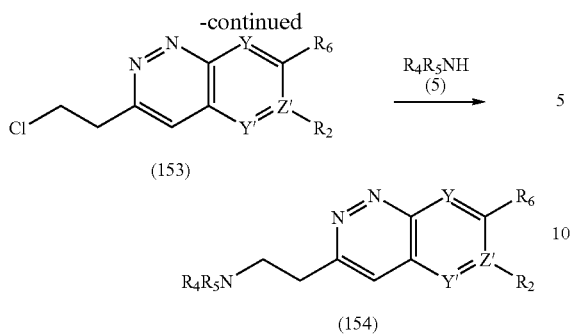

Compounds of formula (154), wherein Y, Y', Z', $R_2$, $R_4$, and $R_5$ are as defined in formula (I) and $R_6$ is aryl or heteroaryl, can be prepared as described in Scheme 22. Compounds of formula (147), purchased or prepared using known methods in the art, can be treated with $NaNO_2$ and acid, such as, but not limited to, concentrated sulfuric acid followed by treatment with KI to provide iodo compounds of formula (148). Iodo compounds of formula (148) can be treated with $SnCl_2$ and an acid such as, but not limited, concentrated HCl to provide compounds of formula (149). Compounds of formula (149) can be treated with but-3-yn-1-ol, copper(I) iodide, base such as, but not limited to triethylamine, and a metal catalyst such as but not limited to $PdCl_2(PPh_3)_2$ to provide alkynes of formula (150). Alkynes of formula (150) can be treated with $NaNO_2$ and an acid such as, but not limited to, 6M HCl to provide compounds of formula (151).

Compounds of formula (151) can be treated with $POCl_3$ to provide chlorides of formula (152). Chlorides of formula (152) can be treated with boronic acids of formula (7) as described in Scheme 1 to provide compounds of formula (153). Compounds of formula (153) can be treated with amines of formula (5) to provide compounds of formula (154).

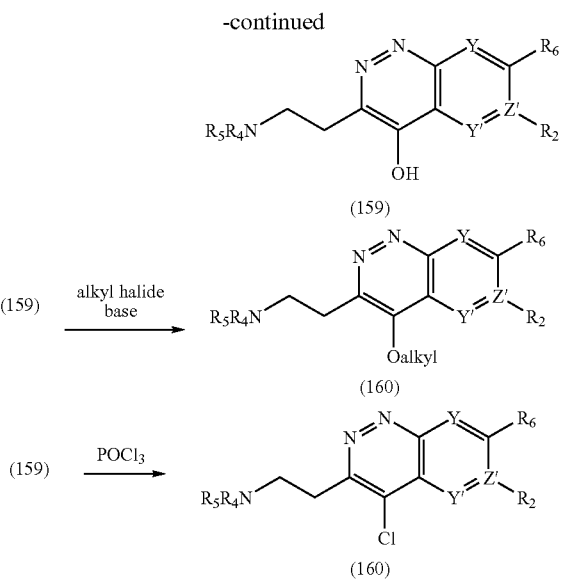

Compounds of formula (159–161), wherein Y, Y', Z', $R_2$, $R_4$, and $R_5$ are as defined in formula (I) and $R_6$ is aryl or heteroaryl, can be prepared as described in Scheme 23. Compounds of formula (149), can be treated with amines of formula (55), copper(I) iodide, a base such as, but not limited to triethylamine, and a metal catalyst such as, but not limited to, $PdCl_2(PPh_3)_2$ to provide alkynes of formula (157). Alkynes of formula (157) can be treated with $NaNO_2$ and an acid such as, but not limited to, 6 M HCl to provide compounds of formula (158). Compounds of formula (158) can be treated with boronic acids of formula (7) as described in Scheme 1 to provide compounds of formula (159). Compounds of formula (159) can be treated with an alkyl halide such as, but not limited to, iodomethane or iodoethane and a base such as, but not limited to, triethylamine to provide compounds of formula (160). Compounds of formula (159) can be treated with phosphorus oxychloride to provide chlorides of formula (161), phosphorus oxybromide may also be used to generate the corresponding bromides.

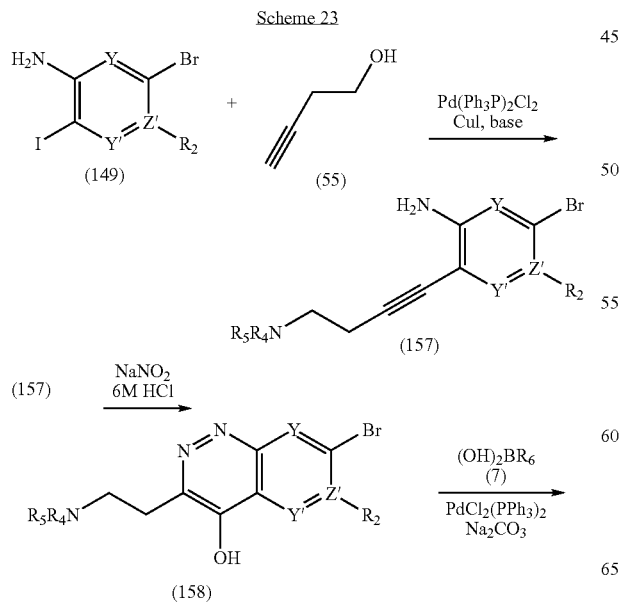

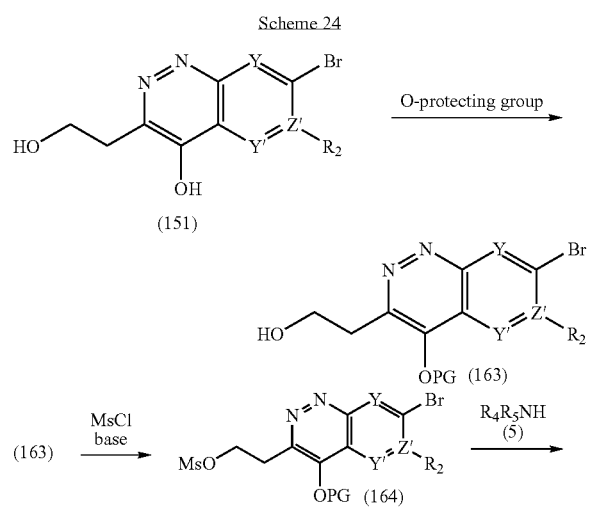

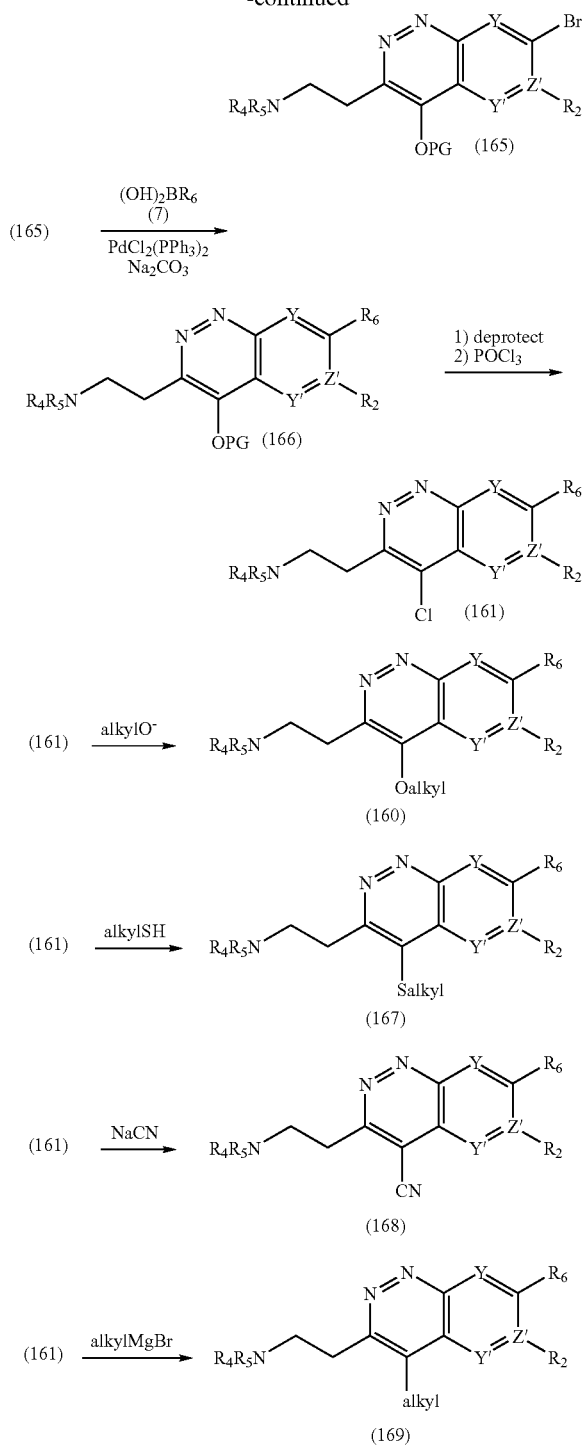

bicarbonate or imidazole to provide compounds of formula (163) wherein PG is the hydroxy protecting group. Compounds of formula (163) can be treated with methanesulfonyl chloride (or toluenesulfonyl chloride) and a base such as, but not limited to, diisopropylamine or triethylamine to provide sulfonates of formula (164). Sulfonates of formula (164) can be treated with amines of formula (5) to provide compounds of formula (165). Compounds of formula (165) can be treated with boronic acids of formula (7) as described in Scheme 1 to provide compounds of formula (166). The hydroxy protecting group of compounds of formula (166) can be removed using methods known to those in the art such as, but not limited to, treatment with fluoride ion, acid, or hydrogenation in the presence of a metal catalyst ($H_2$ and Pd/C) followed by treatment with phosphorus oxychloride to provide chlorides of formula (161), phosphorus oxybromide may also be used to generate the corresponding bromides. Chlorides of formula (161) can be treated with nucleophiles such as, but not limited to, alkoxides, alkyl mercaptans, alkyl grignards, or sodium cyanide to provide compounds of formula (167–169).

The invention also relates to preparing a compound of formula (I)

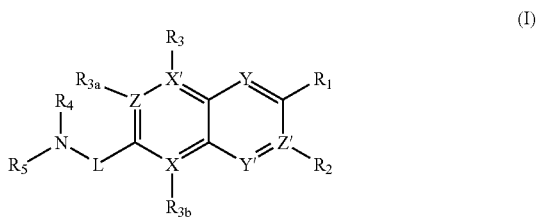

or a pharmaceutically acceptable salt, ester, amide, or prodrug thereof, wherein $R_1$ is $L_2R_6$ wherein $L_2$ is a bond and $R_6$ is 3(2H)-pyridazinon-2-yl; $R_2$, $R_3$, $R_{3a}$, and $R_{3b}$ are hydrogen; L is —[C($R_{16}$)($R_{17}$)]$_n$—; n is 2; $R_{16}$ and $R_{17}$ at each occurrence are hydrogen; $R_4$ and $R_5$ are taken together to form a methylpyrrolidinyl ring of formula (a), wherein one of $R_7$, $R_8$, $R_9$, and $R_{10}$ is methyl and the remaining three substituents are hydrogen; Y and Y' are CH; and X, X', Z, and Z' are C. The process comprises the steps of:

(a) providing a compound (II):

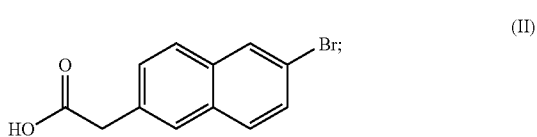

(b) reducing the compound (II) with $BH_3$-THF to provide a compound (III):

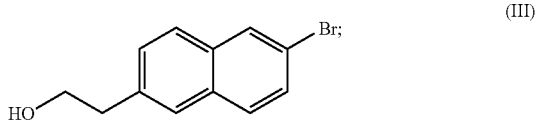

An alternative method for preparing compounds of formula (160–161) and methods for preparation of compounds of formula (167–169), wherein Y, Y', Z', $R_2$, $R_4$, and $R_5$ are as defined in formula (I) and $R_6$ is aryl or heteroaryl, is described in Scheme 24. Compounds of general formula (151), can be treated with a reagent for protecting a hydroxy group known to those of skill in the art such as, but not limited to, tert-butyldimethylsilyl chloride or benzyl bromide, and a base such as, but not limited to, sodium (c) treating the compound of formula (III) with 3(2H)-pyridazinone, copper powder, and base to provide a compound (IV):

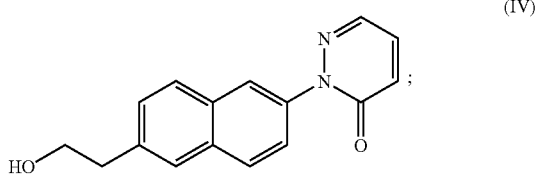

(d) activating the hydroxy group of compound (IV); and reacting the resulting compound with methylpyrrolidine to provide a compound of formula (I).

Compound (II), 6-bromo-naphthalen-2-yl-acetic acid [CAS 3271-06-5] can be prepared by various known methods, for example, Jones et al., J. Amer. Chem. Soc., 70:2843–2848 (1948). Compound (II) can be reduced by treatment with borane-THF, preferably using from about three to four equivalents while maintaining the reaction below 0° C. Compound (III) can be reacted with 3(2H)-pyridazinone by the method described in WO 0024719, Example 62, using about-one equivalent of copper powder and about three equivalents of base. The preferred base is $K_2CO_3$. Compound (IV) can be activated by treatment with methanesulfonyl chloride or toluensulfonyl chloride, preferably in the presence of a base, for example triethylamine. The resulting compound can be reacted with an amine, for example methylpyrrolidine and, more particularly, 2-methylpyrrolidine, to provide a compound within the scope of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof, vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides," as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

Compounds and compositions of the invention are useful for modulating the effects of histamine-3 receptors. In particular, the compounds and compositions of the invention can be used for treating and preventing disorders modulated by the histamine-3 receptors. Typically, such disorders can be ameliorated by selectively modulating the histamine-3 receptors in a mammal, preferably by administering a compound or composition of the invention, either alone or in combination with another active agent as part of a therapeutic regimen.

The compounds of the invention, including but not limited to those specified in the examples, possess an affinity for the histamine-3 receptors. As histamine-3 receptor ligands, the compounds of the invention may be useful for the treatment and prevention of diseases or conditions such as acute myocardial infarction, Alzheimer's disease, asthma, attention-deficit hyperactivity disorder, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, cognitive deficits of schizophrenia, seizures, septic shock, Syndrome X, Tourette's syndrome, vertigo, and sleep disorders.

The ability of the compounds of the invention, including, but not limited to, those specified in the examples, to treat septic shock and cardiovascular disorders, in particular, acute myocardial infarction may be demonstrated by Imamura et al., Circ. Res., 78:475–481 (1996); Imamura et. al., Circ. Res., 78:863–869 (1996); R. Levi and N. C. E. Smith, "Histamine $H_3$-receptors: A new frontier in myocardial ischemia", J. Pharm. Exp. Ther., 292:825–830 (2000); and Hatta, E., K. Yasuda and R. Levi, "Activation of histamine $H_3$ receptors inhibits carrier-mediated norepinephrine release in a human model of protracted myocradial ischemia", J. Pharm. Exp. Ther., 283:494–500 (1997).

The ability of the compounds of the invention, including, but not limited to, those specified in the examples, to treat sleep disorders, in particular, narcolepsy may be demonstrated by Lin et al., Brain Res., 523:325–330 (1990); Monti, et al., Neuropsychopharmacology 15:31–35 (1996); Sakai, et al., Life Sci., 48:2397–2404 (1991); Mazurkiewicz-Kwilecki and Nsonwah, Can. J. Physiol. Pharmacol., 67:75–78 (1989); P. Panula, et al., Neuroscience 44:465–481 (1998); Wada, et al., Trends in Neuroscience 14:415 (1991); and Monti, et al., Eur. J. Pharmacol. 205:283 (1991).

The ability of the compounds of the invention, including, but not limited to, those specified in the examples, to treat cognition and memory process disorders may be demonstrated by Mazurkiewicz-Kwilecki and Nsonwah, Can. J. Physiol. Pharmacol., 67:75–78 (1989); P. Panula, et al., Neuroscience, 82:993–997 (1997); Haas, et al., Behav. Brain Res., 66:41–44 (1995); De Almeida and lzquierdo, Arch. Int. Pharmacodyn., 283:193–198 (1986); Kamei et al., Psychopharmacology, 102:312–318 (1990); Kamei and Sakata, Jpn. J. Pharmacol., 57:437–482 (1991); Schwartz et al., Psychopharmacology, The fourth Generation of Progress. Bloom and Kupfer (eds). Raven Press, New York, (1995) 397; and Wada, et al., Trends in Neurosci., 14:415 (1991).

The ability of the compounds of the invention, including, but not limited to, those specified in the examples, to treat attention-deficit hyperactivity disorder (ADHD) may be demonstrated by Shaywitz et al., Psychopharmacology, 82:73–77 (1984); Dumery and Blozovski, Exp. Brain Res., 67:61–69 (1987); Tedford et al., J. Pharmacol. Exp. Ther., 275:598–604 (1995); Tedford et al., Soc. Neurosci. Abstr., 22:22 (1996); and Fox, et al., Behav. Brain Res., 131: 151–161 (2002).

The ability of the compounds of the invention, including, but not limited to, those specified in the examples, to treat seizures, in particular, epilepsy may be demonstrated by Yokoyama, et al., Eur. J. Pharmacol., 234:129 (1993); Yokoyama and linuma, CNS Drugs 5:321 (1996); Onodera et al., Prog. Neurobiol., 42:685 (1994); R. Leurs, R. C. Vollinga and H. Timmerman, "The medicinal chemistry and therapeutic potential of ligands of the histamine $H_3$ receptor", Progress in Drug Research 45:170–165, (1995); Leurs and Timmerman, Prog. Drug Res., 39:127 (1992); The Histamine $H_3$ Receptor, Leurs and Timmerman (eds), Elsevier Science, Amsterdam, The Netherlands (1998); H. Yokoyama and K. linuma, "Histamine and Seizures: Implications for the treatment of epilepsy", CNS Drugs, 5(5): 321–330 (1995); and K. Hurukami, H. Yokoyama, K. Onodera, K. linuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70–73 (1995).

The ability of the compounds of the invention, including, but not limited to, those specified in the examples, to treat motion sickness, Alzheimer's disease, and Parkinson's disease may be demonstrated by Onodera, et al., Prog. Neurobiol., 42:685 (1994); Leurs and Timmerman, Prog. Drug Res., 39:127 (1992); and The Histamine $H_3$ Receptor, Leurs and Timmerman (eds), Elsevier Science, Amsterdam, The Netherlands (1998).

The ability of the compounds of the invention, including, but not limited to, those specified in the examples, to treat narcolepsy, schizophrenia, depression, and dementia may be demonstrated by R. Leurs, R. C. Vollinga and H. Timmerman, "The medicinal chemistry and therapeutic potential of ligands of the histamine $H_3$ receptor", Progress in Drug Research 45:170–165 (1995); The Histamine $H_3$ Receptor, Leurs and Timmerman (eds), Elsevier Science, Amsterdam, The Netherlands (1998); and Perez-Garcia C, et. al., and Psychopharmacology (Berl) 142(2):215–20 (Feb, 1999).

The ability of the compounds of the invention, including, but not limited to, those specified in the examples, to treat sleep disorders, cognitive dysfunction, mood and attention alteration, vertigo and motion sickness, and treatment of cognitive deficits in psychiatric disorders may be demonstrated by Schwartz, Physiol. Review 71:1–51 (1991).

The ability of the compounds of the invention, including, but not limited to, those specified in the examples, to treat mild cognitive impairment, deficits of memory, deficits of learning and dementia may be demonstrated by C. E. Tedford, in "The Histamine $H_3$ Receptor: a target for new drugs", the Pharmacochemistry Library, vol. 30 (1998) edited by R. Leurs and H. Timmerman, Elsevier (New York). p. 269 and references also contained therein.

The ability of the compounds of the invention, including, but not limited to, those specified in the examples, to treat obesity may be demonstrated by Leurs, et al., Trends in Pharm. Sci., 19:177–183 (1998); E. Itoh, M. Fujimiay, and A. Inui, "Thioperamide, A histamine $H_3$ receptor antagonist, powerfully suppresses peptide YY-induced food intake in rats," Biol. Psych., 45(4):475–481 (1999); S. I. Yates, et al., "Effects of a novel histamine $H_3$ receptor antagonist, GT-2394, on food intake and weight gain in Sprague-Dawley rats," Abstracts, Society for Neuroscience, 102.10: 219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000).

The ability of the compounds of the invention, including, but not limited to, those specified in the examples, to treat inflammation and pain may be demonstrated by Phillips, et al., Annual Reports in Medicinal Chemistry 33:31–40 (1998).

The ability of the compounds of the invention, including, but not limited to, those specified in the examples, to treat migraine may be demonstrated by R. Leurs, R. C. Vollinga and H. Timmerman, "The medicinal chemistry and therapeutic potential of ligands of the histamine $H_3$ receptor," Progress in Drug Research 45:170–165 (1995); Matsubara, et al., Eur. J. Pharmacol., 224:145 (1992); and Rouleau, et al., J. Pharmacol. Exp. Ther., 281:1085 (1997).

The ability of the compounds of the invention, including, but not limited to, those specified in the examples, to treat cancer, in particular, melanoma, cutaneous carcinoma and medullary thyroid carcinoma may be demonstrated by Polish Med. Sci. Mon., 4(5):747 (1998); Adam Szelag, "Role of histamine $H_3$-receptors in the proliferation of neoplastic cells in vitro," Med. Sci. Monit., 4(5):747–755 (1998); and C. H. Fitzsimons, et al., "Histamine receptors signalling in epidermal tumor cell lines with H-ras gene alterations," Inflammation Res., 47 (Suppl 1):S50–S51 (1998).

The ability of the compounds of the invention, including, but not limited to, those specified in the examples, to treat vestibular dysfunctions, in particular, Meniere's disease may be demonstrated by R. Leurs, R. C. Vollinga and H. Timmerman, "The medicinal chemistry and therapeutic potential of ligands of the histamine $H_3$ receptor," Progress in Drug Research 45:170–165 (1995), and Pan, et al., Methods and Findings in Experimental and Chemical Pharmacology 21:771–777 (1998).

The ability of the compounds of the invention, including, but not limited to, those specified in the examples, to treat asthma may be demonstrated by A. Delaunois A., et al., "Modulation of acetylcholine, capsaicin and substance P effects by histamine $H_3$ receptors in isolated perfused rabbit lungs," European Journal of Pharmacology 277(2–3):243–250 (1995); and Dimitriadou, et al., "Functional relationship between mast cells and C-sensitive nerve fibres evidenced by histamine $H_3$-receptor modulation in rat lung and spleen," Clinical Science 87(2):151–163 (1994).

The ability of the compounds of the invention, including, but not limited to, those specified in the examples, to treat allergic rhinitis may be demonstrated by McLeod, et al., Progress in Resp. Research 31:133 (2001).

Compounds of the invention are particularly useful for treating and preventing a condition or disorder affecting the memory or cognition, for example Alzheimer's disease, attention-deficit hyperactivity disorder, schizophrenia, or the cognitive deficits of schizophrenia.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.01 to about 0.1 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

REFERENCE EXAMPLES

Reference Example 1

Preparation of (2R)-2-methylpyrrolidine and (2S)-2-methylpyrrolidine (2R)-2-Methylpyrrolidine tartrate was prepared via resolution of 2-methylpyrrolidine with D-tartaric acid using procedures described by William Gaffield, et al. in Tetrahedron, 37:1861–1869 (1981) or, alternatively, prepared from L-prolinol by methods described by Karrer and Ehrhardt in Helv. Chim. Acta, 34: 2202, 2208 (1951). (2R)-2-methylpyrrolidine hydrobromide also is a suitable source of (2R)-2-methylpyrrolidine, and was prepared using the procedure described by Nijhuis, Walter H. N., et al., J. Org. Chem., 54(1): 209–216,214 (1989). Other procedures describing the synthesis of (2R)-2-methylpyrrolidine and salts thereof can be found in Andres, Jose M., et al. Eur. J. Org. Chem., 9:1719–1726 (2000); and Elworthy, Todd R.; Meyers, A. I., Tetrahedron, 50(20): 6089–6096 (1994).

(2S)-2-Methylpyrrolidine can be substituted for (2R)-2-methylpyrrolidine in the experimental procedures provided herein. The (2S)-2-methylpyrrolidine can be prepared by procedures described in Kim, Mahn-Joo, et al., Bioorg. Med. Chem. Lett. 6(1):71–76 (1996).

Reference Example 2

Preparation of Boronic Acid and Ester Reagents

There are many aryl, heteroaryl, and heterocyclic boronic acids and boronic acid esters that are available commercially or that can be prepared as described in the scientific literature of synthetic organic chemistry. Non-exhaustive examples of boronic acid and boronic acid ester reagents for the synthesis of compounds of formula (I) are provided in Table 1, below, and the following description.

TABLE 1

Examples of Boronic Acid and Boronic Acid Ester Reagents

| Boronic Acid or Boronic Acid Ester | Commercial Source, Chemical Abstracts Number or Literature Reference |
|---|---|
| 2-pyrimidinone-5-boronic acid | Matrix Scientific, Columbia, SC, USA |
| 1H-pyrimidine-2,4-dione-5-boronic acid | Specs, Fleminglaan, the Netherlands |
| pyridine-3-boronic acid | 1692-25-7, Frontier Scientific, Inc., Logan, UT, USA |
| 2,4-dimethoxypyrimidine-5-boronic acid | 89641-18-9, Frontier Scientific, Inc., Logan, UT, USA |
| 2-methoxy-5-pyridine boronic acid | Digital Specialty Chemicals, Dublin, NH |
| pyrimidine-5-boronic acid | S. Gronowitz, et al., "On the synthesis of various thienyl- and selenienylpyrimidines," Chem. Scr. 26(2): 305–309 (1986). |
| pyrimidine-5-boronic acid, pinacol ester | Umemoto, et al., Angew. Chem. Int. Ed. 40(14): 2620–2622 (2001). |

Boronic acid esters of formula (7a):

$$(R_eO)(R_fO)B—R_6 \quad (7a)$$

may serve as synthetic replacements for boronic acids of formula (7) in the Schemes. The substituents represented by $R_e$ and $R_f$ in compounds of formula (7a) may be alkyl, or alternatively $R_e$ and $R_f$ can be taken together to form a ring, which may itself be substituted with alkyl or aryl groups. Examples of suitable compounds of formula (7a) include, but are not limited to $(CH_3O)_2BPh$ and (4-cyanomethylphenyl)boronic acid, pinacol ester (CombiBlocks Inc., San Diego)). Boronic acids of formula (7) and boronic acid esters of formula (7a) are commercially available or can be prepared by methods well known to those skilled in the art of synthetic organic chemistry. For instance, Takagi et al. (Tetrahedron Letters, 43:5649–5651 (2002)) prepared heteroaryl pinacolborane esters of formula (7a) using heteroaromatic compounds and reaction with bis(pinacolborane) in the presence of an iridium catalysis of IrCl[COD] 2-(4,4'-di-t-butyl-2,2'-bipyridine in octane. Other methods have been described wherein aryl halides and heteroaryl halides are transmetallated with alkyl lithiums or Grignard reagents, then treated with trialkylborate esters, then treated with acid to produce compounds of formulae (7) and (7a) (B. T. O'Neill, et al., Organic Letters, 2:4201 (2000); M. D. Sindkhedkar, et al., Tetrahedron, 57:2991 (2001); W. C. Black, et al., Journal of Medicinal Chemistry, 42:1274 (1999); Letsinger; Dandegaonker, J. Amer. Chem. Soc., 81:498–501 (1959); Carroll, F. Ivy, et al. J. Med. Chem., 2229–2237 (2001). Another method is the Miyaura reaction described in Ishiyama, Tatsuo; Ishida, Kousaku, Miyaura, Norio, Tetrahedron, 9813–9816 (2001) in which aryl and heteroaryl halides are reacted with bis(pinacolborane), KOAc, and $Pd_2 dba_3$ and tris-cyclohexylphosphine or $PdCl_2dppf$ (Ishiyama, et al. Tetrahedron, 9813–9816 (2001)). Another method for preparation of compounds of formula (7a) is the reaction described in 0. Baudoin, et al., J. Org. Chem., 65:9268–9271 (2000), in which aryl and heteroaryl halides or triflates are reacted with a dialkoxyborane such as pinacolborane, in the presence of $Et_3N$ and $Pd(OAc)_2$ in dioxane. Compounds of formula (7) and (7a) wherein $R_6$ is a cycloalkyl ring can be prepared, for example, from cycloalkenes (for example, see H. C. Brown, et al., J. Amer. Chem. Soc., 95:2396–2397 (1973) and H. C. Brown, et al., J. Amer. Chem. Soc., 98:1798–1806 (1976)) or cycloalkyl Grignard or cycloalkyl lithium intermediates (see, for example, Graf et al., Tetrahedron, 55:8801–8814 (1999) and Michailow, et al., lzv. Akad. Nauk SSSR Ser. Khim, 76:78 (1959)).

Reference Example 3

Preparation of Stannane-Type Reagents

Many reagents such as $Me_3SnR_6$, $Bu_3SnR_6$, and $R_6ZnCl$ are suitable for reactions under Stille conditions in Scheme 1 and are commercially available. However, where the reagents wherein $R_6$ is heteroaryl, heterocyclic, or aryl are not commercially available, they may be prepared by methods available to one with skill in the art. Examples of such methods include lithium halogen-metal exchange of heteroaryl, heterocyclic or aryl halides, followed by treatment with $Me_3SnCl$ (Li, et al. J. Med. Chem. 1996, 39, 1846), $Bu_3SnCl$, $ZnCl_2$, or $B(OCH_3)_3$ (O'Neill, et al. Org. Lett. 2000, 2, 4201; Sindkhedkar, et al. Tet. 2001, 57, 2991) and magnesium halogen-metal exchange with isopropylmagnesium chloride as described in Knochel, et al. J. Org. Chem. 2000, 65, 4618–4634, followed by treatment with $Me_3SnCl$, $Bu_3SnCl$, or $ZnCl_2$. Heteroaryl halides and triflates can be treated with trimethylstannyl sodium as described in A. O. Koren, et al. J. Med. Chem. 1998, 41, 3690, to give $Me_3SnR_6$. Heteroaryl halides and triflates can be treated wtih hexamethyldistannane as described in W. C. Black, et al. J. Med. Chem. 1999, 42, 1274., to give $Me_3SnR_6$.

EXAMPLES

Example 1

4-(6-{2-[(2R)-2-methyl-1-pyrrolidinyl]ethyl}-2-naphthyl)benzonitrile

Example 1A (6-bromo-2-naphthyl)methanol

To a stirred 1.0 M THF solution of lithium aluminum hydride (108 mL, 108 mmol) was added dropwise over 20 min a solution of methyl 6-bromo-2-naphthoate (18.9 g, 71.3 mmol) in THF (180 mL), while maintaining the reaction temperature below −5° C. When the addition was complete, the reaction mixture was stirred at −10° C. for 1 hr, then quenched by the sequential dropwise addition of distilled water (4 mL), 2 N aqueous $Na_2CO_3$ (4 mL), and distilled water (12 mL). After stirring for 15 min at room temperature, the reaction mixture was filtered. The filter cake was washed with ethyl acetate (3×100 mL) and the combined filtrates were dried ($MgSO_4$) and filtered. This filtrate was concentrated under reduced pressure to give a white solid. Drying under vacuum overnight at 40° C. provided the product (16.84 g, 99% yield). M.p. 149.9–151.6° C. $^1$H NMR ($CDCl_3$, 300 MHz) δ 7.99 (d, J=2 Hz, 1H), 7.79–7.67 (m, 3H), 7.55 (dd, J=2, 12 Hz, 1H), 7.52 (dd, J=2, 12 Hz, 1H), 4.85 (s, 2H). MS (DCI-$NH_3$) [M]$^+$ at 236.

Example 1B 2-bromo-6-(chloromethyl)naphthalene

A stirred solution of the product from Example 1A (30.5 g, 129 mmol) in dioxane (320 mL) under a dry nitrogen atmosphere was chilled to −10° C. Solid anhydrous $ZnCl_2$ (514 mg, 3.77 mmol, 0.03 equiv.) was added in one lot, followed by the dropwise addition of thionyl chloride (19.3 mL, 264 mmol, 2.0 equiv.). The reaction mixture was allowed to warm to room temperature then stirred an additional 2 hr. This reaction mixture was then concentrated under reduced pressure and the residue was partitioned between dichloromethane and saturated aqueous $NaHCO_3$ (500 mL). The organic layer was washed with brine (2×100 mL), dried ($MgSO_4$), and filtered. The filtrate was concentrated under reduced pressure to give a white solid. Drying under vacuum overnight at 40° C. provided the product (32.6 g, 99% yield). M.p. 133.1–134.1° C. $^1$H NMR ($CDCl_3$, 300 MHz) δ 8.00 (d, J=2 Hz, 1H), 7.81–7.67 (m, 3H), 7.56 (dd, J=2, 12 Hz, 1H), 7.54 (dd, J=2, 12 Hz, 1H), 4.73 (s, 2H). MS (DCI-$NH_3$) [M]$^+$ at 254.

Example 1C (6-bromo-2-naphthyl)acetonitrile

A mixture of the product from Example 1B (32.2 g, 126 mmol) and NaCN (7.44 g, 152 mmol, 1.2 equiv.) in acetonitrile (314 mL) and distilled water (32 mL) under a dry nitrogen atmosphere was stirred at reflux for 21 hr. The reaction mixture was cooled to room temperature then concentrated under reduced pressure. The residue was stirred with distilled water (314 mL) for 45 min. The resulting white solid was isolated by filtration and washed with distilled water (1500 mL). Drying under vacuum overnight at 40° C. provided the product (32.2 g, 97% yield). M.p. 119.6–120.6° C. $^1$H NMR ($CDCl_3$, 300 MHz) δ 8.01 (d, J=2 Hz, 1H), 7.82–7.68 (m, 3H), 7.60 (dd, J=2, 12 Hz, 1H), 7.41 (dd, J=2, 12 Hz, 1H), 3.90 (s, 2H). MS (DCI-$NH_3$) [M+$NH_4$]$^+$ at 263, [M+$NH_4$—$NH_3$]$^+$ at 280.

Example 1D (6-bromo-2-naphthyl)acetic acid

A stirred mixture of the product from Example 1C (29.62 g, 120 mmol) in glacial acetic acid (300 mL) and distilled water (150 mL) under a dry nitrogen atmosphere was cooled to −15° C. Concentrated sulfuric acid (120 mL, 4.32 mol, 36.0 equiv.) was added dropwise over 20 min while maintaining the reaction temperature below 10° C. The reaction mixture was then stirred at reflux for 2 hr. After cooling to 35° C., ice (500 g) was added to the mixture and stirring was continued for 45 min. The resulting white solid was isolated by filtration and washed with distilled water (1500 mL). Drying under vacuum overnight at 40° C. provided the product (29.57 g, 93% yield). $^1$H NMR ($CDCl_3$, 300 MHz) δ 7.99 (d, J=2 Hz, 1H), 7.76–7.64 (m, 3H), 7.54 (dd, J=2, 12 Hz, 1H), 7.44 (dd, J=2, 12 Hz, 1H), 3.81 (s, 2H). MS (DCI-$NH_3$) [M+$NH_4$]$^+$ at 282.

Example 1E 2-(6-bromo-2-naphthyl)ethanol

To a stirred, −15° C. solution of the product from Example 1D (28.6 g, 108 mmol) in anhydrous THF (143 mL) under a dry nitrogen atmosphere was added dropwise over 15 min a 1.0 M solution of $BH_3$-THF (409 mL, 409 mmol, 3.8 equiv.) while maintaining the reaction temperature below 0° C. When the addition was complete, the reaction mixture was stirred at −15° C. for 15 min, then allowed to warm to room temperature and stirred an additional 2 hr. The reaction mixture was then cooled to −10° C. and quenched with distilled water (104 mL). After stirring for 15 min at room temperature, the reaction mixture was concentrated under reduced pressure. The residue was partitioned between dichloromethane (350 mL) and distilled water (200 mL) and the aqueous layer was extracted with dichloromethane (2×100 mL). The combined organic extracts were washed with distilled water (3×100 mL), dried ($MgSO_4$) and filtered. The filtrate was concentrated under reduced pressure to give a white solid. Drying under vacuum overnight at 40° C. provided the product (26.1 g, 96% yield). M.p. 102.3–103.1° C. $^1$H NMR ($CDCl_3$, 300 MHz) δ 7.98 (d, J=2 Hz, 1H), 7.74–7.63 (m, 3H), 7.53 (dd, J=2, 12 Hz, 1H), 7.49 (dd, J=2, 12 Hz, 1H), 4.00–3.92 (m, 2H), 3.02 (t, J=6 Hz, 2H), 1.43–1.35 ($t_{br}$, J=6 Hz, 1H). MS (DCI-$NH_3$) [M+$NH_4$]$^+$ at 268.

Example 1F

4-[6-(2-hydroxyethyl)-2-naphthyl]benzonitrile

A mixture of the product from Example 1E (0.60 g, 2.39 mmol), 4-cyanophenylboronic acid (0.42 g, 2.87 mmol, 1.2 equiv.), $PdCl_2(PPh_3)_2$ (34 mg, 0.048 mmol, 0.020 equiv.) and $K_3PO_4H_2O$ (1.38 g, 7.17 mmol, 3.0 equiv.) in isopropanol (40 mL) and distilled water (15 mL) was stirred at 65° C. under a dry nitrogen atmosphere for 1.5 hr. The reaction mixture was cooled to room temperature then concentrated under reduced pressure. The residue was partitioned between ethyl acetate and brine. The aqueous layer was washed with ethyl acetate, and the combined organic extracts were washed with saturated aqueous NH$_4$Cl, dried (MgSO$_4$), and filtered. The filtrate was concentrated under reduced pressure and the residue was purified by column chromatography (7:3 hexane/ethyl acetate). Fractions containing product were combined and concentrated under reduced pressure to provide the product as an off-white solid (0.59 g, 90% yield). $^1$H NMR (CDCl$_3$, 300 MHz) δ 8.04 (d, J=2 Hz, 1H), 7.93–7.68 (m, 8H), 7.44 (dd, J=2, 12 Hz, 1H), 3.98 (t, J=6 Hz, 2H), 3.07 (t, J=6 Hz, 2H). MS (DCI-NH$_3$) [M+NH$_4$]$^+$ at 291, [M+NH$_4$ NH$_3$]$^+$ at 308.

Example 1G

2-[6-(4-cyanophenyl)-2-naphthyl]ethyl 4-methyl benzenesulfonate

A mixture of the product from Example 1F (0.48 g, 1.76 mmol), p-toluenesulfonyl chloride (0.37 g, 1.93 mmol, 1.1 equiv.), and pyridine (3.0 mL, 37.1 mmol, 21.1 equiv.) in anhydrous dichloromethane (20 mL) was stirred at room temperature under a dry nitrogen atmosphere for 3 days. The reaction mixture was concentrated under reduced pressure. The residue was partitioned between ethyl acetate and 10% aqueous citric acid. The aqueous layer was washed with ethyl acetate, and the combined organic extracts were washed with saturated aqueous NaHCO$_3$, dried (MgSO$_4$), and filtered. The filtrate was concentrated under reduced pressure and the residue was purified by column chromatography (6:4 dichloromethane/hexane). Fractions containing product were combined and concentrated under reduced pressure to provide the product as a white solid (0.30 g, 40% yield). $^1$H NMR (CDCl$_3$, 300 MHz) δ 8.01 (d, J=2 Hz, 1H), 7.86–7.75 (m, 6H), 7.72–7.56 (m, 4H), 7.29 (dd, J=2, 12 Hz, 1H), 7.17 (d, J=9 Hz, 2H), 4.34 (t, J=6 Hz, 2H), 3.14 (t, J=6 Hz, 2H), 2.36 (s, 3H). MS (DCI-NH$_3$) [M+NH$_4$]$^+$ at 445.

Example 1H 4-(6-{2-[(2R)-2-methyl-1-pyrrolidinyl]ethyl}-2-naphthyl)benzonitrile

A mixture of the product from Example 1G (0.30 g, 1.08 mmol), (2R)-2-methylpyrrolidine (0.30 g, 3.52 mmol, 5.0 equiv.), and cesium carbonate (0.70 g, 2.1 mmol, 3.0 equiv.) in anhydrous acetonitrile (5 mL) was stirred in a sealed tube at 50° C. under a dry nitrogen atmosphere for 2 days. The reaction mixture was cooled to room temperature then concentrated under reduced pressure. The residue was partitioned between ethyl acetate and saturated aqueous Na$_2$CO$_3$. The aqueous layer was washed with ethyl acetate, and the combined organic extracts were washed with brine, dried (MgSO$_4$), and filtered. The filtrate was concentrated under reduced pressure and the residue was purified by column chromatography (95:5:trace dichloromethane/methanol/N H$_4$OH). Fractions containing product were combined and concentrated under reduced pressure to provide the product as an off-white solid (0.130 g, 54.4% yield). This solid was dissolved in methanol and stirred with one equivalent of L-tartaric acid. The solvent was removed under reduced pressure to give the tartrate salt of the product as a white solid. M.p. 157.4–158.1° C. $^1$H NMR (tartrate, CD$_3$OD, 300 MHz) δ 8.20 (d, J=2 Hz, 1H), 8.01–7.93 (m, 4H), 7.88–7.81 (m, 4H), 7.53 (dd, J=2, 12 Hz, 1H), 4.40 (s, 2H), 3.81–3.63 (m, 2H), 3.63–3.50 (m, 1H), 3.40–3.20 (m, 4H), 2.40–2.27 (m, 1H), 2.18–2.04 (m, 2H), 1.85–1.70 (m, 1H), 1.47 (d, J=6 Hz, 3H). MS (DCI-NH$_3$) [M+H]$^+$ at 341.

Example 2

(2R)-1-[2-(6-bromo-2-naphthyl)ethyl]-2-methylpyrrolidine

Example 2A 2-(6-bromo-2-naphthyl)ethyl trifluoromethanesulfonate

To a stirred, 0° C. solution of the product from Example 1E (1.08 g, 4.3 mmol) and pyridine (0.46 mL, 5.6 mmol, 1.3 equiv.) in anhydrous dichloromethane (40 mL) was added dropwise trifluoromethane sulfonic acid anhydride (0.87 mL, 5.16 mmol, 1.2 equiv.). The reaction mixture was stirred at 0° C. for 1 hr, then treated with ice water (20 mL). The organic layer was isolated, dried (MgSO$_4$), and filtered. The filtrate was concentrated under reduced pressure to give an oil that was purified by elution through a plug of silica gel with 95:5 hexane/ethyl acetate. Fractions containing product were combined and concentrated under reduced pressure to give the product as an off-white solid (1.34 g, 81% yield). $^1$H NMR (CDCl$_3$, 300 MHz) δ 8.00 (d, J=2 Hz, 1H), 7.77–7.64 (m, 3H), 7.56 (dd, J=2, 12 Hz, 1H), 7.35 (dd, J=2, 12 Hz, 1H), 4.73 (t, J=6 Hz, 2H), 3.28 (t, J=6 Hz, 2H). MS (DCI-NH$_3$) [M+NH$_4$]$^+$ at 400, [M+NH$_4$NH$_3$]$^+$ at 417.

Example 2B (2R)-1-[2-(6-bromo-2-naphthyl)ethyl]-2-methylpyrrolidine

A mixture of the product from Example 2A (1.34 g, 3.5 mmol), (2R)-2-methylpyrrolidine (0.90 g, 10.57 mmol, 3.0 equiv.), and cesium carbonate (3.42 g, 10.49 mmol, 3.0 equiv.) in acetonitrile (15 mL) was stirred at 50° C. in a sealed tube for 18 hr. The reaction mixture was cooled to room temperature then concentrated under reduced pressure. The residue was partitioned between ethyl acetate and distilled water. The organic layer was washed with brine, then dried (MgSO$_4$) and filtered. The filtrate was concentrated under reduced pressure to give a beige solid that was dissolved in Et$_2$O. The resulting solution was filtered free of any insoluble material, then treated with HCl (g) to give a white precipitate that was collected by filtration. This hydrochloride salt was dissolved in a minimum of water and sodium hydroxide was added to bring the pH to 14. This basic aqueous mixture was extracted with Et$_2$O. The organic layer was dried (MgSO$_4$) and filtered. The filtrate was concentrated under reduced pressure to provide the free base product as a white solid (0.90 g, 80.8% yield). M.p. (HCl salt) 247.3–250.7° C. $^1$H NMR (free base, CD$_3$OD, 300 MHz) δ 8.00 (d, J=2 Hz, 1H), 7.77–7.67 (m, 3H), 7.52 (dd, J=2, 12 Hz, 1H), 7.42 (dd, J=2, 12 Hz, 1H), 3.32–3.23 (m, 1H), 3.18–3.03 (m, 1H), 3.03–2.87 (m, 2H), 2.48–2.24 (m, 3H), 2.07–1.94 (m, 1H), 1.86–1.73 (m, 2H), 1.52–1.38 (m, 1H), 1.15 (d, J=6 Hz, 3H). MS (DCI-NH$_3$) [M+H]$^+$ at 318.

Example 3

1-[3-(6-{2-[(2R)-2-methyl-1-pyrrolidinyl]ethyl}-2-naphthyl)phenyl]ethanone

Example 3A

1-{3-[6-(2-hydroxyethyl)-2-naphthyl]phenyl}ethanone

A mixture of the product from Example 1E (0.78 g, 3.11 mmol), 3-acetylphenylboronic acid (0.61 g, 3.72 mmol, 1.2 equiv.), PdCl$_2$(PPh$_2$)$_2$ (0.044 g, 0.062 mmol, 0.02 equiv), and K$_3$PO$_4$H$_2$O (1.80 g, 9.35 mmol, 3 equiv) in isopropanol (40 mL) and distilled water (15 mL) was stirred at 65° C. under a dry nitrogen atmosphere for 1.5 hr. The reaction mixture was cooled to room temperature then concentrated under reduced pressure. The residue was partitioned between ethyl acetate and brine. The aqueous layer was washed with ethyl acetate, and the combined organic extracts were washed with saturated aqueous NH$_4$Cl, dried (MgSO$_4$), and filtered. The filtrate was concentrated under reduced pressure and the residue was purified by column chromatography (7:3 hexane/ethyl acetate). Fractions containing product were combined and concentrated under reduced pressure to provide the product as an off-white solid (0.57 g, 63% yield). $^1$H NMR (CD$_3$OD, 300 MHz) δ 8.31 (s, 1H), 8.05 (s, 1H), 8.92–8.98 (m, 4H), 8.72–8.79 (m, 2H), 8.54 (t, J=7 Hz, 1H), 7.4 (d, J=5.7 Hz, 1H), 3.96 (t, J=5.3 Hz, 2H), 3.04 (t, J=5.3 Hz, 2H), 2.67, (s, 3H), 2.48 (bs, 1H). MS (DCI-NH$_3$) [M+H]$^+$ at 291 [M+NH$_4$]$^+$ at 308.

Example 3B

2-[6-(3-acetylphenyl)-2-naphthyl]ethyl methanesulfonate

To a stirred, 0° C. solution of the product from Example 3A (0.44 g, 1.49 mmol) and Et$_3$N (0.30 g, 2.98 mmol, 2.0 equiv), methanesulfonyl chloride (0.24 g, 2.09 mmol, 1.4 equiv) was added dropwise via a syringe. After 15 minutes the ice bath was removed and the reaction mixture was stirred at room temperature for 1.5 hours. The reaction mixture was concentrated under reduced pressure. The residue was partitioned between brine and CH$_2$Cl$_2$. The aqueous layer was washed with CH$_2$Cl$_2$. The combined organic extracts were dried (MgSO$_4$) and filtered. The filtrate was concentrated under reduced pressure to provide the product as an off-white solid (0.547 g, 99.6% yield). $^1$H NMR (CDCl$_3$, 300 MHz) δ 8.28 (s, 1H), 8.05 (s, 1H), 7.87–7.98 (m, 4H), 7.72–7.79 (m, 2H), 7.55 (t, J=5.6 Hz, 1H), 7.38 (d, J=5.6 Hz, 1H), 4.48 (t, J=6 Hz, 2H), 3.22 (t, J=6 Hz, 2H), 2.86 (s, 3H), 2.66 (s, 3H). MS (DCI-NH$_3$) [M+NH$_4$]$^+$ at 386.

Example 3C

1-[3-(6-{2-[(2R)-2-methyl-1-pyrrolidinyl]ethyl}-2-naphthyl)phenyl]ethanone

A mixture of the product from Example 3B (0.55 g, 1.48 mmol), (2R)-2-methylpyrrolidine (0.26 g, 3.05 mmol, 3 equiv), and Cs$_2$CO$_3$ (1.16 g, 3.56 mmol, 2 equiv) in anhydrous acetonitrile (30 mL) was stirred in a sealed tube at 45° C. for 18 hrs. The reaction mixture was cooled to room temperature then concentrated under reduced pressure. The residue was partitioned between ethyl acetate and aqueous 2 N NaOH. The aqueous layer was washed with ethyl acetate. The combined organic layers were dried (MgSO$_4$), and filtered. The filtrate was concentrated under reduced pressure and the residue was purified by column chromatography (95:5:trace dichloromethane/methanol/NH$_4$OH). Fractions containing product were combined and concentrated under reduced pressure to provide the product as an off-white solid (0.115 g, 22% yield). The solid was dissolved in ether and treated with HCl (g) to provide the HCl salt. $^1$H NMR (CD$_3$OD, 300 MHz) δ 8.31 (s, 1H), 8.10 (s, 1H), 7.99 (s, 1H), 7.96 (s, 1H), 7.89 (s, 1H), 7.87 (d, J=113.3 Hz, 1H), 7.75 (d, J=5.8 Hz, 1H), 7.71 (s, 1H), 7.58 (t, J=6.7 Hz, 1H), 7.39 (d, J=5.8 Hz, 1H), 3.2–3.28 (m, 1H), 3.1–3.2 (m, 1H), 2.9–3.03 (m, 2H), 2.67 (s, 3H), 2.37–2.47 (m, 2H), 2.26 (q, J=7 Hz, 1H), 1.94–2.05 (m, 1H), 1.74–1.85 (m, 2H) 1.39–1.52 (m, 1H), 1.17 (d, J=6 Hz, 3H). MS (DCI-NH$_3$) [M+H]$^+$ at 358.

Example 4

2-[3-(6-{2-[(2R)-2-methyl-1-pyrrolidinyl]ethyl}-2-naphthyl)phenyl]-2-pr

To a mixture of the product from Example 3C (0.68 g, 1.91 mmol) in anhydrous THF (10 mL), was added CH$_3$MgCl (0.91 g, 7.64 mmol, 4 equiv) dropwise via a syringe. The reaction mixture was stirred at room temperature for 18 hrs. The reaction was quenched by the addition of aqueous K$_2$HPO$_4$ (25 mL). The reaction mixture was concentrated under reduced pressure. The residue was partitioned between aqueous 2 N NaOH and ethyl acetate. The aqueous layer was washed with ethyl acetate, and the combined organic extracts were dried (MgSO$_4$), and filtered. The filtrate was concentrated under reduced pressure and the residue was purified by column chromatography (90:10:0.1 dichloromethane/methanol/NH$_4$OH). Fractions containing product were combined and concentrated under reduced pressure to provide the product as an off-white solid (0.118 g, 17% yield). The solid was dissolved in ether and treated with HCl (g) to provide the HCl salt. $^1$H NMR (CD$_3$OD, 300 MHz) δ 8.05 (s, 1H), 7.87–7.9 (m, 3H), 7.42 (d, J=6 Hz, 1H), 7.0 (s, 1H), 7.7 (d, J=5.3 Hz, 1H), 7.45–7.49 (m, 1H), 7.42 (s, 1H), 7.4 (s, 1H), 3.2–3.28 (m, 1H), 3.1–3.2 (m, 1H), 2.9–3.03 (m, 2H), 2.37–2.47 (m, 2H), 2.26 (q, J=7 Hz, 1H), 1.94–2.05 (m, 1H), 1.74–1.85 (m, 2H) 1.39–1.52 (m, 1H), 1.61 (s, 6H), 1.17 (d, J=6 Hz, 3H). MS (DCI-NH$_3$) [M+H]$^+$ at 374.

Example 5

6-{2-[(2R)-2-methyl-1-pyrrolidinyl]ethyl}-2-naphthonitrile

A mixture of the product from Example 2B (100 mg, 0.314 mmol), zinc cyanide (22 mg, 0.188 mmol, 0.6 equiv.), Pd$_2$(dba)$_3$ (14 mg, 0.016 mmol, 0.05 equiv.), 1,1'-bis(diphenylphosphino)ferrocene (21 mg, 0.038 mmol, 0.12 equiv.) in DMF (5 mL) and distilled water (0.05 mL) was stirred under a dry nitrogen atmosphere at 120° C. for 24 hr. The reaction mixture was cooled to 80° C. and treated with 4:1:4 saturated aqueous NH$_4$Cl/NH$_4$OH/water, and stirred overnight while cooling to room temperature. The mixture was extracted with ethyl acetate. The organic layer was washed first with 4:1:5 saturated aqueous NH$_4$Cl/NH$_4$OH/water, then with brine. The organic layer was dried (MgSO$_4$), and filtered. The filtrate was concentrated under reduced pressure and the residue was purified by column chromatography (97:3: trace dichloromethane/methanol/NH$_4$OH). Fractions containing product were combined and concentrated under reduced pressure and the residue was dissolved in Et$_2$O. The solution was treated with HCl (g) and the mixture was concentrated under reduced pressure to provide the hydrochloride salt of the product as a white solid (51 mg, 43% yield). M.p. 187.4–188.6° C. $^1$H NMR (CD$_3$OD, 300 MHz) δ 8.38 (s br, 1H), 8.03 (d, J=2 Hz, 1H), 8.00 (d, J=2 Hz, 1H), 7.94 (s$_{br}$, 2H), 7.68 (dd, J=2, 12 Hz, 1H), 7.63 (dd, J=2, 12 Hz, 1H), 3.84–3.67 (m, 2H), 3.63–3.48 (m, 1H), 3.43–3.19 (m, 4H), 2.43–2.29 (m, 1H), 2.24–2.01 (m, 2H), 1.84–1.68 (m, 1H), 1.48 (d, J=7 Hz, 3H). MS (DCI-NH$_3$) [M+H]$^+$ at 265.

Example 6

4-(6-{[(2R)-2-methyl-1-pyrrolidinyl]methyl}-2-naphthyl)benzonitrile

Example 6A

4-[6-(hydroxymethyl)-2-naphthyl]benzonitrile

A mixture of the product from Example 1A (0.119 g, 0.50 mmol), 4-cyanophenylboronic acid (0.088 g, 0.60 mmol, 1.2 equiv.), PdCl$_2$(PPh$_3$)$_2$ (7 mg, 0.001 mmol, 0.020 equiv.) and K$_3$PO$_4$H$_2$O (288 mg, 1.5 mmol, 3.0 equiv.) in isopropanol (10 mL) and distilled water (4 mL) was stirred at 50° C. under a dry nitrogen atmosphere for 1.5 hr. The reaction mixture was cooled to room temperature then concentrated under reduced pressure. The residue was partitioned between ethyl acetate and saturated aqueous NH$_4$Cl. The organic layer was dried (MgSO$_4$), and filtered. The filtrate was concentrated under reduced pressure and the residue was purified by column chromatography (65:35 hexane/ethyl acetate). Fractions containing product were combined and concentrated under reduced pressure to provide the product as a white solid (95 mg, 73% yield). M.p. 174.1–175.5° C. $^1$H NMR (CDCl$_3$, 300 MHz) δ 8.06 (d, J=2 Hz, 1H), 7.97–7.70 (m, 8H), 7.54 (dd, J=2, 12 Hz, 1H), 4.90 (d$_{br}$, J=6 Hz, 2H), 1.78 (t$_{br}$, J=6 Hz, 1H). MS (DCI-NH$_3$) [M+NH$_4$]$^+$ at 277, [M+NH$_4$NH$_3$]$^+$ at 294.

Example 6B

4-[6-(chloromethyl)-2-naphthyl]benzonitrile

A mixture of the product from Example 6A (90 mg, 0.347 mmol), 0.5 M ZnCl$_2$ in THF (0.21 mL, 0.104 mmol, 0.3 equiv.), and thionyl chloride (0.51 mL, 6.94 mmol, 20.0 equiv.) in dioxane (40 mL) was stirred at room temperature under a dry nitrogen atmosphere for 3 hr. The reaction mixture was concentrated under reduced pressure and the residue was partitioned between ethyl acetate and saturated aqueous Na$_2$CO$_3$. The organic layer was dried (MgSO$_4$), and filtered. The filtrate was concentrated under reduced pressure and the residue was purified by column chromatography (95:5 hexane/ethyl acetate). Fractions containing product were combined and concentrated under reduced pressure to provide the product as a white solid (91 mg, 94.4% yield). M.p. 147.5–149.2° C. $^1$H NMR (CDCl$_3$, 300 MHz) δ 8.05 (d, J=2 Hz, 1H), 7.97–7.90 (m, 2H), 7.89–7.84 (m, 1H), 7.84–7.71 (m, 5H), 7.57 (dd, J=2, 12 Hz, 1H), 4.78 (s, 2H). MS (DCI-NH$_3$) [M+NH$_4$]$^+$ at 295, [M+NH$_4$NH$_3$]$^+$ at 312.

Example 6C

4-(6-{[(2R)-2-methyl-1-pyrrolidinyl]methyl}-2-naphthyl)benzonitrile

A mixture of the product from Example 6B (90 mg, 0.324 mmol), (2R)-2-methylpyrrolidine (138 mg, 1.62 mmol, 5.0 equiv.), and cesium carbonate (317 mg, 0.972 mmol, 3.0 equiv.) in acetonitrile (10 mL) in a sealed tube was stirred at 45° C. for 3 hr then for 2 days at room temperature. The reaction mixture was concentrated under reduced pressure. The residue was partitioned between ethyl acetate and distilled water. The organic layer was dried (MgSO$_4$), and filtered. The filtrate was concentrated under reduced pressure and the residue was purified by column chromatography (97:3:trace dichloromethane/methanol/NH$_4$OH). Fractions containing product were combined and concentrated under reduced pressure and the residue was dissolved in Et$_2$O.

The solution was treated with HCl (g) and the precipitate was collected by filtration to provide the hydrochloride salt of the product as a white solid (51 mg, 43% yield). M.p. 212.6–213.6° C. $^1$H NMR (CD$_3$OD, 300 MHz) δ 8.29 (d, J=2 Hz, 1H), 8.15–8.06 (m, 3H), 7.98 (d, J=9 Hz, 2H), 7.93 (dd, J=2, 12 Hz, 1H), 7.86 (d, J=9 Hz, 2H), 7.67 (dd, J=2, 12 Hz, 1H), 4.77 (, J=3 Hz, 1H), 4.37 (d, J=3 Hz, 1H), 3.75–3.61 (m, 1H), 3.46–3.30 (m, 2H), 2.48–2.35 (m, 1H), 2.22–1.92 (m, 2H), 1.86–1.72 (m, 1H), 1.47 (d, J=7 Hz, 3H). MS (DCI-NH$_3$) [M+H]$^+$ at 327.

Example 7

3-(6-{2-[(2R)-2-methyl-1-pyrrolidinyl]ethyl}-2-naphthyl)benzonitrile

Example 7A

3-[6-(2-hydroxyethyl)-2-naphthyl]benzonitrile

The title compound was prepared by the method of Example 3A, substituting 3-cyanophenylboronic acid in place of 3-acetylphenylboronic acid (0.21 g, 96% yield). $^1$H NMR (CDCl$_3$, 300 MHz) δ 8.03–7.97 (m, 2H), 7.97–7.86 (m, 3H), 7.76–7.55 (m, 4H), 7.43 (dd, J=2, 12 Hz, 1H), 3.98 (t, J=6 Hz, 2H), 3.07 (t, J=6 Hz, 2H). MS (DCI-NH$_3$) [M+NH$_4$]$^+$ at 291, [M+NH$_4$NH$_3$]$^+$ at 308.

Example 7B

2-[6-(3-cyanophenyl)-2-naphthyl]ethyl trifluoromethanesulfonate

To a stirred, 0° C. solution of the product from Example 7A (0.21 g, 0.768 mmol) and pyridine (0.08 mL, 1.0 mmol, 1.3 equiv.) in anhydrous dichloromethane (15 mL) was added dropwise trifluoromethane sulfonic acid anhydride (0.16 mL, 0.922 mmol, 1.2 equiv.). The reaction mixture was stirred at 0° C. for 30 minutes, then treated with ice water (20 mL). The organic layer was isolated, dried (MgSO$_4$), and filtered. The filtrate was concentrated under reduced pressure to give an oil that was purified by column chromatography (95:5 to 70:30 hexane/ethyl acetate). Fractions containing product were combined and concentrated under reduced pressure to give the product (60 mg, 19% yield). $^1$H NMR (CDCl$_3$, 300 MHz) δ 8.02–7.87 (m, 5H), 7.76–7.55 (m, 4H), 7.40 (dd, J=2, 12 Hz, 1H), 4.80 (t, J=6 Hz, 2H), 3.32 (t, J=6 Hz, 2H). MS (DCI-NH$_3$) [M+NH$_4$]$^+$ at 423.

Example 7C

3-(6-{2-[(2R)-2-methyl-1-pyrrolidinyl]ethyl}-2-naphthyl)benzonitrile

The title compound was prepared by the method of Example 3C, substituting the product from Example 7B for the product from Example 3B (21 mg, 38% yield). M.p. 228.5–231.6° C. $^1$H NMR (CD$_3$OD, 300 MHz) δ 8.23 (d, J=2 Hz, 1H), 8.20–8.18 (m, 1H), 8.14–8.09 (m, 1H), 8.04–7.98 (m, 2H), 7.90–7.85 (m, 2H), 7.70–7.65 (m, 2H), 7.60 (t, J=7 Hz, 2H), 7.54 (dd, J=2, 12 Hz, 1H), 3.81–3.63 (m, 2H), 3.60–3.48 (m, 1H), 3.40–3.13 (m, 4H), 2.39–2.24

(m, 1H), 2.18–2.00 (m, 2H), 1.82–1.67 (m, 1H), 1.46 (d, J=7 Hz, 3H). MS (DCI-NH$_3$) [M+H]$^+$ at 341.

Example 8

4-(6-{2-[(2R)-2-methyl-1-pyrrolidinyl]ethyl}-2-naphthyl)pyridine

A mixture of the product from Example 2B (50 mg, 0.157 mmol), 4-pyridinylboronic acid (48 mg, 0.393 mmol, 2.5 equiv.), PdCl$_2$(PPh$_3$)$_2$ (6 mg, 0.0085 mmol, 0.054 equiv.) and K$_3$PO$_4$H$_2$O (181 mg, 0.943 mmol, 6.0 equiv.) in isopropanol (5 mL) and distilled water (2 mL) was stirred at 60° C. under a dry nitrogen atmosphere for 1 hr. The reaction mixture was cooled to room temperature then concentrated under reduced pressure. The residue was partitioned between ethyl acetate and saturated aqueous Na$_2$CO$_3$. The organic layer was dried (MgSO$_4$), and filtered. The filtrate was concentrated under reduced pressure and the residue was purified by column chromatography (95:5:trace dichloromethane/methanol/N H$_4$OH). Fractions containing product were combined and concentrated under reduced pressure to provide the product as an off-white solid that was dissolved in Et$_2$O and treated with HCl (g). This mixture was concentrated under reduced pressure to provide the dihydrochloride salt of the product as an off-white, hygroscopic solid (21 mg, 34% yield). $^1$H NMR (CD$_3$OD, 300 MHz) δ 8.90 (d, J=6 Hz, 2H), 8.63 (d, J=2 Hz, 1H), 8.56 (d, J=6 Hz, 2H), 8.15–8.05 (m, 3H), 7.98–7.95 (m, 1H), 7.64 (dd, J=2, 12 Hz, 1H), 3.86–3.69 (m, 2H), 3.65–3.50 (m, 1H), 3.45–3.19 (m, 4H), 2.44–2.30 (m, 1H), 2.28–2.01 (m, 2H), 1.85–1.70 (m, 1H), 1.50 (d, J=6 Hz, 3H). MS (DCI-NH$_3$) [M+H]$^+$ at 317.

Example 9

3-(6-{2-[(2R)-2-methyl-1-pyrrolidinyl]ethyl}-2-naphthyl)pyridine

The title compound was prepared by the method in Example 8, substituting 3-pyridinylboronic acid in place of 4-pyridinylboronic acid (16 mg, 26% yield). $^1$H NMR (CD$_3$OD, 300 MHz) δ 9.35–9.32 (m, 1H), 9.11–9.06 (m, 1H), 8.89–8.85 (m, 1H), 8.41 (d, J=2 Hz, 1H), 8.26–8.20 (m, 1H), 8.08 (t, J=9 Hz, 1H), 7.98–7.93 (m, 2H), 7.62 (dd, J=2, 12 Hz, 1H), 3.86–3.69 (m, 2H), 3.65–3.49 (m, 1H), 3.45–3.22 (m, 4H), 2.43–2.31 (m, 1H), 2.23–2.01 (m, 2H), 1.86–1.71 (m, 1H), 1.51 (d, J=7 Hz, 3H). MS (DCI-NH$_3$) [M+H]$^+$ at 317.

Example 10

(3-fluorophenyl)(6-{2-[(2R)-2-methyl-1-pyrrolidinyl]ethyl}-2-naphthyl)methanol

A 1.7 M solution of t-butyllithium in pentane (0.41 mL, 0.691 mmol, 2.2 equiv.) was added dropwise to a stirred, −78° C. solution of the product from Example 2B (100 mg, 0.314 mmol) in anhydrous THF (3 mL). The reaction mixture was stirred at −78° C. for 20 min then 3-fluorobenzaldehyde (0.04 mL, 0.377 mmol, 1.2 equiv.) was added dropwise to the reaction mixture. After stirring at −78° C. for 10 min, the reaction mixture was allowed to reach room temperature then partitioned between ethyl acetate and saturated aqueous Na$_2$CO$_3$. The organic layer was dried (MgSO$_4$), and filtered. The filtrate was concentrated under reduced pressure and the residue was purified by preparative TLC (95:5:trace dichloromethane/methanol/NH$_4$OH). The band containing product was isolated and eluted with 95:5:trace dichloromethane/methanol/NH$_4$OH. The resulting solution was concentrated under reduced pressure to provide the free base product as a white solid (3.2 mg, 2.5% yield). $^1$H NMR (CD$_3$OD, 300 MHz) δ 7.84–7.72 (m, 3H), 7.66–7.63 (m, 1H), 7.42–7.26 (m, 3H), 7.22–7.13 (m, 2H), 6.98–6.91 (m, 1H), 5.91 (s, 1H), 3.32–3.23 (m, 1H), 3.19–3.09 (m, 2H), 2.51–2.26 (m, 3H), 2.06–1.94 (m, 1H), 1.85–1.74 (m, 2H), 1.52–1.38 (m, 1H), 1.15 (d, J=7 Hz, 3H). MS (DCI-NH$_3$) [M+H]$^+$ at 364.

Example 11

3,5-dimethyl-4-(6-{2-[(2R)-2-methyl-1-pyrrolidinyl]ethyl}-2-naphthyl)isoxazole

The title compound was prepared by the methods of Example 3A–3C, substituting 3,5-dimethyl-4-isoxazolylboronic acid in place of 3-acetylphenylboronic acid in Example 3A (38 mg, 12% yield). $^1$H NMR (CD$_3$OD, 300 MHz) δ 7.95 (dd, J=2, 12, 2H), 7.85 (d$_{br}$, J=12 Hz, 2H), 7.56–7.45 (m, 2H), 3.84–3.65 (m, 2H), 3.63–3.47 (m, 1H), 3.43–3.15 (m, 4H), 2.46 (s, 3H), 2.42–2.26 (m, 1H), 2.30 (s, 3H), 2.21–2.01 (m, 2H), 1.84–1.68 (m, 1H), 1.48 (d, J=7 Hz, 3H). MS (DCI-NH$_3$) [M+H]$^+$ at 335.

Example 12

4-(6-{2-[(2S)-2-(hydroxymethyl)-1-pyrrolidinyl]ethyl}-2-naphthyl)benzonitrile

The title compound was prepared by the method of Example 1H, substituting (2S)-2-pyrrolidinylmethanol in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.51–3.64 (m, 2H), 3.2–3.34 (m, 2H), 2.93–3.1 (m, 2H), 2.69–2.75 (m, 2H), 2.4 (q, J=6 Hz, 1H), 1.9–2.4 (m, 1H), 1.95–2.05 (m, 2H), 1.81–1.91 (m, 1H). MS (DCI-NH$_3$) [M+H]$^+$ at 357.

Example 13

4-(6-{2-[(3R)-3-hydroxy-1-pyrrolidinyl]ethyl}-2-naphthyl)benzonitrile

The title compound was prepared by the method of Example 1H, substituting (3R)-3-pyrrolidinol in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 4.34.4.43 (m, 1H), 2.82–3.08 (m, 6H), 2.67–2.78 (m, 1H), 2.61 (d, J=5.7 Hz, 1H), 2.11–2.24 (m, 1H), 1.71–2.03 (m, 1H). MS (DCI-NH$_3$) [M+H]$^+$ at 343.

Example 14

4-{6-[2-(2-isobutyl-1-pyrrolidinyl)ethyl]-2-naphthyl}benzonitrile

The title compound was prepared by the method of Example 1H, substituting 2-isobutylpyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.31–3.44 (m, 2H), 2.9–3.11 (m, 2H), 2.4–2.53 (m, 2H), 2.31 (q, J=5.7 Hz), 1.9–2.12 (m, 2H), 1.4–1.65 (m, 3H), 1.22–1.36 (m, 1H), 0.92 (d, J=5.6 Hz, 3H), 0.87 (d, J=5.6 Hz, 3H). MS (DCI-NH$_3$) [M+H]$^+$ at 383.

Example 15

4-{6-[2-(2-isopropyl-1-pyrrolidinyl)ethyl]-2-naphthyl}benzonitrile

The title compound was prepared by the method of Example 1H, substituting 2-isopropylpyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.11–3.22 (m, 1H), 2.91–3.1 (m, 2H), 2.46–2.62 (m, 1H), 2.41–2.45 (m, 2H), 1.8–1.93 (m, 1H), 1.68–1.8 (m, 4H), 1.54–1.63 (m 1H), 0.92 (d, J=5.6 Hz, 3H), 0.79 (d, J=5.6 Hz, 3H). MS (DCI-NH$_3$) [M+H]$^+$ at 369.

Example 16

4-(6-{2-[(3R)-3-(dimethylamino)-1-pyrrolidinyl]ethyl}-2-naphthyl)benzonitrile

The title compound was prepared by the method of Example 1H, substituting (3R)-N,N-dimethyl-3-pyrrolidinamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 2.98–3.08 (m, 4H), 2.83–2.95 (m, 3H), 2.72–2.76 (m, 1H) 2.5–2.58 (m, 1H), 2.31 (s, 6H), 2.01–2.13 (m, 1H), 1.75–1.85 (m, 1H). MS (DCI-NH$_3$) [M+H]$^+$ at 370.

Example 17

4-{6-[2-(diethylamino)ethyl]-2-naphthyl}benzonitrile

The title compound was prepared by the method of Example 1H, substituting diethylamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.53 (t, J=3.3 Hz, 2H), 3.31 (q, J=3.6 Hz, 4H), 3.22 (t, J=3.3 Hz, 2H), 1.35 (t, J=3.6 Hz, 6H). MS (DCI-NH$_3$) [M+H]$^+$ at 329.

Example 18

4-{6-[2-(dimethylamino)ethyl]-2-naphthyl}benzonitrile

The title compound was prepared by the method of Example 1H, substituting dimethylamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.49–3.54 (t, J=3.3 Hz, 2H), 3.23–3.28 (t, J=3.3 Hz, 2H), 2.97 (s, 6H). MS (DCI-NH$_3$) [M+H]$^+$ at 301.

Example 19

4-(6-{2-[ethyl(isopropyl)amino]ethyl}-2-naphthyl)benzonitrile

The title compound was prepared by the method of Example 1H, substituting isopropylethylamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.8–3.87 (m, 1H), 3.1–3.57 (m, 6H), 1.31–1.45 (m, 9H). MS (DCI-NH$_3$) [M+H]$^+$ at 343.

Example 20

4-(6-{2-[tert-butyl(methyl)amino]ethyl}-2-naphthyl)benzonitrile

The title compound was prepared by the method of Example 1H, substituting t-butylmethylamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.68–3.75 (m, 1H), 3.3–3.43 (m, 2H), 2.31–3.28 (m, 1H), 3.11–3.19 (m, 1H), 2.7 (s, 3H), 1.45 (s, 9H). MS (DCI-NH$_3$) [M+H]$^+$ at 343.

Example 21

4-(6-{2-[(2S)-2-methyl-1-pyrrolidinyl]ethyl}-2-naphthyl)benzonitrile

The title compound was prepared by the method of Example 1H, substituting (2S)-2-methylpyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.34–3.45 (m, 1H), 3.24–3.35 (m, 1H), 2.97–3.18 (m, 2H), 2.55–2.78 (m, 3H), 2.02–2.15 (m, 1H) 1.82–1.94 (m, 2H), 1.48–1.59 (m, 1H), 1.11 (d, J=6 Hz, 3H). MS (DCI-NH$_3$) [M+H]$^+$ at 341.

Example 22

4-(6-{2-[(2R)-2-methyl-1-piperidinyl]ethyl}-2-naphthyl)benzonitrile

The title compound was prepared by the method of Example 1H, substituting (2R)-2-methylpiperidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 2.86–3.13 (m, 5H), 2.49–2.55 (m, 2H), 1.67–1.81 (m, 4H), 1.33–1.46 (m, 2H), 1.08 (d, J=6 Hz, 3H). MS (DCI-NH$_3$) [M+H]$^+$ at 355.

Example 23

4-{6-[2-(2,5-dihydro-1H-pyrrol-1-yl)ethyl]-2-naphthyl}benzonitrile

The title compound was prepared by the method of Example 1H, substituting 2,5-dihydro-1H-pyrrole in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 5.83, (s, 2H), 3.57 (m, 4H), 2.99 (m, 4H). MS (DCI-NH$_3$) [M+H]$^+$ at 325.

Example 24

4-(6-{2-[methyl(propyl)amino]ethyl}-2-naphthyl)benzonitrile

The title compound was prepared by the method of Example 1H, substituting propylmethylamine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 2.94–3.03 (m, 2H), 2.74–2.81 (m, 2H), 2.45–2.53 (m, 2H), 2.38 (s, 3H), 1.51–1.65 (m, 2H), 0.91 (t, J=6.3 Hz, 3H). MS (DCI-NH$_3$) [M+H]$^+$ at 329.

Example 25

4-(6-{2-[(2-hydroxyethyl)(methyl)amino]ethyl}-2-naphthyl)benzonitrile

The title compound was prepared by the method of Example 1H, substituting 2-(methylamino)ethanol in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.67 (t, J=6 Hz, 2H), 2.96–3.04 (m, 2H), 2.90–2.98 (m, 2H), 2.66 (t, J=5.3 Hz, 2H), 2.42 (s, 3H). MS (DCI-NH$_3$) [M+H]$^+$ at 331.

Example 26

5-(6-{2-[(2R)-2-methyl-1-pyrrolidinyl]ethyl}-2-naphthyl)pyrimidine

Example 26A

[2-(6-bromo-2-naphthyl)ethoxy](tert-butyl)dimethylsilane

A stirred solution of the product from Example 1E (2.51 g, 10 mmol), imidazole (0.715 g, 10.5 mmol, 1.05 equiv), and DMAP (8 mg, 0.066 mmol, 0.0066 equiv.) in anhydrous dichloromethane (65 mL) was chilled at 0° C. under a dry nitrogen atmosphere. A solution of t-butyldimethylsilyl chloride in anhydrous dichloromethane (15 mL) was added slowly to the reaction mixture. When the addition was complete, the reaction mixture was allowed to warm to room temperature and stirred for 18 hr. An aqueous solution of citric acid (10%) was added to the reaction mixture. The organic layer was washed with brine then dried (MgSO$_4$), and filtered. The filtrate was concentrated under reduced pressure and the residue was purified by column chromatography (100% hexane). Fractions containing product were combined and concentrated under reduced pressure to provide the product as a white solid (3.25 g, 89% yield). $^1$H NMR (CDCl$_3$, 300 MHz) δ 7.95 (d, J=2 Hz, 1H), 7.68–7.60 (m, 3H), 7.50 (dd, J=2, 12 Hz, 1H), 7.37 (dd, J=2, 12 Hz, 1H), 3.88 (t, J=6 Hz, 2H), 2.96 (t, J=6 Hz, 2H), 1.46 (s, 9H), –0.04 (s, 6H). MS (DCI-NH$_3$) [M+H]$^+$ at 365, [M+NH$_4$]$^+$ at 382.

Example 26B tert-butyl(dimethyl){2-[6-(4,4,5,5-tetramethyl-1,3,2-dioxaborolan-2-yl)-2-naphthyl]ethoxy}silane A solution of the product from Example 26A (920 mg, 2.518 mmol), Pd(OAc)$_2$, (28 mg, 0.126 mmol, 0.05 equiv.), 2-(dicyclohexylphosphino)biphenyl (176 mg, 0.504 mmol, 0.2 equiv.), and Et$_3$N (1.4 mL, 10.07 mmol, 4 equiv.) in dioxane (15 mL) was stirred under a dry nitrogen atmosphere at room temperature. Pinacolborane (1.1 mL, 7.553 mmol, 3 equiv.) was added dropwise to the reaction mixture. When the addition was complete, the reaction was stirred at 80° C. for 1 hr. After cooling to room temperature, the reaction mixture was concentrated under reduced pressure. The residue was partitioned between saturated aqueous NH$_4$Cl and Et$_2$O. The organic layer was dried (MgSO$_4$), and filtered. The filtrate was concentrated under reduced pressure and the residue was purified by column chromatography (98:2 hexane/ethyl acetate). Fractions containing product were combined and concentrated under reduced pressure to give the product as a yellow solid (660 mg, 64% yield). $^1$H NMR (CDCl$_3$, 300 MHz) δ 8.32 (d, J=2 Hz, 1H), 7.83–7.77 (m, 3H), 7.64–7.62 (m, 1H), 7.33 (dd, J=2, 12 Hz, 1H), 4.51 (t, 5.7 J=Hz, 2H), 3.22 (t, J=5.7 Hz, 2H), 1.39, (s, 12H), 0.86 (s, 9H), 0.04 (s, 6H). MS (DCI-NH$_3$) [M+NH$_4$]$^+$ at 430.

Example 26C

5-[6-(2-{[tert-butyl(dimethyl)silyl]oxy}ethyl)-2-naphthyl]pyrimidine

A solution of the product from Example 26B (206 mg, 0.5 mmol), 5-bromopyrimidine (79.5 mg, 0.5 mmol), Pd(PPh$_3$)$_4$ (28.9 mg, 0.025 mmol, 0.05 equiv.), and Na$_2$CO$_3$ (106 mg, 1 mmol, 2 equiv.) in toluene (10 mL) and distilled water (1.5 mL) was stirred at reflux under a dry nitrogen atmosphere for 3 hr. After cooling to room temperature, the mixture was concentrated under reduced pressure and the residue was partitioned between ethyl acetate and saturated aqueous Na$_2$CO$_3$. The organic layer was dried (MgSO$_4$) and filtered. The filtrate was concentrated under reduced pressure and the residue was purified by column chromatography (8:2 hexane/ethyl acetate). Fractions containing product were combined and concentrated under reduced pressure to give the product as an off-white solid (57 mg, 31%). $^1$H NMR (CDCl$_3$, 300 MHz) δ 9.23 (S$_{br}$, 1H), 9.08 (S$_{br}$, 2H), 8.02 (d, J=2 Hz, 1H), 7.93 (d$_{br}$, J=7 Hz, 1H), 7.86 (d$_{br}$, J=7 Hz, 1H), 7.72 (S$_{br}$, 1H), 7.66 (dd, J=2, 12 Hz, 1H), 7.44 (dd, J=2, 12 Hz, 1H), 3.92 (t, J=6 Hz, 2H), 3.01 (t, J=6 Hz, 2H), 0.88 (s, 9H), –0.02 (s, 6H). MS (DCI-NH$_3$) [M+H]$^+$ at 365.

Example 26D

2-[6-(5-pyrimidinyl)-2-naphthyl]ethanol

A solution of the product from Example 26C (56 mg, 0.154 mmol) and TBAF H$_2$O (48 mg, 0.184 mmol, 1.2 equiv.) in THF (3 mL) was stirred at room temperature under a dry nitrogen atmosphere for 30 min. The mixture was then partitioned between ethyl acetate and saturated aqueous Na$_2$CO$_3$. The organic layer was washed with brine then dried (MgSO$_4$) and filtered. The filtrate was concentrated under reduced pressure to give the title compound as an off-white solid (32 mg, 83% yield) which was used in the next step without further purification.

Example 26E

2-[6-(5-pyrimidinyl)-2-naphthyl]ethyl methanesulfonate

The title compound was prepared by the method of Example 3B, substituting the product from Example 26D in place of the product from Example 3A to give an off-white solid.

Example 26F

5-(6-{2-[(2R)-2-methyl-1-pyrrolidinyl]ethyl}-2-naphthyl)pyrimidine

The title compound was prepared by the method of Example 3C substituting the product from Example 26E in place of the product from Example 3B (17 mg, 36% yield). $^1$H NMR (CD$_3$OD, 300 MHz) δ 9.35 (S$_{br}$, 2H), 9.28 (S$_{br}$, 1H), 8.32 (d, J=2 Hz, 1H), 8.09–8.03 (m, 2H), 7.94–7.88 (m, 2H), 7.60–7.55 (m, 1H), 3.85–3.69 (m, 2H), 3.62–3.50 (m, 1H), 3.44–3.18 (m, 4H), 2.43–2.30 (m, 1H), 2.27–2.01 (m, 2H), 1.84–1.70 (m, 1H), 1.50 (d, J=6 Hz, 3H). MS (DCI-NH$_3$) [M+H]$^+$ at 318.

Example 27

4-(6-{2-[(2R)-2-methyl-1-pyrrolidinyl]ethyl}-2-naphthyl)morpholine

A mixture of the product from Example 2B (318 mg, 1.0 mmol), morpholine (0.87 mL, 1.0 mmol), Pd$_2$(dba)$_3$ (18.3 mg, 0.02 mmol, 0.02 equiv.), (t-Bu)$_3$P (3.6 mg, 0.016 mmol, 0.016 equiv.), and sodium t-butoxide (144.2 mg, 1.5 mmol, 1.5 equiv.) in toluene (2 mL) was stirred at room temperature under a dry nitrogen atmosphere for 66 hr. The reaction mixture was partitioned between ethyl acetate and saturated aqueous Na$_2$CO$_3$. The organic layer was then washed with brine, dried (MgSO$_4$), and filtered. The filtrate was concentrated under reduced pressure and the residue was purified by column chromatography (97:3:trace dichloromethane/methanol/NH$_4$OH). Fractions containing product were combined and concentrated under reduced pressure to provide the product that was dissolved in Et$_2$O and treated with HCl (g). This mixture was concentrated under reduced pressure to provide the dihydrochloride salt of the product as an off-white, hygroscopic solid (100 mg, 31% yield). $^1$H NMR (CD$_3$OD, 300 MHz) δ 8.21 (d, J=6 Hz, 2H), 8.12–8.00 (m, 2H), 7.95 (Sbr, 3H), 7.80 (dd, J=2, 12 Hz, 1H), 7.64 (dd, J=2, 12 Hz, 1H), 4.18–4.13 (m, 4H), 3.94–3.67 (m, 2H), 3.92–3.87 (m, 4H), 3.63–3.47 (m, 1H), 3.47–3.21 (m, 4H), 2.42–2.30 (m, 1H), 2.23–2.00 (m, 2H), 1.85–1.70 (m, 1H), 1.50 (d, J=6 Hz, 3H). MS (DCI-NH$_3$) [M+H]$^+$ at 325.

Example 28

2-(6-{2-[(2R)-2-methyl-1-pyrrolidinyl]ethyl}-2-naphthyl)-1,3-thiazole

Example 28A

2-[6-(2-{[tert-butyl(dimethyl)silyl]oxy}ethyl)-2-naphthyl]-1,3-thiazole

The title compound was prepared by the method in Example 26C, substituting 2-bromothiazole in place of 5-bromopyrimidine (40 mg, 22% yield). $^1$H NMR (CDCl$_3$, 300 MHz) δ 8.44 (d, J=2 Hz, 1H), 8.07 (dd, J=2, 12 Hz, 1H), 7.93 (d, J=3 Hz, 1H), 7.19–7.84 (m, 2H), 7.70–7.68 (m, 1H), 7.42 (dd, J=2, 12, 1H), 7.38 (d, J=3 Hz, 1H), 3.93 (t, J=6 Hz, 2H), 3.02 (t, J=6 Hz, 2H), 0.89 (s, 9H), 0.02 (s, 6H). MS (DCI-NH$_3$) [M+H]$^+$ at 370.

Example 28B

2-[6-(1,3-thiazol-2-yl)-2-naphthyl]ethanol

The title compound was prepared by the method in Example 26D, substituting the product from Example 28A in place of the product from Example 26C.

Example 28C

2-[6-(1,3-thiazol-2-yl)-2-naphthyl]ethyl methanesulfonate

The title compound was prepared by the method of Example 3B, substituting the product from Example 28B in place of the product from Example 3A to give an off-white solid.

Example 28D

2-(6-{2-[(2R)-2-methyl-1-pyrrolidinyl]ethyl}-2-naphthyl)-1,3-thiazole

The title compound was prepared by the method of Example 3C substituting the product from Example 28C in place of the product from Example 3B (hydrochloride salt, 4 mg, 14% yield). $^1$H NMR (CD$_3$OD, 300 MHz) δ 8.55 (d, J=2 Hz, 1H), 8.12 (d, J=3 Hz, 1H), 8.10–8.02 (m, 3H), 7.95–7.92 (m, 1H), 7.89 (d, J=3 Hz, 1H), 7.61 (dd, J=2, 12 Hz, 1H), 3.84–3.69 (m, 2H), 3.64–3.49 (m, 1H), 3.43–3.19 (m, 4H), 2.43–2.30 (m, 1H), 2.23–2.00 (m, 2H), 1.83–1.69 (m, 1H), 1.50 (d, J=6 Hz, 3H). MS (DCI-NH$_3$) [M+H]$^+$ at 323.

Example 29

4-(6-{2-[(2S)-2-(fluoromethyl)-1-pyrrolidinyl]ethyl}-2-naphthyl)benzonitrile The title compound was prepared by the method of Example 1H, substituting (2S)-2-(fluoromethyl)pyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 4.44 (d, J=1.3 Hz, 1H), 4.28 (d, J=1.3 Hz, 1H), 3.18–3.35 (m, 2H), 2.98–3.06 (m, 2H), 2.84–2.99 (m, 1H), 2.69–2.78 (M, 1H), 2.41–2.53 (m, 1H), 1.92–2.03 (m, 1H), 1.75–1.88 (m, 2H), 1.58–1.7 (m, 1H). MS (DCI-NH$_3$) [M+H]$^+$ at 359.

Example 30

(3-fluorophenyl)(6-{2-[(2R)-2-methyl-1-pyrrolidinyl]ethyl}-2-naphthyl)methanone A mixture of the product from Example 10 (3.2 mg, 0.009 mmol) and manganese dioxide (5.4 mg, 0.062 mmol, 7 equiv.) in anhydrous dichloromethane (1 mL) was stirred at room temperature for 3.5 hr. The reaction mixture was filtered through diatomaceous earth and the filtrate was concentrated under reduced pressure. The residue was purified by preparative TLC (95:5:trace dichloromethane/methanol/NH$_4$OH). The band containing product was isolated and eluted with 95:5:trace dichloromethane/methanol/NH$_4$OH. The resulting solution was concentrated under reduced pressure to provide the free base product (0.91 mg, 28.5% yield). $^1$H NMR (CD$_3$OD, 300 MHz) δ 8.27 (d, J=2 Hz, 1H), 8.02–7.86 (m, 4H), 7.65–7.51 (m, 4H), 7.46–7.39 (m, 1H), 3.56–3.37 (m, 2H), 3.26–3.07 (m, 2H), 3.02–2.74 (m, 2H), 2.21–2.10 (m, 1H), 2.02–1.88 (m, 2H), 1.69–1.52 (m, 2H), 1.30 (d, J=6 Hz, 3H). MS (DCI-NH$_3$) [M+H]$^+$ at 362.

Example 31

2-(6-{2-[(2R)-2-Methyl-1-pyrrolidin-1-yl]-ethyl}-2-naphthalen-2-yl)-2-one

Example 31A

(6-Bromo-naphthalen-2-yl)-methanol

To a stirred 1.0 M solution of lithium aluminum hydride (108 mL, 108 mmol) was added dropwise over 20 min a solution of methyl 6-bromo-2-naphthoate (18.9 g, 71.3 mmol) in THF (180 mL), while maintaining the reaction temperature below −5° C. When the addition was complete, the reaction mixture was stirred at −10° C. for 1 hr, then quenched by the sequential dropwise addition of distilled water (4 mL), 2 N aqueous $Na_2CO_3$ (4 mL), and distilled water (12 mL). After stirring for 15 min at room temperature, the reaction mixture was filtered. The filter cake was washed with ethyl acetate (3×100 mL) and the combined filtrates were dried ($MgSO_4$) and filtered. This filtrate was concentrated under reduced pressure to give a white solid. Drying under vacuum overnight at 40° C. provided the product (16.84 g, 99% yield). M.p. 149.9–151.6° C. $^1$H NMR ($CDCl_3$, 300 MHz) δ 7.99 (d, J=2 Hz, 1H), 7.79–7.67 (m, 3H), 7.55 (dd, J=2, 12 Hz, 1H), 7.52 (dd, J=2, 12 Hz, 1H), 4.85 (s, 2H). MS (DCI-$NH_3$) $[M]^+$ at 236.

Example 31B

2-Bromo-6-chloromethyl-naphthalene

A stirred solution of the product from Example 31A (30.5 g, 129 mmol) in dioxane (320 mL) under a dry nitrogen atmosphere was chilled to −10° C. Solid anhydrous $ZnCl_2$ (514 mg, 3.77 mmol, 0.03 equiv.) was added in one lot, followed by the dropwise addition of thionyl chloride (19.3 mL, 264 mmol, 2.0 equiv.). The reaction mixture was allowed to warm to room temperature then stirred an additional 2 hr. This reaction mixture was then concentrated under reduced pressure and the residue was partitioned between dichloromethane and saturated aqueous $NaHCO_3$ (500 mL). The organic layer was washed with brine (2×100 mL), dried ($MgSO_4$), and filtered. The filtrate was concentrated under reduced pressure to give a white solid. Drying under vacuum overnight at 40° C. provided the product (32.6 g, 99% yield). M.p. 133.1–134.1° C. $^1$H NMR ($CDCl_3$, 300 MHz) δ 8.00 (d, J=2 Hz, 1H), 7.81–7.67 (m, 3H), 7.56 (dd, J=2, 12 Hz, 1H), 7.54 (dd, J=2, 12 Hz, 1H), 4.73 (s, 2H). MS (DCI-$NH_3$) $[M]^+$ at 254.

Example 31C (6-Bromo-naphthalen-2-yl)-acetonitrile

A mixture of the product from Example 31B (32.2 g, 126 mmol) and NaCN (7.44 g, 152 mmol, 1.2 equiv.) in acetonitrile (314 mL) and distilled water (32 mL) under a dry nitrogen atmosphere was stirred at reflux for 21 hr. The reaction mixture was cooled to room temperature then concentrated under reduced pressure. The residue was stirred with distilled water (314 mL) for 45 min. The resulting white solid was isolated by filtration and washed with distilled water (1500 mL). Drying under vacuum overnight at 40° C. provided the product (32.2 g, 97% yield). M.p. 119.6–120.6° C. $^1$H NMR ($CDCl_3$, 300 MHz) δ 8.01 (d, J=2 Hz, 1H), 7.82–7.68 (m, 3H), 7.60 (dd, J=2, 12 Hz, 1H), 7.41 (dd, J=2, 12 Hz, 1H), 3.90 (s, 2H). MS (DCI-$NH_3$) $[M+NH_4]^+$ at 263, $[M+NH_4-NH_3]^+$ at 280.

Example 31D (6-Bromo-naphthalen-2-yl)-acetic acid

A stirred mixture of the product from Example 31C (29.62 g, 120 mmol) in glacial acetic acid (300 mL) and distilled water (150 mL) under a dry nitrogen atmosphere was cooled to −15° C. Concentrated sulfuric acid (120 mL, 4.32 mol, 36.0 equiv.) was added dropwise over 20 min while maintaining the reaction temperature below 10° C. The reaction mixture was then stirred at reflux for 2 hr. After cooling to 35° C., ice (500 g) was added to the mixture and stirring was continued for 45 min. The resulting white solid was isolated by filtration and washed with distilled water (1500 mL). Drying under vacuum overnight at 40° C. provided the product (29.57 g, 93% yield). $^1$H NMR ($CDCl_3$, 300 MHz) δ 7.99 (d, J=2 Hz, 1H), 7.76–7.64 (m, 3H), 7.54 (dd, J=2, 12 Hz, 1H), 7.44 (dd, J=2, 12 Hz, 1H), 3.81 (s, 2H). MS (DCI-$NH_3$) $[M+NH_4]^+$ at 282.

Example 31E 2-(6-Bromo-naphthalen-2-yl)-ethanol

To a stirred, −15° C. solution of the product from Example 31D (28.6 g, 108 mmol) in anhydrous THF (143 mL) under a dry nitrogen atmosphere was added dropwise over 15 min a 1.0 M solution of $BH_3$-THF (409 mL, 409 mmol, 3.8 equiv.) while maintaining the reaction temperature below 0° C. When the addition was complete, the reaction mixture was stirred at −15° C. for 15 min, then allowed to warm to room temperature and stirred an additional 2 hr. The reaction mixture was then cooled to −10° C. and quenched with distilled water (104 mL). After stirring for 15 min at room temperature, the reaction mixture was concentrated under reduced pressure. The residue was partitioned between dichloromethane (350 mL) and distilled water (200 mL) and the aqueous layer was extracted with dichloromethane (2×100 mL). The combined organic extracts were washed with distilled water (3×100 mL), dried ($MgSO_4$) and filtered. The filtrate was concentrated under reduced pressure to give a white solid. Drying under vacuum overnight at 40° C. provided the product (26.1 g, 96% yield). M.p. 102.3–103.1° C. $^1$H NMR ($CDCl_3$, 300 MHz) δ 7.98 (d, J=2 Hz, 1H), 7.74–7.63 (m, 3H), 7.53 (dd, J=2, 12 Hz, 1H), 7.49 (dd, J=2, 12 Hz, 1H), 4.00–3.92 (m, 2H), 3.02 (t, J=6 Hz, 2H), 1.43–1.35 (t br, J=6 Hz, 1H). MS (DCI-$NH_3$) $[M+NH_4]^+$ at 268.

Example 31F

2-[6-(2-Hydroxy-ethyl)-naphthalen-2-yl]-2H-pyridazin-3-one

A mixture of the product from Example 31E (500 mg, 1.87 mmol), 2H-pyridazin-3-one (180 mg, 1.87 mmol), copper powder (120 mg, 1.87 mmol), and $K_2CO_3$ (775 mg, 5.61 mmol, 3 equiv.) in pyridine (75 mL) was stirred at reflux under a dry nitrogen atmosphere for 20 hr. The reaction mixture was cooled to room temperature then concentrated under reduced pressure. Residual pyridine was removed by repeated evaporation with toluene. The residue was partitioned between ethyl acetate (350 mL) and saturated aqueous $Na_2CO_3$ The organic layer was washed twice with aqueous $NH_4OH$, dried ($MgSO_4$), filtered, and the filtrate was concentrated under reduced pressure. The residue was purified by column chromatography (75:25 ethyl acetate/hexane) to provide the title compound (270 mg, 54% yield). $^1$H NMR ($CDCl_3$, 300 MHz) δ 8.11 (d, J=2 Hz, 1H), 7.97–7.93 (m, 1H), 7.88 (t, J=9 Hz, 2H), 7.75–7.68 (m, 2H), 7.41 (dd, J=2, 12 Hz, 1H), 7.31–7.24 (m, 1H), 7.10 (dd, J=2, 12 Hz, 1H), 3.97 (t, J=6 Hz, 2H), 3.06 (t, J=6 Hz, 2H). MS (DCI-$NH_3$) $[M+H]^+$ at 267, $[M+NH_4]^+$ at 284.

Example 31G

Methanesulfonic acid 2-[6-(6-oxo-6H-pyridazin-1-yl)-naphthalen-2-yl]-ethyl ester Methanesulfonyl chloride (0.10 mL, 1.33 mmol, 1.3 equiv.) was added dropwise via a syringe to a stirred, 0° C. solution of the product from Example 31F (0.27 g, 1.01 mmol) and Et$_3$N (0.28 mL, 2.02 mmol, 2.0 equiv.). After one hour the ice bath was removed and the reaction mixture was stirred at room temperature for 2 hours. The reaction mixture was concentrated under reduced pressure. The residue was partitioned between EtOAc and saturated aqueous Na$_2$CO$_3$. The aqueous layer was extracted with EtOAc. The combined organic extracts were dried (MgSO$_4$) and filtered. The filtrate was concentrated under reduced pressure then filtered through a pad of silica gel with EtOAc followed by a second removal of solvent to provide the title intermediate as an off-white solid (300 mg, 87% yield). $^1$H NMR (CDCl$_3$, 300 MHz) δ 8.12 (d, J=2 Hz, 1H), 7.97–7.94 (m, 1H), 7.89 (t, J=9 Hz, 2H), 7.76–7.71 (m, 2H), 7.41 (dd, J=2, 12 Hz, 1H), 7.31–7.25 (m, 1H), 7.10 (dd, J=2, 12 Hz, 1H), 4.53 (t, J=6 Hz, 2H), 3.24 (t, J=6 Hz, 2H), 2.83 (s, 3H). MS (DCI-NH$_3$) [M+H]$^+$ at 345, [M+NH$_4$]$^+$ at 362.

Example 31H 2-(6-{2-[(2R)-2-Methyl-1-pyrrolidin-1-yl]-ethyl]-2-naphthalen-2-yl)-2H-pyridazin-3-one A mixture of the product from Example 31G (0.30 g, 0.87 mmol) and (2R)-2-methylpyrrolidine (0.37 g, 4.36 mmol, 5.0 equiv.) in anhydrous acetonitrile (3.5 mL) was stirred in a sealed tube at room temperature for 66 hours. The reaction mixture was concentrated under reduced pressure. The residue was partitioned between ethyl acetate and saturated aqueous Na$_2$CO$_3$. The aqueous layer was extracted with ethyl acetate, and the combined organic extracts were dried (MgSO$_4$) and filtered. The filtrate was concentrated under reduced pressure and the residue was purified by column chromatography (97:3:trace dichloromethane/methanol/NH$_4$OH). Fractions containing product were combined and concentrated under reduced pressure to provide the free base product (220 mg, 75.7% yield). The free base was dissolved in Et$_2$O and HCl gas was bubbled in until pH 2 was achieved. The resulting precipitate was crystallized from MeOH/Et$_2$O to give the hydrochloride salt. M.p. 198.9–201.5° C. $^1$H NMR (CD$_3$OD, 300 MHz) δ 8.12–8.07 (m, 2H), 8.00–7.88 (m, 3H), 7.68 (dd, J=2, 12 Hz, 1H), 7.57–7.49 (m, 2H), 7.13 (dd, J=2, 12 Hz, 1H), 3.84–3.64 (m, 2H), 3.64–3.46 (m, 1H), 3.46–3.13 (m, 4H), 2.43–2.26 (m, 1H), 2.22–1.99 (m, 2H), 1.85–1.67 (m, 1H), 1.48 (d, J=6 Hz, 3H). MS (DCI-NH$_3$) [M+H]$^+$ at 334.

Example 32

2-methoxy-5-(6-{2-[(2R)-2-methyl-1-pyrrolidinyl]ethyl}-2-naphthyl)pyridine

The title compound was prepared by the method in Example 8, substituting 6-methoxy-3-pyridinylboronic acid in place of 4-pyridinylboronic acid (37 mg, 24% yield). $^1$H NMR (CD$_3$OD, 300 MHz) δ 8.50 (d, J=2 Hz, 1H), 8.10–8.05 (m, 2H), 7.98–7.92 (m, 2H), 7.85–7.83 (m, 1H), 7.75 (dd, J=2, 10 Hz, 1H), 7.50 (dd, J=2, 12 Hz, 1H), 6.93 (d, J=9 Hz, 1H), 4.43 (s, 2H), 3.97 (s, 3H), 3.81–3.47 (m, 3H), 3.42–3.17 (m, 4H), 2.41–2.28 (m, 1H), 2.26–2.04 (m, 2H), 1.85–1.71 (m, 1H), 1.47 (d, J=6 Hz, 3H). MS (DCI-NH$_3$) [M+H]$^+$ at 347.

Example 33

4-(6-{2-[(2R)-2-(hydroxymethyl)-1-pyrrolidinyl]ethyl}-2-naphthyl)benzonitrile

The title compound was prepared by the method of Example 1H, substituting (2R)-2-pyrrolidinylmethanol in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.51–3.64 (m, 2H), 3.2–3.34 (m, 2H), 2.93–3.1 (m, 2H), 2.69–2.75 (m, 2H), 2.4 (q, J=6 Hz, 1H), 1.9–2.4 (m, 1H), 1.95–2.05 (m, 2H), 1.81–1.91 (m, 1H). MS (DCI-NH$_3$) [M+H]$^+$ at 357.

Example 34

4-{6-[2-(2-methyl-1-pyrrolidinyl)ethyl]-2-naphthyl}benzonitrile

The title compound was prepared by the method of Example 1H, substituting rac-2-methylpyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.68–3.83 (m, 2H), 3.51–3.61 (m, 1H), 3.17–3.42 (m, 4H), 2.3–2.43 (m, 1H), 2.02–2.12 (m, 2H), 1.68–1.82 (m, 1H), 1.44 (d, J=6 Hz, 3H). MS (DCI-NH$_3$) [M+H]$^+$ at 341.

Example 35

4-{6-[2-(1-pyrrolidinyl)ethyl]-2-naphthyl}benzonitrile

The title compound was prepared by the method of Example 1H, substituting pyrrolidine in place of (2R)-2-methylpyrrolidine. $^1$H NMR (CD$_3$OD, 300 MHz) δ 8.13 (s, 1H), 7.87–7.96 (m, 4H), 7.71–7.85 (m, 4H), 7.41 (d. J=6 Hz, 1H), 3.56–3.62 (m, 1H), 3.1–3.18 (m, 1H), 2.84–2.91 (m, 1H), 2.75–2.8 (m, 1H), 2.66–2.73 (m, 4H), 1.84–1.9 (m, 4H). MS (DCI-NH$_3$) [M+H]$^+$ at 327.

Example 36

4-(6-{2-[(2R)-2-methyl-1-pyrrolidinyl]ethyl}-2-naphthyl)thiomorpholine

The title compound was prepared by the method of Example 27, substituting thiomorpholine in place of morpholine. $^1$H NMR (CD$_3$OD, 300 MHz) δ 7.62–7.69 (m, 2H), 7.53 (s, 1H), 7.21–7.3 (m, 2H), 7.13 (s, 1H), 3.53 (m, 4H), 3.23–4.0 (m, 1H), 3.06–3.16 (m, 1H), 2.82–3.01 (m, 2H), 2.73 (m, 4H), 2.25–2.48 (m, 3H), 1.94–2.04 (m, 1H), 1.72–1.84 (m, 2H), 1.38–1.41 (m, 1H), 1.11 (d, J=6 Hz, 3H). MS (DCI-NH$_3$) (M+H)$^+$ at 341.

Example 37

1-{2-[(6-bromo-2-naphthyl)oxy]ethyl}pyrrolidine

Example 37A 2-bromo-6-(2-bromoethoxy)naphthalene

A round-bottom flask containing 1.0 g (4.5 mmol) of 6-bromo-2-naphthol, 1,2-dibromoethane (135 mmol, 12 mL), potassium hydroxide (5 mL of a 40% solution) and tetrabutylammonium bromide (1.35 mmol, 0.43 g) was heated at 100° C. for 3 h. The reaction mixture was diluted with 150 mL of $CH_2Cl_2$ and washed with water and brine, dried over sodium sulfate and concentrated under vacuum to give the desired compound in 100% as a pale brown solid; $^1$HNMR (300 MHz, $CDCl_3$) δ 3.70 (t, 2H), 4.40 (t, 2H), 7.05–7.90 (m, 6H). MS (DCI) m/z 330 (M+).

Example 37B

1-{2-[(6-bromo-2-naphthyl)oxy]ethyl}pyrrolidine

In a flask containing 0.5 g (1.5 mmol) the product from Example 37A, 10 mL of pyrrolidine was added. After stirring at 80° C. for 3 h, the reaction mixture was concentrated under vacuum. The residue was diluted with 100 mL of $CH_2Cl_2$ and washed sequentially with water, sodium bicarbonate and brine, dried and evaporated under reduced pressure. Silica gel chromatography (MeOH:$CH_2Cl_2$, 95:5) gave the desired material in 98% yield. $^1$HNMR (300 MHz, $CDCl_3$) δ 1.80 (m, 4H), 2.6 (m, 4H), 2.97 (t, 2H), 4.20 (t, 2H), 2.49 (m, 2H) 7.10–7.90 (m, 6H); MS (ESI) m/z 321 $(M+H)^+$.

Example 38

3-{6-[2-(1-pyrrolidinyl)ethoxy]-2-naphthyl}benzonitrile

A mixture of the product from Example 37B (35 mg, 0.11 mmol), 3-cyanophenylboronic acid (22 mg, 0.15 mmol), $PdCl_2(PPh_3)_2$ (4.2 mg, 6 μmol), and isopropanol (0.5 mL) was treated with 2 M aqueous sodium carbonate (80 μL) and heated at 85° C. overnight. The mixture was cooled to room temperature and partitioned between 2 M aqueous NaOH and dichloromethane. The aqueous phase was separated and extracted with dichloromethane. The combined organic phases were filtered through diatomaceous earth, concentrated, and chromatographed through silica with a gradient of 0%/50%/50% to 10%/40%/50% methanol/ethyl acetate/dichloromethane followed by 8% methanol/dichloromethane to provide the title compound. $^1$HNMR (300 MHz, $CD_3OD$) δ 1.86 (m, 4H), 2.73 (m, 4H), 3.01 (t, 2H), 4.28 (t, 2H), 7.22 (dd, 1H), 7.31 (d, 1H), 7.65 (t, 1H), 7.70 (dt, 1H), 7.75 (dd, 1H), 7.85–7.92 (m, 2H), 8.06 (dt, 1H), 8.07–8.13 (m, 2H); MS (ESI) m/z 343 $(M+H)^+$.

Example 39

3-{6-[2-(1-pyrrolidinyl)ethoxy]-2-naphthyl}pyridine

The product from Example 37B and 3-(4,4,5,5-tetramethyl-[1,3,2]dioxaborolan-2-yl)-pyridine were processed as described in Example 38, except that a second column chromatography was done to provide 10 mg of the title compound. $^1$HNMR (300 MHz, $CD_3OD$) δ 1.86 (m, 4H), 2.74 (m, 4H), 3.02 (t, 2H), 4.29 (t, 2H), 7.23 (dd, 1H), 7.31 (d, 1H), 7.56 (ddd, 1H), 7.76 (dd, 1H), 7.86–7.93 (m, 2H), 8.10 (d, 1H), 8.20 (ddd, 1H), 8.52 (dd, 1H), 8.91 (dd, 1H); MS (ESI) m/z 319 $(M+H)^+$.

Example 40

3-(6-{2-[(2R)-2-methyl-1-pyrrolidinyl]ethoxy}-2-naphthyl)benzonitrile

Example 40A (2R)-1-{2-[(6-bromo-2-naphthyl)oxy]ethyl}-2-methylpyrrolidine ((2R)-2-Methylpyrrolidine (L)-tartrate (541 mg, 2.3 mmol) was partitioned between aqueous 2 M NaOH (2.5 mL) and toluene (0.6 mL). The aqueous phase was separated, diluted with brine (0.3 mL), and extracted with toluene (2×0.3 mL). The combined organic phases were dried ($Na_2SO_4$) and carried on to the next step with a toluene rinse (0.3 mL).

The product from Example 37A (495 mg, 1.5 mmol), potassium carbonate (207 mg, 1.5 mmol), and the above toluene solution were suspended into DMF (3 mL) and heated at 50° C. overnight. The reaction mixture was brought to room temperature and partitioned between 0.2 M aqueous NaOH (20 mL) and dichloromethane (10 mL). The aqueous phase was separated and extracted with dichloromethane, and the combined organic phases were washed with 0.2 M aqueous NaOH, dried ($Na_2SO_4$), and filtered quickly through a silica plug with a 0 to 10% methanol/dichloromethane gradient. The filtrate was partitioned between water and 2:1 dichloromethane/hexanes. The aqueous phase was separated and extracted with 20% hexanes/dichloromethane, and the combined organic phases were concentrated and chromatographed through silica with a little hexanes/dichloromethane followed by a gradient of 0 to 10% methanol/dichloromethane. The appropriate fractions were combined and concentrated under high vacuum to provide 451 mg of a 6:1 mixture of title compound and starting dibromide which was used in the next step without further purification; MS (ESI APCI) m/z 334/336 $(M+H)^+$.

Example 40B 3-(6-{2-[(2R)-2-methyl-1-pyrrolidinyl]ethoxy}-2-naphthyl)benzonitrile A mixture of the product from Example 40A (147 mg, approximately 0.38 mmol), 3-cyanophenylboronic acid (96 mg, 0.65 mmol), $PdCl_2(PPh_3)_2$ (28 mg, 0.04 mmol) and isopropanol (2.5 mL) was treated with 2 M aqueous sodium carbonate (700 μL) and heated at 55° C. overnight, then at 85° C. for two days. The mixture was cooled to room temperature and partitioned between 2 M aqueous NaOH (2 mL) and dichloromethane (10 mL). The aqueous phase was separated and extracted with dichloromethane. The combined organic phases were filtered through diatomaceous earth, concentrated, and chromatographed through silica once with a gradient of 0%/50%/50% to 10%/40%/50% methanol/ethyl acetate/dichloromethane, and a second time with a gradient of 0%/0%/100% to 0%/50%/50% to 5%145%150% methanol/ethyl acetate/dichloromethane to provide 28 mg of an orange gum; $^1$HNMR (300 MHz, $CD_{3b}D$) δ 1.10 (d, 3H), 1.48 (m, 1H), 1.75–1.88 (m, 2H), 2.01 (m, 1H), 2.40 (m, 1H), 2.53 (m, 1H), 2.65 (m, 1H), 3.23–3.38 (m, 2H), 4.224.34 (m, 2H), 7.22 (dd, 1H), 7.30 (d, 1H), 7.65 (t, 1H), 7.70 (dt, 1H), 7.75 (dd, 1H), 7.85–7.92 (m, 2H), 8.06 (dt, 1H), 8.07–8.12 (m, 2H); MS (ESI) m/z 357 (M+H)$^+$.

Example 41

3-(6-{2-[(2R)-2-methyl-1-pyrrolidinyl]ethoxy}-2-naphthyl)pyridine

The product from Example 40A and 3-(4,4,5,5-tetramethyl-[1,3,2]dioxaborolan-2-yl)-pyridine were processed as described for Example 40B, except that a single chromatography was conducted with a gradient of 0%/50%/50% to 10%/40%/50% methanol/ethyl acetate/dichloromethane followed by 8% methanol/dichloromethane to provide the title compound. $^1$HNMR (300 MHz, CD$_3$OD) δ 1.10 (d, 3H), 1.47 (m, 1H), 1.75–1.88 (m, 2H), 2.02 (m, 1H), 2.41 (m, 1H), 2.54 (m, 1H), 2.66 (m, 1H), 3.22–3.39 (m, 2H), 4.24–4.33 (m, 2H), 7.22 (dd, 1H), 7.31 (d, 1H), 7.55 (ddd, 1H), 7.76 (dd, 1H), 7.86–7.94 (m, 2H), 8.10 (d, 1H), 8.21 (ddd, 1H), 8.52 (dd, 1H), 8.91 (dd, 1H); MS (ESI) m/z 333 (M+H)$^+$.

Example 42

4-(2-{2-[(2R)-2-methyl-1-pyrrolidinyl]ethyl}-6-quinolinyl)benzonitrile

Example 42A ethyl (6-bromo-2-quinolinyl)acetate

To a solution of diisopropylamine (19.2 g, 0.19 mole) in diethyl ether (200 mL) was added 2.5 M n-butyllithium in hexane (74 mL, 0.185 mole) at −78° C. The clear solution was mixed for 30 min, and followed by addition of 6-bromo-2-methyl-quinoline (13.32 g, 0.060 mole) in ether (200 mL) slowly at −78° C. The brown solution was stirred for 0.5 hour, and ethyl chloroformate (7.45 g, 0.069 mole) in ether (50 mL) was syringed into the mixture slowly so that the internal temperature did not exceed −70° C. The yellow reaction mixture was quenched by addition of 50 mL water, allowed to warm up to rt, and diluted with ethyl acetate (300 mL). The solution was washed with 5% sodium bicarbonate aq. solution (700 mL×3), 25% brine (700 mL), dried over MgSO$_4$, and filtered. The organic was concentrated to ~50 mL volume, and the slurry diluted with heptane (50 mL). The slurry was stirred at 0° C. for 2 h, and the solid was collected by filtration, rinsed with a ice-cold heptane: ethyl acetate (10 mL, 2:1), dried at 50° C. under vacuum to give a yellow solid (12.0 g). Concentration of the mother liquid afforded a 2$^{nd}$ crop of the product (3.6 g). Total yield: 88%; mp: 100–101° C. (uncorrected); MS (ESI): 294, 296 (M+H)$^+$; $^1$H-NMR (CDCl$_3$) δ 8.02 (1H, d, J=8.5 Hz), 7.94 (1H, d, J=2.2 Hz), 7.91 (1H, d, J=8.9 Hz), 7.74 (1H, dd, J=8.9, 2.2 Hz), 7.44 (1H, d, J=8.5 Hz), 4.20 (2H, q, J=7.1 Hz), 4.01 (2H, s), 1.27 (3H, t, J=7.1 Hz); $^{13}$C-NMR (CDCl$_3$) δ 169.7, 154.9, 146.0, 135.1, 132.6, 130.5, 128.9, 127.8, 122.3, 119.9, 61.2, 44.9, 14.5.

Example 42B 2-(6-bromo-2-quinolinyl)ethanol

A 1 L round bottom flask was charged with the product from Example 42A (12.0 g, 0.0408 mole), lithium borohydride (1.78 g, 0.00816 mole) and THF (450 mL) under a nitrogen atmosphere. Ethanol (18.8 g, 0.408 mole) was added slowly at <25° C., and the yellow mixture stirred at rt for 4 hours. Methanol (40 mL) was carefully added and the mixture was concentrated to ~50 mL of volume. The mixture was diluted with ethyl acetate (250 mL), washed with 5% NaHCO$_3$ aq. solution, and water (300 mL). The organic layer was concentrated, azeotroped with ethyl acetate (250 mL×2) to a volume of ~50 mL. The resulting precipitate was diluted with heptane (50 mL), stirred at room temperature overnight, and then at 5° C. for 2 hours. The solid was filtered, rinsed with heptane (20 mL), and dried at 50° C. to give 7.70 g of the product (75% yield); mp: 103–104° C. (uncorrected); MS (ESI): 251, 253 (M+H)$^+$; $^1$H-NMR (CDCl$_3$) δ 7.96 (1H, d, J=8.4 Hz), 7.90 (1H, d, J=2.2 Hz), 7.84 (1H, d, J=8.9 Hz), 7.72 (1H, dd, J=8.9, 2.2 Hz), 7.27 (1H, d, J=8.4 Hz), 4.13 (2H, d, J=5.6 Hz), 3.19 (2H, d, J=5.6 Hz); $^{13}$C-NMR (CDCl$_3$) δ 161.3, 145.4, 135.1, 132.6, 130.1, 129.2, 127.5, 122.4, 119.5, 61.2, 39.7.

Example 42C 2-(6-bromo-2-quinolinyl)ethyl 4-methylbenzenesulfonate

A 500 mL round bottom flask was charged with the product from Example 42B (7.65 g, 0.030 mole), 4-N,N-dimethylaminopyridine (0.36 g, 0.003 mole), dichloromethane (100 mL) and triethylamine (9.3 g, 0.092 mmol). p-Toluenesulfonyl chloride (11.5 g, 0.060 mole) was added in portions, and the solution was stirred at rt for 6 hours. The solution was stripped down to dryness, and the crude product was taken into ethyl acetate (150 mL) and 5% NaHCO$_3$ aq. solution (150 mL). The upper organic was washed with water (150 mL), concentrated, azeotroped with ethyl acetate (250 mL×2) to a volume of ~50 mL. The slurry was diluted with heptane (50 mL), stirred at room temperature overnight, and then at 5° C. for 8 hours. The precipitate was collected by filtration, rinsed with heptane (20 mL), dried at 50° C. under vacuum overnight to afford 10.80 g of the product as an off-white solid; mp 107–109° C.; MS (ESI): 406, 408 (M+H)$^+$; $^1$H-NMR (CDCl$_3$) δ 7.92 (1H, m), 7.91 (1H, m), 7.7 (2H, m), 7.58 (2H, m), 7.25 (1H, d, J=8.4 Hz), 7.09 (2H, m), 4.56 (2H, t, J=6.3 Hz), 3.27 (2H, t, J=6.3 Hz), 2.33 (3H, s); $^{13}$C-NMR (CDCl$_3$) δ 157.2, 145.9, 144.1, 135.0, 132.5, 132.3, 130.3, 129.2, 129.2, 127.7, 127.4, 122.5, 119.6, 69.2, 38.0, 21.8.

Example 42D 6-bromo-2-{2-[(2R)-2-methyl-1-pyrrolidinyl]ethyl}quinoline (2R)-2-Methylpyrrolidine L-tartrate (7.00 g, 0.0298 mole, milled), potassium carbonate (9.04 g, 0.0655 mole, milled), and acetonitrile (190 mL) were combined and heated at 60° C. with agitation for 48 hours. The mixture was allowed to cool to 30° C., and treated with the product from Example 42C (8.00 g, 0.0197 mole). The reaction mixture was heated at −60° C. for 36 hours and then distilled down to −1/4 volume, and isopropyl acetate (200 mL) was added. The mixture was washed with 5% NaHCO$_3$ aq. solution (200 mL×2), and 25% brine (200 mL). The upper organic was dried over anhydrous sodium sulphate, filtered, and the filtrate was concentrated to dryness. The crude product was purified with a short-path silica gel column eluted with heptane:ethyl acetate:TEA (60:40:1) to give 5.8 g (92% yield) of product as an oil, which solidified on standing; mp 49–50° C. (uncorrected); MS (ESI): 319, 311 (M+H)$^+$; $^1$H-NMR (CDCl$_3$) δ 7.95 (1H, d, J=8.5 Hz), 7.91 (1H, d, J=2.2 Hz), 7.89 (1H, d, J=8.9 Hz), 7.72 (1H, dd, J=8.9, 2.2 Hz), 7.35 (1H, d, J=8.5 Hz), 3.23 (2H, m), 3.18 (2H, m), 2.55 (1H, m), 2.38 (1H, m), 2.25 (1H, q, J=8.9 Hz), 1.93 (1H, m), 1.80 (1H, m), 1.71 (1H, m), 1.42 (1H, m), 1.11 (3H, d, J=6.0 Hz); $^{13}$C-NMR (CDCl$_3$) δ 161.3, 146.1, 134.7, 132.3, 130.3, 129.2, 127.6, 122.2, 119.2, 59.9, 54.0, 53.6, 38.6, 33.0, 22.0, 19.4.

Example 42E 4-(2-{2-[(2R)-2-methyl-1-pyrrolidinyl]ethyl}-6-quinolinyl)benzonitrile The product from Example 42D (160 mg, 0.5 mmol), 4-cyanophenylboronic acid (0.75 mmol), and dichlorobis(triphenylphosphine) palladium (II) (35.1 mg, 0.05 mmol) were combined in isopropyl alcohol (5.0 mL) and 0.2 M K$_3$PO$_4$ aq. solution (5.0 mL, 1.0 mmol) and heated at 60° C. for 24 hours. The reaction mixture was allowed to cool to room temperature and diluted with ethyl acetate (20 mL). The organic phase was separated, washed with 5% NaHCO$_3$ (25 mL×3), 25% brine (25 mL), dried over Na$_2$SO$_4$, filtered, and the filtrate concentrated to dryness. The residue was purified by column chromatography (heptane:acetone:CH$_2$Cl$_2$:TEA (60:40:5:1) to provide the title compound. The title compound was treated with one equivalent of L-tartaric acid in IPA:ethanol to give the tartrate salt. mp 164° C.; MS (ESI) 342 (M+H)$^+$; $^1$H NMR (DMSO-d$_6$) δ 8.40 (1H, d), 8.38 (1H, d), 8.12 (1H, d), 8.06 (1H, d), 8.04 (2H, d), 7.98 (2H, d), 7.58 (1H, d), 4.05 (2H, s), 3.63 (1H, m), 3.50 (1H, m), 3.33 (2H, t), 3.15 (2H, m), 2.88 (1H, m), 2.09 (1H, m), 1.86 (2H, m), 1.55 (1H, m), 1.29 (3H, d).

Example 43

6-(4-fluorophenyl)-2-{2-[(2R)-2-methyl-1-pyrrolidinyl]ethyl}quinoline

The title compound was prepared using the procedure described in Example 42E substituting 4-fluorophenylboronic acid for 4-cyanophenylboronic acid. The title compound was treated with HCl in IPA:ethyl acetate to give the dihydrochloride salt. mp 145° C.; MS (ESI) 335 (M+H)$^+$; $^1$H NMR (DMSO-d$_6$) δ 8.88 (1H, d), 8.5 (1H, br), 8.42 (1H, d), 8.37 (1H, d), 7.97 (1H, d), 7.91 (2H, dd), 7.40 (2H, t), 3.93 (1H, br), 3.72 (3H, br), 3.5 (2H, br), 3.26 (1H, br), 2.2 (1H, m), 2.0 (2H, br), 1.7 (1H, br), 1.42 (3H, br).

Example 44

3-(2-{2-[(2R)-2-methyl-1-pyrrolidinyl]ethyl}-6-quinolinyl)benzonitrile

The title compound was prepared using the procedure described in Example 42E substituting 3-cyanophenylboronic acid for 4-cyanophenylboronic acid. The title compound was treated with one equivalent of L-tartaric acid in IPA:ethanol to give the tartrate salt. mp 172° C.; MS (ESI) 342 (M+H)$^+$; $^1$H NMR (DMSO-d$_6$) δ 9.2 (1H, d), 8.61 (1H, d), 8.42 (1H, d), 8.21 (1H, d), 8.19 (1H, d), 8.17 (1H, dt), 7.82 (1H, dt), 7.75 (1H, t), 4.88 (2H, s), 4.06 (1H, m), 3.90 (3H, m), 3.65 (2H, m), 2.40 (1H, m), 2.20 (2H, m), 1.84 (1H, m), 1.59 (3H, d).

Example 45

1-[3-(2-{2-[(2R)-2-methyl-1-pyrrolidinyl]ethyl}-6-quinolinyl)phenyl]ethanone

The title compound was prepared using the procedure described in Example 42E substituting 3-acetylphenylboronic acid for 4-cyanophenylboronic acid. The title compound was treated with HCl in IPA:ethyl acetate to give the dihydrochloride salt. mp 174–175° C.; MS (ESI) 359 (M+H)$^+$; $^1$H NMR (CD$_3$OD) δ 9.14 (1H, d), 8.56, 8.50 (1H, d), 8.4 (2H, m), 8.33, 7.79 (1H, t), 8.14 (1H, dd), 8.05 (1H, dt), 7.74, 7.52 (1H, dt), 7.627.50 (1H, t), 4.02 (1H, m), 3.83 (2H, m), 3.60 (2H, m), 3.41 (1H, m), 2.62 (1H, m), 2.37 (1H, m), 2.15 (3H, m), 1.80 (1H, m), 1.53(3H, s), 1.1 (3H, d).

Example 46

6-(4-methoxyphenyl)-2-{2-[(2R)-2-methyl-1-pyrrolidinyl]ethyl}quinoline

The title compound was prepared using the procedure described in Example 42E substituting 4-methoxyphenylboronic acid for 4-cyanophenylboronic acid. The title compound was treated with HCl in IPA:ethyl acetate to give the dihydrochloride salt. mp 165° C. (dec.); MS (ESI) 347 (M+H)$^+$; $^1$H NMR (CD$_3$OD) δ 9.12 (1H, d), 8.46 (2H, m), 8.36 (1H, d), 8.11 (1H, d), 7.80 (2H, d), 7.10(2H, d), 4.02 (1H, m), 3.90 (3H, s), 3.82 (2H, m), 3.62 (2H, m), 3.41 (1H, m), 2.39 (2H, m), 2.18 (2H, m), 1.82 (1H, m), 1.56 (3H, d).

Example 47

2-{2-[(2R)-2-methyl-1-pyrrolidinyl]ethyl}-6-[4-(trifluoromethyl)phenyl]quinoline The title compound was prepared using the procedure described in Example 42E substituting 4-(triflouromethyl)phenylboronic acid for 4-cyanophenylboronic acid. The title compound was treated with HCl in IPA:ethyl acetate to give the dihydrochloride salt. mp 143–145° C. (dec.); MS (ESI) 385 (M+H)$^+$; $^1$H NMR (DMSO-d$_6$) δ 8.65 (1H, d), 8.50 (1H, s), 8.23 (2H, m), 8.09 (2H, d), 7.91 (2H, d), 7.74 (1H, d), 4.0–3.4 (6H, br, m), 3.22 (1H, br), 2.22 (1H, br), 2.0 (2H, m), 1.70 (1H, m), 1.44 (3H, br).

Example 48

2-{2-[(2R)-2-methyl-1-pyrrolidinyl]ethyl}-6-[4-(methylsulfonyl)phenyl]quinoline

The title compound was prepared using the procedure described in Example 42E substituting 4-(methylsulfonyl)phenylboronic acid for 4-cyanophenylboronic acid. The title compound was treated with HCl in IPA:ethyl acetate to give the dihydrochloride salt. MS (ESI) 395 (M+H)$^+$; $^1$H NMR (CD$_3$OD) δ 9.05 (1H, d), 8.56 (1H, d), 8.45 (1H, dd), 8.38 (1H, d), 8.10 (4H, m), 8.02 (1H, d), 4.03 (1H, br, m), 3.85 (1H, br, m), 3.75 (2H, br, m), 3.62 (2H, br, m), 3.41 (1H, m), 3.18 (3H, s), 2.39 (1H, m), 2.18 (2H, m), 1.82 (1H, m), 1.57 (3H, br, d).

Example 49

6-(3,5-difluorophenyl)-2-{2-[(2R)-2-methyl-1-pyrrolidinyl]ethyl}quinoline

The title compound was prepared using the procedure described in Example 42E substituting 3,5-difluorophenylboronic acid for 4-cyanophenylboronic acid. The title compound was treated with HCl in IPA:ethyl acetate to give the dihydrochloride salt. mp 164–165° C.; MS (ESI) 353 (M+H)$^+$; $^1$H NMR (DMSO-d$_6$) δ 8.72 (1H, d), 8.59 (1H, s), 8.31 (2H, m), 7.76 (1H, d), 7.63 (2H, dd), 7.55 (1H, tt). 3.90 (1H, br), 3.63 (2H, br, m), 3.50 (2H, br, m), 3.23 (1H, br), 2.9–2.6 (1H, br, m), 2.2 (1H, m), 1.98 (2H, br, m), 1.64 (1H, br, m), 1.45 (3H, br).

Example 50

(3-fluorophenyl)2-{2-[(2R)-2-methyl-1-pyrrolidinyl]ethyl}-6-quinolinyl)methanone The product from Example 42D (320 mg, 1.0 mmol) in THF (10 mL) was treated with 2.5M n-butyllithium (0.5 mL, 1.25 mmol) at –78° C. The solution was mixed for 15 min, and treated with a solution of 3-fluoro-N-methoxy-N-methylbenzamide (2.0 mmol) in THF (5.0 mL) at –78° C. The mixture was allowed to warm to room temperature overnight, quenched by 1 mL ethanol, concentrated, and diluted with ethyl acetate. The mixture was washed with 5% NaHCO$_3$ (25 mL×3), 25% brine (25 mL), dried over Na$_2$SO$_4$, filtered, and the filtrate was concentrated to dryness. The residue was purified by column chromatography (heptane:acetone:CH$_2$Cl$_2$:TEA (60:40:5:1) to provide the title compound. The title compound was treated with HCl in IPA:ethyl acetate to give the dihydrochloride salt. mp 162–164° C.(dec.); MS (ESI) 363 (M+H)$^+$; $^1$H NMR (DMSO-d$_6$) δ 8.79 (1H, d), 8.53 (1H, d), 8.30 (1H, d), 8.21 (1H, dd), 7.82 (1H, d), 7.6 (4H, m), 3.9 (1H, br, m), 3.63 (2H, br, m), 3.50 (2H, br, m), 3.21 (1H, br, m), 2.2 (1H, m), 1.98 (2H, br, m), 1.7 (1H, br, m), 1.46 (1H, m), 1.30 (3H, d).

Example 51

2-{2-[(2R)-2-methyl-1-pyrrolidinyl]ethyl}-6-(3-pyridinyl)quinoline

Tetrakis(triphenylphosphine) palladium (0) (28.8 mg, 0.025 mmol), 2-(dicyclohexylphosphino)biphenyl (35.0 mg, 0.10 mmol), 3-pyridinylboronic acid (0.375 mmol), and sodium carbonate (40.0 mg, 0.375 mmol) were combined in 1,2-dimethoxyethane (4 mL) and water (1.5 mL). The mixture was then treated with the product from Example 42D (80 mg, 0.25 mmol) and heated at 80° C. for 24 hours. The reaction mixture was allowed to cool to room temperature and diluted with ethyl acetate (20 mL). The organic layer was separated, washed with 5% NaHCO$_3$ (25 mL×3), 25% brine (25 mL), dried over Na$_2$SO$_4$, filtered, and the filtrate was concentrated to dryness. The residue was purified by column chromatography (heptane:acetone:CH$_2$Cl$_2$:TEA (60:40:5:1) to provide the title compound. The title compound was treated with HCl in IPA:ethyl acetate to give the trihydrochloride salt. mp 205–207° C.; MS (ESI) 318 (M+H)$^+$; $^1$H NMR (DMSO-d$_6$) δ 9.48 (1H, br, s), 9.05 (1H, d), 8.96 (1H, d), 9.00 (1H, d), 8.86 (1H, br, s), 8.60 (1H, d), 8.59 (1H, d), 8.32 (1H, dd), 8.23 (1H, d), 4.08 (1H, br, m), 3.90 (2H, br, m), 3.65 (2H, br, m), 3.46 (1H, q), 2.40 (1H, m), 2.19 (2H, m), 1.84 (1H, m), 1.58 (3H, d).

Example 52

4-(3-{2-[(2R)-2-methyl-1-pyrrolidinyl]ethyl}7-isoquinolinyl)benzonitrile

Example 52A ethyl (6-bromo-1-oxo-2,3-dihydro-1H-inden-2-yl) acetate n-Butyllithium (14 mL, 2 M in pentane) was added dropwise to a solution of diisopropylamine (2.86 g, 28 mmol) in tetrahydrofuran (60 mL) cooled to –70° C. After 30 minutes of stirring at –70° C., the mixture was treated with 6-bromo-1-indanone (4.8 g, 22.7 mmol), prepared according to the procedure described in J. Org. Chem., 49:4226–423 (1984), in two portions over 5 minutes. After 10 minutes, the mixture was allowed to warm to –50° C. and was treated with ethyl bromoacetate (4.8 g, 28 mmol). The mixture was allowed to warm to –10° C. and was stirred at –10 to –15° C. for 1 hour. The reaction was quenched by careful addition of water (60 mL) followed by isopropyl acetate (60 mL). The organic layer was separated, washed with aqueous HCl (50 mL, prepared by adjusting the pH of water to 2 with conc. HCl), and then aqueous potassium carbonate (50 mL, 5%). The organic layer was concentrated under vacuum to provide the title compound which was used in the next step without further purification.

Example 52B

(6-bromo-1-hydroxy-2,3-dihydro-1H-inden-2-yl) acetic acid

The product from Example 52A in THF was treated with tert-butylaminoborane (1.18 g, 13.5 mmol) and heated at 40–45° C. for 2.5 hours. The mixture was treated with sodium hydroxide solution (1.8 g in water, 40 mL) and heating was continued for 30 minutes. The mixture was allowed to cool to room temperature and the aqueous layer was separated. The organic layer was diluted with isopropyl acetate (40 mL) and water (40 mL) and combined with the aqueous layer. The solution was cooled to 0° C. and the pH was adjusted to 2 by addition of concentrated hydrochloric acid. The mixture was filtered and the fitler cake dried at room temperature. The solid was slurried in dichloromethane (6 mL), refiltered, and redried to provide the title compound.

Example 52C methyl (5-bromo-1H-inden-2-yl)acetate

The product from Example 52B (1.35 g, 5 mmol) in methanol (12 mL) was treated with concentrated sulfuric acid (2 mL) and heated to gentle reflux. After 2 hours, additional sulfuric acid was added (1 mL) and heating was continued for another 2 hours. The mixture was concentrated under vacuum and the residue was diluted with water (15 mL). The mixture was cooled to 10° C., filtered, and the filter cake washed with water (5 mL) and dried to provide the title compound. $^1$H NMR (CDCl$_3$) δ 3.42 (s, 2H); 3.55 (s, 2H); 3.74 (s, 3H); 6.65 (m, 1H); 7.22-7.31 (m, 2H), 7.44 (m, 1H).

Example 52D

2-(5-bromo-1H-inden-2-yl)ethanol

The product from Example 52C (1.1 g, 4.1 mmol) in diethyl ether (5 mL) was added dropwise to a suspension of lithium aluminum hydride (0.125 g, 3.3 mmol) in diethyl ether (10 mL) maintaining the internal temperature below 10° C. After stirring for 30 minutes, the reaction mixture was diluted with diethyl ether (10 mL), cooled to 0° C., and treated with saturated aqueous sodium sulfate dropwise. The ethereal solution was decanted, dried with sodium sulfate, filtered, and the filtrate was concentrated to provide the title compound which was used without further purification in the next step. $^1$H NMR (CDCl$_3$) δ 2.77 (m, 2H); 3.32 (s, 2H); 3.88 (t, J=6.5 Hz, 2H); 6.56 (m, 1H), 7.23 (m, 2H); 7.40 (m, 1H).

Example 52E

2-(7-bromo-3-isoquinolinyl)ethanol

The product from Example 52D (0.85 g, 3.5 mmol) in methanol (15 mL) at −70° C. was ozonated until a bluish color developed (~10 minutes). The mixture was treated with dimethylsulfide (0.7 mL, excess) and sodium bicarbonate (0.2 g) and allowed to warm to room temperature. After stirring for 3 hours, the mixture was treated with aqueous ammonium hydroxide (7.4 mL, 28%). After stirring an additional 4 hours, the reaction mixture was concentrated under vacuum and then diluted with dichloromethane (20 mL). The organic layer was separated and evaporated to provide the title compound which was used without further purification in the next step. $^1$H NMR (CDCl$_3$) δ 3.13 (t, J=5.6 Hz, 2H); 4.07 (t, J=5.6 Hz, 2H); 7.47 (s, 1H); 7.61 (d, J=8.7 Hz, 1H); 7.71 (dd, J=1.9, 8.7 Hz, 1H); 9.04 (s, 1H); Anal. Calcd. for C$_{11}$H$_{10}$BrNO: C, 52.41; H, 4.00; N, 5.56. Found: C, 52.51; H, 3.94; N, 5.42.

Example 52F

2-(7-bromo-3-isoquinolinyl)ethyl 4-methylbenzenesulfonate

The product from Example 52E (0.51 g, 2.0 mmol), tosyl chloride (0.68 g, 3.6 mmol), triethylamine (0.55 g, 5.4 mmol), and DMAP (25 mg, 0.2 mmol) were combined in dichloromethane (20 mL) and stirred at room temperature for 6 hours. The mixture was treated with water (0.5 mL), stirred for 2 hours, and then treated with additional water (15 mL). The organic layer was separated, washed with aqueous sodium chloride solution (10 mL, 10%), evaporated in vacuo, and the residue was azeotroped with heptane (15 mL) to provide the title compound which was used in the next step without further purification.

Example 52G

7-bromo-3-{2-[(2R)-2-methyl-1-pyrrolidinyl]ethyl}isoquinoline

The product from Example 52F was dissolved in a solution of (2R)-2-methylpyrrolidine (0.26 g, 3.0 mmol) in acetonitrile (20 mL). The solution was treated with potassium carbonate (0.5 g, 3.6 mmol) and heated at 50–55° C. for 20 hours in a sealed flask. The mixture was allowed to cool to room temperature, filtered, and the filtrate was concentrated in vacuo. The residue was diluted with MTBE (20 mL) and water (20 mL) and the pH was adjusted to 3–3.5 with concentrated HCl. The aqueous layer was separated, extracted with MTBE (10 mL), adjusted to a pH of 8–8.5 with potassium carbonate (20 mL), and extracted with isopropyl acetate (20 mL). The organic layer was separated and concentrated in vacuo. The residue was dissolved in heptane (20 mL), filtered, and the filtrate concentrated under vacuum to provide the title compound. $^1$H NMR (CDCl$_3$) δ 1.10 (d, J=6.1 Hz, 3H); 1.35–1.49 (m, 1H); 1.62–1.85 (m, 2H); 1.85–1.98 (m, 1H); 2.23 (q, J=8.8. Hz, 1H); 2.28–2.42 (m, 1H); 2.46–2.57 (m, 1H); 3.04–3.19 (m, 2H); 3.19–3.30 (m, 2H); 7.47 (s, 1H); 7.60 (d, J=8.8 Hz, 1H), 7.64 7.70 (m, 1H), 8.05 (m, 1H); 9.09 (s, 1H); HRMS Calcd. for [C$_{16}$H$_{19}$BrN$_2$+ H+]: 319.0810. Found: 319.0795.

Example 52H

4-(3-{2-[(2R)-2-methyl-1-pyrrolidinyl]ethyl}-7-isoquinolinyl)benzonitrile

The product from Example 52G (0.2 g, 0.6 mmol), 4-cyanophenylboronic acid (0.22 g, 1.5 mmol), bis(triphenylphosphine)palladium dichloride (55 mg, 0.08 mmol), and potassium phosphate (7 mL, 0.2 M in water) were combined in isopropanol (7 mL) and heated at 60–65° C. for 7 hours in a sealed flask. The mixture was filtered through diatomaceous earth, the filtrate was concentrated in vacuo, and then partitioned between MTBE (10 mL) and water (10 mL). The organic layer was separated, washed with aqueous sodium bicarbonate solution (5%, 10 mL), and then extracted with a solution of 2M HCl (15 mL). The pH of the acidic aqueous layer was adjusted with base using potassium carbonate and extracted with isopropyl acetate (15 mL). The organic layer was evaporated in vacuo and the residue was chased with heptane (10 mL) to provide the title compound. $^1$H NMR (CDCl$_3$) δ 1.12 (d, J=6.0 Hz, 3H); 1.37–1.50 (m, 1H); 1.64–1.85 (m, 2H); 1.85–1.98 (m, 1H); 2.26 (q, J=8.8. Hz, 1H); 2.32–2.43 (m, 1H); 2.50–2.60 (m, 1H), 3.09–3.34 (m, 4H); 7.56 (m, 1H); 7.73–7.81 (m, 4H), 7.84–7.87 (m, 2H), 8.12 (m, 1H); 9.26 (s, 1H); HRMS Calcd. for [C$_{23}$H$_{23}$N$_3$+H$^+$]: 342.1970. Found: 342.1974.

Example 53

3-(3-{2-[(2R)-2-methyl-1-pyrrolidinyl]ethyl}-7-isoquinolinyl)benzonitrile

The title compound was prepared using the procedure described in Example 52H substituting 3-cyanophenylboronic acid for 4-cyanophenylboronic acid. $^1$H NMR (CDCl$_3$) δ 1.15 (d, J=6.1 Hz, 3H); 1.39–1.54 (m, 1H); 1.66–1.87 (m, 2H); 1.88–2.01 (m, 1H); 2.29 (q, J=8.8. Hz, 1H); 2.34–2.47 (m, 1H); 2.52–2.65 (m, 1H), 3.09–3.40 (m, 4H); 7.58 (m, 1H); 7.61 (d, J=7.8 Hz, 1H); 7.64–7.70 (m, 1H), 7.82–7.89 (m, 2H); 7.89–7.95 (m, 1H); 7.97 (m, 1H), 8.10 (m, 1H); 9.27 (s, 1H).

Example 54

6-{2-[(2R)-2-methyl-1-pyrrolidinyl]ethyl}-2-(3-pyridinyl)quinoline

Example 54A

(2R)-2-methyl-1-[2-(4-nitrophenyl)ethyl]pyrrolidine (2R)-2-Methylpyrrolidine L-tartrate (4.0 g, 17.0 mmol), 1-(2-bromoethyl)-4-nitrobenzene (9.8 g, 43 mmol), and potassium carbonate (12 g, 85 mmol), were combined in DMF (20 mL) in a sealed tube at 50° C. and stirred vigorously for 16 hours. The mixture was allowed to cool to room temperature, diluted with diethyl ether (100 mL), washed with water (2 times, 100 mL and then 50 mL), and extracted with 1 M HCl (2 times, 50 mL and 25 mL). The aqueous acidic extractions were combined, washed with diethyl ether (50 mL), cooled to 0° C., adjusted to pH 14 with 50% NaOH solution, and extracted with dichloromethane (3 times, 50 mL). The dichloromethane extractions were combined, dried (MgSO$_4$), filtered, and the filtrate concentrated to provide the title compound. $^1$H NMR (300 MHz, CDCl$_3$) δ 1.08 (d, J=6 Hz, 3H), 1.43 (m, 1H), 1.75 (m, 2H), 1.93 (m, 1H), 2.19 (q, J=9 Hz, 1H), 2.34 (m, 2H), 2.91 (m, 2H), 3.03 (m, 1H), 3.22 (td, J=8, 3 Hz, 1H), 7.38 (d, J=9 Hz, 2H), 8.15 (d, J=9 Hz, 2H); MS (DCI/NH$_3$) m/z 235 (M+H)$^+$.

Example 54B

4-{2-[(2R)-2-methyl-1-pyrrolidinyl]ethyl}aniline

The product from Example 54A (3.85 g, 16.4 mmol) was hydrogenated using 10% Pd/C (0.39 g) in methanol (20 mL) under 1 atm H$_2$ for 16 hours. After the H$_2$ was replaced with N$_2$, the mixture was diluted with methanol (150 mL), stirred for 15 minutes, filtered, and the filtrate was concentrated to provide the title compound. $^1$H NMR (300 MHz, CDCl$_3$) δ 1.11 (d, J=6 Hz, 3H), 1.43 (m, 1H), 1.74 (m, 2H), 1.90 (m, 1H), 2.25 (m, 3H), 2.70 (m, 2H), 2.97 (m, 1H), 3.24 (td, J=9, 3 Hz, 1H), 3.55 (s, 2H), 6.63 (d, J=8 Hz, 2H), 7.01 (d, J=8 Hz, 2H); MS (DCI/NH$_3$) m/z 205 (M+H)$^+$.

Example 54C 2,2-dimethyl-N-(4-{2-[(2R)-2-methyl-1-pyrrolidinyl]ethyl}phenyl)propanamide The product from Example 54B (2.77 g, 14 mmol) was dissolved in anhydrous dichloromethane (70 mL) under nitrogen, treated with triethylamine (2.3 mL, 16 mmol), cooled to 0° C., treated with trimethylacetyl chloride (1.9 mL, 15 mmol), stirred at ambient temperature for 60 hours and treated with 1 M NaOH (40 mL). The layers were separated and the aqueous layer was extracted with dichloromethane (2 times, 40 mL). The combined dichloromethane layers were dried (MgSO$_4$), filtered, and the filtrate was concentrated to provide 4.0 g of the title compound. $^1$H NMR (300 MHz, CDCl$_3$) δ 1.10 (d, J=6 Hz, 3H), 1.31 (s, 9H), 1.44 (m, 1H), 1.76 (m, 2H), 1.92 (m, 1H), 2.18 (q, J=9 Hz, 1H), 2.27 (m, 2H), 2.78 (m, 2H), 2.99 (m, 1H), 3.23 (td, J=9, 3 Hz, 1H), 7.17 (d, J=8 Hz, 2H), 7.44 (d, J=8 Hz, 2H); MS (DCI/NH$_3$) m/z 289 (M+H)$^+$.

Example 54D

N-(2-formyl-4-{2-[(2R)-2-methyl-1-pyrrolidinyl]ethyl}phenyl)-2,2-dimethylpropanamide The product from Example 54C (4.0 g, 13.9 mmol) under nitrogen in anhydrous diethyl ether (140 mL) was treated with N,N,N'N'-tetramethylethylenediamine (6.5 mL, 43 mmol), cooled to −5° C., treated with n-butyllithium (16.7 mL of a 2.5 M solution in hexanes) over 10 minutes, stirred for 4 hours at ambient temperature, cooled to −5° C., treated all at once with anhydrous N,N-dimethylformamide (6.5 mL, 83 mmol), stirred for 16 hours at ambient temperature, diluted with diethyl ether (100 mL), washed with water (75 mL), washed with brine, dried (MgSO$_4$), filtered, and the filtrate was concentrated. The residue was purified by chromatography on silica gel eluting with a gradient of 2%, 3.5%, 5%, and 7.5% (9:1 MeOH:conc NH$_4$OH) in dichloromethane to provide the title compound. $^1$H NMR (300 MHz, CDCl$_3$) δ 1.10 (d, J=6 Hz, 3H), 1.35 (s, 9H), 1.44 (m, 1H), 1.75 (m, 2H), 1.93 (m, 1H), 2.19 (q, J=9 Hz, 1H), 2.31 (m, 2H), 2.85 (m, 2H), 3.01 (m, 1H), 3.23 (td, J=8, 3 Hz, 1H), 7.47 (dd, J=8, 2 Hz, 1H), 7.51 (d, J=2 Hz, 1H), 8.71 (d, J=8 Hz, 1H), 9.92 (s, 1H), 11.31 (s, 1H); MS (DCI/NH$_3$) m/z 317 (M+H)$^+$.

Example 54E 2-amino-5-{2-[(2R)-2-methyl-1-pyrrolidinyl]ethyl}benzaldehyde

The product from Example 54D (2.46 g, 7.8 mmol) in 3M HCl (40 mL) was heated at 80° C. for 4 hours, allowed to cool to room temperature, and carefully poured into a mixture of 1M NaOH (250 mL) and dichloromethane (75 mL). The layers were separated and the aqueous layer was extracted with dichloromethane (2 times, 75 mL). The combined dichloromethane layers were dried (MgSO$_4$), filtered, and the filtrate was concentrated. The residue was purified by chromatography on silica gel eluting with a gradient of 2%, 3.5% and 5% (9:1 MeOH:conc NH$_4$OH) in dichloromethane to provide the title compound. $^1$H NMR (300 MHz, CDCl$_3$) δ 1.12 (d, J=6 Hz, 3H), 1.50 (m, 1H), 1.76 (m, 2H), 1.93 (m, 1H), 2.25 (m, 3H), 2.76 (m, 2H), 2.99 (m, 1H), 3.25 (td, J=9, 3 Hz, 1H), 5.99 (s, 2H), 6.60 (d, J=8 Hz, 1H), 7.19 (dd, J=8, 2 Hz, 1H), 7.31 (d, J=2 Hz, 1H), 9.85 (s, 1H); MS (DCI/NH$_3$) m/z 233 (M+H)$^+$.

Example 54F

6-{2-[(2R)-2-methyl-1-pyrrolidinyl]ethyl}-2-(3-pyridinyl)quinoline

The product from Example 54E (32.5 mg, 0.14 mmol) and 3-acetylpyridine (17 mg, 0.14 mmol) were combined in ethanol (2 mL) and treated with one drop of a saturated solution of potassium hydroxide in ethanol and heated at 80° C. for 16 hours. The mixture was allowed to cool to room temperature and concentrated. The residue was purified by chromatography on silica gel eluting with a gradient 10:1:1 to 6:1:1 to 4:1:1 ethyl acetate:formic acid:water. The fractions containing the product were collected, concentrated, and the residue repurified by chromatography on silica gel eluting with a gradient of 2%, 3.5% and 5% (9:1 MeOH:conc NH$_4$OH) in dichloromethane to provide the title compound. $^1$H NMR (300 MHz, CD$_3$OD) δ 1.17 (d, J=6 Hz, 3H), 1.47 (m, 1H), 1.82 (m, 2H), 2.02 (m, 1H), 2.35 (q, J=9 Hz, 1H), 2.47 (m, 2H), 3.04 (m, 2H), 3.19 (m, 2H), 7.62 (dd, J=8, 5 Hz, 1H), 7.72 (dd, J=9, 2 Hz, 1H), 7.82 (d, J=2 Hz, 1H), 8.04 (d, J=9 Hz, 1H), 8.08 (d, J=9 Hz, 1H), 8.40 (d, J=9 Hz, 1H), 8.60 (dt, J=8, 2 Hz, 1H), 8.64 (dd, J=5, 1 Hz, 1H), 9.32 (d, J=1 Hz, 1H); MS (DCI/NH$_3$) m/z 318 (M+H)$^+$.

Example 55

6-{2-[(2R)-2-methyl-1-pyrrolidinyl]ethyl}-2-(4-pyridinyl)quinoline

The title compound was prepared using the procedure described in Example 54F substituting 4-acetylpyridine acid for 3-acetylpyridine. $^1$H NMR (300 MHz, CDCl$_3$) δ 1.14 (d, J=6 Hz, 3H), 1.48 (m, 1H), 1.78 (m, 2H), 1.96 (m, 1H), 2.25

(q, J=9 Hz, 1H), 2.42 (m, 2H), 3.09 (m, 3H), 3.30 (td, J=9, 3 Hz, 1H), 7.66 (m, 2H), 7.89 (d, J=9 Hz, 1H), 8.05 (dd, J=4, 2 Hz, 2H), 8.12 (d, J=9 Hz, 1H), 8.23 (dd, J=9, 1 Hz, 1H), 8.78 (dd, J=4, 2 Hz, 2H); MS (DCI/NH$_3$) m/z 318 (M+H)$^+$.

Example 56

6-{2-[(2R)-2-methyl-1-pyrrolidinyl]ethyl}-2-(2-pyridinyl)quinoline

The title compound was prepared using the procedure described in Example 54F substituting 2-acetylpyridine acid for 3-acetylpyridine. $^1$H NMR (300 MHz, CDCl$_3$) δ 1.14 (d, J=6 Hz, 3H), 1.46 (m, 1H), 1.77 (m, 2H), 1.94 (m, 1H), 2.25 (q, J=9 Hz, 1H), 2.40 (m, 2H), 3.03 (m, 2H), 3.14 (m, 1H), 3.30 (td, J=9, 3 Hz, 1H), 7.35 (ddd, J=8, 5, 1 Hz, 1H), 7.62 (dd, J=9, 2 Hz, 1H), 7.67 (d, J=1 Hz, 1H), 7.86 (td, J=8, 2 Hz, 1H), 8.10 (d, J=9 Hz, 1H), 8.22 (d, J=9 Hz, 1H), 8.53 (d, J=9 Hz, 1H), 8.63 (d, J=8 Hz, 1H), 8.73 (m, 1H); MS (DCI/NH$_3$) m/z 318 (M+H)$^+$.

Example 57

6-{2-[(2R)-2-methyl-1-pyrrolidinyl]ethyl}-2-(1,3-thiazol-2-yl)quinoline

The product from Example 54E (46 mg, 0.20 mmol) and 1-(1,3-thiazol-2-yl)ethanone (52 mg, 0.41 mmol) were combined in ethanol 0.4 mL and treated with one drop of a saturated solution of potassium hydroxide in ethanol and heated at 80° C. for 16 hours. The mixture was allowed to cool to room temperature and concentrated. The residue was purified by chromatography on silica gel eluting with a gradient of 2% and 3.5% (9:1 MeOH:conc NH$_4$OH) in dichloromethane to provide the title compound. $^1$H NMR (300 MHz, CDCl$_3$) δ 1.13 (d, J=6 Hz, 3H), 1.46 (m, 1H), 1.77 (m, 2H), 1.93 (m, 1H), 2.24 (q, J=9 Hz, 1H), 2.39 (m, 2H), 3.01 (m, 2H), 3.11 (m, 1H), 3.29 (td, J=9, 3 Hz, 1H), 7.48 (d, J=3 Hz, 1H), 7.63 (m, 2H), 7.97 (d, J=3 Hz, 1H), 8.06 (d, J=9 Hz, 1H), 8.19 (d, J=9 Hz, 1H), 8.31 (d, J=9 Hz, 1H); (DCI/NH$_3$) m/z 324 (M+H)$^+$.

Example 58

2-(2,4-dimethyl-1,3-thiazol-5-yl)-6-{2-[(2R)-2-methyl-1-pyrrolidinyl]ethyl}quinoline The title compound was prepared using the procedure described in Example 57 substituting 1-(2,4-dimethyl-1,3-thiazol-5-yl)ethanone for 1-(1,3-thiazol-2-yl)ethanone. $^1$H NMR (300 MHz, CDCl$_3$) δ 1.13 (d, J=6 Hz, 3H), 1.48 (m, 1H), 1.76 (m, 2H), 1.94 (m, 1H), 2.24 (q, J=9 Hz, 1H), 2.39 (m, 2H), 2.72 (s, 3H), 2.75 (s, 3H), 3.01 (m, 2H), 3.12 (m, 1H), 3.29 (td, J=9, 2 Hz, 1H), 7.62 (m, 3H), 7.99 (d, J=9 Hz, 1H), 8.11 (d, J=9 Hz, 1H); (DCI/NH$_3$) m/z 352 (M+H)$^+$.

Example 59

6-{2-[(2R)-2-methyl-1-pyrrolidinyl]ethyl}-2-(2-pyrazinyl)quinoline

The title compound was prepared using the procedure described in Example 57 substituting 1-(2-pyrazinyl)ethanone for 1-(1,3-thiazol-2-yl)ethanone. $^1$H NMR (300 MHz, CDCl$_3$) δ 1.14 (d, J=6 Hz, 3H), 1.46 (m, 1H), 1.78 (m, 2H), 1.94 (m, 1H), 2.25 (q, J=9 Hz, 1H), 2.40 (m, 2H), 3.05 (m, 2H), 3.16 (m, 1H), 3.30 (td, J=9, 3 Hz, 1H), 7.65 (dd, J=8, 2 Hz, 1H), 7.68 (br. s., 1H). 8.13 (d, J=8 Hz, 1H), 8.24 (d, J=8 Hz, 1H), 8.46 (d, J=9 Hz, 1H), 8.63 (d, J=2 Hz, 1H), 8.66 (dd, J=3, 2 Hz, 1H), 9.86 (d, J=1 Hz, 1H); (DCI/NH$_3$) m/z 319 (M+H)$^+$.

Example 60

1-[6-(6-{2-[(2R)-2-methyl-1-pyrrolidinyl]ethyl}-2-quinolinyl)-2-pyridinyl}ethanone The title compound was prepared using the procedure described in Example 57 substituting 2,6-diacetylpyridine for 1-(1,3-thiazol-2-yl)ethanone. $^1$H NMR (300 MHz, CDCl$_3$) δ 1.14 (d, J=6 Hz, 3H), 1.48 (m, 1H), 1.78 (m, 2H), 1.95 (m, 1H), 2.26 (q, J=9 Hz, 1H), 2.41 (m, 2H), 2.88 (s, 3H), 3.04 (m, 2H), 3.17 (m, 1H), 3.31 (td, J=9, 3 Hz, 1H), 7.64 (dd, J=9, 2 Hz, 1H), 7.69 (d, J=2 Hz, 1H), 8.00 (t, J=8 Hz, 1H), 8.10 (m, 2H), 8.25 (d, J=9 Hz, 1H), 8.66 (d, J=9 Hz, 1H), 8.88 (dd, J=8, 1 Hz, 1H); (DCI/NH$_3$) m/z 360 (M+H)$^+$.

Example 61

4-(2-{2-[(2R)-2-methyl-1-pyrrolidinyl]ethyl}-6-quinoxalinyl)benzonitrile and 4-(3-{2-[(2R)-2-methyl-1-pyrrolidinyl]ethyl}-6-quinoxalinyl)benzonitrile Example 61A 4-bromo-1,2-benzenediamine 4-Bromo-2-nitroaniline (10 g, 46 mmol) in THF (120 mL) was treated with 1% Pt/C (1.0 g) and hydrogenated at room temperature under 40 psi of H$_2$ pressure. After 2 hours, the reaction was filtered and the filtrate concentrated to provide the title compound which was used without further purification in the next step. MS 188 (M+H)$^+$; $^1$H NMR (400 MHz, CDCl$_3$) δ 6.77–6.81 (m, 2H), 6.54 (d, J=8.4 Hz, 1H), 3.28 (br, 4H).

Example 61B 7-bromo-2-methylquinoxaline and 6-bromo-2-methylquinoxaline

The product from Example 61A (9.4 g, 50 mmol) in acetonitrile (100 mL) was treated with 40% aqueous pyruvic aldehyde (11.0 mL, 60 mmol) dropwise. After stirring at room temperature for 2 hours, the mixture was concentrated and the residue was suspended in IPAc (100 mL) and filtered. The filtrate was washed with 20% brine, dried with Na$_2$SO$_4$, filtered, and the filtrate was concentrated. The residue was purified by silica gel column chromatography eluting with heptane:EtOH:MeOH (8:2:1) to provide the title compounds. MS 224 (M+H)$^+$; $^1$H NMR (400 MHz, CDCl$_3$) δ 8.73 (s, 1H), 8.72 (s, 1H), 8.23 (d, J=2.2 Hz, 1H), 8.18 (d, J=2.1 Hz, 1H), 7.75–7.93 (m, 4H), 2.78 (s, 3H), 2.76 (s, 3H); $^{13}$C NMR (400 MHz, CDCl$_3$) δ 154.32, 153.73, 146.34, 145.83, 142.28, 141.17, 140.45, 139.34, 133.17, 132.15, 131.15, 130.75, 130.16, 129.71, 123.66, 122.38, 22.89.

Example 61C

4-(2-methyl-6-quinoxalinyl)benzonitrile and

4-(3-methyl-6-quinoxalinyl)benzonitrile

4-Cyanophenylboronic acid (588 mg, 4.0 mmol), cesium carbonate (2.2 g, 7.0 mmol), and cesium fluoride (608 mg, 4.0 mmol) were combined in $H_2O$ (15 mL) and treated with the products from Example 61B (446 mg, 2.0 mmol) in toluene (10 mL) and heated at 80° C. for 3 hours. The reaction mixture was allowed to cool to room temperature and filtered through a pad of celite. The filtrate was partitioned between IPAc (60 mL) and $H_2O$ (50 mL). The organic layer was separated, washed with 20% brine, dried with $Na_2SO_4$, filtered, and the filtrate was concentrated under vacuum to provide the title compounds which were used in the next step without further purification. MS 246 $(M+H)^+$; $^1H$ NMR (400 MHz, $CDCl_3$) δ 8.71 (s, 1H), 8.69 (s, 1H), 8.02–8.20 (m, 4H), 7.84–7.90 (m, 2H), 7.70–7.76 (m, 8H), 2.73 (s, 6H); $^{13}C$ NMR (400 MHz, $CDCl_3$) δ 154.34, 154.10, 146.47, 147.17, 143.80, 142.93, 141.74, 140.62, 140.39, 140.18, 139.16, 132.49, 130.16, 129.74, 129.25, 128.71, 128.63, 128.06, 127.77, 127.74, 127.66, 127.59, 127.22, 126.73, 118.39, 118.37, 111.61, 111.51, 22.96.

Example 61D

4-(2-{2-[(2R)-2-methyl-1-pyrrolidinyl]ethyl}-6-quinoxalinyl)benzonitrile and

4-(3-{2-[(2R)-2-methyl-1-pyrrolidinyl]ethyl}-6-quinoxalinyl)benzonitrile (2R)-2-Methylpyrrolidine hydrochloride 5 (973 mg, 8.0 mmol) and 37% aqueous solution of formaldehyde (0.57 mL, 7.0 mmol) were combined in EtOH (20 mL) and heated in a sealed tube at 85° C. for 1 hour. The mixture was allowed to cool to room temperature, treated with the products from Example 61C (500 mg, 2.0 mmol), and heated at 85° C. overnight. The mixture was allowed to cool to room and concentrated to dryness under vacuum. The residue was partitioned between IPAc (50 mL) and 20% brine (40 mL). The organic layer was separated, dried with $Na_2SO_4$, filtered, and the filtrate was concentrated under vacuum. The residue was purified by silica gel column chromatography eluting with heptane:acetone:$CH_2Cl_2$:$Et_3N$ (60:40:3:1) to provide the title compounds. MS 343 $(M+H)^+$; $^1H$ NMR (400 MHz, $CDCl_3$) δ 8.74 (s, 1H), 7.72 (s, 1H), 8.16 (m, 2H), 8.06 (m, 2H), 7.85 (m, 2H), 7.70 (m, 4H), 3.17 (m, 8H), 2.52 (m, 2H), 2.31 (m, 2H), 2.17 (m, 2H), 1.83 (m, 2H), 1.65 (m, 4H), 1.32 (m, 2H). $^{13}C$ NMR (400 MHz, $CDCl_3$) δ 156.63, 156.41, 146.45, 145.16, 143.73, 143.70, 141.75, 141.53, 140.81, 140.60, 139.89, 139.04, 132.38, 129.66, 129.36, 128.42, 127.68, 127.65, 127.55, 137.13, 126.86, 118.29, 111.48, 111.40, 59.87, 53.93, 52.89, 35.83, 32.90, 21.98, 19.25.

Example 62

7-(2,6-difluoro-3-pyridinyl)-3-{2-[(2R)-2-methyl-1-pyrrolidinyl]ethyl}isoquinoline

Example 62A methyl 5-bromo-2-iodobenzoate

To a stirred slurry of methyl 2-iodo-benzoate (5.0 g, 0.019 mol) and N-bromosuccinimide (3.74 g, 0.021 mol) in acetic acid (10 mL) was added concentrated $H_2SO_4$ (10 mL) dropwise, keeping the temperature at 20–40° C. The mixture was stirred at room temperature for 88 hours and then heated at 50° C. for 4 hours. The mixture was cooled to 10° C., treated with 40 g of ice water, and extracted with 50 mL of $CH_2Cl_2$. The organic phase was washed in succession with 2×50 mL 5% $NaHCO_3$, 50 mL 10% $Na_2S_2O_3$, 50 mL water, and concentrated to colorless oil. The residue was purified by column chromatography (silica gel, 10:90 EtOAc:hexane) to provide the title compound. $^1H$ NMR ($CDCl_3$, 400 MHz) δ 7.92 (d, J=4 Hz, 1H), 7.83 (d, J=8 Hz, 1H), 7.27 (dd, J=8, 4 Hz, 1H), 3.92 (s, 3H); MS (DCI/$NH_3$) $[M+NH_4]^+$ at 358, $[M+NH_3—NH_4]^+$ at 375.

Example 62B

(5-bromo-2-iodophenyl)methanol

To a stirred mixture of $NaBH_4$ (11.18 g, 0.296 mol) in EtOH (200 mL) at 5° C. was added the product from Example 62A (50.4 g, 0.148 mol) in THF (100 mL). The mixture was alowed to warm to room temperature and stirred for 18 hours. The mixture was treated with additional $NaBH_4$ (8.4 g, 0.222 mol) and was stirred for 22 hours. The mixture was cooled to 0° C., treated with 100 mL of 15% aqueous citric acid slowly, and extracted with 600 mL of $CH_2Cl_2$. The organic phase was washed with 200 mL of 15% NaCl and concentrated to provide the title compound. $^1H$ NMR ($CDCl_3$, 400 MHz) δ 7.64 (d, J=8 Hz, 1H), 7.61 (d, J=4 Hz, 1H), 7.12 (dd, J=4, 8 Hz, 1H), 4.63 (d, J=8 Hz, 2H), 1.98 (t, J=8 Hz, 1H). MS (DCI/$NH_3$) $[M+NH_4]^+$ at 330, $[M+NH_4—H_2O]^+$ at 312.

Example 62C

5-bromo-2-iodobenzaldehyde

A solution of oxalyl chloride (1.53 g, 0.012 mol) in $CH_2Cl_2$ (15 mL) was cooled to –70° C., and DMSO (1.41 g, 0.018 mol) in $CH_2Cl_2$ (15 mL) was added at –65 to –70° C. The mixture was stirred under nitrogen for 10 minutes at –70° C. and then treated with the product from Example 62B (2.35 g, 7.5 mmol) in 60 mL $CH_2Cl_2$. The slurry was stirred at –65° C. for 15 minutes and treated with triethylamine (3.8 g, 0.037 mol). The mixture was allowed to warm to –10° C. over 1 hour. The mixture was treated with 20 mL of water and allowed to warm to room temperature. The organic layer was separated and concentrated to provide the title compound. $^1H$ NMR ($CDCl_3$, 400 MHz) δ 9.97 (s, 1H), 7.97 (d, J=4 Hz, 1H), 7.79 (d, J=8 Hz, 1H), 7.40 (dd, J=4, 8 Hz, 1H). MS (DCI/$NH_3$) $[M+NH_4]^+$ at 328.

Example 62D

N-[(1E)-(5-bromo-2-iodophenyl)methylene]-N-(tert-butyl)amine

The product from Example 62C (2.28 g, 7.3 mmol) in THF (10 mL) was treated with t-butylamine (1.61 g, 22.0 mmol) and stirred under nitrogen at room temperature for 40 hours. The mixture was concentrated under reduced pressure and the residue was dissolved in 30 mL of methylene chloride. The methylene chloride was washed with 10 mL water and concentrated to provide the title compound which was used in the next step without further purification. $^1H$ NMR ($CDCl_3$, 400 MHz) δ 8.29 (s, 1H), 8.05 (d, J=4 Hz, 1H), 7.66 (d, J=8 Hz, 1H), 7.19 (dd, J=4, 8 Hz, 1H), 1.34 (s, 9H). MS (DCI/$NH_3$) 366 $[M+H]^+$.

Example 62E 2-(7-bromo-3-isoquinolinyl)ethanol

The product from Example 62D (1.3 g, 3.6 mmol), 3-butyn-1-ol (0.3 g, 4.3 mmol), CuI (0.04 g, 0.2 mmol), and PdCl$_2$(PPh$_3$)$_2$ (0.08 g, 0.1 mmol) were combined in toluene (15 mL). The mixture was treated with diisopropylamine (0.54 g, 5.3 mmol) and stirred at room temperature for 4 hours. The mixture was then treated with additional CuI (0.07 g, 0.4 mmol) and heated at 100° C. for 4 hours. The mixture was allowed to cool to room temperature, diluted with 30 mL CH$_2$Cl$_2$, and filtered. The filtrate was washed with 2×10 mL 15% NaCl and concentrated under reduced pressure. The residue was purified by column chromatography (silica gel, 10:90 MeOH:CHCl$_3$) to provide the title compound. $^1$H NMR (CDCl$_3$, 400 MHz) δ 9.08 (s, 1H), 8.09 (d, J=4 Hz, 1H), 7.73 (dd, J=8, 4 Hz, 1H), 7.63 (d, J=8 Hz, 1H), 7.48 (s, 1H), 4.08 (t, J=4 Hz, 2H), 3.92 (s, 1H), 3.15 (t, J=4 Hz, 2H). $^{13}$C NMR (CDCl$_3$, 100 MHz) δ 153.8, 150.3, 134.5, 133.8, 129.4, 127.6, 120.0, 118.6, 62.3, 39.4. MS (DCI/NH$_3$) 252, 254 [M+H]$^+$.

Example 62F 7-bromo-3-{2-[(2R)-2-methyl-1-pyrrolidinyl]ethyl}isoquinoline

The product from Example 62E (0.5 g, 2.0 mmol) and triethylamine (0.5 g, 4.9 mmol) were combined in THF (15 mL) at −15° C. The mixture was treated with methanesulfonyl chloride (0.24 g, 2.1 mmol) and stirred at 0–10° C. for 2 hours. The mixture was treated with additional methanesulfonyl chloride (0.2 mmol) and stirred at room temperature for 16 hours. The mixture was treated with (2R)-2-methylpyrrolidine hydrochloride (0.72 g, 6.0 mmol) and K$_2$CO$_3$ (0.27 g, 2.0 mmol) in acetonitrile (25 mL) and then the mixture was heated at 60° C. for 20 hours. The mixture was allowed to cool to room temperature and was concentrated under reduced pressure. The residue was dissolved in 20 mL CH$_2$Cl$_2$, washed with 5 mL of water and concentrated under reduced pressure. The residue was purified by column chromatography (silica gel, 10:90 MeOH:CHCl$_3$) to provide the title compound. $^1$H NMR (CDCl$_3$, 400 MHz) δ 9.10 (s, 1H), 8.09 (d, J=4 Hz, 1H), 7.72 (dd, J=12, 4 Hz, 1H), 7.64 (d, J=12 Hz, 1H), 7.58 (s, 1H), 3.46–3.40 (m, 2H), 3.34–3.29 (m, 2H), 2.91–1.85 (m, 1H), 2.81–2.68 (m, 1H), 2.59–2.49 (m, 1H), 2.11–2.02 (m, 1H), 2.00–1.91 (m, 1H), 1.88–1.79 (m, 1H), 1.71–1.61 (m, 1H), 1.32 (d, J=8 Hz, 3H). $^{13}$C NMR (CDCl$_3$, 100 MHz) δ 152.5, 150.6, 134.5, 133.6, 129.2, 127.8, 127.7, 120.0, 118.7, 61.7, 53.7, 53.4, 36.0, 32.4, 21.9, 17.9. MS (DCI/NH$_3$) 319, 321 [M+H]$^+$.

Example 62G 7-(2,6-difluoro-3-pyridinyl)-3-{2-[(2R)-2-methyl-1-pyrrolidinyl]ethyl}isoquinolin The product from Example 62F (0.30 g, 0.9 mmol), 2,6-difluoro-3-pyridineboronic acid (0.3 g, 1.9 mmol), 2-(dicyclohexylphosphino)biphenyl (66 mg, 0.2 mmol), and PdCl$_2$(PPh$_3$)$_2$ (66 mg, 0.1 mmol) were combined in isopropanol (15 mL). The mixture was treated with a solution of Na$_2$CO$_3$ (0.15 g, 1.4 mmol, in 5 mL water) and heated at 65° C. for 16 hours. After cooling to room temperature, the mixture was diluted with 20 mL of CH$_2$Cl$_2$ and filtered. The filtrate was washed with 10 mL of 15% NaCl and concentrated under reduced pressure. The residue was purified by column chromatography (silica gel, 10:90:1 MeOH:CHCl$_3$:Et$_3$N) to provide the title compound. $^1$H NMR (CDCl$_3$, 400 MHz) δ 9.25 (s, 1H), 8.11–8.05 (m, 2H), 7.85 (d, J=10 Hz, 1H), 7.81–7.78 (m, 1H), 7.58 (s, 1H), 6.98 (dd, J=10 Hz, 1H), 3.34–3.27 (m, 2H), 3.22–3.15 (m, 2H), 2.65–2.56 (m, 1H), 2.45–2.40 (m, 1H), 2.33–2.27 (m, 1H), 2.01–1.91 (m, 1H), 1.87–1.80 (m, 1H), 1.77–1.70 (m, 1H), 1.52–1.42 (m, 1H), 1.16 (d, J=8 Hz, 3H); $^{13}$C NMR (CDCl$_3$, 400 MHz) δ 158.9, 154.6, 151.9, 144.6, 144.5, 135.6, 130.7, 130.2, 127.3, 126.7, 126.6, 118.1, 1006.8, 106.5, 60.2, 54.2, 54.1, 37.5, 32.9, 22.0, 19.2.

Example 63

3-{2-[(2R)-2-methyl-1-pyrrolidinyl]ethyl}-7-(3-pyridinyl)isoquinoline

Example 63A

2-[7-(3-pyridinyl)-3-isoquinolinyl]ethanol

The product from Example 62E (0.3 g, 1.2 mmol), 3-pyridineboronic acid (0.22 g, 1.8 mmol), 2-(dicyclohexylphosphino)biphenyl (80 mg, 0.2 mmol), and PdCl$_2$(PPh$_3$)$_2$ (80 mg, 0.1 mmol) were combined in isopropanol (15 mL) and treated with a solution of Na$_2$CO$_3$ (0.19 g, 1.8 mmol) in water (5 mL) and heated at 65° C. for 16 hours. After cooling to room temperature, the mixture was diluted with 20 mL of CH$_2$Cl$_2$ and filtered. The filtrate was washed with 10 ml 15% NaCl and concentrated under reduced pressure. The residue was purifed by column chromatography (silica gel, 10:90 MeOH:CHCl$_3$) to provide the title compound. $^1$H NMR (CDCl$_3$, 400 MHz) δ 9.24 (s, 1H), 8.95 (d, J=4 Hz, 1H), 8.65 (dd, J=2, 8 Hz, 1H), 8.13 (bs, 1H), 7.98 (2 m, 1H), 7.91–7.86 (m, 2H), 7.55 (s, 1H), 7.44–7.41 (2d, 1H), 4.11 (t, J=4 Hz, 2H), 3.19 (t, J=4 Hz, 2H); $^{13}$C NMR (CDCl$_3$, 400 MHz) δ 153.9, 151.7, 148.6, 148.0, 135.9, 135.5, 135.4, 134.2, 129.5, 127.2, 126.9, 125.4, 123.5, 118.5, 62.4, 39.4.

Example 63B

3-{2-[(2R)-2-methyl-1-pyrrolidinyl]ethyl}-7-(3-pyridinyl)isoquinoline

The product from Example 63A (0.25 g, 1.0 mmol) and triethylamine (0.15 g, 1.5 mmol) in methylene chloride (10 mL) at −5° C. were treated with methanesulfonyl chloride (0.12 g, 1.2 mmol) and stirred at 0° C. for 2 hours and then stirred at room temperature for 15 hours. The mixture was concentrated under reduced pressure and the residue was treated with K$_2$CO$_3$ (0.21 g, 1.5 mmol) and (2R)-2-methylpyrrolidine (0.13 g, 1.5 mmol) in acetonitrile (15 mL), and then heated at 60° C. for 5 hours. The mixture was concentrated under reduced pressure and the residue was dissolved in 30 mL methylene chloride, washed with 10 mL 15% NaCl, and concentrated under reduced pressure. The residue was purified by column chromatography (silica gel, 10:90:1 MeOH:CHCl$_3$:Et$_3$N) to provide the title compound. $^1$H NMR (CDCl$_3$, 400 MHz) δ 9.27 (s, 1H), 8.95 (m, 1H), 8.64 (dd, J=2, 4 Hz, 1H), 8.12 (s, 1H), 7.98 (m, 1H), 1.90–1.86 (m, 2H), 7.56 (s, 1H), 7.44–7.40 (m, 1H), 3.37–3.28 (m, 2H), 3.26–3.18 (m, 2H), 2.68–2.61 (m, 2H), 2.51–2.46 (m, 1H), 2.38–2.31 (m, 1H), 2.00–1.93 (m, 1H), 1.88–1.82 (m, 1H), 1.80–1.72 (m, 1H), 1.55–1.46 (m, 1H), 1.14 (d, 3H); $^{13}$C NMR (CDCl$_3$, 400 MHz) δ 9.27 153.8, 151.9, 148.4, 147.9, 135.6, 135.5, 135.4, 134.1, 129.1, 127.0, 126.9, 125.2, 123.4, 118.2, 60.4, 54.1, 54.0, 37.2, 32.8, 21.9, 19.0.

Example 64

3-(benzyloxy)-2-methyl-6-{2-[(2R)-2-methyl-1-pyrrolidinyl]ethyl}quinoline

The title compound was prepared using the procedure described in Example 57 substituting 1-(benzyloxy)acetone for 1-(1,3-thiazol-2-yl)ethanone. $^1$H NMR (300 MHz, CDCl$_3$) δ 1.13 (d, J=6.1 Hz, 3H), 1.46 (m, 1H), 1.75 (m, 1H), 1.94 (m, 1H), 2.23 (q, J=8.8 Hz, 1H), 2.37 (m, 2H), 2.70 (s, 3H), 2.97 (m, 2H), 3.11 (m, 1H), 3.28 (m, 1H), 5.20 (s, 2H), 7.31 (s, 1H), 7.35–7.46 (m, 5H), 7.50 (m, 3H), 7.89 (d, J=8.5 Hz, 1H); (DCI/NH$_3$) m/z 361 (M+H)$^+$.

Example 65

2-cyclopropyl-6-{2-[(2R)-2-methyl-1-pyrrolidinyl]ethyl}quinoline

The title compound was prepared using the procedure described in Example 57 substituting 1-cyclopropylethanone for 1-(1,3-thiazol-2-yl)ethanone. $^1$H NMR (300 MHz, CDCl$_3$) δ 1.02–1.16 (m, 4H), 1.12 (d, J=6.1 Hz, 3H), 1.45 (m, 1H), 1.76 (m, 2H), 1.93 (m, 1H), 2.23 (m, 2H), 2.37 (m, 2H), 2.98 (m, 2H), 3.10 (m, 1H), 3.28 (m, 1H), 7.13 (d, J=8.5 Hz, 1H), 7.50–7.56 (m, 2H), 7.88 (d, J=8.5 Hz, 1H), 7.93 (d, J=8.5 Hz, 1H); (DCI/NH$_3$) m/z 281 (M+H)$^+$.

Example 66

4-(6-{2-[(2R)-2-methyl-1-pyrrolidinyl]ethyl}-2-quinolinyl)benzonitrile

The title compound was prepared using the procedure described in Example 57 substituting 4-acetylbenzonitrile for 1-(1,3-thiazol-2-yl)ethanone. $^1$H NMR (400 MHz, CDCl$_3$) δ 1.13 (d, J=5.8 Hz, 3H), 1.46 (m, 1H), 1.73 (m, 1H), 1.83 (m, 1H), 1.95 (m, 1H), 2.25 (q, J=8.6 Hz, 1H), 2.40 (m, 2H), 3.03 (m, 2H), 3.14 (m, 1H), 3.29 (dt, J=8.4, 2.3 Hz, 1H), 7.66 (m, 2H), 7.81 (d, J=8.6 Hz, 2H), 7.86 (d, J=8.3 Hz, 1H), 8.09 (d, J=8.6 Hz, 1H), 8.22 (d, J=8.29 Hz, 1H), 8.29 (d, J=8.59 Hz, 2H); (DCI/NH$_3$) m/z 342 (M+H)$^+$.

Example 67

2,6-dimethyl-5-(6-{2-[(2R)-2-methyl-1-pyrrolidinyl]ethyl}-2-quinolinyl)nicotinonitrile The title compound was prepared using the procedure described in Example 57 substituting 5-acetyl-2,6-dimethylnicotinonitrile for 1-(1,3-thiazol-2-yl)ethanone. $^1$H NMR (300 MHz, CDCl$_3$) δ 1.14 (d, J=6.10 Hz, 3H), 1.48 (m, 1H), 1.77 (m, 2H), 1.95 (m, 1H), 2.25 (q, J=8.70 Hz, 1H), 2.40 (m, 2H), 2.69 (s, 3H), 2.82 (s, 3H), 3.10 (m, 3H), 3.30 (m, 1H), 7.50 (d, J=8.48 Hz, 1H), 7.68 (dd, J=2.03, 8.48 Hz, 1H), 7.71 (bs, 1H), 8.06 (d, J=8.48 Hz, 1H), 8.06 (s, 1H), 8.22 (d, J=8.48 Hz, 1H); (DCI/NH$_3$) m/z 371 (M+H)$^+$.

Example 68

2-(3-methyl-2-pyrazinyl)-6-{2-[(2R)-2-methyl-1-pyrrolidinyl]ethyl}quinoline

The title compound was prepared using the procedure described in Example 57 substituting 1-(3-methyl-2-pyrazinyl)ethanone for 1-(1,3-thiazol-2-yl)ethanone. $^1$H NMR (300 MHz, CDCl$_3$) δ 1.14 (d, J=6.10 Hz, 3H), 1.47 (m, 1H), 1.77 (m, 2H), 1.95 (m, 1H), 2.25 (q, J=8.81 Hz, 1H), 2.41 (m, 2H), 2.94 (s, 3H), 3.10 (m, 3H), 3.31 (td, J=8.39, 2.54 Hz, 1H), 7.66 (dd, J=8.65, 1.86 Hz, 1H), 7.70 (d, J=2.00 Hz, 1H), 8.02 (d, J=8.48 Hz, 1H), 8.09 (d, J=8.48 Hz, 1H), 8.25 (d, J=8.82 Hz, 1H), 8.53 (m, 2H); (DCI/NH$_3$) m/z 333 (M+H)$^+$.

Example 69 ethyl 5-(6-{2-[(2R)-2-methyl-1-pyrrolidinyl]ethyl}-2-quinolinyl)-3-isoxazolecarboxylate The title compound was prepared using the procedure described in Example 57 substituting ethyl 5-acetyl-3-isoxazolecarboxylate for 1-(1,3-thiazol-2-yl)ethanone. $^1$H NMR (300 MHz, CDCl$_3$) δ 1.13 (d, J=6.10 Hz, 3H), 1.45 (m, 1H), 1.46 (t, J=7.12 Hz, 3H), 1.77 (m, 2H), 1.95 (m, 1H), 2.24 (q, J=8.48 Hz, 1H), 2.38 (m, 2H), 2.97–3.22 (m, 3H), 3.29 (m, 1H), 4.50 (q, J=7.12 Hz, 2H), 7.46 (s, 1H), 7.68 (m, 2H), 8.02 (d, J=8.48 Hz, 1H), 8.09 (d, J=8.82 Hz, 1H), 8.25 (d, J=8.48 Hz, 1H); (DCI/NH$_3$) m/z 380 (M+H)$^+$.

Example 70

5-(6-{2-[(2R)-2-methyl-1-pyrrolidinyl]ethyl}-2-quinolinyl)-2-thiophenecarbonitrile The title compound was prepared as the major product using the procedure described in Example 57 substituting 5-acetyl-2-thiophenecarbonitrile for 1-(1,3-thiazol-2-yl)ethanone. $^1$H NMR (300 MHz, CDCl$_3$) δ 1.13 (d, J=5.76 Hz, 3H), 1.46 (m, 1H), 1.76 (m, 2H), 1.95 (m, 1H), 2.23 (q, J=8.59 Hz, 1H), 2.40 (m, 2H), 3.01 (m, 2H), 3.14 (m, 1H), 3.28 (dt, 1H), 7.64 (m, 4H), 7.77 (d, J=8.81 Hz, 1H), 8.01 (d, J=9.15 Hz, 1H), 8.15 (d, J=9.15 Hz, 1H); (DCI/NH$_3$) m/z 348 (M+H)$^+$.

Example 71 ethyl 5-(6-{2-[(2R)-2-methyl-1-pyrrolidinyl]ethyl}-2-quinolinyl)-2-thiophenecarboximidoate The title compound was prepared as a minor product using the procedure described in Example 57 substituting 5-acetyl-2-thiophenecarbonitrile for 1-(1,3-thiazol-2-yl)ethanone. $^1$H NMR (300 MHz, CDCl$_3$) δ 1.13 (d, J=6.10 Hz, 3H), 1.44 (t, J=7.12 Hz, 3H), 1.46 (m, 1H), 1.77 (m, 2H), 1.95 (m, 1H), 2.24 (q, J=8.82 Hz, 1H), 2.39 (m, 2H), 3.00 (m, 2H), 3.12 (m, 1H), 3.29 (m, 1H), 4.34 (q, J=7.46 Hz, 2H), 7.60 (m, 4H), 7.77 (d, J=8.48 Hz, 1H), 8.01 (d, J=9.16 Hz, 1H), 8.10 (d, J=8.48 Hz, 1H); (DCI/NH$_3$) m/z 394 (M+H)$^+$.

Example 72

2-(2,4-dimethyl-1,3-oxazol-5-yl)-6-{2-[(2R)-2-methyl-1-pyrrolidinyl]ethyl}quinloine The title compound was prepared using the procedure described in Example 57 substituting 1-(2,4-dimethyl-1,3-oxazol-5-yl)ethanone for 1-(1,3-thiazol-2-yl)ethanone. $^1$H NMR (300 MHz, CD$_3$OD) δ 1.20 (d, J=6.10 Hz, 3H), 1.50

(m, 1H), 1.85 (m, 2H), 2.05 (m, 1H), 2.44 (m, 1H), 2.55 (s, 3H), 2.56 (m, 2H), 2.65 (s, 3H), 3.05 (m, 2H), 3.29 (m, 2H), 7.67 (dd, J=8.65, 1.86 Hz, 1H), 7.75 (d, J=1.86 Hz, 1H), 7.80 (d, J=8.48 Hz, 1H), 7.98 (d, J=8.48 Hz, 1H), 8.29 (d, J=8.81 Hz, 1H); (DCI/NH$_3$) m/z 336 (M+H)$^+$.

Example 73 ethyl 3-methyl-5-(6-{2-[(2R)-2-methyl-1-pyrrolidinyl]ethyl}-2-quinolinyl)-4-isoxazolecarboxylate The title compound was prepared using the procedure described in Example 57 substituting ethyl 5-acetyl-3-methyl-4-isoxazolecarboxylate for 1-(1,3-thiazol-2-yl)ethanone. $^1$H NMR (300 MHz, CD$_3$OD) δ 1.18 (d, J=6.10 Hz, 3H), 1.19 (t, J=7.12 Hz, 3H), 1.48 (m, 1H), 1.82 (m, 2H), 2.03 (m, 1H), 2.37 (m, 1H), 2.52 (m, 2H), 2.53 (s, 3H), 3.07 (m, 2H), 3.21 (m, 1H), 3.31 (m, 1H), 4.29 (q, J=7.12 Hz, 2H), 7.78 (dd, J=8.82, 2.03 Hz, 1H), 7.89 (d, J=1.36 Hz, 1H), 7.98 (d, J=8.48 Hz, 1H), 8.07 (d, J=8.82 Hz, 1H), 8.45 (d, J=8.82 Hz, 1H); (DCI/NH$_3$) m/z 394 (M+H)$^+$.

Example 74

4-(7-{2-[(2R)-2-methyl-1-pyrrolidinyl]ethyl}-3-isoquinolinyl)benzonitrile

Example 74A 4-(7-bromo-3-isoquinolinyl)benzonitrile

The product from Example 62D (3.6 mmol), 4-cyanophenylacetylene (4.3 mmol), CuI (0.2 mmol), PdCl$_2$(PPh$_3$)$_2$ (0.1 mmol), and diisopropylamine (5.3 mmol) can be combined in toluene (15 mL) and processed as described in Example 62E to provide the title compound.

Example 74B

4-[7-(2-hydroxyethyl)-3-isoquinolinyl]benzonitrile

The product from Example 74A (4 mmol) is dissolved in 20 mL THF and is cooled to –60° C. under nitrogen. n-BuLi (4.4 mmol) is added dropwise, and the mixture is stirred at –60° C. for additional 30 minutes. A solution of ethylene oxide (20 mmol) in 10 ml THF is added and the mixture is allowed to warm to 10° C. and is stirred to complete the reaction. The mixture iss cooled back down to 0° C. and is slowly quenched with 2N HCl to pH=3. The solvent is removed under vacuum and the residue is dissolved in 20 mL methylene chloride, is washed with water, and is concentrated under reduced pressure. The residue is chromatographed on silica gel (5:95 MeOH:CHCl$_3$) to provide the title compound.

Example 74C 4-(7-{2-[(2R)-2-methyl-1-pyrrolidinyl]ethyl}-3-isoquinolinyl)benzonitrile The product from Example 74B, methanesulfonyl chloride, and (2R)-2-methylpyrrolidine hydrochloride are pro-cessed as described in Example 62F to provide the title compound.

Example 75

6-{2-[(2R)-2-Methyl-1-pyrrolidinyl]ethyl}-2-(4-methoxyphenyl)quinoxaline and

7-{2-[(2R)-2-Methyl-1-pyrrolidinyl]ethyl}-2-(4-methoxyphenyl)quinoxaline

Example 75A

N-(4-{2-[(2R)-2-Methyl-1-pyrrolidinyl]ethyl}phenyl)acetamide

The product from Example 54B (0.47 g, 2.3 mmol) in acetic acid:water (1:1) at 0° C. was treated with acetic anhydride (0.44 mL, 4.6 mmol) and heated at 100° C. for 45 minutes. The mixture was allowed to cool to room temperature, concentrated, and the residue was partitioned between 1 M NaOH and dichloromethane. The phases were separated and the aqueous phase was extracted with dichloromethane (3 times). The dichloromethane layers were combined, dried (MgSO$_4$), filtered, and the filtrate was concentrated to provide the title compound. $^1$H NMR (300 MHz, CDCl$_3$) δ 1.10 (d, J=6 Hz, 3H), 1.43 (m, 1H), 1.76 (m, 2H), 1.92 (m, 1H), 2.16 (s, 3H), 2.25 (m, 3H), 2.77 (m, 2H), 2.99 (m, 1H), 3.23 (td, J=9, 3 Hz, 1H), 7.16 (d, J=8 Hz, 2H), 7.40 (d, J=8 Hz, 2H); (DCI/NH$_3$) m/z 247 (M+H)$^+$.

Example 75B

N-(4-{2-[(2R)-2-methyl-1-pyrrolidinyl]ethyl}-2-nitrophenyl)acetamide

The product from Example 75A (0.58 g, 2.4 mmol) in acetic anhydride (2.2 mL) and concentrated sulfuric acid (0.16 mL) was cooled to 0° C. and treated dropwise with 90% nitric acid (0.115 mL, 2.4 mmol). After stirring at ambient temperature for 16 hours, the mixture was diluted with water, cooled to 0° C., the pH adjusted using 1 M NaOH, and extracted with dichloromethane (3 times). The combined dichloromethane layers were dried (MgSO$_4$), filtered, and the filtrate was concentrated to provide the title compound. $^1$H NMR (300 MHz, CDCl$_3$) δ 1.08 (d, J=6 Hz, 3H), 1.43 (m, 1H), 1.74 (m, 2H), 1.92 (m, 1H), 2.18 (q, J=9 Hz, 1H), 2.28 (s, 3H), 2.32 (m, 1H), 2.84 (m, 2H), 3.02 (m, 1H), 3.21 (td, J=8, 3 Hz, 1H), 7.51 (dd, J=9, 2 Hz, 1H), 8.07 (d, J=2 Hz, 1H), 8.65 (d, J=9 Hz, 1H), 10.23 (s, 1H); (DCI/NH$_3$) m/z 292 (M+H)$^+$.

Example 75C

4-{2-[(2R)-2-methyl-1-pyrrolidinyl]ethyl}-2-nitroaniline

The product from Example 75B (0.60 g, 2.1 mmol) in 3M HCl (12 mL) was heated at 80° C. for 2 hours, cooled to 0° C., the pH was adjusted by the slow addition of 1 M NaOH, and extracted with dichloromethane (4 times). The combined dichloromethane layers were dried (MgSO$_4$), filtered, and the filtrate was concentrated to provide the title compound. $^1$H NMR (300 MHz, CDCl$_3$) δ 1.13 (d, J=6 Hz, 3H), 1.47 (m, 1H), 1.77 (m, 2H), 1.95 (m, 1H), 2.29 (m, 3H), 2.76 (dd, J=9, 7 Hz, 2H), 3.00 (m, 1H), 3.25 (td, J=8, 3 Hz, 1H), 5.97 (s, 2H), 6.75 (d, J=9 Hz, 1H), 7.26 (dd, J=9, 2 Hz, 1H), 7.96 (d, J=2 Hz, 1H); (DCI/NH$_3$) m/z 250 (M+H)$^+$.

Example 75D

4-{2-[(2R)-2-methyl-1-pyrrolidinyl]ethyl}-1,2-benzenediamine

The title compound was prepared using the procedure described in Example 54B substituting the product from Example 75C for the product from Example 54A to provide the title compound. $^1$H NMR (300 MHz, CDCl$_3$) δ 1.15 (d, J=6 Hz, 3H), 1.47 (m, 1H), 1.83 (m, 3H), 2.30 (m, 3H), 2.70 (m, 2H), 3.00 (m, 1H), 3.27 (m, 5H), 6.59 (m, 3H); (DCI/NH$_3$) m/z 220 (M+H)$^+$.

Example 75E

6-{2-[(2R)-2-methyl-1-pyrrolidinyl]ethyl}quinoxaline

The product from Example 75D (14.6 mg, 0.067 mmol) was treated with 0.075 mL of a 1 M solution of glyoxal in ethanol (made by diluting 0.4 g of a 40% weight solution of glyoxal in water with ethanol to a total volume of 6.9 mL) and heated at 80° C. for 16 hours. The mixture was allowed to cool to room temperature and concentrated. The residue was chromatographed on silica gel eluting with a gradient of 2% and 3.5% (9:1 MeOH:conc NH$_4$OH) in dichloromethane to provide the title compound. $^1$H NMR (300 MHz, CD$_3$OD) δ 1.15 (d, J=6 Hz, 3H), 1.47 (m, 1H), 1.80 (m, 2H), 2.03 (m, 1H), 2.34 (q, J=9 Hz, 1H), 2.48 (m, 2H), 3.07 (m, 2H), 3.25 (m, 2H), 7.80 (dd, J=9, 2 Hz, 1H), 7.95 (d, J=2 Hz, 1H), 8.04 (d, J=9 Hz, 1H), 8.84 (d, J=2 Hz, 1H), 8.86 (d, J=2 Hz, 1H); (DCI/NH$_3$) m/z 242 (M+H)$^+$.

Example 75F

6-{2-[(2R)-2-Methyl-1-pyrrolidinyl]ethyl}-2-(4-methoxyphenyl)quinoxaline and

7-{2-[(2R)-2-Methyl-1-pyrrolidinyl]ethyl}-2-(4-methoxyphenyl)quinoxaline

The product from Example 75D and oxo(4-methoxyphenyl)acetaldehyde (chemical abstracts number 16208-17-6) is processed as described in Example 75E to provide the title compounds.

Example 76

6-{2-[(2R)-2-methyl-1-pyrrolidinyl]ethyl}-2-phenylquinoxaline and

7-{2-[(2R)-2-methyl-1-pyrrolidinyl]ethyl}-2-phenylquinoxaline

The product from Example 75D and oxo(phenyl)acetaldehyde is processed as described in Example 75E to provide the title compounds.

Example 77

6-{2-[(2R)-2-methyl-1-pyrrolidinyl]ethyl}-2-(3-pyridinyl)quinazoline

Example 77A

N-(2-formyl-4-{2-[(2R)-2-methyl-1-pyrrolidinyl]ethyl}phenyl)nicotinamide

The product from Example 54E (35 mg, 0.15 mmol) and triethylamine (0.051 mL, 0.36 mmol) were combined in dichloromethane (0.5 mL) and treated with nicotinoyl chloride hydrochloride (30 mg, 0.17 mmol). After stirring at ambient temperature for 16 hours, the mixture was concentrated and the residue purified by chromatography on silica gel eluting with a gradient of 2% and 3.5% (9:1 MeOH:conc NH$_4$OH) in dichloromethane to provide the title compound. $^1$H NMR (300 MHz, CDCl$_3$) δ 1.11 (d, J=6 Hz, 3H), 1.45 (m, 1H), 1.77 (m, 2H), 1.94 (m, 1H), 2.22 (q, J=9 Hz, 1H), 2.35 (m, 2H), 2.90 (m, 2H), 3.06 (m, 1H), 3.25 (m, 1H), 7.48 (dd, J=8, 5 Hz, 1H), 7.56 (dd, J=8, 2 Hz, 1H), 7.60 (d, J=2 Hz, 1H), 8.34 (dt, J=8, 2 Hz, 1H), 8.83 (m, 2H), 9.32 (d, J=2 Hz, 1H), 9.99 (s, 1H), 12.09 (s, 1H); MS (DCI/NH$_3$) m/z 338 (M+H)$^+$.

Example 77B

6-{2-[(2R)-2-methyl-1-pyrrolidinyl]ethyl}-2-(3-pyridinyl)quinazoline

The product from Example 77A (25 mg, 0.074 mmol) in saturated aqueous ammonium chloride (3 mL) was heated at 80° C. for 16 hours. The mixture was allowed to cool to room temperature, adjusted to pH 14 with 1 M NaOH, and extracted with dichloromethane (3 times). The combined dichloromethane layers were dried (MgSO$_4$), filtered, and the filtrate was concentrated. The residue was purified by chromatography on silica gel eluting with a gradient of 2% and 3.5% (9:1 MeOH:conc NH$_4$OH) in dichloromethane to provide the title compound. $^1$H NMR (300 MHz, CDCl$_3$) δ 1.13 (d, J=6 Hz, 3H), 1.47 (m, 1H), 1.75 (m, 2H), 1.96 (m, 1H), 2.25 (q, J=9 Hz, 1H), 2.41 (m, 2H), 3.10 (m, 3H), 3.29 (m, 1H), 7.45 (dd, J=8, 5 Hz, 1H), 7.78 (d, J=1 Hz, 1H), 7.83 (dd, J=8, 2 Hz, 1H), 8.03 (d, J=8 Hz, 1H), 8.73 (d, J=4 Hz, 1H), 8.85 (dt, J=8, 2 Hz, 1H), 9.43 (d, J=1 Hz, 1H), 9.80 (s, 1H); MS (DCI/NH$_3$) m/z 319 (M+H)$^+$.

Example 78

6-Methyl-2-{6-[2-((2R)-2-methyl-pyrrolidin-1-yl)-ethyl]-naphthalen-2-yl}-2H-pyridazin 3-one The title compound was prepared by the method of Example 31F, substituting 1-[2-(6-bromo-naphthalen-2-yl)-ethyl]-(2R)-2-methyl-pyrrolidine (Example 2B, 60 mg, 0.19 mmol) in place of 2-(6-bromo-naphthalen-2-yl)-ethanol (Example-31 E) and substituting 6-methyl-2H-pyridazin-3-one (41.5 mg, 0.38 mmol, 2 equiv.) in place of 2H-pyridazin-3-one. Column chromatography (95:5:trace dichloromethane/methanol/NH$_4$OH) provided free base product that was dissolved in Et$_2$O. HCl gas was bubbled into this solution to provide the monohydrochloride salt of the title compound (25 mg, 34% yield). $^1$H NMR (CD$_3$OD, 300 MHz) δ 8.08 (d, J=2 Hz, 1H), 7.98 (s, 1H), 7.95 (s, 1H), 7.88–7.92 (m, 1H), 7.67 (dd, J=2, 8 Hz, 1H), 7.54 (dd, J=2, 8 Hz, 1H), 7.48 (d, J=9 Hz, 1H), 7.05 (d, J=9 Hz, 1H), 3.85–3.70 (m, 2H), 3.60–3.51 (m, 1H), 3.40–3.15 (m, 4H), 2.42 (s, 3H), 2.42–2.26 (m, 1H), 2.25–1.99 (m, 2H), 1.85–1.67 (m, 1H), 1.49 (d, J=6 Hz, 3H). MS (DCI-NH$_3$) [M+H]$^+$ at 348.

Example 79

5-{6-[2-((2R)-2-Methyl-pyrrolidin-1-yl)-ethyl]-naphthalen-2-yl}-pyrimidine-2-carbonitrile Example 79A 5-Bromo-pyrimidine-2-carbonitrile A mixture of 5-bromo-2-iodopyrimidine (1.85 g, 6.49 mmol) and CuCN (0.64 g, 7.14 mmol, 1.1 equiv.) in pyridine (13 mL) was stirred at 80° C. for 3 hours, then an additional 15 hours at room temperature. Volatiles were removed under reduced pressure and the residue was partitioned between dichloromethane and brine. The organic layer was dried (MgSO$_4$) and filtered. The filtrate was concentrated under reduced pressure and the residue was purified by column chromatography (95:5 hexane/ethyl acetate) to provide the title intermediate as an off-white solid (0.63 g, 53% yield). M.p. 119.6–121.5° C., $^1$H NMR (CDCl$_3$, 300 MHz) δ 8.93 (s, 2H). MS (DCI-NH$_3$) [M+NH$_4$]$^+$ at 201.

Example 79B

5-Trimethylstannanyl-pyrimidine-2-carbonitrile

A mixture of 5-bromo-pyrimidine-2-carbonitrile (Example 79A, 276 mg, 1.50 mmol), hexamethylditin (639 mg, 1.95 mmol, 1.3 equiv.) and Pd(PPh$_3$)$_4$ (55 mg, 0.15 mmol, 0.1 equiv.) in toluene (5 mL) was stirred at reflux for 3 hours, then an additional 15 hours at room temperature under a dry nitrogen atmosphere. Volatiles were removed under reduced pressure and the residue was partitioned between dichloromethane and aqueous KF (10 g in 100 mL). The organic layer was dried (MgSO$_4$) and filtered. The filtrate was concentrated under reduced pressure and the residue was purified by column chromatography (100% dichloromethane) to provide the title intermediate as a white solid (219 mg, 54% yield). $^1$H NMR (CDCl$_3$, 300 MHz) δ 8.81 (s, 2H), 0.45 (s, 9H). MS (DCI-NH$_3$) [M+H]$^+$ at 270, [M+NH$_4$]$^+$ at 287.

Example 79C

5-[6-(2-Hydroxy-ethyl)-naphthalen-2-yl]-pyrimidine-2-carbonitrile

A mixture of 5-trimethylstannanyl-pyrimidine-2-carbonitrile (Example 79B, 200 mg, 0.75 mmol, 1.1 equiv.), 2-(6-bromo-naphthalen-2-yl)-ethanol (Example 31E, 171 mg, 0.679 mmol), cesium fluoride (227 mg, 1.49 mmol, 2.2 equiv.) and Pd[P(t-Bu)$_3$]$_2$ (10.4 mg, 0.02 mmol, 0.03 equiv.) in p-dioxane (10 mL) was stirred at 85° C. for 72 hours. Volatiles were removed under reduced pressure and the residue was partitioned between ethyl acetate and aqueous KF (10 g in 100 mL). The organic layer was dried (MgSO$_4$) and filtered. The filtrate was concentrated under reduced pressure and the residue was purified by column chromatography (70:30 hexane/ethyl acetate) to provide the title intermediate as a white solid (35.5 mg, 19% yield). $^1$H NMR (CD$_3$OD, 300 MHz) δ 9.33 (s, 2H), 8.31 (d, J=2 Hz, 1H), 7.99 (t, J=9 Hz, 1H), 7.94 (s, 1H), 7.86 (dd, J=2, 9 Hz, 1H), 7.79 (br s, 1H), 7.50 (dd, J=2, 9 Hz, 1H), 3.88 (t, J=7 Hz, 2H), 3.02 (t, J=7 Hz, 2H). MS (DCI-NH$_3$) [M+H]$^+$ at 276, [M+NH$_4$]$^+$ at 293.

Example 79D

5-{6-[2-((2R)-2-Methyl-pyrrolidin-1-yl)-ethyl]-naphthalen-2-yl}-pyrimidine-2-carbonitrile The title compound was prepared by the methods of Examples 3B and 3C substituting 5-[6-(2-hydroxy-ethyl)-naphthalen-2-yl]-pyrimidine-2-carbonitrile (Example 79C, 35.5 mg, 0.13 mmol) in place of 1-{3-[6-(2-hydroxyethyl)-2-naphthyl]phenyl}ethanone (Example 3A) for the mesylate formation and substituting the crude mesylate thus formed (~45 mg, 0.13 mmol) in place of 2-[6-(3-acetylphenyl)-2-naphthyl]ethyl methanesulfonate (Example 3B). Column chromatography (97:3:trace dichloromethane/methanol/NH$_4$OH) provided free base product that was dissolved in Et$_2$O. HCl gas was bubbled into this solution to provide the monohydrochloride salt of the title compound (3.8 mg, 9% yield over two steps). $^1$H NMR (CD$_3$OD, 300 MHz) δ 9.33 (s, 2H), 8.36 (d, J=2 Hz, 1H), 8.06 (dd, J=2, 8 Hz, 2H), 8.07–7.90 (m, 2H), 7.58 (dd, J=2, 8 Hz, 1H), 3.85–3.69 (m, 2H), 3.63–3.51 (m, 1H), 3.44–3.18 (m, 4H), 2.43–2.31 (m, 1H), 2.25–2.01 (m, 2H), 1.85–1.71 (m, 1H), 1.50 (d, J=6 Hz, 3H). MS (DCI-NH$_3$) [M+H]$^+$ at 343, [M+NH$_4$]$^+$ at 360.

Example 80

1-{6-[2-(2(R)-Methyl-pyrrolidin-1-yl)-ethyl]-naphthalen-2-yl}-1H-pyridin-2-one

Example 80A

1-[6-(2-Hydroxy-ethyl)-naphthalen-2-yl]-1H-pyridin-2-one

A mixture of 2-(6-bromo-naphthalen-2-yl)-ethanol (Example 31E, 100 mg, 0.40 mmol), 2-hydroxy-pyridine (57 mg, 0.60 mmol, 1.5 equiv.), copper powder (25 mg, 0.40 mmol), and K$_2$CO$_3$ (165 mg, 1.20 mmol, 3 equiv.) in pyridine (2 mL) was stirred at reflux under a dry nitrogen atmosphere for 18 hr. The reaction mixture was cooled to room temperature then concentrated under reduced pressure. Residual pyridine was removed by repeated evaporation with toluene. The residue was partitioned between ethyl acetate and aqueous NH$_4$OH (2×50 mL) then washed with brine. The organic layer was dried (MgSO$_4$), filtered, and the filtrate was concentrated under reduced pressure. The residue was purified by column chromatography (100% ethyl acetate) to provide the title intermediate as a white solid (30 mg, 28% yield). $^1$H NMR (CDCl$_3$, 300 MHz) δ 7.80 (d, J=9 Hz, 1H), 7.72 (d, J=9 Hz, 1H), 7.71 (s, 1H), 7.63 (s, 1H), 7.42 (dd, J=2, 8 Hz, 1H), 7.39–7.30 (m, 3H), 6.62 (dd, J=1, 10 Hz, 1H), 6.20 (dt, J=1, 6 Hz, 1H), 3.84 (t, J=6 Hz, 2H), 2.95 (t, J=6 Hz, 2H). MS (DCI-NH$_3$) [M+H]$^+$ at 266, [M+NH$_4$]$^+$ at 283.

Example 80B

1-{6-[2-(2(R)-Methyl-pyrrolidin-1-yl)-ethyl]-naphthalen-2-yl}-1H-pyridin-2-one

Methanesulfonyl chloride (0.01 mL, 0.136 mmol, 1.2 equiv.) was added dropwise via a syringe to a stirred, −30° C. solution of 1-[6-(2-hydroxy-ethyl)-naphthalen-2-yl]-1H- pyridin-2-one (Example 80A, 30 mg, 0.113 mmol) and Et₃N (0.024 mL, 0.17 mmol, 1.5 equiv.). After two hours stirring at room temperature, the reaction mixture was concentrated under reduced pressure. The residue was partitioned between EtOAc and saturated aqueous Na₂CO₃. The organic extract was dried (MgSO₄) and filtered. The filtrate was concentrated under reduced pressure and the residue was crystallized from Et₂O/hexane (20 mg, 52% yield). This mesylate (20 mg, 0.058 mmol), (2R)-2-methylpyrrolidine (14.9 mg, 0.058 mmol, 3.0 equiv.), and cesium carbonate (19 mg, 0.058 mmol) in anhydrous acetonitrile (3.5 mL) were stirred in a sealed tube at 60° C. for 18 hours. The reaction mixture was concentrated under reduced pressure. The residue was partitioned between ethyl acetate and saturated aqueous Na₂CO₃. The organic layer was dried (MgSO₄) and filtered. The filtrate was concentrated under reduced pressure and the residue was purified by column chromatography (97:3:trace, dichloromethane/methanol/NH₄OH). Fractions containing product were combined and concentrated under reduced pressure to provide the free base. This free base was dissolved in Et₂O and HCl gas was bubbled in to precipitate the hydrochloride salt of the title compound. $^1$H NMR (CD₃OD, 300 MHz) δ 8.08–7.96 (m, 2H), 7.93 (s, 2H), 7.76–7.66 (m, 2H), 7.60–7.51 (m, 2H), 6.70 (d, J=9 Hz, 1H), 6.56 (dt, J=1, 6 Hz, 1H), 3.83–3.68 (m, 2H), 3.64–3.49 (m, 1H), 3.43–3.18 (m, 4H), 2.43–2.30 (m, 1H), 2.22–2.02 (m, 2H), 1.84–1.69 (m, 1H), 1.49 (d, J=6 Hz, 3H). MS (DCI-NH₃) [M+H]⁺ at 333.

Example 81

5-{6-[2-(2(R)-Methyl-pyrrolidin-1-yl)-ethyl]-naphthalen-2-yl}-nicotinonitrile

Example 81A

5-[6-(2-Hydroxy-ethyl)-naphthalen-2-yl]-nicotinonitrile

A mixture of 5-(4,4,5,5-tetramethyl-[1,3,2]dioxaborolan-2-yl)-nicotinonitrile (220 mg, 0.956 mmol, 1.2 equiv.), 2-(6-bromo-naphthalen-2-yl)-ethanol (Example 31E, 200 mg, 0.8 mmol), Na₂CO₃ (253 mg, 2.39 mmol, 3 equiv.), biphenyl-2-yl-dicyclohexyl-phosphane (7 mg, 0.02 mmol, 0.025 equiv.), and PdCl₂(PPh₃)₂ (27.9 mg, 0.04 mmol, 0.05 equiv.) in isopropanol (20 mL) and water (8 mL) was stirred at 80° C. for one hour. The reaction mixture was then concentrated under reduced pressure and the residue was partitioned between ethyl acetate and saturated aqueous Na₂CO₃. The organic layer was dried (MgSO₄) and filtered. The filtrate was concentrated under reduced pressure to give a crude solid that was purified by column chromatography (1:1 hexane/ethyl acetate) to provide the title intermediate (166 mg, 76% yield). $^1$H NMR (CD₃OD, 300 MHz) δ 9.19 (d, J=2 Hz, 1H), 8.88 (d, J=2 Hz, 1H), 8.57 (t, J=2 Hz, 1H), 8.20 (d, J=2 Hz, 1H), 7.99–7.90 (m, 2H), 7.79 (dd, J=2, 9 Hz, 1H), 7.76 (br s, 1H), 7.48 (dd, J=2, 9 Hz, 1H), 3.88 (t, J=7 Hz, 2H), 3.02 (t, J=7 Hz, 2H). MS (DCI-NH₃) [M+H]⁺ at 275, [M+NH₄]⁺ at 292.

Example 81B

Methanesulfonic acid 2-[6-(5-cyano-pyridin-3-yl)-naphthalen-2-yl]-ethyl ester Methanesulfonyl chloride (0.056 mL, 0.726 mmol, 1.2 equiv.) was added to a stirred, −30° C. solution of 5-[6-(2-hydroxy-ethyl)-naphthalen-2-yl]-nicotinonitrile (Example 81A, 190 mg, 0.539 mmol) under a dry nitrogen atmosphere. Triethylamine (0.13 mL, 0.908 mmol, 1.5 equiv.) was added dropwise to the chilled solution, then the reaction mixture was stirred at room temperature for 18 hours. The reaction mixture was partitioned between ethyl acetate and saturated aqueous Na₂CO₃. The organic layer was dried (MgSO₄) and filtered. The filtrate was concentrated under reduced pressure to give the title intermediate (192 mg, 90% yield). $^1$H NMR (CDCl₃, 300 MHz) δ 9.22 (d, J=2 Hz, 1H), 8.90 (d, J=2 Hz, 1H), 8.60 (t, J=2 Hz, 1H), 8.25 (br s, 1H), 8.00 (t, J=8 Hz, 2H), 7.87–7.81 (m, 2H), 7.52 (dd, J=2, 8 Hz, 1H), 7.31–7.25 (m, 1H), 4.55 (t, J=6 Hz, 2H), 3.25 (t, J=6 Hz, 2H), 2.95 (s, 3H). MS (DCI-NH₃) [M+H]⁺ at 353, [M+NH₄]⁺ at 370.

Example 81C

5-{6-[2-(2(R)-Methyl-pyrrolidin-1-yl)-ethyl]-naphthalen-2-yl}-nicotinonitrile

Methanesulfonic acid 2-[6-(5-cyano-pyridin-3-yl)-naphthalen-2-yl]-ethyl ester (Example 81B, 190 mg, 0.54 mmol), (2R)-2-methylpyrrolidine (138 mg, 1.62 mmol, 3.0equiv.), and cesium carbonate (176 mg, 0.54 mmol) in anhydrous acetonitrile (6 mL) were stirred in a sealed tube at 50° C. for 18 hours. The reaction mixture was concentrated under reduced pressure. The residue was partitioned between ethyl acetate and saturated aqueous Na₂CO₃. The organic layer was washed with brine, then dried (MgSO₄), and filtered. The filtrate was concentrated under reduced pressure and the residue was purified by column chromatography (98:2: trace dichloromethane/methanol/N H₄OH). Fractions containing product were combined and concentrated under reduced pressure to provide the free base of the title compound as a white solid (105.9 mg, 57% yield). This free base was dissolved in methanol and treated with excess dioxane-HCl. Ether was added to induce crystallization of the dihydrochloride salt of the title compound. $^1$H NMR (CD₃OD, 300 MHz) δ 9.26 (br s, 1H), 8.97 (br s, 1H), 8.68 (s, 1H), 8.29 (s, 1H), 8.05 (s, 1H), 8.02 (s, 1H), 7.90 (br s, 1H), 7.88 (dd, J=2, 9 Hz, 1H), 7.56 (d, J=8 Hz, 1H), 3.84–3.49 (m, 7H), 2.45–2.30 (m, 1H), 2.27–1.99 (m, 2H), 1.84–1.69 (m, 1H), 1.50 (d, J=6 Hz, 3H). MS (DCI-NH₃) [M+H]⁺ at 342.

Example 82

4-Methyl-1-{6-[2-(2(R)-methyl-pyrrolidin-1-yl)-ethyl]-naphthalen-2-yl}-1H-pyridin-2-one Example 82A 1-[6-(2-Hydroxy-ethyl)-naphthalen-2-yl]-4-methyl-1H-pyridin-2-one A mixture of 2-(6-bromo-naphthalen-2-yl)-ethanol (Example 31E, 200 mg, 0.796 mmol), 2-hydroxy-4-methylpyridine (130 mg, 1.195 mmol, 1.5 equiv.), copper powder (50.6 mg, 0.796 mmol), and K₂CO₃ (330.2 mg, 2.389 mmol, 3 equiv.) in pyridine (5 mL) was stirred at reflux under a dry nitrogen atmosphere for 62 hr. The reaction mixture was cooled to room temperature then concentrated under reduced pressure. Residual pyridine was removed by repeated evaporation with toluene. The residue was partitioned between ethyl acetate and aqueous NH₄OH then washed with brine (3×50 mL). The organic layer was dried (MgSO₄), filtered, and the filtrate was concentrated under reduced pressure. The residue was purified by column chromatography (100% ethyl acetate) to provide the title intermediate as a white solid (70 mg, 31% yield). $^1$H NMR (CD$_3$OD, 300 MHz) δ 7.94 (d, J=9 Hz, 1H), 7.88 (d, J=9 Hz, 1H), 7.84 (d, J=2 Hz, 1H), 7.80 (br s, 1H), 7.59 (d, J=7 Hz, 1H), 7.49 (dd, J=2, 9 Hz, 1H), 7.44 (dd, J=2, 9 Hz, 1H), 6.49 (br s, 1H), 6.40 (dd, J=2, 7 Hz, 1H), 3.87 (t, J=7 Hz, 2H), 3.04 (t, J=7 Hz, 2H), 2.32 (s, 3H). MS (DCI-NH$_3$) [M+H]$^+$ at 280.

Example 82B

4-Methyl-1-{6-[2-(2(R)-methyl-pyrrolidin-1-yl)-ethyl]-naphthalen-2-yl}-1H-pyridin-2-one Methanesulfonyl chloride (0.03 mL, 0.301 mmol, 1.2 equiv.) was added dropwise via a syringe to a stirred, 0° C. solution of 1-[6-(2-hydroxy-ethyl)-naphthalen-2-yl]4-methyl-1H-pyridin-2-one (Example 82A, 70 mg, 0.251 mmol) in anhydrous THF (10 mL) under a dry nitrogen atmosphere. Triethylamine (1.0 mL, 7.175 mmol, 28.6 equiv.) was then added. After two hours of stirring at 0° C., the reaction mixture was concentrated under reduced pressure. The residue was partitioned between EtOAc and saturated aqueous Na$_2$CO$_3$. The organic extract was dried (MgSO$_4$) and filtered. The filtrate was concentrated under reduced pressure. This crude mesylate (~89 mg, 0.249 mmol), (2R)-2-methylpyrrolidine (64 mg, 0.747 mmol, 3.0 equiv.), and cesium carbonate (81 mg, 0.249 mmol) in anhydrous acetonitrile (5 mL) were stirred in a sealed tube at 50° C. for 18 hours. The reaction mixture was concentrated under reduced pressure. The residue was partitioned between ethyl acetate and saturated aqueous Na$_2$CO$_3$. The organic layer was dried (MgSO$_4$) and filtered. The filtrate was concentrated under reduced pressure and the residue was purified by column chromatography (97:3:trace dichloromethane/methanol/NH$_4$OH). Fractions containing product were combined and concentrated under reduced pressure to provide the free base. This free base was dissolved in Et$_2$O and the solution was treated with HCl-dioxane to precipitate the hydrochloride salt of the title compound (15 mg, 16% yield). $^1$H NMR (CD$_3$OD, 300 MHz) δ 8.00 (d, J=9 Hz, 1H), 7.98 (d, J=9 Hz, 1H), 7.93–7.89 (m, 2H), 7.62 (d, J=7 Hz, 1H), 7.56 (dd, J=2, 9 Hz, 1H), 7.51 (dd, J=2, 9 Hz, 1H), 6.52 (br s, 1H), 6.45 (dd, J=2, 7 Hz, 1H), 3.83–3.68 (m, 2H), 3.61–3.49 (m, 1H), 3.43–3.17 (m, 4H), 2.43–2.30 (m, 1H), 2.33 (s, 3H), 2.24–1.99 (m, 2H), 1.83–1.69 (m, 1H), 1.49 (d, J=6 Hz, 3H). MS (DCI-NH$_3$) [M+H]$^+$ at 347.

Example 83

2-{6-[2-((2R)-2-Methyl-pyrrolidin-1-yl)-ethyl]-naphthalen-2-yl}-pyrazine

Example 83A

2-(6-Pyrazin-2-yl-naphthalen-2-yl)-ethanol

A mixture of 2-tributylstannanyl-pyrazine (323 mg, 0.876 mmol, 1.1 equiv.), 2-(6-bromo-naphthalen-2-yl)-ethanol (Example 31E, 200 mg, 0.796 mmol), cesium fluoride (266 mg, 1.75 mmol, 2.2 equiv.) and Pd[P(t-Bu)$_3$]$_2$ (12.2 mg, 0.024 mmol, 0.03 equiv.) in p-dioxane (10 mL) was stirred at 85° C. for 2.5 hours. Volatiles were removed under reduced pressure and the residue was partitioned between ethyl acetate and aqueous KF (10 g in 100 mL). The organic layer was washed consecutively with saturated aqueous Na$_2$CO$_3$ and brine, then dried (MgSO$_4$) and filtered. The filtrate was concentrated under reduced pressure and the residue was purified by column chromatography (1:1 hexane/ethyl acetate) to provide the title intermediate as a beige solid (42.5 mg, 21% yield). $^1$H NMR (CD$_3$OD, 300 MHz) δ 9.25 (d, J=1 Hz, 1H), 8.72–8.70 (m, 1H), 8.58 (d, J=2 Hz, 1H), 8.54 (d, J=3 Hz, 1H), 8.17 (dd, J=2, 9 Hz, 1H), 7.97 (d, J=2 Hz, 1H), 7.94 (d, J=2 Hz, 1H), 7.77 (br s, 1H), 7.48 (dd, J=2, 8 Hz, 1H), 3.88 (t, J=7 Hz, 2H), 3.02 (t, J=7 Hz, 2H). MS (DCI-NH$_3$) [M+H]$^+$ at 251, [M+NH$_4$]$^+$ at 268.

Example 83B

2-{6-[2-((2R)-2-Methyl-pyrrolidin-1-yl)-ethyl]-naphthalen-2-yl}-pyrazine

Methanesulfonyl chloride (0.005 mL, 0.067 mmol, 1.2 equiv.) was added dropwise via a syringe to a stirred, 0° C. solution of 2-(6-pyrazin-2-yl-naphthalen-2-yl)-ethanol (Example 83A, 14 mg, 0.056 mmol) in anhydrous THF (10 mL) under a dry nitrogen atmosphere. Triethylamine (0.023 mL, 0.167 mmol, 3 equiv.) was then added. After 18 hours at −20° C., the reaction mixture was dried (MgSO$_4$) and filtered. The filtrate was concentrated under reduced pressure. This crude mesylate (~18 mg, 0.056 mmol), (2R)-2-methylpyrrolidine (190 mg, 2.237 mmol, 40 equiv.), and cesium carbonate (182 mg, 0.559 mmol, 10 equiv.) in anhydrous acetonitrile (5 mL) were stirred in a sealed tube at 40° C. for 62 hours. The reaction mixture was concentrated under reduced pressure. The residue was partitioned between ethyl acetate and saturated aqueous Na$_2$CO$_3$. The organic layer was dried (MgSO$_4$) and filtered. The filtrate was concentrated under reduced pressure and the residue was purified by column chromatography (97:3:trace dichloromethane/methanol/NH$_4$OH). Fractions containing product were combined and concentrated under reduced pressure to provide the free base. This free base was dissolved in methanol and the solution was treated with HCl gas. The hydrochloride salt of the title compound was obtained on evaporation of solvent (4.5 mg, 23% yield). $^1$H NMR (CD$_3$OD, 300 MHz) δ 9.29 (br s, 1H), 8.79–8.74 (m, 1H), 8.64 (br s, 1H), 8.58 (d, J=2 Hz, 1H), 8.24 (dd, J=2, 9 Hz, 1H), 8.03 (t, J=9 Hz, 2H), 7.90 (br s, 1H), 7.55 (dd, J=2, 9 Hz, 1H), 3.84–3.68 (m, 2H), 3.64–3.49 (m, 1H), 3.44–3.17 (m, 4H), 2.43–2.30 (m, 1H), 2.27–2.00 (m, 2H), 1.84–1.68 (m, 1H), 1.50 (d, J=7 Hz, 3H). MS (DCI-NH$_3$) [M+H]$^+$ at 318.

Example 84

2-{6-[2-((2R)-2-Methyl-2,5-dihydro-pyrrol-1-yl)-ethyl]-naphthalen-2-yl}-2H-3-one

Example 84A

(2S)-2-Hydroxymethyl-2,5-dihydro-pyrrole-1-carboxylic acid tert-butyl ester The title intermediate can be prepared reductively from the corresponding carboxylic acid or its methyl ester.

From the carboxylic acid: Employing the literature (Rodriguez, M., et. al., Tetrahedron Letters, 1991, 32(7), 923–926) procedure; 2,5-Dihydro-pyrrole-1, (2R)-2-dicarboxylic acid 1-tert-butyl ester (970 mg, 4.549 mmol) was dissolved in anhydrous DME (5 mL). This solution was chilled to −20° C. under a dry nitrogen atmosphere. To this stirred solution was slowly added first 4-methyl-morpholine (0.5 mL, 4.549 mmol) then isobutyl chloroformate (0.6 mL, 4.549 mmol). After stirring at −20° C. for one minute, a solution of sodium borohydride (516 mg, 13.647 mmol, 3 equiv.) in water (5 mL) was rapidly added and stirring was continued while the reaction mixture warmed to −5° C. where it was maintained for 25 minutes. The reaction mixture was then diluted with water and extracted with ethyl acetate. The organic layer was washed with brine, dried (MgSO$_4$), and filtered. The filtrate was concentrated under reduced pressure and the residue was purified by column chromatography (4:1 hexane/ethyl acetate) to give the title intermediate (386 mg, 42% yield). $^1$H NMR (CDCl$_3$, 300 MHz) δ 5.90–5.72 (m, 1H), 5.69–5.56 (m, 1H), 4.80–4.60 (m, 1H), 4.28–3.99 (m, 2H), 3.78 (dd, J=2, 9 Hz, 1H), 3.65–3.51 (m, 1H), 1.49 (s, 9H). MS (DCI-NH$_3$) [M+H]$^+$ at 200, [M+NH$_4$]$^+$ at 217.

From the methyl carboxylate: Sodium borohydride 333 mg, 8.80 mmol, 2 equiv.) was added in one lot to a stirred, 0° C. solution of 2,5-dihydro-pyrrole-1, (2R)-2-dicarboxylic acid 1-tert-butyl ester 2-methyl ester (1.0 g, 4.40 mmol) in THF (3 mL) and methanol (2 mL). The reaction mixture was stirred at 0° C. for 15 min then at room temperature for 18 hr. After an aqueous work-up as above and column chromatography as above the title intermediate was obtained (524 mg, 60% yield).

Example 84B (2R)-2-Methyl-2,5-dihydro-pyrrole-1-carboxylic acid tert-butyl ester Methanesulfonyl chloride (0.24 mL, 3.13 mmol, 1.2 equiv.) was added dropwise to a stirred, 0° C. solution of (2S)-2-hydroxymethyl-2,5-dihydro-pyrrole-1-carboxylic acid tert-butyl ester (Example 84A, 520 mg, 2.61 mmol) and triethylamine (1.1 mL, 7.83 mmol, 3 equiv.) in anhydrous THF (50 mL) under a dry nitrogen atmosphere. The reaction mixture was stirred at 0° C. for 15 min then at room temperature for 18 hours. The reaction mixture was concentrated under reduced pressure and the residue was partitioned between ethyl acetate and water. The organic layer was washed with saturated aqueous Na$_2$CO$_3$, then dried (MgSO$_4$), and filtered. The filtrate was concentrated under reduced pressure and the crude mesylate (~660 mg, 91% yield) was immediately reduced:

A solution of the crude mesylate (~660 mg, 2.38 mmol) in THF (10 mL) was stirred at 0° C. under a dry nitrogen atmosphere. Lithium triethylborohydride (1.0 M in THF, 7.14 mL, 7.14 mmol, 3 equiv.) was added dropwise. Stirring at 0° C. was continued for 20 min after the addition, then the reaction mixture was stirred at room temperature for 18 hours. The reaction was quenched by the careful, sequential addition of water (1.38 mL), 3 N NaOH (2.75 mL), and 30% aqueous hydrogen peroxide (2.75 mL). After stirring for 30 min, the reaction was treated with saturated aqueous Na$_2$SO$_3$ and stirred vigorously overnight. The organic layer was dried (MgSO$_4$) and filtered. The filtrate was concentrated under reduced pressure and the residue was purified by column chromatography (gradient:100% hexane to 95:5 hexane/ethyl acetate) to provide the title intermediate (282 mg, 65% yield). $^1$H NMR (CDCl$_3$, 300 MHz) δ 5.77–5.62 (m, 2H), 4.63–4.42 (m, 1H), 4.27–3.98 (m, 2H), 1.48 (s, 9H), 1.34–1.19 (m, 3H). MS (DCI-NH$_3$) [M+H]$^+$ at 184, [M+NH$_4$]$^+$ at 201.

Example 84C (2R)-2-Methyl-2,5-dihydro-1H-pyrrole

Trifluoroacetic acid (1.8 mL, 22.92 mmol, 15 equiv.) was added dropwise to a stirred, room temperature solution of (2R)-2-methyl-2,5-dihydro-pyrrole-1-carboxylic acid tert-butyl ester (Example 84B, 280 mg, 1.528 mmol) in dichloromethane (5 mL). The reaction mixture was stirred at room temperature under a dry nitrogen atmosphere for 18 hours. The reaction mixture was concentrated under reduced pressure to give the crude title intermediate as its trifluoroacetic acid salt (~300 mg, 100% yield). $^1$H NMR (CD$_3$OD, 300 MHz) δ 5.92 (s, 2H), 4.94–4.49 (m, 1H), 4.12–3.97 (m, 2H), 1.44 (d, J=7 Hz, 3H). MS (DCI-NH$_3$) [M+H]$^+$ at 84.

Example 84D

2-{6-[2-((2R)-2-Methyl-2,5-dihydro-pyrrol-1-yl)-ethyl]-naphthalen-2-yl}-2H-pyridazin-3-one A mixture of methanesulfonic acid 2-[6-(6-oxo-6H-pyridazin-1-yl)-naphthalen-2-yl]-ethyl ester (Example 31G, 205 mg, 0.595 mmol), (2R)-2-methyl-2,5-dihydro-1H-pyrrole, trifluoroacetic acid salt (Example 84C, ~300 mg, 1.52 mmol, 2.55 equiv.), and cesium carbonate (1.49 g, 4.56 mmol, 3 equiv.) in anhydrous acetonitrile (10 mL) was stirred in a sealed tube at room temperature for 90 hours then at 45° C. for another 18 hours. The reaction mixture was concentrated under reduced pressure. The residue was partitioned between ethyl acetate and saturated aqueous Na$_2$CO$_3$. The aqueous layer was washed with ethyl acetate, and the combined organic extracts were dried (MgSO$_4$) and filtered. The filtrate was concentrated under reduced pressure and the residue was purified by column chromatography (98:2:trace dichloromethane/methanol/NH$_4$OH). Fractions containing product were combined and concentrated under reduced pressure to provide the free base product (69 mg, 35% yield). $^1$H NMR (CD$_3$OD, 300 MHz) δ 8.04 (dd, J=2, 4 Hz, 1H), 8.04 (d, J=2 Hz, 1H), 7.92 (d, J=9 Hz, 1H), 7.88 (d, J=9 Hz, 1H), 7.79 (br s, 1H), 7.62 (dd, J=2, 9 Hz, 1H), 7.51 (dd, J=3, 9 Hz, 1H), 7.48 (dd, J=2, 9 Hz, 1H), 7.12 (dd, J=2, 9 Hz, 1H), 5.83–5.68 (m, 2H), 3.91–3.81 (m, 1H), 3.66–3.54 (m, 1H), 3.40–3.30 (m, 1H), 3.21–3.08 (m, 1H), 3.08–2.91 (m, 2H), 2.86–2.73 (m, 1H), 1.22 (d, J=7 Hz, 3H). MS (DCI-NH$_3$) [M+H]$^+$ at 332.

Example 85

4-(6-{2-[(2-Dimethylamino-ethyl)-methyl-amino]-ethyl}-naphthalen-2-yl)-benzonitrile

Example 85A

Methanesulfonic acid 2-[6-(4-cyano-phenyl)-naphthalen-2-yl]-ethyl ester A stirred, 0° C. solution of 4-[6-(2-hydroxy-ethyl)-2-naphthyl]benzonitrile (Example 1F, 460 mg, 1.683 mmol) and triethylamine (0.94 mL, 6.732 mmol, 4 equiv.) in anhydrous THF (10 mL) was treated with methanesulfonyl chloride (0.17 mL, 2.188 mmol, 1.3 equiv.) under a dry nitrogen atmosphere. The reaction mixture was stirred at room temperature for one hour, then the reaction mixture was diluted with water and extracted with ethyl acetate (3×20 mL). The combined organic extracts were washed with saturated aqueous Na$_2$CO$_3$ and then with brine. The organic layer was dried (MgSO$_4$) and filtered. The filtrate was concentrated under reduced pressure to give the title intermediate (305 mg, 52% yield). $^1$H NMR (CDCl$_3$, 300 MHz) δ 8.04 (d, J=2 Hz, 1H), 7.94–7.87 (m, 2H), 7.84–7.69 (m, 6H), 7.43 (dd, J=2, 8 Hz, 1H), 4.54 (t, J=7 Hz, 2H), 3.26 (t, J=7 Hz, 2H), 2.88 (s, 3H). MS (DCI-NH$_3$) [M+NH$_4$]$^+$ at 369.

Example 85B 4-(6-{2-[(2-Dimethylamino-ethyl)-methyl-amino]-ethyl}-naphthalen-2-yl)-benzonitrile A mixture of methanesulfonic acid 2-[6-(4-cyano-phenyl)-naphthalen-2-yl]-ethyl ester (Example 85A, 150 mg, 0.427 mmol) and N,N,N'-trimethylethylenediamine (0.17 mL, 1.280 mmol, 3 equiv.) in anhydrous acetonitrile (1 mL) was stirred at room temperature in a sealed tube for 66 hours. The reaction mixture was partitioned between ethyl acetate and saturated aqueous $Na_2CO_3$. The organic layer was dried ($MgSO_4$) and filtered. The filtrate was concentrated under reduced pressure and the residue was purified by column chromatography (gradient: 98:2 to 97:3:trace dichloromethane/methanol/$NH_4OH$) to give the free base product (28.7 mg, 19% yield). The free base was dissolved in methanol and treated with a methanol solution containing one equivalent of L-tartaric acid. The tartrate salt of the title compound crystallized from the methanol solution. $^1$H NMR ($CD_3OD$, 300 MHz) δ 8.17 (d, J=2 Hz, 1H), 7.97–7.82 (m, 4H), 7.86–7.77 (m, 4H), 7.48 (dd, J=2, 8 Hz, 1H), 4.39 (s, tartrate, 2H), 3.17–2.90 (m, 8H), 2.69 (s, 6H), 2.54 (s, 3H). MS (DCI-$NH_3$) [M+H]$^+$ at 358.

Example 86

4-{6-[2-(4-Methyl-piperazin-1-yl)-ethyl]-naphthalen-2-yl}-benzonitrile

A mixture of methanesulfonic acid 2-[6-(4-cyano-phenyl)-naphthalen-2-yl]-ethyl ester (150 mg, 0.427 mmol) and 1-methylpiperazine (0.14 mL, 1.280 mmol, 3 equiv.) in anhydrous acetonitrile (1 mL) was stirred at room temperature in a sealed tube for 66 hours. The reaction mixture was partitioned between ethyl acetate and saturated aqueous $Na_2CO_3$. The organic layer was dried ($MgSO_4$) and filtered. The filtrate was concentrated under reduced pressure and the residue was purified by column chromatography (97:3:trace dichloromethane/methanol/$NH_4OH$) to give the free base product. $^1$H NMR ($CD_3OD$, 300 MHz) δ 8.16 (br s, 1H), 7.97–7.89 (m, 4H), 7.86–7.81 (m, 2H), 7.79 (dd, J=2, 8 Hz, 2H), 7.74 (br s, 1H), 7.44 (dd, J=2, 8 Hz, 1H), 3.05–2.97 (m, 2H), 2.77–2.43 (m, 10H), 2.31 (s, 3H). MS (DCI-$NH_3$) [M+H]$^+$ at 356. The free base was dissolved in methanol and treated with a methanol solution containing one equivalent of L-tartaric acid. The tartrate salt of the title compound crystallized from the methanol solution (101 mg, 66% yield).

Example 87

2-(2,5-Dimethyl-furan-3-yl)-6-{2-[(2R)-2-methyl-1-pyrrolidinyl]ethyl}-quinoline

The title compound was prepared using the procedure described in Example 57 using 1-(2,5-dimethyl-furan-3-yl)-ethanone for 1-(1,3-thiazol-2-yl)-ethanone. $^1$H NMR (300 MHz, $CD_3OD$) δ 1.19 (d, J=6 Hz, 3H), 1.51 (m, 1H), 1.84 (m, 2H), 2.06 (m, 1H), 2.31 (s, 3H), 2.48 (m, 3H), 2.63 (s, 3H), 3.06 (m, 3H), 3.21 (m, 1H), 7.33 (d, J=9 Hz, 1H), 7.34 (d, J=3 Hz, 1H), 7.72 (dd, J=9 Hz, J=3 Hz, 1H), 7.82 (s, 1H), 8.16 (d, J=9 Hz, 1H), 8.39 (d, J=3 Hz, 1H); (DCI/$NH_3$) m/z 335 (M+H)$^+$.

Example 88

6-{2-[(2R)-2-methyl-1-pyrrolidinyl]ethyl}-2-(4-methylsulfanyl-phenyl)-quinoline

The title compound was prepared using the procedure described in Example 57 using 1-(4-methylsulfanyl-phenyl)-ethanone for 1-(1,3-thiazol-2-yl)-ethanone. $^1$H NMR (300 MHz, $CD_3OD$) δ 1.17 (d, J=6 Hz, 3H), 1.48 (m, 1H), 1.84 (m, 2H), 2.05 (m, 1H), 2.49 (m, 3H), 2.55 (s, 3H), 2.63 (s, 3H), 3.06 (m, 2H), 3.17 (m, 1H), 3.21 (m, 1H), 7.41 (d, J=9 Hz, 2H), 7.68 (dd, J=9 Hz, J=3 Hz, 1H), 7.77 (d, J=3 Hz, 1H), 7.94 (d, J=9 Hz, 1H), 8.03 (d, J=9 Hz, 1H), 8.05 (d, J=9 Hz, 1H), 8.33 (d, J=9 Hz, 1H); (DCI/$NH_3$) m/z 363 (M+H)$^+$.

Example 89

2-(6-Methyl-pyridin-3-yl)-6-{2-[(2R)-2-methyl-1-pyrrolidinyl]ethyl}-quinoline

The title compound was prepared using the procedure described in Example 57 using 1-(6-methyl-pyridin-3-yl)-ethanone (reference: S. P. Tanis et al., J. Med. Chem. 39, 1996, 5053–5063) for 1-(1,3-thiazol-2-yl)-ethanone. $^1$H NMR (300 MHz, $CD_3OD$) δ 1.17 (d, J=6 Hz, 3H), 1.48 (m, 1H), 1.84 (m, 2H), 2.04 (m, 1H), 2.38 (m, 1H), 2.49 (m, 3H), 2.63 (s, 3H), 3.06 (m, 2H), 3.19 (m, 1H), 7.47 (d, J=9 Hz, 1H), 7.70 (dd, J=9 Hz, J=3 Hz, 1H), 7.80 (d, J=3 Hz, 1H), 8.00 (d, J=9 Hz, 1H), 8.07 (d, J=9 Hz, 1H), 8.37 (d, J=9 Hz, 1H), 8.47 (dd, J=9 Hz, J=3 Hz, 1H), 9.17 (d, J=3 Hz, 1H); (DCI/$NH_3$) m/z 332 (M+H)$^+$.

Example 90

2-(1,3-Dimethyl-1H-pyrazol-4-yl)-6-{2-[(2R)-2-methyl-1-pyrrolidinyl]ethyl}-quinoline The title compound was prepared using the procedure described in Example 57 using 1-(1,3-dimethyl-1H-pyrazol-4-yl)-ethanone (reference: P. Schenone et al., J. Heterocycl. Chem. 19, 1982, 1355–1361) for 1-(1,3-thiazol-2-yl)-ethanone. $^1$H NMR (300 MHz, $CD_3OD$) δ 1.32 (d, J=6 Hz, 3H), 1.63 (m, 1H), 1.97 (m, 2H), 2.17 (m, 1H), 2.60 (s, 3H), 2.85 (m, 2H), 3.12 (m, 3H), 3.47 (m, 2H), 3.90 (s, 3H), 7.66 (dd, J=9 Hz, J=3 Hz, 1H), 7.69 (d, J=9 Hz, 1H), 7.76 (d, J=2 Hz, 1H), 7.96 (d, J=9 Hz, 1H), 8.12 (s, 1H), 8.22 (d, J=9 Hz, 1H); (DCI/$NH_3$) m/z 335 (M+H)$^+$.

Example 91

6-{2-[(2R)-2-methyl-1-pyrrolidinyl]ethyl}-2-thiophen-3-yl-quinoline

The title compound was prepared using the procedure described in Example 57 using 1-thiophen-3-yl-ethanone (reference: E. Campaigne et al., J. Amer. Chem. Soc. 70, 1948, 1555) for 1-(1,3-thiazol-2-yl)-ethanone. $^1$H NMR (300 MHz, $CD_3OD$) δ 1.27 (d, J=6 Hz, 3H), 1.61 (m, 1H), 1.92 (m, 2H), 2.12 (m, 1H), 2.70 (m, 2H), 3.06 (m, 3H), 3.24 (m, 1H), 3.45 (m, 1H), 7.56 (dd, J=9 Hz, J=9 Hz, 1H), 7.68 (dd, J=9 Hz, J=3 Hz, 1H), 7.78 (s, 1H), 7.88 (d, J=6 Hz, 1H), 7.94 (d, J=9 Hz, 1H), 8.03 (d, J=9 Hz, 1H), 8.18 (m, 1H), 8.28 (d, J=9 Hz, 1H); (DCI/$NH_3$) m/z 323 (M+H)$^+$.

Example 92

6-{2-[(2R)-2-methyl-1-pyrrolidinyl]ethyl}-2-pyrimidin-5-yl-quinoline

The title compound was prepared using the procedure described in Example 57 using 1-pyrimidin-5-yl-ethanone (reference: I. I. Naumenko et al., Chem. Heterocycl. Compd. (Engl. Transl.) 17, 1981, 710–714) for 1-(1,3-thiazol-2-yl)-ethanone. $^1$H NMR (300 MHz, CD$_3$OD) δ 1.16 (d, J=6 Hz, 3H), 1.50 (m, 1H), 1.84 (m, 2H), 2.04 (m, 1H), 2.35 (m, 1H), 2.46 (m, 2H), 3.12 (m, 3H), 3.21 (m, 1H), 7.74 (dd, J=9 Hz, J=3 Hz, 1H), 7.82 (d, J=3 Hz, 1H), 8.10 (d, J=6 Hz, 2H), 8.43 (d, J=9 Hz, 1H), 9.25 (s, 1H), 9.56 (s, 2H); (DCI/NH$_3$) m/z 319 (M+H)$^+$.

Example 93

2-(2,6-Dimethyl-pyridin-3-yl)-6-{2-[(2R)-2-methyl-1-pyrrolidinyl]ethyl}quinoline The title compound was prepared using the procedure described in Example 57 using 1-(2,6-dimethyl-pyridin-3-yl)-ethanone (reference K. Franke Angew. Chem. 67, 1955, 395) for 1-(1,3-thiazol-2-yl)-ethanone. $^1$H NMR (300 MHz, CD$_3$OD) δ 1.17 (d, J=6 Hz, 3H), 1.48 (m, 1H), 1.82 (m, 2H), 2.01 (m, 1H), 2.35 (m, 1H), 2.47 (m, 2H), 2.54 (s, 3H), 2.59 (s, 3H), 3.07 (m, 3H), 3.19 (m, 1H), 7.29 (d, J=9 Hz, 1H), 7.63 (d, J=9 Hz, 1H), 7.73 (dd, J=9 Hz, J=3 Hz, 1H), 7.81 (d, J=6 Hz, 1H), 7.84 (d, J=3 Hz, 1H), 8.00 (d, J=9 Hz, 1H), 8.40 (d, J=9 Hz, 1H); (DCI/NH$_3$) m/z 346 (M+H)$^+$.

Example 94

1-[2,6-Dimethyl-5-(6-{2-[(2R)-2-methyl-1-pyrrolidinyl]ethyl}-quinolin-2-2-yl)-pyridine-3-yl]-ethanone The title compound was prepared using the procedure described in Example 57 using 3,5-diacetyl-2,6-dimethylpyridine for 1-(1,3-thiazol-2-yl)ethanone. The product was dissolved in water and treated with two equivalents of L-tartaric acid. The solvent was removed via lyopholization to give the ditartrate salt of the product as a white foam. $^1$H NMR (CD$_3$OD) δ ppm 1.49 (d, J=6.78 Hz, 3H), 1.81 (m, 1H), 2.13 (m, 2H), 2.35 (m, 1H), 2.60 (s, 3H), 2.64 (s, 3H), 2.76 (s, 3H), 3.36 (m, 4H), 3.59 (m, 1H), 3.74 (m, 2H), 4.47 (s, 4H), 7.77 (d, J=8.48 Hz, 1H), 7.82 (dd, J=8.65, 1.87 Hz, 1H), 7.99 (d, J=1.70 Hz, 1H), 8.10 (d, J=8.82 Hz, 1H), 8.32 (s, 1H), 8.47 (d, J=8.48 Hz, 1H). MS (DCI-NH$_3$) [M+H]$^+$ at 388.

Example 95

6-{2-[(2R)-2-methyl-1-pyrrolidinyl]ethyl}-2-(2H-pyrazol-3-yl)-quinoline

The title compound was prepared using the procedure described in Example 57 using 1-(1H-pyrazol-5-yl)ethan-1-one hydrochloride for 1-(1,3-thiazol-2-yl)ethanone and using 5 drops of the saturated solution of potassium hydroxide in ethanol. $^1$H NMR (CDCl$_3$) δ ppm 1.14 (d, J=6.10 Hz, 3H), 1.48 (m, 1H), 1.77 (m, 2H), 1.93 (m, 1H), 2.25 (q, J=8.82 Hz, 1H), 2.40 (m, 2H), 3.01 (m, 2H), 3.14 (m, 1H), 3.30 (m, 1H), 6.92 (s, 1H), 7.61 (m, 1H), 7.63 (s, 1H), 7.70 (d, J=2.03 Hz, 1H), 7.81 (d, J=8.82 Hz, 1H), 8.02 (d, J=8.48 Hz, 1H), 8.14 (d, J=8.48 Hz, 1H). MS (DCI-NH$_3$) [M+H]$^+$ at 307.

Example 96

2-(3-Bromo-isoxazol-5-yl)-6-{2-[(2R)-2-methyl-1-pyrrolidinyl]ethyl}-quinoline

The title compound was prepared using the procedure described in Example 57 using 1-(3-bromo-isoxazol-5-yl)-ethanone (reference: M. D. Amici et al., J. Org. Chem. 1989, 54 (11), 2646–2650) for 1-(1,3-thiazol-2-yl)ethanone. $^1$H NMR (CDCl$_3$) δ ppm 1.13 (d, J=6.10 Hz, 3H), 1.47 (m, 1H), 1.78 (m, 2H), 1.95 (m, 1H), 2.24 (q, J=8.59 Hz, 1H), 2.40 (m, 2H), 3.08 (m, 3H), 3.29 (m, 1H), 7.14 (s, 1H), 7.67 (dd, 1H), 7.69 (s, 1H), 7.96 (d, J=8.48 Hz, 1H), 8.06 (d, J=9.16 Hz, 1H), 8.24 (d, J=8.48 Hz, 1H). MS (DCI-NH$_3$) [M+H]$^+$ at 386.

Example 97

2-(6-Chloro-pyridin-3-yl)-6-{2-[(2R)-2-methyl-1-pyrrolidinyl]ethyl}-quinoline

The title compound was prepared using the procedure described in Example 57 using 1-(6-chloro-3-pyridinyl)-1-ethanone for 1-(1,3-thiazol-2-yl)ethanone. $^1$H NMR (CDCl$_3$) δ ppm 1.14 (d, J=5.76 Hz, 3H), 1.47 (m, 1H), 1.78 (m, 2H), 1.94 (m, 1H), 2.25 (q, J=8.70 Hz, 1H), 2.40 (m, 2H), 3.03 (m, 2H), 3.15 (m, 1H), 3.30 (m, 1H), 7.48 (d, J=8.48 Hz, 1H), 7.65 (dd, 1H), 7.67 (s, 1H), 7.83 (d, J=8.48 Hz, 1H), 8.08 (d, J=8.48 Hz, 1H), 8.21 (d, J=8.48 Hz, 1H), 8.51 (dd, J=8.31, 2.54 Hz, 1H), 9.11 (dd, J=2.71, 0.68 Hz, 1H). MS (DCI-NH$_3$) [M+H]$^+$ at 352.

Example 98

2-(3,5-Dimethyl-thiophen-2-yl)-6-{2-[(2R)-2-methyl-1-pyrrolidinyl]ethyl}-quinoline The title compound was prepared using the procedure described in Example 57 using 1-(3,5-dimethyl-2-thienyl)ethan-1-one for 1-(1,3-thiazol-2-yl)ethanone. $^1$H NMR (CDCl$_3$) δ ppm 1.14 (d, J=6.10 Hz, 3H), 1.47 (m, 1H), 1.77 (m, 2H), 1.95 (m, 1H), 2.25 (m, 1H), 2.39 (m, 2H), 2.49 (s, 3H), 2.54 (s, 3H), 3.00 (m, 2H), 3.11 (m, 1H), 3.29 (m, 1H), 6.64 (s, 1H), 7.56 (dd, 1H), 7.58 (s, 1H), 7.63 (d, J=8.82 Hz, 1H), 7.99 (d, J=8.14 Hz, 1H), 8.05 (d, J=8.82 Hz, 1H). MS (DCI-NH$_3$) [M+H]$^+$ at 351.

Example 99

6-{2-[(2R)-2-methyl-1-pyrrolidinyl]ethyl}-2-thiophen-2-yl-quinoline

The title compound was prepared using the procedure described in Example 57 using 2-acetylthiophene for 1-(1,3-thiazol-2-yl)ethanone. $^1$H NMR (CDCl$_3$) δ ppm 1.15 (d, J=6.10 Hz, 3H), 1.49 (m, 1H), 1.77 (m, 2H), 1.96 (m, 1H), 2.26 (q, J=8.70 Hz, 1H), 2.41 (m, 2H), 3.02 (m, 2H), 3.14 (m, 1H), 3.30 (m, 1H), 7.15 (dd, J=5.09, 3.73 Hz, 1H), 7.45 (dd, J=5.09, 1.02 Hz, 1H), 7.58 (dd, 1H), 7.59 (s, 1H), 7.71 (dd, J=3.73, 1.02 Hz, 1H), 7.77 (d, J=8.82 Hz, 1H), 8.01 (d, J=8.48 Hz, 1H), 8.08 (d, J=8.82 Hz, 1H). MS (DCI-NH$_3$) [M+H]$^+$ at 323.

Example 100

2-Furan-3-yl-6-{2-[(2R)-2-methyl-1-pvrrolidinyl]ethyl}-quinoline

The title compound was prepared using the procedure described in Example 57 using 1-furan-3-yl-ethanone (reference: J. M. McNamara et al., Tetrahedron 1984, 40 (22), 4685–4692) for 1-(1,3-thiazol-2-yl)ethanone. $^1$H NMR (CDCl$_3$) δ ppm 1.14 (d, J=6.10 Hz, 3H), 1.47 (m, 1H), 1.77 (m, 2H), 1.95 (m, 1H), 2.25 (q, J=8.82 Hz, 1H), 2.40 (m, 2H), 3.01 (m, 2H), 3.14 (m, 1H), 3.35 (m, 1H), 7.10 (dd, J=1.87, 0.85 Hz, 1H), 7.54 (t, J=1.70 Hz, 1H), 7.57 (d, J=8.48 Hz, 1H), 7.58 (dd, 1H), 7.60 (s, 1H), 8.00 (d, J=8.14 Hz, 1H), 8.07 (d, J=7.80 Hz, 1H), 8.13 (m, 1H). MS (DCI-NH$_3$) [M+H]$^+$ at 307.

Example 101

2-(4,5-Dihydro-thiazol-2-yl)-6-{2-[(2R)-2-methyl-1-pyrrolidinyl]ethyl}-quinoline The title compound was prepared using the procedure described in Example 57 using 2-acetyl-2-thiazoline for 1-(1,3-thiazol-2-yl)ethanone. $^1$H NMR (CDCl$_3$) δ ppm 1.13 (d, J=6.10 Hz, 3H), 1.46 (m, 1H), 1.76 (m, 2H), 1.94 (m, 1H), 2.24 (q, J=8.59 Hz, 1H), 2.40 (m, 2H), 3.02 (m, 2H), 3.13 (m, 1H), 3.29 (m, 1H), 3.41 (t, J=8.48 Hz, 2H), 4.60 (t, J=8.48 Hz, 2H), 7.63 (dd, J=8.48, 2.03 Hz, 1H), 7.65 (s, 1H), 8.11 (d, J=8.82 Hz, 1H), 8.13 (s, 2H). MS (DCI-NH$_3$) [M+H)$^+$ at 326.

Example 102

1-[4-(6-{2-[(2R)-2-methyl-1-pyrrolidinyl]ethyl}-quinolin-2-yl)-phenyl]-ethanone

The title compound was prepared using the procedure described in Example 57 using 1,4-diacetylbenzene for 1-(1,3-thiazol-2-yl)ethanone. $^1$H NMR (CDCl$_3$) δ ppm 1.15 (d, J=5.76 Hz, 3H), 1.48 (m, 1H), 1.79 (m, 2H), 1.95 (m, 1H), 2.26 (q, 1H), 2.42 (m, 2H), 2.67 (s, 3H), 3.04 (m, 2H), 3.15 (m, 1H), 3.31 (m, 1H), 7.64 (dd, J=8.48, 2.03 Hz, 1H), 7.67 (s, 1H), 7.90 (d, J=8.48 Hz, 1H), 8.11 (m, 3H), 8.20 (d, J=8.48 Hz, 1H), 8.27 (m, 2H). MS (DCI-NH$_3$) [M+H]$^+$ at 359.

Example 103

3-(6-{2-[(2R)-2-methyl-1-pyrrolidinyl]ethyl}-quinolin-2-yl)-2-trifluoromethyl-pyridin-4-ol The title compound was prepared using the procedure described in Example 57 using 1-(4-hydroxy-2-trifluoromethyl-pyridin-3-yl)-ethanone (reference: L. S. Vasil'ev et al., Russ. Chem.BI. 1996, 45 (11), 2574–2577) for 1-(1,3-thiazol-2-yl)ethanone. $^1$H NMR (CD$_3$OD) δ ppm 1.43 (d, J=6.44 Hz, 3H), 1.73 (m, 1H), 2.06 (m, 2H), 2.29 (m, 1H), 3.10–3.75 (m, 7H), 6.93 (d, J=5.76 Hz, 1H), 7.52 (d, J=8.48 Hz, 1H), 7.70 (dd, J=8.65, 1.87 Hz, 1H), 7.88 (d, J=1.70 Hz, 1H), 8.01 (d, J=8.82 Hz, 1H), 8.23 (d, J=6.10 Hz, 1H), 8.33 (d, J=8.48 Hz, 1H). MS (DCI-NH$_3$) [M+H]$^+$ at 402.

Example 104

2-(3,5-Dimethyl-1H-pyrazol-4-yl)-6-{2-[(2R)-2-methyl-1-pyrrolidinyl]ethyl}-quinoline The title compound was prepared using the procedure described in Example 54F using 1-(3,5-dimethyl-1H-pyrazol-4-yl)-ethanone (reference: E. E. Emelina et al., Russ. J. Org. Chem. 1994, 30(10), 1637–1639) for 3-acetylpyridine. $^1$H NMR (CDCl$_3$) δ ppm 1.17 (d, J=5.76 Hz, 3H), 1.51 (m, 1H), 1.80 (m, 2H), 1.97 (m, 1H), 2.28 (m, 1H), 2.44 (m, 2H), 2.51 (s, 3H), 2.51 (s, 3H), 3.05 (m, 2H), 3.15 (m, 1H), 3.32 (m, 1H), 7.47 (d, J=8.48 Hz, 1H), 7.59 (dd, J=8.48, 2.03 Hz, 1H), 7.63 (s, 1H), 8.01 (d, J=8.81 Hz, 1H), 8.10 (d, J=8.81 Hz, 1H). MS (DCI-NH$_3$) [M+H]$^+$ at 335.

Example 105

6-{2-[(2R)-2-methyl-1-pyrrolidinyl]ethyl}-2-(1H-pyrazol-4-yl)-quinoline

The title compound was prepared using the procedure described in Example 57 using 1-(1H-pyrazol-4-yl)-ethanone (reference: G. Heinisch et al., Monatsh. Chem. 1988, 119, 253–262) for 1-(1,3-thiazol-2-yl)ethanone. $^1$H NMR (CDCl$_3$) δ ppm 1.16 (d, J=6.10 Hz, 3H), 1.48 (m, 1H), 1.76 (m, 1H), 1.94 (m, 2H), 2.29 (q, J=8.36 Hz, 1H), 2.44 (m, 2H), 3.02 (m, 2H), 3.22 (m, 1H), 3.38 (m, 1H), 7.53 (d, J=8.48 Hz, 1H), 7.56 (s, 1H), 7.57 (dd, 1H), 7.97 (d, J=7.46 Hz, 1H), 8.00 (d, J=8.14 Hz, 1H), 8.08 (s, 2H), 11.14 (br. s, 1H). MS (DCI-NH$_3$) [M+H]$^+$ at 307.

Example 106

2,6-Dimethyl-5-(6-{2-[(2R)-2-methyl-1-pyrrolidinyl]ethyl}-quinolin-2-yl)-nicotinamide

Example 106A

5-Acetyl-2,6-dimethyl-1,4-dihydro-pyridine-3-carbonitrile

A mixture of 3-aminocrotonitrile (2.0 g, 24 mmol), 2,4-pentanedione (4.9 g, 49 mmol), paraformaldehyde (1.5 g, 49 mmol) and piperidine (12 drops) in ethanol (100 mL) was heated to reflux for 4 hours, cooled and concentrated to dryness. The residue was treated with diethyl ether (150 mL). The solid was collected and washed with ether. The solid was triturated with dichloromethane (2×100 mL). The combined dichloromethane triturations were concentrated to provide 2.5 g of the title compound. $^1$H NMR (DMSO-d$_6$) δ ppm 1.92 (t, J=1.02 Hz, 3H), 2.09 (s, 3H), 2.10 (s, 3H), 3.20 (s, 2H), 8.65 (s, 1H). MS (DCI-NH$_3$) [M+H]$^+$ at 177.

Example 106B 5-acetyl-2,6-dimethylnicotinonitrile

The product from Example 106A (1.0 g, 5.7 mmol) was treated with toluene (15 mL), treated with barium manganate (3.0 g, 12 mmol), stirred over night at ambient temperature and filtered. The filtrate was concentrated and chromatographed (using 20:1 and then 3:2 hexane:ethyl acetate) to provide 0.9 g of the title compound. $^1$H NMR (CDCl$_3$) δ ppm 2.60 (s, 3H), 2.79 (s, 3H), 2.79 (s, 3H), 8.16 (s, 1H). MS (DCI-NH$_3$) [M+H]$^+$ at 175.

Example 106C

2,6-Dimethyl-5-(6-{2-[(2R)-2-methyl-1-pyrrolidinyl]ethyl}-quinolin-2-yl)-nicotinamide The title compound was prepared using the procedure described in Example 57 using 5-acetyl-2,6-dimethylnicotinonitrile for 1-(1,3-thiazol-2-yl)ethanone providing the product from Example 67 which eluted first and the title compound which eluted second. $^1$H NMR (CDCl$_3$) δ ppm 1.18 (d, J=5.43 Hz, 3H), 1.53 (m, 1H), 1.80 (m, 2H), 1.98 (m, 1H), 2.2–2.6 (m, 3H), 2.65 (s, 3H), 2.78 (s, 3H), 3.09 (m, 2H), 3.19 (m, 1H), 3.33 (m, 1H), 5.75 (s, 1H), 5.90 (s, 1H), 7.52 (d, J=8.48 Hz, 1H), 7.66 (dd, J=8.65, 1.87 Hz, 1H), 7.71 (s, 1H), 7.94 (s, 1H), 8.06 (d, J=8.82 Hz, 1H), 8.19 (d, J=8.14 Hz, 1H). MS (DCI-NH$_3$) [M+H]$^+$ at 389.

Example 107

2-[2-(2R-Methyl-pyrrolidin-1-yl)-ethyl]-6-pyridin-4-1-quinoline

The title compound was prepared using the procedure described in Example 51 using 4-pyridinylboronic acid for 3-pyridinylboronic acid. The title compound was treated with HCl in ethyl acetate to give the corresponding trihydrochloride salt. mp 145–147° C. (uncorrected); MS (ESI) 318 (M+H)$^+$; $^1$H NMR (trihydrochloride, CD$_3$OD, 400 MHz) δ 9.12 (1H, m), 9.03 (2H, d), 8.94 (1H, d), 8.65 (2H, d), 8.61 (1H, d), 8.53 (1H, d), 8.12 (1H, d), 4.10 (1H, br), 3.90 (1H, br), 3.80 (1H, br), 3.62 (2H, br), 3.42 (1H, m), 2.40 (1H, m), 2.3–2.1 (3H, m), 1.82 (1H, br, m), 1.58 (3H, d).

Example 108

6-(6-Methoxy-pyridin-3-yl)-2-[2(R)-(2-methyl-pyrrolidin-1-yl)-ethyl]-quinoline The title compound was prepared using the procedure described in Example 51 using 6-methoxy-pyridin-3-ylboronic acid for 3-pyridinylboronic acid.

The title compound was treated with L-tartaric acid in IPA to give the corresponding tartrate. mp 132–134° C. (uncorrected); MS (ESI) 348 (M+H)$^+$; $^1$H NMR (tartrate, DMSO-d$_6$, 400 MHz) δ 8.62 (1H, d), 8.37 (1H, d), 8.24 (1H, d), 8.18 (1H, dd), 8.08 (1H, dd), 8.04 (1H, d), 7.52 (1H, d), 6.94 (1H, d), 4.05, 3.90 (2H, s), 3.80–3.4 (3H, m), 3.32 (3H, m), 3.04 (1H, q), 2.13 (1H, m), 1.90 (2H, m), 1.60 (1H, m), 1.35, 1.03 (3H, d).

Example 109

6-(2,6-Difluoro-pyridin-3-yl)-2-[2-(2R-methyl-pyrrolidin-1-yl)-ethyl]-quinoline The title compound was prepared using the procedure described in Example 51 using 2,6-difluoro-pyridin-3-ylboronic acid for 3-pyridinylboronic acid.

The title compound was treated with L-tartaric acid in IPA to give the corresponding tartrate. mp 142–143° C. (uncorrected); MS (ESI) 354 (M+H)$^+$; $^1$H NMR (tartrate, DMSO-d$_6$, 400 MHz) δ 8.62 (1H, q), 8.60 (1H, d), 8.21 (1H, s), 8.08 (1H, d), 7.94 (1H, d), 8.04 (1H, d), 7.59 (1H, d), 7.35 (1H, dd), 4.00 (2H, s), 3.80–3.4 (3H, m), 3.38 (1H, m), 3.25 (2H, m), 2.96 (1H, q), 2.12 (1H, m), 1.89 (2H, m), 1.59 (1H, m), 1.32 (3H, d).

Example 110

6-(6-Chloro-pyridin-3-yl)-2-[2-(2(R)-methyl-pyrrolidin-1-yl)-ethyl]-quinoline The title compound was prepared using the procedure described in Example 51 using 2-chloro-5-trimethylstannanyl-pyridine for 3-pyridinylboronic acid. The title compound was treated with L-tartaric acid in IPA to give the corresponding tartrate. mp 167–168° C. (uncorrected); MS (ESI) 352 (M+H)$^+$; $^1$H NMR (tartrate, CD$_3$OD, 400 MHz) δ 8.87 (1H, d), 8.40 (1H, d), 8.05 (1H, d), 8.02 (1H, dd), 8.13 (1H, d), 8.08 (1H, dd), 7.59 (1H, d), 7.57 (1H, d), 4.40 (2H, s), 4.05 (1H, br, m), 3.78 (1H, br, m), 3.63 (1H, br, m), 3.6–3.4 (3H, m), 3.35 (1H, m), 2.35 (1H, m), 2.14 (2H, m), 1.82 (1H, m), 1.58, 1.15 (3H, d).

Example 111

6-(2,6-Dichloro-pyridin-3-yl)-2-[2-(2(R)-methyl-pyrrolidin-1-yl)-ethyl]-quinoline The title compound was prepared using the procedure described in Example 51 using 2,6-dichloro-pyridin-3-ylboronic acid for 3-pyridinylboronic acid.

The title compound was treated with HCl in ethyl acetate to give the corresponding dihydrochloride. mp 105–107° C. (uncorrected); MS (ESI) 386 (M+H)$^+$; $^1$H NMR (dihydrochloride, DMSO-d$_6$, 400 MHz) δ 8.52 (1H, d), 8.19 (1H, s), 8.15 (1H, d), 8.10 (1H, d), 7.94 (1H, dd), 7.75 (1H, d), 7.68 (1H, d), 3.90 (2H, br, m), 3.66 (1H, br, m), 3.50 (3H, br, m), 3.22 (1H, br, m), 2.22 (1H, br, m), 1.96 (2H, br, m), 1.66 (1H, br, m), 1.45 (3H, br, d).

Example 112

2-[2-(2(R)-Methyl-pyrrolidin-1-yl)-ethyl]-6-pyrazin-2-yl-quinoline

The title compound was prepared using the procedure described in Example 51 using 2-tri-tert-butylstannanyl-pyrazine for 3-pyridinylboronic acid. MS (ESI) 319 (M+H)$^+$; $^1$H NMR (CDCl$_3$, 400 MHz) δ 9.20 (1H, d), 8.70 (1H, t), 8.58 (1H, d), 8.50 (1H, d), 8.37 (1H, dd), 8.20 (1H, d), 8.19 (1H, d), 7.43 (1H, d), 3.4–3.2 (4H, m), 2.65 (1H, br, m), 2.45 (1H, br, m), 2.34 (1H, br, m), 1.95 (1H, br, m), 1.82 (1H, br, m), 1.75 (1H, br, m), 1.50 (1H, br, m), 1.15 (3H, d).

Example 113

2-[2-(2(R)-Methyl-pyrrolidin-1-yl)-ethyl]-6-pyrimidin-5-yl-quinoline

The title compound was prepared using the procedure described in Example 51 using 5-tri-tert-butylstannanyl-pyrimidine for 3-pyridinylboronic acid.

The title compound was treated with HCl in ethyl acetate to give the corresponding trihydrochloride. mp 160–162° C. (uncorrected); MS (ESI) 319 (M+H)$^+$; $^1$H NMR (trihydrochloride, DMSO-d$_6$, 400 MHz) δ 9.32 (2H, s), 9.26 (1H, s), 8.70 (1H, d), 8.52 (1H, d), 8.38 (1H, dd), 8.30 (1H, d), 7.82 (1H, d), 3.92 (1H, m), 3.65 (3H, br, m), 3.50 (2H, br, m), 3.22 (1H, br, m), 2.10 (1H, m), 2.00 (2H, br, m), 1.70 (1H, br, m), 1.50 (3H, br, d).

Example 114

6-(2,4-Dimethoxy-pyrimidin-5-yl)-2-[2-(2(R)-methyl-pyrrolidin-1-yl)-ethyl]-quinoline The title compound was prepared using the procedure described in Example 51 using 2,6-dimethoxypyrimidin-5-ylboronic acid for 3-pyridinylboronic acid. MS (ESI) 379 (M+H)$^+$; $^1$H NMR (CDCl$_3$, 400 MHz) δ 8.34 (1H, s), 8.10 (1H, d), 8.07 (1H, d), 7.88 (1H, d), 7.82 (1H, dd), 7.38 (1H, d), 4.06 (3H, s), 4.05 (3H, s), 3.30 (2H, m), 3.22 (2H, m), 2.60 (1H, m), 2.42 (1H, m), 2.30 (1H, q), 1.95 (1H, m), 1.80 (1H, m), 1.72 (1H, m), 1.43 (1H, m), 1.13 (3H, d).

Example 115

Dimethyl-(4-{2-[2-(2(R)-methyl-pyrrolidin-1-yl)-ethyl]-quinolin-6-yl}-phenyl)-amine The title compound was prepared using the procedure described in Example 51 using 4-dimethylaminophenylboronic acid for 3-pyridinylboronic acid.

The title compound was treated with L-tartaric acid in IPA to give the corresponding tartrate. mp 155–156° C. (uncorrected); MS (ESI) 360 (M+H)$^+$; $^1$H NMR (tartrate, DMSO-d$_6$, 400 MHz) δ 8.30 (1H, d), 8.10 (1H, d), 8.02 (1H, dd), 7.95 (1H, d), 7.68 (2H, d), 7.47 (1H, d), 6.83 (2H, d), 4.00 (2H, s), 3.60 (1H, m), 3.48 (1H, m), 3.27 (2H, m), 3.12 (2H, m), 2.97 (6H, s), 2.82 (1H, m), 2.08 (1H, m), 1.83 (2H, m), 1.52 (1H, m), 1.28 (3H, d).

Example 116

1-(4-{2-[2-(2(R)-Methyl-pyrrolidin-1-yl)-ethyl]-quinolin-6-yl}-phenyl)-ethanone

The title compound was prepared using the procedure described in Example 51 using 4-acetylphenylboronic acid for 3-pyridinylboronic acid. The title compound was treated with L-tartaric acid in IPA to give the corresponding tartrate. mp 152–154° C. (uncorrected); MS (ESI) 359 (M+H)$^+$; $^1$H NMR (tartrate, CD$_3$OD, 400 MHz) δ 8.40 (1H, d), 8.24 (1H, s), 8.11 (2H, d), 8.09 (2H, m), 7.92 (2H, d), 7.55 (1H, d), 4.39 (2H, s), 4.01 (1H, m), 3.79 (1H, m), 3.63 (1H, m), 3.53 (1H, m), 3.50 (2H, m), 3.31 (1H, m), 2.64 (3H, s), 2.38 (1H, m), 2.12 (2H, m), 1.82 (1H, m), 1.58 (3H, d).

Example 117

6-(4-Chloro-phenyl)-2-[2-(2(R)-methyl-pyrrolidin-1-yl)-ethyl]-quinoline

The title compound was prepared using the procedure described in Example 51 using 4-chlorophenylboronic acid for 3-pyridinylboronic acid. The title compound was treated with HCl in ethyl acetate to give the corresponding dihydrochloride. mp 154–155° C. (uncorrected); MS (ESI) 351 (M+H)$^+$; $^1$H NMR (dihydrochloride, DMSO-d$_6$, 400 MHz) δ 8.70 (1H, d), 8.43 (1H, s), 8.27 (2H, s), 7.90 (2H, d), 7.81 (1H, d), 7.60 (2H, d), 3.90 (1H, br, m), 3.63 (3H, br, m), 3.50 (2H, br, m), 3.23 (1H, br, m), 2.20 (1H, s), 2.00 (2H, m), 1.68 (1H, m), 1.42 (3H, br, d).

Example 118

6-(2,6-Dimethyl-pyridin-3-yl)-2-[2-(2(R)-methyl-pyrrolidin-1-yl)-ethyl]-quinoline The title compound was prepared using the procedure described in Example 51 using 2,6-dimethyl-3-(4,4,5,5-tetramethyl-[1,3,2]dioxaborolan-2-yl)-pyridine for 3-pyridinylboronic acid. The title compound was treated with HCl in ethyl acetate to give the corresponding trihydrochloride. mp 176–177° C. (uncorrected); MS (ESI) 346 (M+H)$^+$; $^1$H NMR (trihydrochloride, CD$_3$OD, 400 MHz) δ 9.08 (1H, d), 8.46 (2H, d), 8.42 (1H, d), 8.18 (1H, dd), 8.14 (1H, d), 7.89 (1H, d), 4.08 (1H, m), 3.90 (1H, m), 3.82 (2H, m), 3.65 (2H, br, m), 3.42 (11H, m), 2.87 (3H, s), 2.75 (3H, s), 2.39 (1H, m), 2.18 (2H, br, m), 1.83 (1H, br, m), 1.58 (3H, d).

Example 119

6-(5-Methoxy-pyridin-3-yl)-2-[2-(2(R)-methyl-pyrrolidin-1-yl)-ethyl]-quinoline

The title compound was prepared using the procedure described in Example 51 using 3-methoxy-5-(4,4,5,5-tetramethyl-[1,3,2]d ioxaborolan-2-yl)-pyridine for 3-pyridinylboronic acid. MS (ESI) 348 (M+H)$^+$; $^1$H NMR (CDCl$_3$, 400 MHz) δ 8.57 (1H, s), 8.34 (1H, d), 8.12 (2H, d), 7.96 (1H, d), 7.90 (1H, dd), 7.48 (1H, dd), 7.40 (1H, d), 3.95 (3H, s), 3.76, 3.63 (1H, m), 3.4–3.2 (3H, m), 2.64 (1H, m), 2.45 (1H, m), 2.32 (1H, q), 1.95 (1H, m), 1.82 (1H, m), 1.73 (1H, m), 1.45 (1H, m), 1.15 (3H, d).

Example 120

6-(3,5-Dimethyl-isoxazol-4-yl)-2-[2-(2(R)-methyl-pyrrolidin-1-yl)-ethyl]-quinoline The title compound was prepared using the procedure described in Example 51 using 3,5-dimethyl-isoxazol-4-ylboronic acid for 3-pyridinylboronic acid. The title compound was treated with HCl in ethyl acetate to give the corresponding trihydrochloride. mp 174–175° C. (uncorrected); MS (ESI) 336 (M+H)$^+$; $^1$H NMR (trihydrochloride, DMSO-d$_6$, 400 MHz) δ 8.72 (1H, d), 8.30 (1H, d), 8.18 (1H, d), 7.97 (1H, dd), 7.83 (1H, d), 3.90 (1H, br, m), 3.65 (2H, br, m), 3.52 (2H, br, m), 3.23 (1H, br, m), 2.50 (3H, s), 2.32 (3H, s), 2.20 (2H, br, m), 2.00 (2H, br, m), 1.70 (1H, br, m), 1.45 (3H, br, d).

Example 121

4-{2-[2-(2(R)-Methyl-pyrrolidin-1-yl)-ethyl]-quinolin-6-yl}-benzoic acid methyl ester The title compound was prepared using the procedure described in Example 51 using 4-methoxycarbonylphenylboronic acid for 3-pyridinylboronic acid. The title compound was treated with HCl in ethyl acetate to give the corresponding dihydrochloride. mp 172–174° C. (uncorrected); MS (ESI) 375 (M+H)$^+$; $^1$H NMR (diihydrochloride, DMSO-d$_6$, 400 MHz) δ 8.86 (1H, d), 8.60 (1H, s), 8.39 (2H, s), 8.12 (2H, d), 8.04 (2H, d), 7.95 (1H, d), 3.95 (1H, br, m), 3.90 (3H, s), 3.70 (2H, br, m), 3.52 (2H, br, m), 3.24 (1H, br, m), 2.20 (2H, m), 2.00 (2H, br, m), 1.68 (1H, br, m), 1.45 (3H, br, d).

Example 122

2-[2-(2(R)-Methyl-pyrrolidin-1-yl)-ethyl]-6-(4-methylsulfanyl-phenyl)-quinoline The title compound was prepared using the procedure described in Example 51 using 4-methylsulfanylphenylboronic acid for 3-pyridinylboronic acid.

The title compound was treated with HCl in ethyl acetate to give the corresponding dihydrochloride. mp 158–159° C. (uncorrected); MS (ESI) 363 (M+H)$^+$; $^1$H NMR (dihydrochloride, DMSO-d$_6$, 400 MHz) 68.79 (1H, d), 8.43 (1H, s), 8.31 (2H, br, s), 7.88 (1H, d), 8.02 (2H, d), 7.43 (2H, d), 3.95 (1H, br, m), 3.67 (2H, br, m), 3.50 (3H, br, m), 3.23 (1H, br, m), 2.53 (3H, s), 2.20 (1H, m), 2.00 (2H, br, m), 1.68 (1H, br, m), 1.45 (3H, br, d).

Example 123

6-(6-Fluoro-pyridin-3-yl)-2-[2-(2(R)-methyl-pyrrolidin-1-yl)-ethyl]-quinoline The title compound was prepared using the procedure described in Example 51 using 2-fluoro-5-(4,4,5,5-tetramethyl-[1,3,2]dioxaborolan-2-yl)-pyridine for 3-pyridinylboronic acid. The title compound was treated with HCl in ethyl acetate to give the corresponding trihydrochloride. mp 162–163° C. (uncorrected); MS (ESI) 336 (M+H)$^+$; $^1$H NMR (trihydrochloride, DMSO-d$_6$, 400 MHz) δ 8.93 (1H, d), 8.77 (1H, d), 8.58 (1H, d), 8.50 (1H, td), 8.40 (2H, m), 7.96 (1H, d), 7.40 (1H, dd), 3.95 (1H, br, m), 3.71 (2H, br, m), 3.52 (2H, br, m), 3.24 (1H, br, m), 3.05 (1H, m), 2.20 (1H, m), 2.00 (2H, br, m), 1.68 (1H, br, m), 1.45 (3H, br, d).

Example 124

5-{2-[2-(2(R)-Methyl-pyrrolidin-1-yl)-ethyl]-quinolin-6-yl}-nicotinonitrile

The title compound was prepared using the procedure described in Example 51 using 5-(4,4,5,5-tetramethyl-[1,3,2]d ioxaborolan-2-yl)-nicotinonitrile for 3-pyridinylboronic acid. The title compound was treated with L-tartaric acid in IPA to give the corresponding tartrate. mp 100–102° C.; MS (ESI) 343 (M+H)$^+$; $^1$H NMR (tartrate, DMSO-d$_6$, 400 MHz) δ 9.36 (1H, d), 9.05 (1H, d), 8.81 (1H, dd), 8.49 (1H, d), 8.37 (1H, d), 8.20 (1H, dd), 8.09 (1H, d), 7.59 (1H, d), 4.04 (2H, s), 3.65 (1H, m), 3.49 (1H, m), 3.36 (2H, m), 3.17 (2H, m), 2.89 (1H, m), 2.09 (1H, m), 1.88 (2H, br, m), 1.56 (1H, br, m), 1.28, 1.05 (3H, d).

Example 125

2,4-Dimethoxy-5-{6-[2-((2R)-methyl-pyrrolidin-1-yl)-ethyl]-naphthalen-2-yl}-pyrimidine

Example 125A

2-[6-(2,4-Dimethoxy-pyrimidin-5-yl)-naphthalen-2-yl]-ethanol A mixture of the product from Example 1E (0.1020 g, 0.41 mmol), 2,4-dimethoxypyrimidin-5-yl-boronic acid (0.0920 g, 0.50 mmol), dichlorobis (triphenylphosphine)-palladium (II) (0.0096 g, 0.014 mmol), and K$_3$PO$_4$.H$_2$O in isopropyl alcohol (5 mL) and H$_2$O (2 mL) was stirred at 65° C. for 2 hours. The reaction mixture was cooled to room temperature then concentrated under reduced pressure. The residue was partitioned between brine and ethyl acetate. The aqueous layer was washed with ethyl acetate, and the combined organic extracts were dried (MgSO$_4$), and filtered. The filtrate was concentrated under reduced pressure and the residue was purified by column chromatography (7:3 hexane/ethyl acetate). Fractions containing product were combined to provide (0.0376 g, 30% yield). $^1$H NMR (CDCl$_3$, 300 MHz), δ 8.37 (s, 1H), 7.95 (s, 1H), 7.86–7.82 (d, J=6 Hz, 2H), 7.71 (s, 1H), 7.64–7.59 (d, J=9 Hz, 1H), 7.46–7.6 (s, J=9 Hz, 1H), 4.08 (s, 3H), 4.06 (s, 3H), 3.89–3.84 (t, J=7.5 Hz, 2H), 3.30–2.98 (t, J=7.5 Hz, 2H). MS (DCI-NH$_3$) [M+H]$^+$ at 311.

Example 125B

Methanesulfonic acid 2-[6-(2,4-dimethoxy-pyrimidin-5-yl)-naphthalen-2-yl]-ethyl ester The compound was prepared by the method in Example 3B, using 2-[6-(2,4-dimethoxy-pyrimidin-5-yl)-naphthalen-2-yl]-ethanol for 1-{3-[6-(2-hydroxyethyl)-2-naphthyl]phenyl}ethanone (39 mg, 84% yield). $^1$H NMR (CD$_3$OD, 300 MHz), δ 8.38 (s, 1H), 7.98 (s, 1H), 7.9–7.86 (d, J=9 Hz, 2H), 7.7 (s, 1H), 7.66–7.61 (d, J=6 Hz, 1H), 7.49–7.44 (d, J=6 Hz, 1H), 4.57–4.52 (t, J=7.5 Hz, 2H), 4.08 (s, 3H), 4.06 (s, 3H), 3.27–3.19 (t, J=7.5 Hz, 2H). MS (DCI-NH$_3$) [M+H]$^+$ at 389.

Example 125C 2,4-Dimethoxy-5-{6-[2-((2R)-methyl-pyrrolidin-1-yl)-ethyl]-naphthalen-2-yl}-pyrimidine The title compound was prepared by the method in Example 3C using, methanesulfonic acid 2-[6-(2,4-dimethoxy-pyrimidin-5-yl)-napthalen-2-yl]-ethyl ester for 2-[6-(3-acetylphenyl)-2-naphthyl]ethyl methanesulfonate (0.0063 g, 14% yield). $^1$H NMR (CD$_3$OD, 300 MHz), δ 8.38 (s, 1H), 7.98 (s, 1H), 7.9–7.86 (d, J=9 Hz, 2H), 7.7 (s, 1H), 7.66–7.61 (d, J=6 Hz, 1H), 7.49–7.44 (d, J=6 Hz, 1H), 4.08 (s, 3H), 4.06 (s, 3H), 3.18–3.11 (m, 2H), 3.09–2.96 (m, 2H), 2.51–2.4 (m, 2H), 2.39–2.31 (m, 1H), 2.10–1.91 (m, 1H), 1.89–1.76 (m, 2H), 1.55–1.4 (m, 1H), 1.15 (d, J=6 Hz, 3H). MS (DCI-NH$_3$) [M+H]$^+$ at 378.

Example 126

2,6-Difluoro-3-{6-[2-((2R)-2-methyl-pyrrolidin-1-yl)-ethyl]-naphthalen-2-yl}-pyridine

Example 126A

2-[6-(2,6-Difluoro-pyridin-3-yl)-naphthalen-2-yl]-ethanol

The compound was prepared by the method in Example 125A using 2,6-difluoropyrid-3-yl-boronic acid for 2,4-dimethoxypyrimidin-5-yl-boronic acid (23 mg, 20% yield). $^1$H NMR (CD$_3$OD, 300 MHz), δ 8.32–8.25 (m, 1H), 8.04, (s, 1H), 7.91–7.87 (m, 2H), 7.74, (s, 1H), 7.67–7.62 (d, J=6 Hz, 1H), 7.48–7.45 (d, J=6.6 Hz, 1H), 7.15–7.1 (d, J=5.4 Hz, 1H), 3.92–3.85 (t, J=6 Hz, 2H), 3.06–2.99 (t, J=6 Hz, 2H). MS (DCI-NH$_3$) [M+H]$^+$ at 286.

Example 126B

Methanesulfonic acid 2-[6-(2,6-difluoro-pyridin-3-yl)-naphthalen-2-yl]-ethyl ester The compound was prepared using the method in Example 3B using, 2-[6-(2,6-difluoro-pyridin-3-yl)-naphthalen-2-yl]-ethanol for 1-{3-[6-(2-hydroxyethyl)-2-naphthyl]phenyl}ethanone (24 mg, 82% yield). $^1$H NMR (CD$_3$OD, 300 MHz), 8.34–8.25 (m, 1H), 8.05 (s, 1H), 7.97–7.9 (m, 2H), 7.82 (s, 1H), 7.72–7.67 (d, J=6 Hz, 1H), 7.54–7.48 (d, J=7.8 Hz, 1H), 7.17–7.11 (d, J=6 Hz, 1H), 4.57–4.52 (t, J=6 Hz, 2H), 4.15–4.06 (t, J=6 Hz, 2H), 2.94 (s, 3H). MS (DCI-NH$_3$) [M+NH$_4$]$^+$ at 381.

Example 126C 2,6-Difluoro-3-{6-[2-((2R)-2-methyl-pyrrolidin-1-yl)-ethyl]-naphthalen-2-yl}-pyridine The title compound was prepared using the method in Example 3C using, methanesulfonic acid 2-[6-(2,6-difluoro-pyridin-3-yl)-naphthalen-2-yl]-ethyl ester for 2-[6-(3-acetylphenyl)-2-naphthyl]ethyl methanesulfonate. $^1$H NMR (CD$_3$OD, 300 MHz), δ 8.34–8.25 (m, 1H), 8.05 (s, 1H), 7.97–7.9 (m, 2H), 7.82 (s, 1H), 7.72-7.67 (d, J=6 Hz, 1H), 7.54–7.48 (d, J=7.8 Hz, 1H), 7.17–7.11 (d, J=6 Hz, 1H), 3.18–3.11 (m, 2H), 3.09–2.96 (m, 2H), 2.51–2.4 (m, 2H), 2.39–2.31 (m, 1H), 2.10–1.91 (m, 1H), 1.89–1.76 (m, 2H), 1.55–1.4 (m, 1H), 1.15 (d, J=6 Hz, 3H). MS (DCI-NH$_3$) [M+H]$^+$ at 353.

Example 127

Cyclopropyl-(3-{6-[2-((2R)-2-methyl-pyrrolidin-1-yl)-ethyl]-naphthalen-2-yl}-phenyl)-methanone

Example 127A (3-Bromo-phenyl)-cyclopropyl-methanone

A mixture of 1-(3-bromo-phenyl)-4-chloro-1-oxo-butane (1.0 g, 3.82 mmol) and a 1.0 M solution of sodium bis(trimethylsilyl)amide (4.21 mL, 4.21 mmol, 1.1 equiv.) in toluene (10 mL) was stirred at room temperature for 3 h. The reaction mixture was concentrated under reduced pressure and the residue was partitioned between ethyl acetate and brine. The organic layer was dried (MgSO$_4$), and filtered. The filtrate was concentrated under reduced pressure and the residue was purified by column chromatography (98:2 hexane/ethyl acetate) to provide the title intermediate (0.53 g, 62% yield). $^1$H NMR (CDCl3, 300 MHz), δ 8.14 (t, J=1.7 Hz, 1H) 7.95–7.92 (m, 1H), 7.71–7.67 (m, 1H), 7.36 (t, J=7.8 Hz, 1H), 2.66–2.58 (m, 1H), 1.29–1.24 (m, 2H), 1.11–1.05 (m, 2H). MS (DCI-NH$_3$) [M+H]$^+$ at 225.

Example 127B (3-{6-[2-(tert-Butyl-dimethyl-silanyloxy)-ethyl]-naphthalen-2-yl}-phenyl)-cyclopropyl-methanone The compound was prepared using the method in 26C substituting (3-bromo-phenyl)-cyclopropyl-methanone in place of 5-bromopyrimidine (71 mg, 61% yield). $^1$H NMR (CDCl$_3$, 300 MHz), δ 8.35 (s, 1H) 8.09–8.02 (m, 2H), 7.94–7.87 (m, 3H), 7.79–7.71 (m, 2H), 7.83–7.58 (t, J=8.1 Hz, 1H), 7.45–7.4 (d, J=7.5 Hz, 1H), 4.03–3.96 (q, J=6 Hz, 2H), 3.1–3.04 (t, J=6 Hz, 2H), 2.71–2.69 (m, 1H), 1.35–1.28 (m, 2H), 1.15–1.08 (m, 2H), 0.87 (s, 9H), –0.02 (s, 3H). MS (DCI-NH$_3$) [M+H]$^+$ at 431.

Example 127C cyclopropyl-{3-[6-(2-hydroxy-ethyl)-naphthalen-2-yl]-phenyl}-methanone The compound was prepared by the method in 26D using (3-{6-[tert-butyl-dimethyl-silanyloxy)-ethyl]-naphthalen-2-yl}-phenyl)-cyclopropyl-methanone for 5-[6-(2-{[tert-butyl(dimethyl)silyl]oxy}ethyl)-2-naphthyl]pyrimidine (71 mg, 61% yield). $^1$H NMR (CDCl$_3$, 300 MHz), δ 8.35 (s, 1H) 8.09–8.02 (m, 2H), 7.94–7.87 (m, 3H), 7.79–7.71 (m, 2H), 7.83–7.58 (t, J=8.1 Hz, 1H), 7.45–7.4 (d, J=7.5 Hz, 1H), 4.03–3.96 (q, J=6 Hz, 2H), 3.1–3.04 (t, J=6 Hz, 2H), 2.71–2.69 (m, 1H), 1.35–1.28 (m, 2H), 1.15–1.08 (m, 2H). MS (DCI-NH$_3$) [M+H]$^+$ at 317.

Example 127D

Methanesulfonic acid 2-[6-(3-cyclopropanecarbonyl-phenyl)-naphthalen-2-yl]-ethyl ester The compound was prepared using the method in 3B using cyclopropyl-{3-[6-(2-hydroxy-ethyl)-naphthalen-2-yl]-phenyl}-methanone for 1-{3-[6-(2-hydroxyethyl)-2-naphthyl]phenyl}ethanone (68 mg, 76% yield). $^1$H NMR (CDCl$_3$, 300 MHz), δ 8.35 (s, 1H) 8.09–8.02 (m, 2H), 7.94–7.87 (m, 3H), 7.79–7.71 (m, 2H), 7.83–7.58 (t, J=8.1 Hz, 1H), 7.45–7.4 (d, J=7.5 Hz, 1H), 4.1–4.05 (t, J=6 Hz, 2H), 3.6 (s, 3H), 3.17–3.02 (t, J=6 Hz, 2H), 2.71–2.69 (m, 1H), 1.35–1.28 (m, 2H), 1.15–1.08 (m, 2H). MS (DCI-NH$_3$) [M+NH$_4$]$^+$ at 412.

Example 127E

Cyclopropyl-(3-{6-[2-((2R)-2-methyl-pyrrolidin-1-yl)-ethyl]-naphthalen-2-yl}-phenyl)-methanone The title compound was prepared using the method in 3C using methane sulfonic acid 2-[6-(3-cyclopropanecarbonyl-phenyl)-naphthalen-2-yl]-ethyl ester for 2-[6-(3-acetylphenyl)-2-naphthyl]ethyl methanesulfonate (3.9 mg, 6% yield). $^1$H NMR (CD$_3$OD, 300 MHz), δ 8.35 (s, 1H) 8.09–8.02 (m, 2H), 7.94–7.87 (m, 3H), 7.79–7.71 (m, 2H), 7.83–7.58 (t, J=8.1 Hz, 1H), 7.45–7.4 (d, J=7.5 Hz, 1H), 3.29-3.18 (m, 1H), 3.09–2.91 (m, 3H), 2.6–2.39 (m, 3H), 2.1–1.98 (m, 1H), 2.9–2.77 (m, 1H), 2.58–2.42 (m, 1H), 1.35–1.32 (m, 2H), 1.22–1.12 (m, 6H), 1.96–1.83 (m, 1H). MS (DCI-NH$_3$) [M+H]$^+$ at 384.

Example 128

3-Methoxy-6-{6-[2-((2R)-2-methyl-pyrrolidin-1-yl)-ethyl]-naphthalen-2-yl}-pyridazine

Example 128A

3-{6-[2-(tert-Butyl-dimethyl-silanyloxy)-ethyl]-naphthalen-2-yl}-6-methoxy-pyridazine The compound was prepared using the method in 26C using 3-chloro-6-methoxy-pyridazine for 5-bromopyrimidine (64 mg, 76% yield). $^1$H NMR (CDCl$_3$, 300 MHz), δ 8.43 (s, 1H), 8.24–8.2 (d, J=7.5 Hz, 1H), 7.96–7.81 (m, 3H), 7.63 (s, 1H), 7.44–7.41 (d, J=6 Hz, 1H), 7.12–7.07 (d, J=9

Hz, 1H), 4.96‑4.86 (m, 2H), 4.22 (s, 3H), 3.03–2.91 (m, 2H), 0.87 (s, 9H), −0.02 (s, 6H). MS (DCI-NH$_3$) [M+H]$^+$ at 395.

Example 128B

2-[6-(6-Methoxy-pyridazin-3-yl)-naphthalen-2-yl]-ethanol

The compound was prepared by the method in 26D using 3-{6-[2(tert-butyl-dimethyl-silanyloxy)-ethyl]-naphthalen-2-yl}-6-methoxy-pyridazine for 5-[6-(2-{[tert-butyl(dimethyl)silyl]oxy}ethyl)-2-naphthyl]pyrimidine (6.7 mg, 37% yield). $^1$H NMR (CDCl$_3$, 300 MHz), δ 8.43 (s, 1H), 8.24–8.2 (d, J=7.5 Hz, 1H), 7.96–7.81 (m, 3H), 7.63 (s, 1H), 7.44–7.41 (d, J=6 Hz, 1H), 7.12–7.07 (d, J=9 Hz, 1H), 4.22 (s, 3H), 4.03 (q, J=5.4 Hz, 2H), 3.09–3.04 (d, J=5.4 Hz, 2H). MS (DCI-NH$_3$) [M+H]$^+$ at 281.

Example 128C

Methanesulfonic acid 2-[6-(6-methoxy-pyridazin-3-yl)-naphthalen-2-yl]-ethyl ester The compound was prepared by the method in Example 3B using 2-[6-(6-methoxy-pyridazin-3-yl)-naphthalen-2-yl]-ethanol for 1-{3-[6-(2-hydroxyethyl)-2-naphthyl]phenyl}ethanone (14 mg, 64% yield). $^1$H NMR (CDCl$_3$, 300 MHz), δ 8.43 (s, 1H), 8.24–8.2 (d, J=7.5 Hz, 1H), 7.96–7.81 (m, 3H), 7.63 (s, 1H), 7.44–7.41 (d, J=6 Hz, 1H), 7.12–7.07 (d, J=9 Hz, 1H), 4.57‑4.52 (t, J=6 Hz, 2H), 4.22 (s, 3H), 4.15–4.06 (t, J=6 Hz, 2H) 2.94 (s, 3H). MS (DCI-NH$_3$) [M+NH$_4$]$^+$ at 359.

Example 128D

3-Methoxy-6-{6-[2-((2R)-2-methyl-pyrrolidin-1-yl)-ethyl]-naphthalen-2-yl}-pyridazine The title compound was prepared using the method in 1H using methanesulfonic acid 2-[6-(6-methoxy-pyridazin-3-yl)-naphthalen-2-yl]-ethyl ester for 2-[6-(4-cyanophenyl)-2-naphthyl]ethyl 4-methylbenzenesulfonate (3 mg, 22% yield). $^1$H NMR (CD$_3$OD, 300 MHz), δ 8.43 (s, 1H), 8.24–8.2 (d, J=7.5 Hz, 1H), 7.96–7.81 (m, 3H), 7.63 (s, 1H), 7.44–7.41 (d, J=6 Hz, 1H), 7.12–7.07 (d, J=9 Hz, 1H), 4.17 (s, 3H), 3.18–3.11 (m, 2H), 3.09–2.96 (m, 2H), 2.51–2.4 (m, 2H), 2.39–2.31 (m, 1H), 2.10–1.91 (m, 1H), 1.89–1.76 (m, 2H), 1.55–1.4 (m, 1H), 1.15 (d, J=6 Hz, 3H). MS (DCI-NH$_3$) [M+NH$_4$]$^+$ at 348.

Example 129

4-{6-[2-(2-Methyl-piperidin-1-vi)-ethyl]-naphthalen-2-yl}-benzonitrile

The title compound was prepared by the method described in Example 1H using 2-methylpiperidine in place of (2R)-2-methylpyrrolidine (9 mg, 8.4% yield). $^1$H NMR (CD$_3$OD, 300 MHz), δ 8.17 (s, 1H), 7.97–7.91 (m, 4H), 7.87–7.75 (m, 4H), 7.45 (d, J=6 Hz, 1H), 3.13–2.86 (m, 5H), 2.55–2.49 (m, 2H), 1.81–1.67 (m, 4H), 1.46–1.33 (m, 2H), 1.08 (d, J=6 Hz, 3H). MS (DI-NH$_3$) [M+H]$^+$ at 355.

Example 130

4-{6-[2-((2R)-2-Ethyl-pyrrolidin-1-yl)-ethyl]-naphthalen-2-yl}-benzonitrile

The title compound was prepared by the method in 1H using (2R)-2-ethylpyrrolidine for (2R)-2-methylpyrrolidine (13 mg, 7.5% yield). $^1$H NMR (CD$_3$OD, 300 MHz), δ 8.17 (s, 1H), 7.97–7.91 (m, 4H), 7.87–7.75 (m, 4H), 7.45 (d, J=6 Hz, 1H), 3.29–3.17 (m, 2H), 3.19–2.95 (m, 2H), 2.49–2.42 (m, 2H), 2.41–2.31 (m, 1H), 2.14–1.99 (m, 1H), 1.89–1.78 (m, 2H), 1.63–1.42 (m, 2H), 1.31–1.2 (m, 1H), 0.99–0.89 (m, 3H). MS (DCI-NH$_3$) [M+H]$^+$ at 355.

Example 131

2-{6-[2-((2S)-2-Methyl-pyrrolidin-1-yl)-ethyl]-naphthalen-2-yl}-2H-pyridazin-3-one The title compound was prepared by the method in Example 31H substituting (2S)-2-methylpyrrolidine in place of (2R)-2-methylpyrrolidine (42 mg, 30% yield). $^1$H NMR (HCl salt, CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.32–3.20 (m, 2H), 3.16–2.99 (m, 2H), 3.83–3.51 (m, 3H), 2.17–2.02 (m, 1H), 1.95–1.82 (m, 2H), 1.52–1.48 (m, 1H), 1.23 (d, J=2 Hz, 3H). MS (DCI-NH$_3$) [M+H]$^+$ at 334.

Example 132

2-[6-(2-Piperidin-1-yl-ethyl)-naphthalen-2-yl]-2H-pyridazin-3-one

The title compound was prepared by the method in Example 31H substituting piperidine in place of (2R)-2-methylpyrrolidine (42 mg, 50% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.1–3.0 (m, 2H), 2.84–2.75 (m, 2H), 2.63–2.58 (m, 4H) 1.74–1.60 (m, 4H), 1.60–1.51 (m, 2H). MS (DCI-NH$_3$) [M+H]$^+$ at 334.

Example 133

2-{6-[2-(tert-Butyl-methyl-amino)-ethyl]-naphthalen-2-yl}-2H-pyridazin-3-one

The title compound was prepared by the method in Example 31H substituting methyl(t-butyl)amine in place of (2R)-2-methylpyrrolidine (26 mg, 31% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.1 (s, 3H), 3.01–2.9 (m, 4H), 1.23 (s, 9H). MS (DCI-NH$_3$) [M+H]$^+$ at 336.

Example 134

2-[6-(2-Diethylamino-ethyl)-naphthalen-2-yl]-2H-pyridazin-3-one

The title compound was prepared by the method in Example 31H substituting diethylamine in place of (2R)-2-methylpyrrolidine (11 mg, 14% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.1 (m, 4H), 3.0–2.91 (m, 4H), 1.26–1.19 (m, 6H). MS (DCI-NH$_3$) [M+H]$^+$ at 322.

Example 135

2-[6-(2-Morpholin-4-yl-ethyl)-naphthalen-2-yl]-2H-pyridazin-3-one

The title compound was prepared by the method in Example 31H substituting morpholine in place of (2R)-2-methylpyrrolidine (27 mg, 34% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.75–3.69 (m, 2H), 3.69–3.62 (m, 1H), 3.61–3.49 (m, 1H), 3.06–2.99 (m, 2H), 2.75–2.71 (m, 2H), 2.61–2.58 (m, 4H). MS (DCI-NH$_3$) [M+H]$^+$ at 336.

Example 136

2-{6-[2-(Ethyl-methyl-amino)-ethyl]-naphthalen-2-yl}-2H-pyridazin-3-one

The title compound was prepared by the method in Example 31H using ethylmethylamine for (2R)-2-methylpyrrolidine (30 mg, 37% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.07–2.98 (m, 2H), 2.85–2.77 (m, 2H), 2.69–2.6 (m, 2H), 2.41 (s, 3H), 1.17 (t, J=6 Hz, 3H). MS (DCI-NH$_3$) [M+H]$^+$ at 308.

Example 137

2-{6-[2-((2S)-2-Fluoromethyl-pyrrolidin-1-yl)-ethyl]-naphthalen-2-yl}-2H-pyridazin-3-one The title compound was prepared by the method in Example 31H substituting (S)-2-fluoromethylpyrrolidine in place of (2R)-2-methylpyrrolidine (21 mg, 24% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 4.58–4.51 (m, 2H), 4.48–4.29 (d, J=36 Hz, 1H), 3.33–3.21 (m, 2H), 3.06–2.99 (m, 2H), 2.8–2.71 (m, 1H), 2.54–2.42 (m, 1H), 2.02–1.95 (m, 1H), 1.88–1.79 (m, 1H), 1.71–1.59 (m, 1H), 1.33–1.29 (m, 1H). MS (DCI-NH$_3$) [M+H]$^+$ at 352.

Example 138

2-{6-[2-((2S)-2-Hydroxymethyl-pyrrolidin-1-yl)-ethyl]-naphthalen-2-yl}-2H-pyridazin-3-one The title compound was prepared by the method in Example 31H substituting (S)-prolinol in place of (2R)-2-methylpyrrolidine (67 mg, 32% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.66 (m, 2H), 3.17–3.0 (m, 3H), 2.99–2.93 (m, 1H), 2.79–2.73 (m, 1H), 2.11–2.02 (m, 1H), 1.97–1.82 (m, 3H), 1.8–1.72 (m, 1H). MS (DCI-NH$_3$) [M+H]$^+$ at 350.

Example 139

2-{6-[2-((R)-2-Ethyl-pyrrolidin-1-yl)-ethyl]-naphthalen-2-yl}-2H-pyridazin-3-one The title compound was prepared by the method in Example 31H substituting (2R)-2-ethylpyrrolidine in place of (2R)-2-methylpyrrolidine (3.1 mg, 5.7% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.29–3.17 (m, 2H), 3.19–2.95 (m, 2H), 2.49–2.42 (m, 2H), 2.41–2.31 (m, 1H), 2.14–1.99 (m, 1H), 1.89–1.78 (m, 2H), 1.63–1.42 (m, 2H), 1.31–1.2 (m, 1H), 0.99–0.89 (m, 3H). MS (DCI-NH$_3$) [M+H]$^+$ at 348.

Example 140

2-[6-(2-Azetidin-1-yl-ethyl)-naphthalen-2-yl]-2H-pyridazin-3-one

The title compound was prepared by the method in Example 31H substituting azetidine in place of (2R)-2-methylpyrrolidine (1.3 mg, 2.5% yield). $^1$H NMR (CD$_3$OD, 300 MHz), 6–8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.44–3.2 (m, 6H), 1.36–1.29 (m, 2H), 1.18–1.23 (d, J=4.5 Hz, 2H). MS (DCI-NH$_3$) [M+H]$^+$ at 306.

Example 141

2-{6-[2-((2S)-2-Fluoromethyl-azetidin-1-yl)-ethyl]-naphthalen-2-yl}-2H-pyridazin-3-one The title compound was prepared by the method in Example 31H substituting (2S)-2-fluoromethylazetidine in place of (2R)-2-methylpyrrolidine (1.7 mg, 3.4% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.24–2.8 (m, 5H), 2.76–2.62 (m, 1H), 2.09–1.93 (m, 1H), 1.68–1.53 (m, 1H), 1.3–1.2 (m, 2H), 0.98–0.91 (m, 1H). MS (DCI-NH$_3$) [M+H]$^+$ at 337.

Example 142

2-{6-[2-((2S)-2-Hydroxymethyl-azetidin-1-yl)-ethyl]-naphthalen-2-yl}-2H-pyridazin-3-one The title compound was prepared by the method in Example 31H using (2S)-2-hydroxymethylazetidine for (2R)-2-methylpyrrolidine (2 mg, 3.7% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 4.08–3.98 (m, 1H), 4.0–3.73 (m, 3H), 3.55–3.45 (m, 1H), 3.42–3.34 (m, 1H), 3.24–3.14 (m, 1H), 3.09–2.98 (m, 2H), 2.33–2.98 (m, 2H), 1.34–1.22 (m, 1H). MS (DCI-NH$_3$) [M+H]$^+$ at 336.

Example 143

2-{6-[2-((2R,5R)-2,5-Dimethyl-pyrrolidin-1-yl)-ethyl]-naphthalen-2-yl}-2H-pridazin-3-one The title compound was prepared by the method in Example 31H using (2R, 5R)-2,5-dimethylpyrrolidine for (2R)-2-methylpyrrolidine (2 mg, 3.7% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.51–3.49 (m, 1H), 3.15–3.05 (m, 1H), 2.39–2.28 (m, 4H), 1.86–1.76 (m, 4H), 1.39–1.46 (d, J=5.1 Hz, 6H). MS (DCI-NH$_3$) [M+H]$^+$ at 348.

Example 144

2-{6-[2-((2R,6S)-2,6-Dimethyl-piperidin-1-yl)-ethyl]-naphthalen-2-yl}-2H-pyridazin-3-one The title compound was prepared by the method in Example 31H substituting (2R,6S)-2,6-dimethylpiperidine in place of (2R)-2-methylpyrrolidine (1.2 mg, 2.4% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.61–3.18 (m, 7H), 2.1–1.91 (m, 1H), 1.9–1.84 (m, 1H), 1.74–1.58 (m, 3H) 1.5–1.44 (d, J=3.6 Hz, 6H). MS (DCI-NH$_3$) [M+H]$^+$ at 362.

Example 145

2-{6-[2-((R)-3-Hydroxy-piperidin-1-yl)-ethyl]-naphthalen-2-yl}-2H-pyridazin-3-one The title compound was prepared by the method in Example 31H substituting (3R)-3-hydroxypiperidine in place of (2R)-2-methylpyrrolidine (1.3 mg, 2.8% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.78–3.67 (m, 1H), 3.1–2.99 (m, 3H), 2.91–2.81 (m, 1H), 2.8–2.72 (m, 2H), 2.22–2.01 (m, 1H), 1.99–1.89 (m, 1H), 1.86–1.78 (m, 1H), 1.69–1.54 (m, 1H), 1.36–1.22 (m, 1H). MS (DCI-NH$_3$) [M+H]$^+$ at 350.

Example 146

2-{6-[2-((R)-2-Methyl-piperidin-1-yl)-ethyl]-naphthalen-2-yl}-2H-pyridazin-3-one The title compound was prepared by the method in Example 31H substituting (R)-2-methylpiperidine in place of (2R)-2-methylpyrrolidine (9.2 mg, 1.8% yield). $^1$H NMR (CD$_3$OD, 300 MHz), δ 8.12–8.06 (m, 2H), 7.97–7.89 (m, 2H), 7.82 (s, 1H), 7.68–7.62 (m, 1H), 7.55–7.46 (m, 2H), 7.15 (dd, J=2, 12 Hz, 1H), 3.14–2.88 (m, 5H), 2.66–2.49 (m, 2H), 1.8–1.56 (m, 4H), 1.46–1.34 (m, 2H), 1.22–1.19 (d, J=4.8 Hz, 3H). MS (DCI-NH$_3$) [M+H]$^+$ at 348.

Example 147

2,6-Dimethyl-3-{6-[2-((2R)-2-methyl-pyrrolidin-1-yl)-ethyl]-naphthalen-2-yl}-pyridine Example 147A 2-[6-(2,6-Dimethyl-pyridin-3-yl)-naphthalen-2-yl]-ethanol The compound was prepared by the method in Example 1F substituting 2,6-dimethylpyridyl-3-boronic acid in place of para-cyanophenyl boronic acid (78 mg, 35% yield). $^1$H NMR (CD$_3$OD, 300 MHz), δ 8.09–8.05 (m, 1H), 7.99–7.87 (m, 2H), 7.82–7.79 (m, 1H), 7.66–7.62 (m, 1H), 7.53–7.44 (m, 2H), 7.22–7.13 (m, 1H), 4.844.51 (t, J=6 Hz, 2H), 3.05–2.98 (t, J=6 Hz, 2H), 2.56 (s, 3H), 2.06 (s, 3H). MS (DCI-NH$_3$) [M+H]$^+$ at 278.

Example 147B

Methanesulfonic acid 2-[6-(2,6-dimethyl-pyridin-3-yl)-naphthalen-2-yl]-ethyl ester The compound was prepared by the method in Example 3B substituting 2-[6-(2,6-dimethyl-pyridin-3-yl)-naphthalen-2-yl]-ethanol in place of 4-[6-(2-hydroxy-ethyl)-naphthalen-2-yl]-benzonitrile (0.9763 g, 97% yield). $^1$H NMR (CD$_3$OD, 300 MHz), δ 8.09–8.05 (m, 1H), 7.99–7.87 (m, 2H), 7.82–7.79 (m, 1H), 7.66–7.62 (m, 1H), 7.53–7.44 (m, 2H), 7.22–7.13 (m, 1H), 4.57–4.52 (t, J=7.5 Hz, 2H), 4.08 (s, 3H), 3.27–3.19 (t, J=7.5 Hz, 2H). MS (DCI-NH$_3$) [M+H]$^+$ at 356.

Example 147C 2,6-Dimethyl-3-{6-[2-((2R)-2-methyl-pyrrolidin-1-yl)-ethyl]-naphthalen-2-yl}-pyridine The title compound was prepared by the method in Example 3C substituting methanesulfonic acid 2-[6-(2,6-dimethyl-pyridin-3-yl)-naphthalen-2-yl]-ethyl ester in place of methanesulfonic acid 2-[6-(4-cyano-phenyl)-naththalen-2-yl]-ethyl ester (12 mg, 12% yield). $^1$H NMR (CD$_3$OD, 300 MHz), δ 8.09–8.05 (m, 1H), 7.99–7.87 (m, 2H), 7.82–7.79 (m, 1H), 7.66–7.62 (m, 1H), 7.53–7.44 (m, 2H), 7.22–7.13 (m, 1H), 4.08 (s, 3H), 4.06 (s, 1H), 3.18–3.11 (m, 2H), 3.09–2.96 (m, 2H), 2.55 (s, 3H), 2.45 (s, 3H), 2.51–2.4 (m, 2H), 2.39–2.31 (m, 1H), 2.10–1.91 (m, 1H), 1.89–1.76 (m, 2H), 1.55–1.4 (m, 1H), 1.15 (d, J=6 Hz, 3H). MS (DCI-NH$_3$) [M+H]$^+$ at 345.

Example 148

5-{6-[2-((R)-2-Methyl-pyrrolidin-1-yl)-ethyl]-naphthalen-2-yl}-thiazole

Example 148A 2-(6-Thiazol-5-yl-naphthalen-2-yl)-ethanol

A mixture of the product from Example 1 E (206 mg, 0.82 mmol), 2-trimethylsilyl-5-tributylytin-thiazole (369 mg, 0.82 mmol), dichlorobis-(triphenylphosphine)-palladium (II) (30 mg, 0.43 mmol), and lithium chloride (123 mg, 2.9 mmol), were stirred at 100° C. in 25 mL toluene overnight. The reaction was cooled to room temperature then diluted with 5 mL aqueous KF. The aq. layer was extracted with ethyl acetate. The organic layer was dried over MgSO$_4$ and solid was removed by filtration. The resulting brown oil was purified by column chromatography 1:1 hexane/ethyl acetate (0.081 g, 39% yield). $^1$H NMR (CCl$_3$D, 300 MHz), δ 8.84 (s, 1H), 8.16 (s, 1H), 8.0 (s, 1H), 7.89–7.82 (m, 2H), 7.71–7.66 (m, 2H), 7.45–7.4 (m, 1H), 4.1–3.94 (t, J=5.7 Hz, 2H), 3.09–3.02 (t, J=5.7 Hz, 2H). MS (DCI-NH$_3$) [M+H]$^+$ at 256.

Example 148B

Methanesulfonic acid 2-(6-thiazol-5-yl-naphthalen-2-yl)-ethyl ester The compound was prepared by the method in Example 3B substituting 2-(6-thiazol-5-yl-naphthalen-2-yl)-ethanol in place of 4-[6-(2-hydroxy-ethyl)-naphthalen-2-yl]-benzonitrile (91 mg, 86% yield). $^1$H NMR (CCl$_3$D, 300 MHz), δ 8.84 (s, 1H), 8.16 (s, 1H), 8.0 (s, 1H), 7.89–7.82 (m, 2H), 7.71–7.66 (m, 2H), 7.45–7.4 (m, 1H), 4.57–4.52 (t, J=7.5 Hz, 2H), 4.08 (s, 3H), 3.27–3.19 (t, J=7.5 Hz, 2H). MS (DCI-NH$_3$) [M+H]$^+$ at 334.

Example 148C

5-{6-[2-((R)-2-Methyl-pyrrolidin-1-yl)-ethyl]-naphthalen-2-yl}-thiazole

The title compound was prepared by the method in Example 3C substituting methanesulfonic acid 2-(6-thiazol-5-yl-naphthalen-2-yl)-ethyl ester in place of methanesulfonic acid 2-[6-(4-cyano-phenyl)-naththalen-2-yl]-ethyl ester (53 mg, 50% yield). $^1$H NMR (CD$_3$OD, 300 MHz), δ 8.84 (s, 1H), 8.16 (s, 1H), 8.0 (s, 1H), 7.89–7.82 (m, 2H), 7.71–7.66 (m, 2H), 7.45–7.4 (m, 1H), 4.08 (s, 3H), 4.06 (s, 1H), 3.18–3.11 (m, 2H), 3.09–2.96 (m, 2H), 2.55 (s, 3H), 2.45 (s, 3H), 2.51–2.4 (m, 2H), 2.39–2.31 (m, 1H), 2.10–1.91 (m, 1H), 1.89–1.76 (m, 2H), 1.55–1.4 (m, 1H), 1.15 (d, J=6 Hz, 3H). MS (DCI-NH$_3$) [M+H]$^+$ at 323.

Example 149

2-{6-[2-((R)-2-Methyl-pyrrolidin-1-yl)-ethyl]-naphthalen-2-yl}-pyrimidine

Example 149A

2-[6-(tert-Butyl-dimethyl-silanyloxyethyl)-naphthalen-2-yl]-pyrimidine

The compound was prepared by the method in Example 26C substituting 2-bromopyrimidine in place of 5-bromopyrimidine (157 mg, 60% yield), $^1$H NMR (CD$_3$OD, 300 MHz), δ 8.95 (s, 1H), 8.92–8.89 (m, 2H), 8.54–8.51 (m, 1H), 8.07–7.94 (m, 3H), 7.55–7.51 (m, 1H), 7.42–7.38 (m, 1H), 4.96–4.86 (m, 2H), 3.03–2.91 (m, 2H), 0.87 (s, 9H), −0.02 (s, 6H). MS (DCI-NH$_3$) [M+H]$^+$ at 365.

Example 149B (6-Pyrimidin-2-yl-naphthalen-2-yl)-ethanol

The compound was prepared by the method in Example 26D substituting 2[6-[(tert-butyl-dimethyl-silanyloxy]ethyl)-naphthalen-2-yl]-pyrimidine in place of 5-[6-(2-{[tert-butyl(dimethyl)silyl]oxy}ethyl)-2-naphthyl]-pyrimidine (56 mg, 72% yield. $^1$H NMR (CD$_3$OD, 300 MHz), δ 8.95 (s, 1H), 8.92–8.89 (m, 2H), 8.54–8.51 (m, 1H), 8.07–7.94 (m, 3H), 7.55–7.51 (m, 1H), 7.42–7.38 (m, 1H), 4.1–3.94 (t, J=5.7 Hz, 2H), 3.09–3.02 (t, J=5.7 Hz, 2H). MS (DCI-NH$_3$) [M+H]$^+$ at 237.

Example 149C

Methanesulfonic acid 2-(6-pyrimidin-2-yl-naphthalen-2-yl)-ethyl ester

The title compound was prepared by the method of Example 3B, using the product from Example 149B in place of the product from Example 3A to give an off-white solid.

Example 149D

2-{6-[2-((R-2-Methyl-pyrrolidin-1-yl)-ethyl]-naphthalen-2-yl}-pyrimidine

The title compound was prepared by the method of Example 3C using the product from Example 149C in place of the product from Example 3B (56 mg, 41% yield). $^1$H NMR (CD$_3$OD, 300 MHz), δ 8.95 (s, 1H), 8.92–8.89 (m, 2H), 8.54–8.51 (m, 1H), 8.07–7.94 (m, 3H), 7.55–7.51 (m, 1H), 7.42–7.38 (m, 1H), 3.24–3.28 (m, 1H), 3.12–3.01 (m, 1H), 2.75–2.55 (m, 3H), 2.45–2.34 (m, 2H), 2.09–1.98 (m, 1H), 1.91–1.78 (m, 2H), 1.56–1.41 (m, 1H), 1.19 (d, J=6 Hz, 3H). MS (DCI-NH$_3$) [M+H]$^+$ at 318.

Example 150

3-Chloro-6-{6-[2-((R)-2-methyl-pyrrolidin-1-yl)-ethyl]-naphthalen-2-yl}-pyridazine Example 150A 3-[6-(tert-Butyl-dimethyl-silanyloxyethyl)-naphthalen-2-yl]-6-chloro-pyridazine The compound was prepared using the method in Example 26C using 3,6-dichloropyridazine for 5-bromopyrimidine (63 mg, 32% yield). $^1$H NMR (CD$_3$OD, 300 MHz), δ 8.63 (s, 1H), 8.37–8.33 d, J=9 Hz, 1H), 8.29–8.24 (d, J=9 Hz, 1H), 8.09–8.02 (m, 1H), 7.94–7.88 (m, 1H), 7.89–7.79 (m, 1H), 7.49–7.43 (m, 2H), 4.96–4.86 (m, 2H), 3.03–2.91 (m, 2H), 0.87 (s, 9H), −0.02 (s, 6H). MS (DCI-NH$_3$) [M+H]$^+$ at 400.

Example 150B

[6-(6-Chloro-pyridazin-3-yl)-naphthalen-2-yl]-methanol

The compound was prepared using the method in Example 26D using 2,6-(tert-butyl-dimethyl-silanyloxyethyl)-naphthalen-2-yl]-6-chloro-pyridazine for 5-[6-(2-{[tert-butyl(dimethyl)silyl]oxy}ethyl)-2-naphthyl]pyrimidine (29 mg, 68% yield). $^1$H NMR (CD$_3$OD, 300 MHz), δ 8.63 (s, 1H), 8.37–8.33 (d, J=9 Hz, 1H), 8.29–8.24 (d, J=9 Hz, 1H), 8.09–8.02 (m, 1H), 7.94–7.88 (m, 1H), 7.89–7.79 (m, 1H), 7.49–7.43 (m, 2H), 4.1–3.94 (t, J=5.7 Hz, 2H), 3.09–3.02 (t, J=5.7 Hz, 2H). MS (DCI-NH$_3$) [M+H]$^+$ at 271.

Example 150C

Methanesulfonic acid 6-(6-chloro-pyridazin-3-yl)-naphthalen-2-ylethyl ester

The title compound was prepared by the method of Example 3B, using the product from Example 150B in place of the product from Example 3A to give an off-white solid.

Example 150D

3-Chloro-6-{6-[2-((R)-2-methyl-pyrrolidin-1-yl)-ethyl]-naphthalen-2-yl}-pyridazine The title compound was prepared by the method of Example 3C using the product from Example 150C in place of the product from Example 3B (3.2 mg, 16% yield). $^1$H NMR (CD$_3$OD, 300 MHz), δ 8.63 (s, 1H), 8.37–8.33 d, J=9 Hz, 1H), 8.29–8.24 (d, J=9 Hz, 1H), 8.09–8.02 (m, 1H), 7.94–7.88 (m, 1H), 7.89–7.79 (m, 1H), 7.49–7.43 (m, 2H), 3.24–3.28 (m, 1H), 3.12–3.01 (m, 1H), 2.75–2.55 (m, 3H), 2.45–2.34 (m, 2H), 2.09–1.98 (m, 1H), 1.91–1.78 (m, 2H), 1.56–1.41 (m, 1H), 1.19 (d, J=6 Hz, 3H). MS (DCI-NH$_3$) [M+H]$^+$ at 352.

Example 151

5-{6-[2-((R)-2-Methyl-pyrrolidin-1-yl)-ethyl]-naphthalen-2-yl}-pyrimidin-2-ylamine Example 151A 5-[6-(tert-Butyl-dimethyl-silanyloxyethyl)-naphthalen-2-yl]-pyrimidin-2-ylamine The compound was prepared using the method in Example 26C using 2-amino-5-iodopyrimidine for 5-bromopyrimidine (85 mg, 46% yield). $^1$H NMR (CD$_3$OD, 300 MHz), δ 8.79 (s, 2H), 8.1 (s, 1H), 7.98–7.95 (m, 2H), 7.84 (s, 1H), 7.77–7.74 (d, J=6 Hz, 1H), 7.52–7.47 (d, J=6 Hz, 1H), 4.96–4.86 (m, 2H), 3.03–2.91 (m, 2H), 0.87 (s, 9H), −0.02 (s, 6H). MS (DCI-NH$_3$) [M+H]$^+$ at 380.

Example 151B

[6-(2-Amino-pyrimidin-5-yl)-naphthalen-2-yl]-ethanol

The compound was prepared using the method in Example 26D using 5-[6-(tert-butyl-dimethyl-silanyloxy-ethyl)-naphthalen-2-yl]-pyrimidin-2-ylamine for 5-[6-(2-{[tert-butyl(dimethyl)silyl]oxy}ethyl)-2-naphthyl]pyrimidine (29 mg, 68% yield). $^1$H NMR (CD$_3$OD, 300 MHz), δ 8.79 (s, 2H), 8.1 (s, 1H), 7.98–7.95 (m, 2H), 7.84 (s, 1H), 7.77–7.74 (d, J=6 Hz, 1H), 7.52–7.47 (d, J=6 Hz, 1H), 4.1–3.94 (t, J=5.7 Hz, 2H), 3.09–3.02 (t, J=5.7 Hz, 2H). MS (DCI-NH$_3$) [M+H]$^+$ at 252.

Example 151C

Methanesulfonic acid 6-(2-amino-pyrimidin-5-yl)-naphthalen-2-ylethyl ester

The title compound was prepared by the method of Example 3B, using the product from Example 151 B in place of the product from Example 3A to give an off-white solid.

Example 151D

5-{6-[2-((R)-2-Methyl-pyrrolidin-1-yl)-ethyl]-naphthalen-2-yl}-pyrimidin-2-ylamine The title compound was prepared by the method of Example 3C using the product from Example 151C in place of the product from Example 3B (5.4 mg, 23% yield), $^1$H NMR (CD$_3$OD, 300 MHz), δ 8.79 (s, 2H), 8.1 (s, 1H), 7.98–7.95 (m, 2H), 7.84 (s, 1H), 7.77–7.74 (d, J=6 Hz, 1H), 7.52–7.47 (d, J=6 Hz, 1H), 3.24–3.28 (m, 1H), 3.12–3.01 (m, 1H), 2.75–2.55 (m, 3H), 2.45–2.34 (m, 2H), 2.09–1.98 (m, 1H), 1.91–1.78 (m, 2H), 1.56–1.41 (m, 1H), 1.19 (d, J=6 Hz, 3H). MS (DCI-NH$_3$) [M+H]$^+$ at 333.

Example 152

2-Methyl-5-{6-[2-((2R)-2-methyl-pyrrolidin-1-yl)-ethyl]-naphthalen-2-yl}-pyridine

Example 152A

5-[6-(tert-Butyl-dimethyl-silanyloxyethyl)-naphthalen-2-yl]-2-methyl-pyridine

The compound was prepared using the method in Example 26C using 5-bromo-2-methylpyridine for 5-bromopyrimidine (61 mg, 26% yield). $^1$H NMR (CD$_3$OD, 300 MHz), δ 9.13 (s, 1H), 9.88–9.84 (d, J=9, 1H), 8.35 (s, 1H), 8.1–7.98 (m, 3H), 7.94–7.89 (m, 2H), 7.62–7.57 (d, J=6 Hz, 1H), 4.96–4.86 (m, 2H), 3.03–2.91 (m, 2H), 2.66 (s, 3H), 0.87 (s, 9H), −0.02 (s, 6H). MS (DCI-NH$_3$) [M+H]$^+$ at 378.

Example 152B

[6-(6-Methyl-pyridin-3-yl)-naphthalen-2-yl]-ethanol

The compound was prepared by the method in Example 26D substituting 5-[6-(tert-butyl-dimethyl-silanyloxyethyl)-naphthalen-2-yl]-2-methyl-pyridine in place of 5-[6-(2-{[tert-butyl(dimethyl)silyl]oxy}ethyl)-2-naphthyl]pyrimidine (29 mg, 68% yield). $^1$H NMR (CD$_3$OD, 300 MHz), δ 9.13 (s, 1H), 9.88–9.84 (d, J=9, 1H), 8.35 (s, 1H), 8.1–7.98 (m, 3H), 7.94–7.89 (m, 2H), 7.62–7.57 (d, J=6 Hz, 1H), 4.1–3.94 (t, J=5.7 Hz, 2H), 3.09–3.02 (t, J=5.7 Hz, 2H), 2.64 (s, 3H). MS (DCI-NH$_3$) [M+H]$^+$ at 250.

Example 152C

Methanesulfonic Acid 6-(6-methyl-pyridin-3-yl)-naphthalen-2-ylethyl Ester

The title compound was prepared by the method of Example 3B, using the product from Example 152B in place of the product from Example 3A to give an off-white solid.

Example 152D

2-Methyl-5-{6-[2-((2R)-2-methyl-pyrrolidin-1-yl)-ethyl]-naphthalen-2-yl}-pyridine The title compound was prepared by the method of Example 3C substituting the product from Example 152C in place of the product from Example 3B (4.8 mg, 17% yield). $^1$H NMR (CD$_3$OD, 300 MHz), δ 9.13 (s, 1H), 9.88–9.84 (d, J=9 Hz, 1H), 8.35 (s, 1H), 8.1–7.98 (m, 3H), 7.94–7.89 (m, 2H), 7.62–7.57 (d, J=6 Hz, 1H), 3.24–3.28 (m, 1H), 3.12–3.01 (m, 1H), 2.84 (s, 3H), 2.75–2.55 (m, 3H), 2.45–2.34 (m, 2H), 2.09–1.98 (m, 1H), 1.91–1.78 (m, 2H), 1.56–1.41 (m, 1H), 1.19 (d, J=6 Hz, 3H). MS (DCI-NH$_3$) [M+H]$^+$ at 331.

Example 153

3-Bromo-7-(2-pyrrolidin-1-yl-ethyl)-[1,5]naphthyridine

Example 153A 3,7-Dibromo-1,5-naphthyridine

To a stirred solution of 1.3 g (10 mmol) of 1,5-naphthyridine in 60 mL of CCl$_4$ was added 4.30 g (23 mmol) of bromine in 6 mL of CCl$_4$ and the mixture was refluxed for 1 hr. Pyridine (0.79 g, 10 mmol) in 10 mL of CCl$_4$ was added over a period of 0.5 hr to the refluxing mixture and the mixture was heated for an additional 12 hr, cooled and filtered. The dark green solid was treated with 100 mL of 10% solution of NaOH for 1 hr and the resulting solution was extracted with chloroform. The chloroform and the CCl$_4$ reaction solution were combined, dried over Na$_2$SO$_4$ filtered and evaporated under reduced pressure. The residue was chromatographed using 5% ethyl acetate in CCl$_4$ (25% yield). M.p. 238–239° C. $^1$H NMR (CDCl$_3$, 300 MHz) δ 8.80 (m, 2H), 9.10 (m, 2H). MS (ESI) [M+H]$^+$ at 288.

Example 153B

Tributyl-(2-ethoxy-vinyl)-stannane

The title compound was prepared as described by Wollenberg et al *J. Am. Chem. Soc.* 1977, 99, 7365.

Example 153C

3-Bromo-7-(2-ethoxy-vinyl)-[1,5]naphthyridine

A solution of 3,7-dibromo-1,5-naphthyridine (0.5 g, 1.74 mmol), tributyl-2-ethoxy-vinylstannane (1.91 mmol, 0.69 g), LiCl (8.7 mmol, 0.37 g) and 0.085 g of PdCl$_2$(PPh$_3$)$_2$ in 50 mL of toluene was heated at 95° C. for 16 hr. After cooling off, 20 mL of a 2 M solution of KF was added to the mixture and stirring was continued for 0.5 hr. The mixture was diluted with 100 mL of $CH_2Cl_2$ and washed successively with a saturated solution of sodium bicarbonate, brine and water. The organic layer was dried over sodium sulfate, filtered and evaporated under reduced pressure. The residue was chromatographed using 5% MeOH in $CH_2Cl_2$ to give the desired material in 55% yield. $^1$H NMR (CDCl$_3$, 300 MHz) δ 1.40 (m, 3H), 4.05 (m, 2H), 5.85 (s, 1H), 7.25 (s, 1H), 8.15 (m, 1H), 8.55 (m, 1H), 8.85 (m, 2H). MS (ESI) [M+H]$^+$ at 280.

Example 153D (7-Bromo-[1,5]naphthyridin-3-yl)-acetaldehyde

To a mixture of the product from Example 153C (0.25 g, 0.89 mmol) in 15 mL of THF was added 1.5 mL of HCl (6N). The mixture was heated to reflux for 5 hr, cooled and the pH adjusted to 8.0 with NaOH. The mixture was diluted with 75 mL of $CH_2Cl_2$ and washed successively with a saturated solution of sodium bicarbonate, brine and water. The organic layer was dried over sodium sulfate, filtered and evaporated under reduced pressure to give the desired product in 95% yield. $^1$H NMR (CDCl$_3$, 300 MHz) δ 3.75 (m, 2H), 8.25 (m, 1H), 8.60 (m, 1H), 8.85 (m, 1H), 9.00 (m, 1H), 9.90 (s, 1H). MS (ESI) [M+H]$^+$ at 252.

Example 153E

3-Bromo-7-(2-pyrrolidin-1-yl-ethyl)-[1,5]naphthyridine

To a stirred solution of the product from Example 153D (0.1 g, 0.4 mmol), acetic acid (0.4 mmol, 0.025 g) and pyrrolidine (0.44 mmol, 0.031 g) in dry THF (5 ml) NaBH(OAc)$_3$ was added (0.6 mmol, 0.127 g). After 12 hr at room temperature the mixture was diluted with 50 mL of $CH_2Cl_2$ and washed successively with a saturated solution of sodium bicarbonate, brine and water. The organic layer was dried over sodium sulfate, filtered and evaporated under reduced pressure. The residue was purified over silica using 10% MeOH in $CH_2Cl_2$. The desired compound was obtained in 40%. $^1$H NMR (CDCl$_3$, 300 MHz) δ 1.60 (m, 4H), 2.20 (m, 4H), 2.75 (m, 4H), 8.30 (m, 1H), 8.40 (m, 1H), 8.90 (m, 1H), 9.05 (m, 1H). MS (ESI) [M+H]$^+$ at 307.

Example 154

3-Bromo-7-[2-(2R-2-methyl-pyrrolidin-1-yl)-ethyl]-[1,5]naphthyridine

The title compound was prepared by the method described in Example 153E, using (2R)-2-methylpyrrolidine in place of pyrrolidine. $^1$H NMR (CDCl$_3$, 300 MHz) δ 1.20 (d, J=7 Hz, 3H), 1.50 (m, 4H), 2.20 (m, 2H), 2.40 (m, 1H), 2.60 (m, 2H), 2.75 (m, 2H), 8.25 (m, 1H), 8.45 (m, 1H), 8.85 (m, 1H), 9.15 (m, 1H). MS (ESI) [M+H]$^+$ at 321.

Example 155

3-Bromo-7-(2-piperidin-1-yl-ethyl)-[1,5]naphthyridine

The title compound was prepared by the method described in Example 153E, using piperidine in place of pyrrolidine. $^1$H NMR (CDCl$_3$, 300 MHz) δ 1.45–1.60 (m, 6H), 1.50 (m, 4H), 2.30 (m, 4H), 8.30 (m, 1H), 8.40 (m, 1H), 8.95 (m, 1H), 9.10 (m, 1H). MS (ESI) [M+H]$^+$ at 321.

Example 156

3-(2,6-Dimethyl-pyridin-3-yl)-7-[2-(2R-2-methyl-pyrrolidin-1-yl)-ethyl]-[1,5]naphyridine The product from Example 154 (50 mg, 0.16 mmol), 2,6-dimethyl-3-(4,4,5,5-tetramethyl-[1,3,2]dioxaborolan-2-yl)-pyridine (0.21 mmol, 0.048 g), Pd(PPh$_3$)$_2$Cl$_2$ (0.007 g, 0.008 mmol), and 1 M Na$_2$CO$_3$ (0.42 mL, 0.42 mmol) in isopropanol (5 mL) was heated to 90° C. under a dry nitrogen atmosphere for 24 hr. After cooling, the reaction mixture was filtered through diatomaceous earth and concentrated under reduced pressure. The crude material was purified by column chromatography using a mixture of dichloromethane/methanol/NH$_4$OH (90:10:1) to afford the product (53% yield). $^1$H NMR (DMSO-D$_6$, 300 MHz) δ 1.25 (d, J=7 Hz, 3H), 1.55 (m, 2H), 1.60 (m, 2H), 2.25 (m, 2H), 2.35 (m, 1H), 2.50 (s, 3H), 2.55 (s, 3H), 2.60–2.70 (m, 4H), 7.20 (m, 1H), 7.95 (m, 1H), 8.30 (m, 1H), 8.70 (m, 1H), 8.90 (m, 1H), 9.25 (m, 1H). MS (ESI) [M+H]$^+$ at 347.

Example 157

3-(2,4-Dimethoxy-pyrimidin-5-yl)-7-[2-(2R-2-methyl-pyrrolidin-1-yl)-ethyl]-[1,5naphtyridine The title compound was prepared by the method described in Example 156, using 2,4-dimethoxypyrimidin-5-ylboronic acid in place of 2,6-dimethyl-3-(4,4,5,5-tetramethyl-[1,3,2]dioxaborolan-2-yl)-pyridine. $^1$H NMR (CDCl$_3$, 300 MHz) δ 1.20 (d, J=7 Hz, 3H), 1.50 (m, 2H), 1.65 (m, 2H), 2.20 (m, 2H), 2.35 (m, 1H), 2.65–2.70 (m, 4H), 3.85 (s, 6H), 8.30 (m, 1H), 8.70 (m, 1H), 8.80 (s, 1H), 8.90 (m, 1H), 9.25 (m, 1H). MS (ESI) [M+H]$^+$ at 380.

Example 158

3-(2,6-Dimethyl-pyridin-3-yl)-7-(2-pyrrolidin-1-yl-ethyl)-[1,5]naphthyridine

The title compound was prepared by the method described in Example 156, using the product from Example 153E in place of the product from Example 154. $^1$H NMR (CDCl$_3$, 300 MHz) δ 1.55 (m, 4H), 2.35 (m, 4H), 2.50 (s, 3H), 2.55 (s, 3H) 2.60–2.70 (m, 4H), 7.25 (m, 1H), 7.90 (m, 1H), 8.30 (m, 1H), 8.70 (m, 1H), 8.90 (m, 1H), 9.25 (m, 1H). MS (ESI) [M+H]$^+$ at 333.

Example 159

3-(2,4-Dimethoxy-pyrimidin-5-yl)-7-(2-pyrrolidin-1-yl-ethyl)-[1,5]naphthyridine

The title compound was prepared by the method described in Example 156, using 2,4-dimethoxypyrimidin-5-ylboronic acid and the product from Example 153E in place of 2,6-dimethyl-3-(4,4,5,5-tetramethyl-[1,3,2]dioxaborolan-2-yl)-pyridine and the product from Example 154. $^1$H NMR (CDCl$_3$, 300 MHz) δ 1.55 (m, 2H), 1.65 (m, 2H), 2.50 (m, 4H), 2.60–2.65 (m, 4H), 3.80 (s, 3H), 3.85 (s, 3H), 8.35 (m, 1H), 8.70 (m, 1H), 8.85 (s, 1H), 8.90 (m, 1H), 9.20 (m, 1H). MS (ESI) [M+H]$^+$ at 366.

Example 160

3-(2,6-Dimethyl-pyridin-3-yl)-7-(2-piperidin-1-yl-ethyl)-[1,5]naphthyridine

The title compound was prepared by the method described in Example 156, using the product from Example 155 in place of the product from Example 154. $^1$H NMR (CDCl$_3$, 300 MHz) δ 1.45–160 (m, 6H), 2.75 (m, 4H), 2.30 (s, 3H), 2.35 (s, 3H) 2.55–2.65 (m, 4H), 7.20 (m, 1H), 7.95 (m, 1H), 8.20 (m, 1H), 8.65 (m, 1H), 8.95 (m, 1H), 9.15 (m, 1H). MS (ESI) [M+H]$^+$ at 347.

Example 161

3-(2,4-Dimethoxy-pyrimidin-5-yl)-7-(2-piperidin-1-yl-ethyl)-[1,5]naphthyridine The title compound was prepared by the method described in Example 156, using 2,4-dimethoxypyrimidin-5-ylboronic acid and the product from Example 155 in place of 2,6-dimethyl-3-(4,4,5,5-tetramethyl-[1,3,2]dioxaborolan-2-yl)-pyridine and the product from Example 154. $^1$H NMR (CDCl$_3$, 300 MHz) δ 1.40–1.55 (m, 6H), 2.45 (m, 4H), 2.65 (m, 4H), 3.70 (s, 3H), 3.80 (s, 3H), 8.35 (m, 1H), 8.75 (m, 1H), 8.80 (s, 1H), 8.95 (m, 1H), 9.30 (m, 1H). MS (ESI) [M+H]$^+$ at 380.

Example 162

3-[2-(2(R)-Methyl-pyrrolidin-1-yl)-ethyl]-7-pyridin-4-yl-isoquinoline

The title compound was prepared by the method described in Example 62G, using 4-pyridineboronic acid in place of 2,6-difluoro-3-pyridineboronic acid. $^1$H NMR (CDCl$_3$, 400 MHz) δ 9.29 (s, 1H), 8.71 (dd, 2H), 8.20 (d, 1H), 7.93 (dd, 1H), 7.88 (d, J=8 Hz, 1H), 7.62–7.61 (m, 3H), 3.41–3.34 (m, 2H), 3.28–3.25 (m, 2H), 2.84–2.79 (m, 1H), 2.79–2.69 (m, 1H), 2.61–2.50 (m, 1H), 2.43–2.37 (m, 1H), 2.04–1.50 (m, 3H), 1.22 (m, 3H). $^{13}$C NMR (CDCl$_3$, 400 MHz) δ 152.1, 150.1, 147.0, 136.1, 136.0, 128.7, 127.0, 125.6, 121.4, 118.4, 60.8, 53.9, 46.2, 36.9, 32.7, 22.0, 18.7, 10.4. MS (DCI-NH$_3$) [M+H]$^+$ at 318.

Example 163

7-(6-Methoxy-pyridin-3-yl)-3-[2-(2(R)-methyl-pyrrolidin-1-yl)-ethyl]-isoquinoline The title compound was prepared by the method described in Example 62G, using 2-methoxy-5-pyridineboronic acid in place of 2,6-difluoro-3-pyridineboronic acid. $^1$H NMR (CDCl$_3$, 400 MHz) δ 9.24 (s, 1H), 9.49 (d, J=3 Hz, 1H), 8.04 (s, 1H), 7.89 (dd, J=3, 12 Hz, 1H), 7.83 (s, 2H), 7.55 (s, 1H), 6.87 (d, J=12 Hz, 1H), 4.01 (s, 3H), 3.35–3.15 (m, 4H), 2.67–2.58 (m, 2H), 2.45–2.28 (m, 2H), 2.00–1.46 (m, 3H), 1.17 (d, 3H). $^{13}$C NMR (CDCl$_3$, 400 MHz) δ 163.4, 151.8, 144.9, 137.1, 135.7, 135.2, 129.1, 128.9, 127.2, 126.7, 124.3, 118.1, 110.9, 60.3, 54.1, 53.8, 46.3, 37.2, 32.9, 22.0, 19.2. MS (DCI-NH$_3$) [M+H]$^+$ at 347.

Example 164

3-[2-(2(R)-Methyl-pyrrolidin-1-yl)-ethyl]-7-pyrimidin-5-yl-isoquinoline

The title compound was prepared by the method described in Example 62G, using 5-(4,4,5,5-tetramethyl-[1,3,2]dioxaborolan-2-yl)-pyrimidine in place of 2,6-difluoro-3-pyridineboronic acid. $^1$H NMR (CDCl$_3$, 400 MHz) δ 9.29 (s, 1H), 9.26 (s, 1H), 9.07 (s, 2H), 8.15 (s, 1H), 7.93 (d, J=12 Hz, 1H), 7.87 (dd, J=3, 12 Hz, 1H), 7.64 (s, 1H), 3.44–3.28 (m, 4H), 2.91–2.41 (m, 3H), 2.07–1.54 (m, 4H), 1.30 (d, J=8 Hz, 3H). $^{13}$C NMR (CDCl$_3$, 400 MHz) δ 157.3, 154.6, 152.0, 135.9, 133.3, 132.2, 128.5, 127.5, 127.0, 125.6, 118.5, 61.1, 53.9, 53.8, 36.7, 32.6, 21.9, 18.5. MS (DCI-NH$_3$) [M+H]$^+$ at 319.

Example 165

7-(6-Fluoro-pyridin-3-yl)-3-[2-(2(R)-methyl-pyrrolidin-1-yl)-ethyl]-isoquinoline The title compound was prepared by the method described in Example 62G, using 2-fluoro-5-(4,4,5,5-tetramethyl-[1,3,2]dioxaborolan-2-yl)-pyridine in place of 2,6-difluoro-3-pyridineboronic acid. $^1$H NMR (CDCl$_3$, 400 MHz) δ 9.26 (s, 1H), 8.53 (m, 1H), 8.11–8.06 (m, 2H), 7.88 (d, J=8 Hz, 1H), 7.84 (d, J=8 Hz, 1H), 7.61 (s, 1H), 7.06 (dd, J=4, 12 Hz, 1H), 3.40–3.26 (m, 3H), 2.88–2.82 (m, 1H), 2.79–2.72 (m, 1H), 2.63–2.58 (m, 1H), 2.46–2.39 (m, 1H), 2.06–1.52 (m, 4H), 1.27 (d, 3H). $^{13}$C NMR (CDCl$_3$, 400 MHz) δ 164.0, 161.6, 153.2, 151.9, 145.7, 145.5, 139.5, 139.4, 135.5, 134.5, 133.7, 133.6, 129.0, 127.0, 127.0, 125.2, 116.3, 109.7, 109.3, 60.9, 53.8, 46.2, 36.7, 32.6, 21.9, 18.5. MS (DCI-NH$_3$) [M+H]$^+$ at 336.

Example 166

5-{3-[2-(2(R)-Methyl-pyrrolidin-1-yl)-ethyl]-isoquinolin-7-yl}-nicotinonitrile The title compound was prepared by the method described in Example 62G, using 5-(4,4,5,5-tetramethyl-[1,3,2]dioxaborolan-2-yl)-nicotinonitrile in place of 2,6-difluoro-3-pyridineboronic acid. $^1$H NMR (CDCl$_3$, 400 MHz) δ 9.30 (s, 1H), 9.15 (d, J=2 Hz, 1H), 8.90 (d, J=2 Hz, 1H), 8.26 (m, 1H), 8.16 (d, J=2 Hz, 1H), 7.94 (d, J=8 Hz, 1H), 7.86 (dd, J=2, 12 Hz, 1H), 7.65 (s, 1H), 3.44–3.29 (m, 3H), 2.93–2.88 (q, J=8 Hz, 1H), 2.82–2.75 (m, 1H), 2.66–2.60 (m, 1H), 2.49–2.42 (m, 1H), 2.07–1.54 (m, 4H), 1.29 (d, J=8 Hz, 3H). $^{13}$C NMR (CDCl$_3$, 400 MHz) δ 154.0, 152.0, 151.0, 150.5, 136.9, 135.9, 135.7, 133.4, 128.5, 127.5, 126.9, 125.9, 118.2, 116.1, 110.0, 61.0, 53.8, 53.7, 36.6, 32.5, 21.9, 18.2. MS (DCI-NH$_3$) [M+H]$^+$ at 343.

Example 167

7-(3-Chloro-pyridin-4-yl)-3-[2-(2(R)-methyl-pyrrolidin-1-yl)-ethyl]-isoquinoline The title compound was prepared by the method described in Example 62G, using 3-chloro-4-pyridineboronic acid in place of 2,6-difluoro-3-pyridineboronic acid. $^1$H NMR (CDCl$_3$, 400 MHz) δ 9.25 (s, 1H), 8.72 (s, 1H), 8.57 (d, J=4 Hz, 1H), 8.05 (s, 1H), 7.88 (d, J=8 Hz, 1H), 7.78 (dd, J=2, 12, Hz, 1H), 7.65 (s, 1H), 7.37 (d, J=4 Hz, 1H), 3.47–3.27 (m, 4H), 2.87–2.47 (m, 3H), 2.08–1.60 (m, 4H), 1.31 (d, J=8 Hz, 3H). $^{13}$C NMR (CDCl$_3$, 400 MHz) δ 153.4, 151.9, 149.6, 147.5, 146.1, 135.7, 134.3, 130.4, 129.7, 127.6, 126.4, 126.0, 124.9, 118.4, 61.1, 53.6, 53.5, 35.3, 35.0, 32.4, 32.3, 21.7, 18.1. MS (DCI-NH$_3$) [M+H]$^+$ at 352.

Example 168

7-Bromo-3-[2-((2R)-2-methyl-pyrrolidin-1-yl)-ethyl]-cinnolin-4-ol

Example 168A

4-Bromo-1-iodo-2-nitro-benzene

NaNO$_2$ (0.83 g, 12.00 mmol) was gradually added to conc. H$_2$SO$_4$ (9 mL). The resulting mixture was stirred and heated to 70° C. for 15 minutes then cooled to room temperature (r.t.). Next, 4-bromo-2-nitroaniline (2.4 g, 11.00 mmol) was dissolved in glacial acetic acid (22 mL) and added dropwise to the HSO$_3$NO solution, while maintaining reaction temperature below 40° C. After addition, the resulting mixture was stirred at r.t. for 30 minutes and poured into a 70° C. solution of KI (2.0 g, 12.00 mmol) dissolved in 20 mL of water. The temperature was maintained while stirring for 20 minutes and then diluted with 150 mL water and filtered. The precipitate was washed with 50 mL water and dried under vacuum to provide the product in 86% yield as an orange solid, which was used without further purification. $^1$H NMR (CDCl$_3$, 300 MHz) δ 8.00 (d, J=3 Hz, 1H), 7.91 (d, J=9 Hz, 1H), 7.42 (dd, J=3, 9 Hz, 1H). MS (DCI-NH$_3$) [M+H]$^+$ at 328.8.

Example 168B

5-Bromo-2-iodo-phenylamine

To a 15–18° C. stirred solution of SnCl$_2$ (5.20 g, 27.44 mmol), dissolved in 10 mL conc. HCl, was quickly added a solution of Example 168A (1.8 g, 5.49 mmol) in ethanol (14-mL). The resulting mixture was heated to 55° C. for 15 minutes, cooled in an ice bath, made basic by addition of a saturated KOH solution, and extracted with 250 mL CHCl$_3$. The organic phase was dried with Na$_2$SO$_4$, filtered, and the filtrate was concentrated under reduced pressure. The residue was purified by column chromatography (100% hexanes to 50/50 hexanes/dichloromethane) to provide the product as a white solid in 74% yield. $^1$H NMR (CDCl$_3$, 300 MHz) δ 7.47 (d, J=9 Hz, 1H), 6.88 (d, J=3 Hz, 1H), 6.62 (dd, J=3, 9 Hz, 1H), 4.00 (bs, 1H). MS (DCI-NH$_3$) [M]$^+$ at 297.

Example 168C

5-Bromo-2-[4-((2R)-2-methyl-pyrrolidin-1-yl)-but-1-ynyl]-phenylamine

A solution of Example 168B (0.2 g, 0.67 mmol), 1-but-3-ynyl-(2R)-2-methyl-pyrrolidine (7.4 mL as a 0.1 M solution in acetonitrile, 0.74 mmol), and triethylamine (10 mL, 72.0 mmol) was degassed with nitrogen for 10 minutes while stirring at r.t. Next, Pd(PPh$_3$)$_2$Cl$_2$ (0.010 g, 0.013 mmol) and CuI (0.003 g, 0.013 mmol) were added and the resulting mixture was degassed for an additional. 10 minutes, sealed, and stirred at r.t. for 18 hours. Contents were then concentrated under reduced pressure and the residue was dissolved in 100 mL dichloromethane, washed twice with each: 50 mL sat. NaHCO$_3$, 50 mL water, and 50 mL brine, dried with Na$_2$SO$_4$, and concentrated under reduced pressure. The crude material was purified by column chromatography (100% dichloromethane to 95:5 dichloromethane/methanol) to afford the product in 30% yield as a light yellow oil. $^1$H NMR (CD$_3$OD, 300 MHz) δ 7.03 (d, J=9 Hz, 1H), 6.88 (d, J=3 Hz, 1H), 6.68 (dd, J=3, 9 Hz, 1H), 3.41–3.20 (m, 2H), 2.79–2.52 (m, 5H), 2.12–2.04 (m, 1H), 1.92–1.82 (m, 2H), 1.56–1.47 (m, 1H), 1.25 (d, J=6 Hz, 3H). MS (ESI) [M+H]$^+$ at 308.

Example 168D

7-Bromo-3-[2-((2R)-2-methyl-pyrrolidin-1-yl)-ethyl]-cinnolin-4-ol

To a mixture of Example 168C (0.10 g, 0.325 mmol) in 2 mL of water was added 1.5 mL 6 M HCl. The resulting solution was cooled to 0° C. and NaNO$_2$ (0.034 g, 0.488 mmol), dissolved in 1 mL water, was added dropwise. The resulting mixture was stirred for 30 minutes at 0° C. and subsequently heated to 90° C. for one hour. After cooling, contents were filtered and the precipitate was washed with 10 mL water and dried under reduced pressure to provide the product in 47% yield as a brown solid in HCl salt form, which was used without further purification. $^1$H NMR (CD$_3$OD, 300 MHz) δ 8.10 (d, J=9 Hz, 1H), 7.82 (d, J=3 Hz, 1H), 7.60 (dd, J=3, 9 Hz, 1H), 3.89–3.76 (m, 2H), 3.58–3.53 (m, 1H) 3.42–3.23 (m, 4H), 2.38–2.30 (m, 1H), 2.16–2.06 (m, 2H), 1.83–1.75 (m, 1H), 1.51 (d, J=6 Hz, 3H). MS (ESI) [M]$^+$ at 336.

Example 169

4-{3-[2-(2-Methyl-pyrrolidin-1-yl)-ethyl]-cinnolin-7-yl}-benzonitrile

Example 169A 4-(2-Amino-4-bromo-phenyl)-but-3-yn-1-ol

The title compound was prepared using the procedure described in Example 168C, using 3-butyn-1-ol instead of 1-but-3-ynyl-(2R)-2-methyl-pyrrolidine. $^1$H NMR (CD$_3$OD, 300 MHz) δ 7.03 (d, J=9 Hz, 1H), 6.88 (d, J=3 Hz, 1H), 6.68 (dd, J=3, 9 Hz, 1H), 3.73 (t, J=6 Hz, 2H), 2.65 (t, J=6 Hz, 2H). MS (DCI-NH$_3$) [M]$^+$ at 240 [M+NH$_3$]$^+$ at 257.

Example 169B

7-Bromo-3-(2-hydroxy-ethyl)-cinnolin-4-ol

The title compound was prepared by the method described in Example 168D, using the product from Example 169A in place of the product from Example 168C. $^1$H NMR (CD$_3$OD, 300 MHz) δ 8.07 (d, J=9 Hz, 1H), 7.77 (d, J=3 Hz, 1H), 7.54 (dd, J=3, 9 Hz, 1H), 3.92 (t, J=6 Hz, 2H), 3.02 (t, J=6 Hz, 2H). MS (DCI-NH$_3$) [M]$^+$ at 269.

Example 169C

7-Bromo-4-chloro-3-(2-chloro-ethyl)-cinnoline

To a stirred mixture of the product from Example 169B (0.20 g, 0.744 mmol) in chlorobenzene (5 mL) was added POCl$_3$ (0.10 mL, 1.11 mmol) and anhydrous pyridine (0.018 mL, 0.223 mmol). The resulting mixture was heated to 100° C. for 1 hour, cooled to r.t., and subsequently concentrated under reduced pressure. The residue was neutralized with 10 mL of a sat. K$_2$CO$_3$ solution, extracted twice with 25 mL dichloromethane, and concentrated. The crude material was purified by column chromatography (50:50 hexanes/dichloromethane to 100% dichloromethane) to afford the product in 42% yield as a brown solid. $^1$H NMR (CDCl$_3$, 300 MHz) δ 8.14 (d, J=9 Hz, 1H), 7.54 (d, J=3 Hz, 1H), 7.49 (dd, J=3, 9 Hz, 1H), 3.95 (t, J=6 Hz, 2H), 3.28 (t, J=6 Hz, 2H). MS (DCI-NH$_3$) [M+H]$^+$ at 307.

Example 169D

4-[3-(2-Chloro-ethyl)-cinnolin-7-yl]-benzonitrile

A mixture of the product from Example 169C (0.095 g, 0.312 mmol), 4-cyanophenylboronic acid (0.046 g, 0.343 mmol), Pd(PPh$_3$)$_2$Cl$_2$ (0.011 g, 0.016 mmol), and 1 M Na$_2$CO$_3$ (0.778 mL, 0.778 mmol) in de-gassed isopropanol/toluene (5 mL, 1:1) was heated to 90° C. under a dry nitrogen atmosphere for 24 hours. After cooling, the reaction mixture was diluted with 20 mL water, extracted twice with 25 mL dichloromethane, and concentrated under reduced pressure. The crude material was purified by column chromatography (100% dichloromethane to 99:1 dichloromethane/methanol) to afford the product in 50% yield as a brown-orange solid. $^1$H NMR (CDCl$_3$, 300 MHz) δ 8.76 (d, J=3 Hz, 1H), 8.02 (dd, J=3, 9 Hz, 1H), 7.96 (d, J=9 Hz, 1H), 7.87 (q, J=9 Hz, 4H), 7.80 (s, 1H), 4.14 (t, J=6 Hz, 2H), 3.69 (t, J=6 Hz, 2H). MS (DCI-NH$_3$) [M−Cl]$^+$ at 258, [M+H]$^+$ at 294.

Example 169E

4-{3-[2-((rac)-2-Methyl-pyrrolidin-1-yl)-ethyl]-cinnolin-7-yl}-benzonitrile

Racemic 2-methylpyrrolidine (0.5 mL, neat) was added to the product from Example 169D (0.01 g, 0.034 mmol) and heated to 65° C. in a sealed tube for 18 hours. After cooling, the reaction mixture was concentrated under reduced pressure and purified by column chromatography (100% dichloromethane to 95:5 dichloromethane/methanol) to afford the product in 43% yield as a brown-yellow semi-solid. $^1$H NMR (CD$_3$OD, 300 MHz) δ 8.72 (m, 1H), 8.20 (dd, J=3, 9 Hz, 1H), 8.16 (s, 1H), 8.11 (d, J=9 Hz, 1H), 8.06 (d, J=9 Hz, 2H), 7.91 (d, J=9 Hz, 2H), 3.58–3.46 (m, 4H), 2.85–2.65 (m, 2H), 2.57–2.51 (m, 1H), 2.03–1.90 (m, 1H), 1–0.89–1.83 (m, 2H), 1.56–1.50 (m, 1H), 1.21 (d, J=6 Hz, 3H). MS (ESI) [M+H]$^+$ at 343.

Example 170

7-Bromo-4-chloro-3-[2-((2R)-2-methyl-pyrrolidin-1-yl)-ethyl]-cinnoline

The title compound was prepared by the method described in Example 169C, using the product from Example 168D in place of the product from Example 169B. $^1$H NMR (CD$_3$OD, 300 MHz) δ 8.69 (d, J=3 Hz, 1H), 8.21 (d, J=9 Hz, 1H), 8.07 (dd, J=3, 9 Hz, 1H), 3.63–3.58 (m, 2H), 3.46–3.30 (m, 2H), 2.73–2.64 (m, 1H), 2.55–2.42 (m, 2H), 2.06–1.95 (m, 1H), 1.84–1.77 (m, 2H), 1.48–1.41 (m, 1H), 1.14 (d, J=6 Hz, 3H). MS (ESI) [M]$^+$ at 354.

Example 171

4-{4-Hydroxy-3-[2-((2R)-2-methyl-pyrrolidin-1-yl)-ethyl]-cinnolin-7-yl}-benzonitrile A mixture of the product from Example 168D (0.30 g, 0.805 mmol), 4-cyanophenylboronic acid (0.15 g, 1.05 mmol), Pd(PPh$_3$)$_2$Cl$_2$ (0.03 g, 0.04 mmol), and 1 M Na$_2$CO$_3$ (2.01 mL, 2.01 mmol) in isopropanol (15 mL) was heated to 90° C. under a dry nitrogen atmosphere for 2 days. After cooling, the reaction mixture was filtered through celite and concentrated under reduced pressure. The crude material was purified by column chromatography (100% dichloromethane to 90:10 dichloromethane/methanol) to afford the product in 33% yield as a light brown solid. $^1$H NMR (CD$_3$OD, 300 MHz) δ 8.29 (d, J=9 Hz, 1H), 7.95 (q, J=9 Hz, 4H), 7.83 (d, J=3 Hz, 1H), 7.75 (dd, J=3, 9 Hz, 1H), 3.49–3.42 (m, 2H), 3.17–3.12 (m, 2H), 2.78–2.73 (m, 2H), 2.62–2.59 (m, 1H), 2.12–2.09 (m, 1H), 1.92–1.84 (m, 2H), 1.61–1.53 (m, 1H), 1.25 (d, J=6 Hz, 3H). MS (ESI) [M+H]$^+$ at 359.

Example 172

4-{4-Isopropoxy-3-[2-((2R)-2-methyl-pyrrolidin-1-yl)-ethyl]-cinnolin-7-yl}-benzonitrile The title compound was prepared by the method described in Example 171, using the product from Example 170 in place of the product from Example 168D. $^1$H NMR (CD$_3$OD, 300 MHz) δ 8.69 (d, J=3 Hz, 1H), 8.32 (d, J=9 Hz, 1H), 8.19 (dd, J=3, 9 Hz, 1H), 8.06 (d, J=9 Hz, 2H), 7.92, (d, J=9 Hz, 2H), 4.88–4.77 (m, 1H), 3.71–3.49 (m, 4H), 3.06–2.91 (m, 2H), 2.81–2.73 (m, 1H), 2.19–2.10 (m, 1H), 1.97–1.90 (m, 2H), 1.61–1.53 (m, 1H), 1.48 (d, J=6 Hz, 6H), 1.25 (d, J=6 Hz, 3H). MS (ESI) [M+H]$^+$ at 401.

Example 173

4-{3-[2-(4-Methyl-piperazin-1-yl)-ethyl]-cinnolin-7-yl}-benzonitrile

The title compound was prepared by the method described in Example 169E, using 1-methylpiperazine in place of 2-methylpyrrolidine. $^1$H NMR (CD$_3$OD, 300 MHz) δ 8.70 (m, 1H), 8.19 (dd, J=3, 9 Hz, 1H), 8.13 (s, 1H), 8.11–8.01 (m, 3H), 7.91 (d, J=9 Hz, 2H), 3.44 (t, J=6 Hz, 2H), 2.95 (t, J=6 Hz, 2H), 2.75–2.45 (m, 8H), 2.28 (s, 3H). MS (ESI) [M+H]$^+$ at 358.

Example 174

4-[3-(2-Piperidin-1-yl-ethyl)-cinnolin-7-yl]-benzonitrile

The title compound was prepared by the method described in Example 169E, using piperidine in place of 2-methylpyrrolidine. $^1$H NMR (CD$_3$OD, 300 MHz) δ 8.70 (m, 1H), 8.19 (dd, J=3, 9 Hz, 1H), 8.13 (s, 1H), 8.12–8.04 (m, 3H), 7.91 (d, J=9 Hz, 2H), 3.44 (t, J=6 Hz, 2H), 2.91 (t, J=6 Hz, 2H), 2.61 (m, 4H), 1.65 (m, 4H), 1.51 (m, 2H). MS (ESI) [M+H]$^+$ at 343.

Example 175

4-[3-(2-Pyrrolidin-1-yl-ethyl)-cinnolin-7-yl]-benzonitrile

The title compound was prepared by the method described in Example 20169E, using pyrrolidine in place of 2-methylpyrrolidine. $^1$H NMR (CD$_3$OD, 300 MHz) δ 8.71 (m, 1H), 8.20 (dd, J=3, 9 Hz, 1H), 8.15 (s, 1H), 8.11 (d, J=9 Hz, 1H), 8.06 (d, J=9 Hz, 2H), 7.92 (d, J=9 Hz, 2H), 3.50 (t, J=9 Hz, 2H), 3.21 (t, J=9 Hz, 2H), 2.85 (m, 4H), 1.90 (m, 4H). MS (ESI) [M+H]$^+$ at 329.

Example 176

4-{3-[2-((2R)-2-Methyl-pyrrolidin-1-yl)-ethyl]-cinnolin-7-yl}-benzonitrile (2R)-2-methylpyrrolidine (L)-tartrate (0.100 g, 0.425 mmol) was partitioned between toluene (0.5 mL) and 5 M NaOH/brine (1:1, 1 mL total). The organic phase was then added to the product from Example 169D (0.01 g, 0.034 mmol) and heated to 85° C. in a sealed tube for 48 hours. After cooling, the reaction mixture was concentrated under reduced pressure and purified by column chromatography (100% dichloromethane to 95:5 dichloromethane/methanol) to afford the product in 27% yield as a yellow solid. $^1$H NMR (CD$_3$OD, 300 MHz) δ 8.73 (m, 1H), 8.21 (dd, J=3, 9 Hz, 1H), 8.14 (s, 1H), 8.12 (d, J=9 Hz, 1H), 8.06 (d, J=9 Hz, 2H), 7.92 (d, J=9 Hz, 2H), 3.72–3.48 (m, 4H), 3.15–2.90 (m, 2H), 2.86–2.75 (m, 1H), 2.21–2.10 (m, 1H), 1.98–1.91 (m, 2H), 1.67–1.60 (m, 1H), 1.31 (d, J=6 Hz, 3H). MS (ESI) [M+H]$^+$ at 343.

Example 177

4-{3-[2-((2R)-2-Hydroxymethyl-pyrrolidin-1-yl)-ethyl]-cinnolin-7-yl}-benzonitrile The title compound was prepared by the method described in Example 169E, using pyrrolidin-(2R)-2-yl-methanol in place of 2-methylpyrrolidine. $^1$H NMR (CD$_3$OD, 300 MHz) δ 8.71 (m, 1H), 8.19 (dd, J=3, 9 Hz, 1H), 8.15 (s, 1H), 8.10 (d, J=9 Hz, 1H), 8.06 (d, J=9 Hz, 2H), 7.91 (d, J=9 Hz, 2H), 3.58–3.43 (m, 4H), 2.92 (m, 1H), 2.73 (m, 1H), 2.48 (m, 1H), 2.01–1.92 (m, 2H), 1.85–1.67 (m, 4H). MS (ESI) [M+H]$^+$ at 359.

Example 178

4-[3-(2-Morpholin-4-yl-ethyl)-cinnolin-7-yl]-benzonitrile

The title compound was prepared by the method described in Example 169E, using morpholine in place of 2-methylpyrrolidine. $^1$H NMR (CD$_3$OD, 300 MHz) δ 8.70 (m, 1H), 8.19 (dd, J=3, 9 Hz, 1H), 8.14 (s, 1H), 8.10 (d, J=9 Hz, 1H), 8.05 (d, J=9 Hz, 2H), 7.91 (d, J=9 Hz, 2H), 3.70 (t, J=4.5 Hz, 4H), 3.44 (t, J=9 Hz, 2H), 2.94 (t, J=9 Hz, 2H), 2.61 (t, J=4.5 Hz, 4H). MS (ESI) [M+H]$^+$ at 345.

Example 179

4-{3-[2-(4-Methyl-piperidin-1-yl)-ethyl]-cinnolin-7-yl}-benzonitrile

The title compound was prepared by the method described in Example 169E, using 4-methylpiperidine in place of 2-methylpyrrolidine. $^1$H NMR (CD$_3$OD, 300 MHz) δ 8.71 (m, 1H), 8.19 (dd, J=3, 9 Hz, 1H), 8.13 (s, 1H), 8.10 (d, J=9 Hz, 1H), 8.05 (d, J=9 Hz, 2H), 7.91 (d, J=9 Hz, 2H), 3.47 (t, J=6 Hz, 2H), 3.14 (m, 2H), 3.00, (m, 2H), 2.26 (m, 2H), 1.73, (m, 2H), 1.48–1.44 (m, 1H), 1.32–1.28 (m, 2H), 0.96 (d, J=6 Hz, 3H). MS (ESI) [M+H]$^+$ at 357.

Example 180

4-{3-[2-(Ethyl-methyl-amino)-ethyl]-cinnolin-7-yl}-benzonitrile

The title compound was prepared by the method described in Example 169E, using ethyl-methyl-amine in place of 2-methylpyrrolidine. $^1$H NMR (CD$_3$OD, 300 MHz) δ 8.70 (m, 1H), 8.19 (dd, J=3, 9 Hz, 1H), 8.13 (s, 1H), 8.10 (d, J=9 Hz, 1H), 8.06 (d, J=9 Hz, 2H), 7.91 (d, J=9 Hz, 2H), 3.43 (t, J=6 Hz, 2H), 2.99 (t, J=6 Hz, 2H), 2.61 (q, J=9 Hz, 2H), 2.40 (s, 3H), 1.12 (t, J=9 Hz, 3H). MS (ESI) [M+H]$^+$ at 317.

Example 181

7-(2,6-Dimethyl-pyridin-3-yl)-3-[2-((2R)-2-methyl-pyrrolidin-1-yl)-ethyl]-cinnoline A mixture of the product from Example 169C (0.100 g, 0.328 mmol), 2,6-dimethyl-3-(4,4,5,5-tetramethyl-[1,3,2]dioxaborolan-2-yl)-pyridine (0.077 g, 0.328 mmol), Pd(PPh$_3$)$_2$Cl$_2$ (0.012 g, 0.017 mmol), and 1 M Na$_2$CO$_3$ (0.820 mL, 0.820 mmol) in de-gassed isopropanol/toluene (5 mL, 1:1) was heated to 90° C. under a dry nitrogen atmosphere for 24 hours. After cooling, the reaction mixture was filtered, diluted with 20 mL water, extracted twice with 25 mL dichloromethane, and concentrated under reduced pressure. Next, (2R)-2-methylpyrrolidine (L)-tartrate (0.100 g, 0.425 mmol) was partitioned between toluene (0.5 mL) and 5M NaOH/brine (1:1, 1 mL total). The toluene phase (0.5 mL) was subsequently added to a solution of the above crude material in acetonitrile (3 mL) and the resulting mixture was heated to 85° C. in a sealed tube for 48 hours. Upon cooling, the mixture was concentrated under reduced pressure and purified by column chromatography (100% dichloromethane to 95:5 dichloromethane/methanol) to provide the title compound. $^1$H NMR (CD$_3$OD, 300 MHz) δ 8.38 (m, 1H), 8.19 (s, 1H), 8.06 (d, J=9 Hz, 1H), 7.84 (dd, J=3, 9 Hz, 1H), 7.76 (d, J=9 Hz, 1H), 7.27 (d, J=9 Hz, 1H), 3.52–3.28 (m, 4H), 2.78–2.62 (m, 2H), 2.59 (s, 3H), 2.52 (s, 3H), 2.46–2.39 (m, 1H), 2.08–1.98 (m, 1H), 1.86–1.78 (m, 2H), 1.56–1.42 (m, 1H), 1.18 (d, J=6 Hz, 3H). MS (ESI) [M+H]$^+$ at 347.

Example 182

7-(2,4-Dimethoxy-pyrimidin-5-yl)-3-[2-((2R)-2-methyl-pyrrolidin-1-yl)-ethyl]-cinnoline The title compound was prepared by the method described in Example 181, using 2,4-dimethoxypyrimidine-5-boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.59 (m, 1H), 8.56 (s, 1H), 8.16 (s, 1H), 8.06–8.00 (m, 2H), 4.12 (s, 3H), 4.08 (s, 3H), 3.58–3.38 (m, 4H), 2.87–2.52 (m, 3H), 2.16–2.05 (m, 1H), 1.91–1.83 (m, 2H), 1.58–1.47 (m, 1H), 1.22 (d, J=6 Hz, 3H). MS (ESI) [M+H]$^+$ at 380.

Example 183

7-(6-Methoxy-pyridin-3-yl)-3-[2-((2R)-2-methyl-pyrrolidin-1-yl)-ethyl]-cinnoline The title compound was prepared by the method described in Example 181, using 2-methoxy-5-pyridine boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.64 (m, 2H), 8.23–7.98 (m, 3H), 8.12 (d, J=9 Hz, 1H), 6.99 (d, J=9 Hz, 1H), 4.01 (s, 3H), 3.82–3.46 (m, 4H), 3.26–3.20 (m, 2H), 3.04–2.98 (m, 1H), 2.38–2.24 (m, 1H), 2.17–2.04 (m, 2H), 1.78–1.70 (m, 1H), 1.42 (d, J=6 Hz, 3H). MS (ESI) [M+H]$^+$ at 349.

Example 184

3-{3-[2-((2R)-2-Methyl-pyrrolidin-1-yl)-ethyl]-cinnolin-7-yl}-benzonitrile

The title compound was prepared by the method described in Example 181, using 3-cyanophenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.731 (m, 1H), 8.28–8.13 (m, 5H), 7.83 (dd, J=3, 9 Hz, 1H), 7.76 (d, J=9 Hz, 1H), 3.82–3.60 (m, 4H), 3.41–3.28 (m, 2H), 3.18–3.06 (m, 1H), 2.36–2.21 (m, 1H), 2.13–2.02 (m, 2H), 1.78–1.71 (m, 1H), 1.41 (d, J=6 Hz, 3H). MS (ESI) [M+H]$^+$ at 343.

Example 185

5-{3-[2-((2R)-2-Methyl-pyrrolidin-1-yl)-ethyl]-cinnolin-7-yl}-nicotinonitrile The title compound was prepared by the method described in Example 181, using 5-(4,4,5,5-tetramethyl-[1,3,2]dioxaborolan-2-yl)-nicotinonitrile in place of 2,6-dimethyl-3-(4,4,5,5-tetramethyl-[1,3,2]dioxaborolan-2-yl)-pyridine. $^1$H NMR (CD$_3$OD, 300 MHz) δ 9.36 (m, 1H), 9.03 (m, 1H), 8.84 (s, 1H), 8.78 (m, 1H), 8.28–8.24 (m, 2H), 8.19 (d, J=9 Hz, 1H), 4.16–3.97 (m, 1H), 3.82–3.57 (m, 5H), 3.38–3.26 (m, 1H), 2.41–2.32 (m, 1H), 2.29–2.17 (m, 2H), 1.84–1.78 (m, 1H), 1.43 (d, J=6 Hz, 3H). MS (ESI) [M+H]$^+$ at 344.

Example 186

7-(4-Fluoro-phenyl)-3-[2-((2R)-2-methyl-pyrrolidin-1-yl)-ethyl]-cinnoline

The title compound was prepared by the method described in Example 181, using 4-fluorophenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.62 (m, 1H), 8.21–8.07 (m, 3H), 7.92–7.87 (m, 2H), 7.33–7.25 (m, 2H), 4.03–3.95 (m, 1H), 3.83–3.53 (m, 5H), 3.07–2.99 (m, 1H), 2.41–2.30 (m, 1H), 2.18–2.10 (m, 2H), 1.82–1.77 (m, 1H), 1.43 (d, J=6 Hz, 3H). MS (ESI) [M+H]$^+$ at 336.

Example 187

2-{3-[2-((2R)-2-Methyl-pyrrolidin-1-yl)-ethyl]-cinnolin-7-yl}-pyrrole-1-carboxylic acid tert-butyl ester The title compound was prepared by the method described in Example 181, using 1-(t-butoxycarbonyl)pyrrole-2-boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.36 (m, 1H), 8.19 (s, 1H), 7.96 (d, J=9 Hz, 1H), 7.87 (dd, J=3, 9 Hz, 1H), 7.47 (m, 1H), 6.47 (m, 1H), 6.37 (m, 1H), 4.03–3.95 (m, 1H), 3.82–3.51 (m, 5H), 3.27–3.23 (m, 1H), 2.38–2.27 (m, 1H), 2.18–2.06 (m, 2H), 1.82–1.77 (m, 1H), 1.42 (d, J=6 Hz, 3H), 1.38 (s, 9H). MS (ESI) [M+H]$^+$ at 407.

Example 188

(3-{3-[2-((2R)-2-Methyl-pyrrolidin-1-yl)-ethyl]-cinnolin-7-yl}-phenyl)-methanol The title compound was prepared by the method described in Example 181, using 3-(hydroxymethyl)phenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.62 (m, 1H), 8.19–8.03 (m, 3H), 7.83–7.76 (m, 2H), 7.57–7.43 (m, 2H), 4.76 (s, 2H), 3.58–3.38 (m, 4H), 2.84–2.45 (m, 3H), 2.12–2.02 (m, 1H), 1.92–1.82 (m, 2H), 1.57–1.46 (m, 1H), 1.21 (d, J=6 Hz, 3H). MS (ESI) [M+H]$^+$ at 348.

Example 189

7-(3,5-Difluoro-phenyl)-3-[2-((2R)-2-methyl-pyrrolidin-1-yl)-ethyl]-cinnoline The title compound was prepared by the method described in Example 181, using 3,5-difluorophenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.60 (m, 1H), 8.22 (s, 1H), 8.10–8.03 (m, 2H), 7.81–7.75 (m, 1H), 7.23–7.17 (m, 2H), 4.05–3.96 (m, 1H), 3.82–3.51 (m, 5H), 3.27–3.23 (m, 1H), 2.38–2.27 (m, 1H), 2.18–2.06 (m, 2H), 1.82–1.77 (m, 1H), 1.42 (d, J=6 Hz, 3H). MS (ESI) [M+H]$^+$ at 354.

Example 190

3-[2-((2R)-2-Methyl-pyrrolidin-1-yl)-ethyl]-7-thiophen-3-yl-cinnoline

The title compound was prepared by the method described in Example 181, using 3-thiophene boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.63 (m, 1H), 8.28 (dd, J=3, 9 Hz, 1H), 8.18 (s, 1H), 8.05 (m, 2H), 7.76 (m, 1H), 7.63 (m, 1H), 4.05–3.96 (m, 1H), 3.83–3.52 (m, 5H), 3.27–3.23 (m, 1H), 2.41–2.30 (m, 1H), 2.18–2.06 (m, 2H), 1.83–1.77 (m, 1H), 1.43 (d, J=6 Hz, 3H). MS (ESI) [M+H]$^+$ at 324.

Example 191

7-(4-Chloro-phenyl)-3-[2-((2R)-2-methyl-pyrrolidin-1-yl)-ethyl]-cinnoline

The title compound was prepared by the method described in Example 181, using 4-chlorophenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.64 (m, 1H), 8.21–8.06 (m, 3H), 7.88–7.82 (m, 2H), 7.60–7.54 (m, 2H), 4.03–3.96 (m, 1H), 3.83–3.53 (m, 5H), 3.07–2.99 (m, 1H), 2.41–2.30 (m, 1H), 2.18–2.09 (m, 2H), 1.82–1.76 (m, 1H), 1.44 (d, J=6 Hz, 3H). MS (ESI) [M+H]$^+$ at 352.

Example 192

7-(4-Ethoxy-phenyl)-3-[2-((2R)-2-methyl-pyrrolidin-1-yl)-ethyl]-cinnoline

The title compound was prepared by the method described in Example 181, using 4-ethoxyphenyl boronic acid in place of 2,6-dimethyl-3-(4,4,5,5-tetramethyl-[1,3,2]dioxaborolan-2-yl)-pyridine. $^1$H NMR (CD$_3$OD, 300 MHz) δ 8.59 (m, 1H), 8.21 (dd, J=3, 9 Hz, 1H), 8.18 (s, 1H), 8.06 (d, J=9 Hz, 1H), 7.82–7.78 (m, 2H), 7.10–7.06 (m, 2H), 4.14 (q, J=6 Hz, 2H), 4.05–3.97 (m, 1H), 3.83–3.55 (m, 5H), 3.07–2.98 (m, 1H), 2.41–2.30 (m, 1H), 2.19–2.07 (m, 2H), 1.82–1.76 (m, 1H), 1.44 (t, J=6 Hz, 3H), 1.41 (d, J=6 Hz, 3H). MS (ESI) [M+H]$^+$ at 362.

Example 193

3-[2-((2R)-2-Methyl-pyrrolidin-1-yl)-ethyl]-7-(1H-pyrrol-2-yl)-cinnoline

To a solution of the product from Example 187 (0.007 g, 0.017 mmol) in tetrahydrofuran (2 mL), was added NaOMe (0.03 mL, 25% in methanol) and stirred at r.t. for 3 hours. The reaction mixture was then concentrated under reduced pressure, re-dissolved in water (2 mL), extracted with ethyl acetate (2 mL), dried with Na$_2$SO$_4$, and concentrated to afford the product in 76% yield as a yellowish solid. $^1$H NMR (CD$_3$OD, 300 MHz) δ 8.31 (m, 1H), 8.02 (dd, J=3, 9 Hz, 1H), 7.90 (s, 1H), 7.79 (d, J=9 Hz, 1H), 6.89 (m, 1H), 6.71 (m, 1H), 6.18 (m, 1H), 3.33–3.19 (m, 4H), 2.53–2.22 (m, 3H), 1.96–1.87 (m, 1H), 1.77–1.64 (m, 2H), 1.43–1.37 (m, 1H), 1.06 (d, J=6 Hz, 3H). MS (ESI) [M+H]$^+$ at 307.

Example 194

2-(1,5-Dimethyl-1H-pyrazol-4-yl)-6-{2-[(2R)-2-methyl-1-pyrrolidinyl]ethyl}-quinoline The title compound was prepared using the procedure described in Example 57-using 1-(1,5-dimethyl-1H-pyrazol-4-yl)-ethanone (reference P. Schenone et al., J. Heterocycl. Chem. 19, 1982, 1355–1361) for 1-(1,3-thiazol-2-yl)-ethanone. $^1$H NMR (300 MHz, CD$_3$OD) δ 1.20 (d, J=6 Hz, 3H), 1.5 (m, 1H), 1.84 (m, 2H), 2.07 (m, 1H), 2.60 (m, 3H), 2.72 (s, 3H), 3.05 (m, 2H), 3.23 (m, 1H), 3.35 (m, 1H), 3.1 (s, 3H), 7.64 (dd, J=9 Hz, J=3 Hz, 1H), 7.69 (d, J=9 Hz, 1H), 7.73 (d, J=1.70 Hz, 1H), 7.94 (d, J=9 Hz, 1H), 7.96 (d, J=1.70 Hz, 1H), 8.22 (d, J=9 Hz, 1H); (DCI/NH$_3$) m/z 335 (M+H)$^+$.

Example 195

Determination of Biological Activity

To determine the effectiveness of representative compounds of this invention as histamine-3 receptor ligands (H$_3$ receptor ligands), the following tests were conducted according to methods previously described (European Journal of Pharmacology, 188:219–227 (1990); Journal of Pharmacology and Experimental Therapeutics, 275:598–604 (1995); Journal of Pharmacology and Experimental Therapeutics, 276:1009–1015 (1996); and Biochemical Pharmacology, 22:3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid N$_2$ and stored at −70° C. until used in assays. Rat cortical membranes (12 mg wet weight/tube) were incubated with (3H)-N-α-methylhistamine (~0.6 nM) with or without H$_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 µM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and K$_i$ values were determined using the Cheng-Prusoff equation.

Generally, representative compounds of the invention demonstrated binding affinities in the above assay from about 810 nM to about 0.12 nM. Preferred compounds of the invention bound to histamine-3 receptors with binding affinities from about 100 nM to about 0.12 nM. More preferred compounds of the invention bound to histamine-3 receptors with binding affinities from about 20 nM to about 0.12 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula:

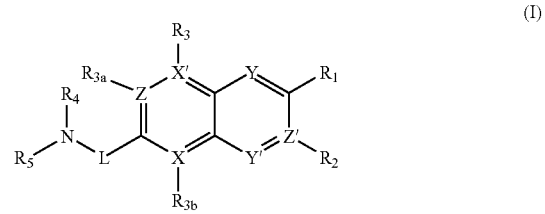

(I)

or a pharmaceutically acceptable salt, ester, amide, or prodrug thereof, wherein:

Y, and Y' are each independently selected from the group consisting of CH and CF;

X, X', Z, and Z' are each;

one of $R_1$ and $R_2$ is selected from the group consisting of halogen, cyano, and $L_2R_6$;

the other of $R_1$ and $R_2$ is selected from the group consisting of hydrogen, alkyl, alkoxy, aryl, cycloalkyl, halogen, cyano, and thioalkoxy, $R_3$ is selected from the group consisting of hydrogen, alkyl, alkoxy, halogen, cyano, and thioalkoxy;

$R_{3a}$ is selected from the group consisting of hydrogen, methyl, alkoxy, halogen, and cyano;

$R_{3b}$ is selected from the group consisting of hydrogen, alkyl, alkoxy, halogen, hydroxy, cyano, and thioalkoxy;

$R_4$ and $R_5$ are each independently selected from the group consisting of alkyl, haloalkyl, hydroxyalkyl, alkoxyalkyl, cycloalkyl, cycloalkylalkyl, and $(NR_AR_B)$alkyl, or $R_4$ and $R_5$ taken together with the nitrogen atom to which each is attached form a non-aromatic ring of the formula:

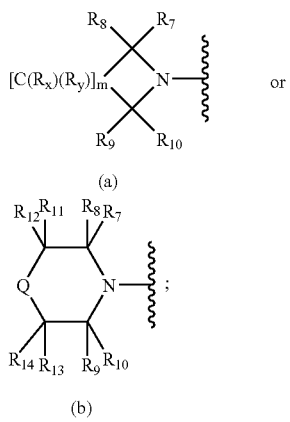

(a)

(b)

$R_6$ is selected from the group consisting of aryl, heteroaryl, heterocycle, and cycloalkyl;

$R_7$, $R_8$, $R_9$, and $R_{10}$ at each occurrence are each independently selected from the group consisting of hydrogen, hydroxyalkyl, fluoroalkyl, and alkyl; or one of the pair $R_7$ and $R_8$ or the pair $R_9$ and $R_{10}$ is taken together to form a $C_3$–$C_6$ ring, wherein 0, 1, or 2 heteroatoms selected from 0, N, or S replace a carbon atom in the ring;

$R_{11}$, $R_{12}$, $R_{13}$, and $R_{14}$ are each independently selected from the group consisting of hydrogen, hydroxy, hydroxyalkyl, alkyl, and fluoro;

Q is selected from the group consisting of a bond, O, S, and $NR_{15}$;

L is —$[C(R_{16})(R_{17})]_n$— or —$[C(R_{16})(R_{17})]_pO$—;

$L_2$ is selected from the group consisting of a bond, —C(=O)—, —S—, —$[C(R_{18})(R_{19})]_q$—, —NH— and —N(alkyl)—;

$R_{15}$ is selected from the group consisting of hydrogen, alkyl, acyl, amido, and formyl;

$R_{16}$ and $R_{17}$ at each occurrence are independently selected from the group consisting of hydrogen, alkyl, alkoxy, and fluoro;

$R_{18}$ and $R_{19}$ at each occurrence are each independently selected from the group consisting of hydrogen, hydroxy, alkyl, alkoxy, and fluoro;

$R_x$ and $R_y$ at each occurrence are independently selected from the group consisting of hydrogen, hydroxy, alkyl, alkoxy, alkylamino, dialkylamino, and fluoro, or one of $R_x$ or $R_y$ represents a covalent bond when taken together with $R_x$ or $R_y$ on an adjacent carbon atom such that a double bond is represented between the adjacent carbon atoms;

m is an integer from 1 to 5;

n is an integer from 1 to 6;

p is an integer from 2 to 6; and q is an integer from 1 to 4.

2. The compound of claim 1, wherein $R_1$ is bromo, cyano, or $L_2R_6$.

3. The compound of claim 1, wherein $R_1$ is $L_2R_6$, $L_2$ is —CH(OH)—, —C(=O)—, or a bond, and $R_6$ is aryl, heteroaryl, heterocycle, or cycloalkyl.

4. The compound of claim 1, wherein $R_1$ is $L_2R_6$, $L_2$ is a bond, and $R_6$ is aryl wherein the aryl is phenyl substituted with 0, 1, or 2 substituents selected from the group consisting of cyano, halogen, —$NR_AR_B$, alkoxy, hydroxyalkyl, alkylcarbonyl, alkoxycarbonyl, cycloalkylcarbonyl, alkylsulfonyl, haloalkyl, and thioalkoxy.

5. The compound of claim 1, wherein $R_1$ is $L_2R_6$, $L_2$ is a bond, and $R_6$ is selected from the group consisting of furyl, imidazolyl, isothiazolyl, isoxazolyl, oxadiazolyl, oxazolyl, pyrazinyl, pyrazolyl, pyridazinyl, pyridazinonyl, pyridinonyl, pyridinyl, pyrimidinyl, pyrrolyl, tetrazolyl, thiadiazolyl, thiazolyl, thienyl, triazinyl, and triazolyl, substituted with 0, 1, 2, or 3 substituents selected from the group consisting of —$NR_AR_B$, halogen, alkyl, cyano, alkoxyimino, alkoxycarbonyl, $(NR_AR_B)$carbonyl, alkylcarbonyl, haloalkyl, and alkoxy.

6. The compound of claim 1, wherein $R_1$ is $L_2R_6$, $L_2$ is a bond, and $R_6$ is selected from the group consisting of azepanyl, azetidinyl, aziridinyl, azocanyl, dihydrothiazolyl, morpholinyl, piperazinyl, piperidinyl, pyrrolidinyl, pyrrolinyl, thiomorpholinyl, tetrahydropyridinyl, tetrahydrofuryl, and tetrahydropyranyl.

7. The compound of claim 1, wherein $R_4$ and $R_5$ are each independently selected from methyl, ethyl, and propyl.

8. The compound of claim 1, wherein $R_4$ and $R_5$ taken together with the nitrogen atom to which each is attached form a 4- to 8-membered non-aromatic ring represented by formula (a).

9. The compound of claim 8, wherein the 4- to 8-membered non-aromatic ring is selected from the group consisting of azetidinyl, azepanyl, azepinyl, pyrrolidinyl, pyrrolinyl, piperidinyl, piperazinyl, and tetrahydropyridinyl, substituted with 0, 1, or 2 substituents selected from the group consisting of alkyl, hydroxyalkyl, fluoroalkyl, and —$NR_AR_B$.

10. The compound of claim 8, wherein at least one substituent represented by $R_7$, $R_8$, $R_9$, and $R_{10}$ is selected from the group consisting of alkyl, halogen, fluoroalkyl, and hydroxyalkyl or at least one substituent represented by $R_x$ or R is selected from the group consisting of hydrogen, hydroxy, and fluoro.

11. The compound of claim 8, wherein the 4- to 8-membered non-aromatic ring is selected from the group consisting of methylpyrrolidinyl, ethylpyrrolidinyl, dimethylaminopyrrolidinyl, isopropylpyrrolidinyl, isobutylpyrrolidinyl, hydroxymethylpyrrolidinyl, and fluoromethylpyrrolidinyl.

12. The compound of claim 1, wherein $R_4$ and $R_5$ taken together with the nitrogen atom to which each is attached form morpholinyl or thiomorpholinyl.

13. The compound of claim 1, wherein at least one substituent represented by $R_7$, $R_8$, $R_9$, and $R_{10}$ is hydroxyalkyl, fluoroalkyl, or alkyl.

14. The compound of claim 1, wherein at least one substituent represented by $R_7$, $R_8$, $R_9$, and $R_{10}$ is methyl, ethyl, fluoromethyl, or hydroxymethyl.

15. The compound of claim 1, wherein one substituent represented by $R_7$, $R_8$, $R_9$, and $R_{10}$ is alkyl and the other three substituents are hydrogen.

16. The compound of claim 1, wherein $R_{11}$, $R_{12}$, $R_{13}$, and $R_{14}$ are each hydrogen.

17. The compound of claim 1, wherein $R_{11}$ and $R_{12}$ each are hydrogen, and $R_{13}$ and $R_{14}$ are each independently selected from the group consisting of hydrogen and alkyl.

18. The compound of claim 1, wherein $R_{15}$ is selected from the group consisting of hydrogen, alkyl, amido, and formyl.

19. The compound of claim 1, wherein $R_{16}$ and $R_{17}$ are hydrogen.

20. The compound of claim 1, wherein $R_{18}$ and $R_{19}$ are hydrogen.

21. The compound of claim 1, wherein m is 2 or 3.
22. The compound of claim 1, wherein n is 2 or 3.
23. The compound of claim 1, wherein p is 2.
24. The compound of claim 1, wherein q is 1.
25. The compound of claim 1, wherein
Y and Y' are CH;
X, X', Z, and Z' are C; and
$R_2$, $R_3$, $R_{3a}$, and $R_{3b}$ are hydrogen.
26. The compound of claim 1, wherein:
$R_1$ is $L_2R_6$ wherein $L_2$ is a bond and $R_6$ is heteroaryl or heterocycle;
$R_2$, $R_3$, $R_{3a}$, and $R_{3b}$ are hydrogen;
L is —$[C(R_{16})(R_{17})]_n$—;
n is 2;
$R_{16}$ and $R_{17}$ at each occurrence are hydrogen;
$R_4$ and $R_5$ are taken together to form a methylpyrrolidinyl ring of formula (a), wherein one of $R_7$, $R_8$, $R_9$, and $R_{10}$ is methyl and the remaining three substituents are hydrogen;
Y and Y' are CH; and
X, X', Z, and Z' are C.
27. The compound of claim 26, wherein $R_1$ is a heteroaryl group selected from 2H-pyridazin-3-one-2-yl.
28. The compound of claim 1, selected from the group consisting of
4-(6-{2-[(2R)-2-methyl-1-pyrrolidinyl]ethyl}-2-naphthyl)benzonitrile;
(2R)-1-[2-(6-bromo-2-naphthyl)ethyl]-2-methylpyrrolidine;
1-[3-(6-{2-[(2R)-2-methyl-1-pyrrolidinyl]ethyl}-2-naphthyl)phenyl]ethanone;
2-[3-(6-{2-[(2R)-2-methyl-1-pyrrolidinyl]ethyl}-2-naphthyl)phenyl]-2-propanol;
6-{2-[(2R)-2-methyl-1-pyrrolidinyl]ethyl}-2-naphthonitrile;
4-(6-{[(2R)-2-methyl-1-pyrrolidinyl]methyl}-2-naphthyl)benzonitrile;
3-(6-{2-[(2R)-2-methyl-1-pyrrolidinyl]ethyl}-2-naphthyl)benzonitrile;
4-(6-{2-[(2R)-2-methyl-1-pyrrolidinyl]ethyl}-2-naphthyl)pyridine;
3-(6-{2-[(2R)-2-methyl-1-pyrrolidinyl]ethyl}-2-naphthyl)pyridine;
(3-fluorophenyl)(6-{2-[(2R)-2-methyl-1-pyrrolidinyl]ethyl}-2-naphthyl)methanol;
3,5-dimethyl-4-(6-{2-[(2R)-2-methyl-1-pyrrolidinyl]ethyl}-2-naphthyl)isoxazole;
4-(6-{2-[(2S)-2-(hydroxymethyl)-1-pyrrolidinyl]ethyl}-2-naphthyl)benzonitrile;
4-(6-{2-[(3R)-3-hydroxy-1-pyrrolidinyl]ethyl}-2-naphthyl)benzonitrile;
4-{6-[2-(2-isobutyl-1-pyrrolidinyl)ethyl]-2-naphthyl}benzonitrile;
4-{6-[2-(2-isopropyl-1-pyrrolidinyl)ethyl]-2-naphthyl}benzonitrile;
4-(6-{2-[(3R)-3-(dimethylamino)-1-pyrrolidinyl]ethyl}-2-naphthyl)benzonitrile;
4-{6-[2-(diethylamino)ethyl]-2-naphthyl}benzonitrile;
4-{6-[2-(dimethylamino)ethyl]-2-naphthyl}benzonitrile;
4-(6-{2-[ethyl(isopropyl)amino]ethyl}-2-naphthyl)benzonitrile;
4-(6-{2-[tert-butyl (methyl)amino]ethyl}-2-naphthyl)benzonitrile;
4-(6-{2-[(2S)-2-methyl-1-pyrrolidinyl]ethyl}-2-naphthyl)benzonitrile;
4-(6-{2-[(2R)-2-methyl-1-piperidinyl]ethyl}-2-naphthyl)benzonitrile;
4-{6-[2-(2,5-dihydro-1H-pyrrol-1-yl)ethyl]-2-naphthyl}benzonitrile;
4-(6-{2-[methyl(propyl)amino]ethyl}-2-naphthyl)benzonitrile;
4-(6-{2-[(2-hydroxyethyl)(methyl)amino]ethyl}-2-naphthyl)benzonitrile;
5-(6-{2-[(2R)-2-methyl-1-pyrrolidinyl]ethyl}-2-naphthyl)pyrimidine;
4-(6-{2-[(2R)-2-methyl-1-pyrrolidinyl]ethyl}-2-naphthyl)morpholine;
2-(6-{2-[(2R)-2-methyl-1-pyrrolidinyl]ethyl}-2-naphthyl)-1, 3-thiazole;
4-(6-{2-[(2S)-2-(fluoromethyl)-1-pyrrolidinyl]ethyl}-2-naphthyl)benzonitrile;
(3-fluorophenyl)(6-{2-[(2R)-2-methyl-1-pyrrolidinyl]ethyl}-2-naphthyl)methanone;
2-(6-{2-[(2R)-2-methyl-1-pyrrolidin-1-yl]-ethyl}-2-naphthalen-2-yl)-2H-pyridazin-3-one;
2-methoxy-5-(6-{2-[(2R)-2-methyl-1-pyrrolidinyl]ethyl}-2-naphthyl)pyridine;
4-(6-{2-[(2R)-2-(hydroxymethyl)-1-pyrrolidinyl]ethyl}-2-naphthyl)benzonitrile;
4-{6-[2-(2-methyl-1-pyrrolidinyl)ethyl]-2-naphthyl}benzonitrile;
4-{6-[2-(1-pyrrolidinyl)ethyl]-2-naphthyl}benzonitrile;
4-(6-{2-[(2R)-2-methyl-1-pyrrolidinyl]ethyl}-2-naphthyl)thiomorpholine;
1-{2-[(6-bromo-2-naphthyl)oxy]ethyl}pyrrolidine;
3-{6-[2-(1-pyrrolidinyl)ethoxy]-2-naphthyl}benzonitrile;
3-{6-[2-(1-pyrrolidinyl)ethoxy]-2-naphthyl}pyridine;
3-(6-{2-[(2R)-2-methyl-1-pyrrolidinyl]ethoxy}-2-naphthyl)benzonitrile;
3-(6-{2-[(2R)-2-methyl-1-pyrrolidinyl]ethoxy}-2-naphthyl)pyridine;
6-methyl-2-{6-[2-((2R)-2-methyl-pyrrolidin-1-yl)-ethyl]-naphthalen-2-yl}-2H-pyridazin-3-one;
5-{6-[2-((2 R)-2-methyl-pyrrolidin-1-yl)-ethyl]-naphtha-len-2-yl}-pyrimidine-2-carbonitrile;
1-{6-[2-(2(R)-methyl-pyrrolidin-1-yl)-ethyl]-naphthalen-2-yl}-1H-pyridin-2-one;
5-{6-[2-(2(R)-methyl-pyrrolidin-1-yl)-ethyl]-naphthalen-2-yl}-nicotinonitrile;
4-methyl-1-{6-[2-(2(R)-methyl-pyrrolidin-1-yl)-ethyl]-naphthalen-2-yl}-1H-pyridin-2-one;
2-{6-[2-((2R)-2-methyl-pyrrolidin-1-yl)-ethyl]-naphthalen-2-yl}-pyrazine;
2-{6-[2-((2R)-2-methyl-2,5-dihydro-pyrrol-1-yl)-ethyl]-naphthalen-2-yl}-2H-pyridazin-3-one;

4-(6-{2-[(2-dimethylamino-ethyl)-methyl-amino]-ethyl}-naphthalen-2-yl)-benzonitrile;

4-{6-[2-(4-methyl-piperazin-1-yl)-ethyl]-naphthalen-2-yl}-benzonitrile;

2,4-dimethoxy-5-{6-[2-((2R)-methyl-pyrrolidin-1-yl)-ethyl]-naphthalen-2-yl}-pyrimidine;

2,6-difluoro-3-{6-[2-((2R)-2-methyl-pyrrolidin-1-yl)-ethyl]-naphthalen-2-yl}-pyridine;

cyclopropyl-(4-{6-[2-((2R)2-methyl-pyrrolidin-1-yl)-ethyl]-naphthalen-2-yl}-phenyl)-methanone;

3-methoxy-6-{6-[2-((2R)2-methyl-pyrrolidin-1-yl)-ethyl]-naphthalen-2-yl}-pyridazine;

4-{6-[2-(2-methyl-piperidin-1-yl)-ethyl]-naphthalen-2-yl}-benzonitrile;

4-{6-[2-((2R)-2-ethyl-pyrrolidin-1-yl)-ethyl]-naphthalen-2-yl}-benzonitrile;

2-{6-[2-((2S)-2-methyl-pyrrolidin-1-yl)-ethyl]-naphthalen-2-yl}-2H-pyridazin-3-one;

2-[6-((2R)-2-piperidin-1-yl-ethyl)-naphthalen-2-yl]-2H-pyridazin-3-one;

2-{6-[2-(tert-butyl-methyl-amino)-ethyl]-naphthalen-2-yl}-2H-pyridazin-3-one;

2-[6-(2-diethylamino-ethyl)-naphthalen-2-yl]-2H-pyridazin-3-one;

2-[6-(2-morpholin-4-yl-ethyl)-naphthalen-2-yl]-2H-pyridazin-3-one;

2-{6-[2-(ethyl-methyl-amino)-ethyl]-naphthalen-2-yl}-2H-pyridazin-3-one;

2-{6-[2-((2S)-2-fluoromethyl-pyrrolidin-1-yl)-ethyl]-naphthalen-2-yl}-2H-pyridazin-3-one;

2-{6-[2-(2-hydroxymethyl-pyrrolidin-1-yl)-ethyl]-naphthalen-2-yl}-2H-pyridazin-3-one;

2-{6-[2-((R)-2-ethyl-pyrrolidin-1-yl)-ethyl]-naphthalen-2-yl}-2H-pyridazin-3-one;

2-[6-(2-azetidin-1-yl-ethyl)-naphthaten-2-yl]-2H-pyridazin-3-one;

2-{6-[2-((2S)-2-fluoromethyl-azetidin-1-yl)-ethyl]-naphthalen-2-yl}-2H-pyridazin-3-one;

2-{6-[2-((2S)-2-hydroxymethyl-azetidin-1-yl)-ethyl]-naphthalen-2-yl}-2H-pyridazin-3-one;

2-{6-[2-((2R,5R)-2,5-Dimethyl-pyrrolidin-1-yl)-ethyl]-naphthalen-2-yl}-2H-pyridazin-3-one;

2-{6-[2-((2R,6S)-2,6-dimethyl-piperidin-1-yl)-ethyl]-naphthalen-2-yl}-2H-pyridazin-3-one;

2-{6-[2-((R)-3-hydroxy-piperidin-1-yl)-ethyl]-naphthalen-2-yl}-2H-pyridazin-3-one;

2-{6-[2-((R)-2-methyl-pipendin-1-yl)-ethyl]-naphthalen-2-yl}-2H-pyridazin-3-one;

2,6-dimethyl-3-{6-[2-((2R)-2-methyl-pyrrolidin-1-yl)-ethyl]-naphthalen-2-yl}-pyridine;

5-{6-[2-((R)-2-methyl-pyrrolidin-1-yl)-ethyl]-naphthalen-2-yl}-thiazole;

2-{6-[2-((R)-2-methyl-pyrrolidin-1-yl)-ethyl]-naphthalen-2-yl}-pyrimidine;

3-chloro-6-{6-[2-((R)-2-methyl-pyrrolidin-1-yl)-ethyl]-naphthalen-2-yl}-pyridazine;

5-{6-[2-((R)-2-methyl-pyrrolidin-1-yl)-ethyl]-naphthalen-2-yl}-pyrimidin-2-ylamine; and 2-methyl-5-{6-[2-((2R)2-methyl-pyrrolidin-1-yl)-ethyl]-naphthalen-2-yl}-pyridine.

29. The compound of claim 1, that is 2-(6-{2-[(2R)-2-methyl-1-pyrrolidin-1-yl]-ethyl}-2-naphthalen-2-yl)-2H-pyridazin-3-one or 2-(6-{2-[(2R)-2-methyl-1-pyrrolidinyl]ethyl}-2-naphthyl)-3(2H)-pyridazinone.

30. A pharmaceutical composition comprising a therapeutically effective amount of a compound of claim 1 in combination with a pharmaceutically acceptable carrier.

31. A method of treating a condition or disorder modulated by the histamine-3 receptors in a mammal comprising administering an effective amount of a compound of claim 1, wherein the condition or disorder is Alzheimer's disease, attention-deficit hyperactivity disorder or schizophrenia.

* * * * *

UNITED STATES PATENT AND TRADEMARK OFFICE
CERTIFICATE OF CORRECTION

PATENT NO.       : 7,153,889 B2
APPLICATION NO.  : 10/689735
DATED            : December 26, 2006
INVENTOR(S)      : Altenbach et al.

Page 1 of 1

It is certified that error appears in the above-identified patent and that said Letters Patent is hereby corrected as shown below:

Col. 153, line 3
 replace "X, X', Z, and Z' are each:"
 with --X, X', Z, and Z' are each C:--.

Col. 153, line 7
 replace "selected from 0, N, or S replace a carbon atom in the"
 with --selected from O, N, or S replace a carbon atom in the--.

Col. 154, line 55
 replace "Ris selected from the group consisting of hydrogen"
 with --R is selected from the group consisting of hydrogen--.

Col. 156, line 13
 replace "4-(6-{2-[tert-butyl   (methyl)amino]ethyl}-2-naphthyl)"
 with --4-(6-{2-[tert-butyl(methyl)amino]ethyl}-2-naphthyl)--.

Col. 156, line 56
 replace "5-{6-[2-((2 R)-2-methyl-pyrrolidin-1-yl)ethyl]-naphthalen"
 with --5-{6-[2-((2R)-2-methyl-pyrrolidin-1-yl)ethyl]-naphthalen--.

Col. 157, line 7
 replace "2,   6-difluoro-3-{6-[2-((2R)-2-methyl-pyrrolidin-1-yl)-"
 with --2,6-difluoro-3-{6-[2-((2R)-2-methyl-pyrrolidin-1-yl)- --.

Signed and Sealed this

Ninth Day of September, 2008

JON W. DUDAS
*Director of the United States Patent and Trademark Office*